US012383499B2

(12) United States Patent
Nel et al.

(10) Patent No.: US 12,383,499 B2
(45) Date of Patent: Aug. 12, 2025

(54) SCALE UP SYNTHESIS OF SILICASOME NANOCARRIERS

(71) Applicant: The Regents of the University of California, Oakland, CA (US)

(72) Inventors: Andre E. Nel, Sherman Oaks, CA (US); Huan Meng, Los Angeles, CA (US); Xiangsheng Liu, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 16/235,950

(22) Filed: Dec. 28, 2018

(65) Prior Publication Data
US 2019/0216736 A1    Jul. 18, 2019

Related U.S. Application Data

(60) Provisional application No. 62/612,671, filed on Jan. 1, 2018.

(51) Int. Cl.
*A61K 9/1271* (2025.01)
*A61K 9/1277* (2025.01)
(Continued)

(52) U.S. Cl.
CPC .......... *A61K 9/1271* (2013.01); *A61K 9/1277* (2013.01); *A61K 9/5115* (2013.01);
(Continued)

(58) Field of Classification Search
CPC .. A61K 9/1271; A61K 9/1277; A61K 9/5115; A61K 9/5192; A61K 31/4745; A61P 35/00
See application file for complete search history.

(56) References Cited

U.S. PATENT DOCUMENTS

| 4,737,323 A | 4/1988 | Martin et al. |
| 5,670,631 A | 9/1997 | Bayerl et al. |

(Continued)

FOREIGN PATENT DOCUMENTS

| AU | 2017206077 B2 | 11/2021 |
| EP | 2964201 A1 | 1/2016 |

(Continued)

OTHER PUBLICATIONS

US Office Action (Restriction Requirement), dated Feb. 3, 2017, issued in U.S. Appl. No. 14/772,740.
(Continued)

*Primary Examiner* — Benjamin J Packard
*Assistant Examiner* — Lucy M Tien
(74) *Attorney, Agent, or Firm* — Mark S. Cohen; PEARL COHEN ZEDEK LATZER BARATZ LLP

(57) ABSTRACT

In order to facilitate the approval and commercialization of silicasome drug delivery systems (e.g. irinotecan silicasomes) it is necessary to scale up synthesis of the drug-loaded silicasomes. In this regard, it was discovered that the synthesis protocols used for laboratory synthesis of drug-loaded silicasomes (e.g., 500 mg/batch) do not scale to large scale silicasome production, because the resulting products were too heterogeneous for use as pharmaceuticals. Accordingly, new methods are provided herein that effectively afford the large-scale production of mesoporous silica nanoparticles (MSNPs) and lipid bilayer coated MSNPs (silicasomes).

26 Claims, 55 Drawing Sheets
(49 of 55 Drawing Sheet(s) Filed in Color)
Specification includes a Sequence Listing.

(51) Int. Cl.
 *A61K 9/51* (2006.01)
 *A61K 31/4745* (2006.01)
 *A61P 35/00* (2006.01)
(52) U.S. Cl.
 CPC ........ *A61K 9/5192* (2013.01); *A61K 31/4745* (2013.01); *A61P 35/00* (2018.01)

(56) References Cited

U.S. PATENT DOCUMENTS

| | | | |
|---|---|---|---|
| 6,296,870 | B1 | 10/2001 | Needham et al. |
| 6,868,343 | B1 | 3/2005 | Bayerl et al. |
| 8,734,816 | B2 | 5/2014 | Liu et al. |
| 8,758,811 | B2 | 6/2014 | Ho et al. |
| 8,992,984 | B1 | 3/2015 | Brinker et al. |
| 9,532,949 | B2 | 1/2017 | Zeinelden et al. |
| 9,579,283 | B2 | 2/2017 | Brinker et al. |
| 10,143,660 | B2 | 12/2018 | Nel et al. |
| 10,343,903 | B2 | 7/2019 | Zink et al. |
| 10,765,636 | B2 | 9/2020 | Nel et al. |
| 10,828,255 | B2 | 11/2020 | Nel et al. |
| 11,096,900 | B2 | 8/2021 | Nel et al. |
| 2003/0035842 | A1 | 2/2003 | Kazakov et al. |
| 2004/0005352 | A1 | 1/2004 | Lopez et al. |
| 2005/0249795 | A1 | 11/2005 | Zhang et al. |
| 2006/0154069 | A1 | 7/2006 | Lin et al. |
| 2007/0116753 | A1 | 5/2007 | Hong et al. |
| 2008/0175992 | A1 | 7/2008 | Plieth et al. |
| 2010/0255103 | A1 | 10/2010 | Liong et al. |
| 2010/0284924 | A1 | 11/2010 | Zink et al. |
| 2010/0310465 | A1 | 12/2010 | Zink et al. |
| 2011/0104073 | A1 | 5/2011 | Zeng et al. |
| 2011/0123601 | A1 | 5/2011 | Ho et al. |
| 2011/0268791 | A1 | 11/2011 | Liu et al. |
| 2012/0021034 | A1 | 1/2012 | Zink et al. |
| 2012/0207795 | A1 | 8/2012 | Zink et al. |
| 2013/0046274 | A1 | 2/2013 | Zink et al. |
| 2013/0195963 | A1 | 8/2013 | Serda et al. |
| 2014/0079774 | A1 | 3/2014 | Brinker et al. |
| 2014/0138278 | A1 | 5/2014 | Kennedy |
| 2014/0301951 | A1 | 10/2014 | Liu et al. |
| 2015/0272885 | A1 | 10/2015 | Ashley et al. |
| 2016/0008283 | A1 | 1/2016 | Nel et al. |
| 2017/0095418 | A1 | 4/2017 | Zink et al. |
| 2017/0173169 | A1 | 6/2017 | Yantasee et al. |
| 2018/0098945 | A1 | 4/2018 | Nel et al. |
| 2019/0160015 | A1 | 5/2019 | Nel et al. |
| 2020/0383929 | A1 | 12/2020 | Nel et al. |
| 2021/0077397 | A1 | 3/2021 | Nel et al. |
| 2022/0160644 | A1 | 5/2022 | Nel et al. |

FOREIGN PATENT DOCUMENTS

| | | | |
|---|---|---|---|
| WO | WO 2006/015757 | A1 | 2/2006 |
| WO | WO 2006/032136 | A1 | 3/2006 |
| WO | WO 2010/078569 | A2 | 7/2010 |
| WO | WO 2012/009448 | A2 | 1/2012 |
| WO | WO 2012/149376 | A2 | 11/2012 |
| WO | WO 2013/012891 | A1 | 1/2013 |
| WO | WO 2014/138278 | A1 | 9/2014 |
| WO | WO 2017/013250 | A1 | 1/2017 |
| WO | WO 2017/120537 | A1 | 7/2017 |
| WO | WO 2019/133884 | A1 | 7/2019 |

OTHER PUBLICATIONS

US Office Action dated Jun. 2, 2017, issued in U.S. Appl. No. 14/772,740.
US Final Office Action dated Feb. 20, 2018, issued in U.S. Appl. No. 14/772,740.
US Advisory Action dated Jun. 1, 2018, issued in U.S. Appl. No. 14/772,740.
US Office Action dated Aug. 7, 2018, issued in U.S. Appl. No. 14/772,740.
US Final Office Action dated Apr. 1, 2019, issued in U.S. Appl. No. 14/772,740.
US Office Action dated Nov. 27, 2019, issued in U.S. Appl. No. 14/772,740.
US Office Action dated Jan. 31, 2018 issued in U.S. Appl. No. 15/798,287.
US Office Action dated May 29, 2018 issued in U.S. Appl. No. 15/798,287.
US Notice of Allowance dated Jul. 19, 2018 issued in U.S. Appl. No. 15/798,287.
US Office Action dated Sep. 4, 2019 issued in U.S. Appl. No. 16/164,030.
US Miscellaneous Communication dated Apr. 22, 2020 issued in U.S. Appl. No. 16/164,030.
US Examiner Initiated Interview Summary dated Apr. 23, 2020 issued in U.S. Appl. No. 16/164,030.
U.S. Appl. No. 14/253,030 Office Action dated Dec. 9, 2016.
U.S. Appl. No. 14/253,030 Response as filed on May 9, 2017.
PCT International Search Report and Written Opinion dated Jun. 24, 2014 issued in PCT/US2014/020857.
PCT International Report on Patentability and Written Opinion dated Sep. 17, 2015 issued in PCT/US2014/020857.
European Extended Search Report dated Jul. 27, 2016 issued in Application No. EP 14 760 467.2.
European Office Action dated Aug. 23, 2018 issued in Application No. EP 14 760 467.2.
PCT International Search Report and Written Opinion dated Apr. 18, 2017 issued in PCT/US2017/012625.
PCT International Preliminary Report on Patentability and Written Opinion dated Jul. 10, 2018 issued in PCT/US2017/012625.
European Extended Search Report dated Aug. 7, 2019 issued in Application No. EP 17736481.7.
PCT International Search Report and Written Opinion dated Mar. 27, 2019 issued in PCT/US18/67970.
Abigerges et al. (1995) "Phase I and pharmacologic studies of the camptothecin analog irinotecan administered every 3 weeks in cancer patients." *Clin Oncol* 13:210-221.
Al Shamsi et al. (2010) "Biocompatibility of calcined mesoporous silica particles with cellular bioenergetics in murine tissues." *Chem Res Toxicol* 23(11):1796-1805.
Angelos et al. (2007) "Mesostructured silica supports for functional materials and molecular machines." *Adv Funct Mater* 17:2261-2271.
Argyo, et al. (2013) "Multifunctional Mesoporous Silica Nanoparticles as a Universal Platform for Drug Delivery." *Chem. Mater.*, 26(1): 435-451.
Arruebo et al. (2006) "Development of Magnetic Nanostructured Silica-Based Materials as Potential Vectors for Drug-Delivery Applications." *Chem Mater* 18:1911-1919.
Arruebo et al. (Published Jul. 18, 2006) "Sustained release of doxorubicin from zeolite-magnetite nanocomposited prepared by mechanical activation." *Nanotechnology* 17:4057-4064.
Aryal, et al. (2011) "Polymeric Nanoparticles with Precise Ratiometric Control over Drug Loading for Combination Therapy." *Mol. Pharmaceutics* 8:1401-1407.
Ashley et al. (2011) "The targeted delivery of multicomponent cargos to cancer cells by nanoporous particle-supported lipid bilayers." *Nature Materials* 10(5):389-397.
Ashley et al. (2012) "Delivery of Small Interfering RNA by Peptide-Targeted Mesoporous Silica Nanoparticle-Supported Lipid Bilayers." *ACS Nano* 6:2174-2188.
Awasthi et al. (2013) "Comparative Benefits of Nab-Paclitaxel over Gemcitabine or Polysor-bate-Based Docetaxel in Experimental Pancreatic Cancer." *Carcinogenesis* 34: 2361-2369.
Bagwe et al. (Apr. 25, 2006) "Surface Modification of Silica Nanoparticles to Reduce Aggregation and Nonspecific Binding." *Langmuir* 22:4357-4362.
Baker et al. (2008) "Irinophore C, a Novel Nanoformulation of Irinotecan, Alters Tumor Vascular Function and Enhances the Distribution of 5-Fluorouracil and Doxorubicin." *Clin. Cancer Res.* 14:7260-7271.
Barbe et al. (2004) "Silica particles: A novel drug-delivery system." *Adv Mater* 16:1959-1966.

(56) References Cited

OTHER PUBLICATIONS

Bardelle (1993) "Membrane binding kinetics of factor VIII indicate a complex binding process." *J Biol Chem.* 268(12): 8815-24.
Bayerl, et al. (1990) "Physical Properties of Single Phospholipid Bilayers Adsorbed to Micro Glass Beads. A New Vesicular Model System Studied by 2H-Nuclear Magnetic Resonance." *Biophys. J.*, 58: 357-362.
Bourzac, K. (2012) "Nanotechnology: Carrying Drugs." *Nature*, 491: S58-S60.
Brigger et al. (2002) "Nanoparticles in cancer therapy and diagnosis." *Advanced Drug Delivery Reviews* 54:631-651.
Brumm et al. (1996) "The effect of increasing membrane curvature on the phase transition and mixing behavior of a dimyristoyl-sn-glycero-3-phosphatidylcholine/distearoyl-sn-glycero-3-phosphatidylcholine lipid mixture as studied by Fourier transform infrared spectroscopy and differential scanning calorimetry." *Biophys J.* 70: 1373-1379.
Buck et al. (2004) "Engineering Lipobeads: Properties of the Hydrogel Core and the Lipid Bilayer Shell" *Biomacromolecules*, 5: 2230-2237.
Buranda et al. (2003) "Biomimetic Molecular Assemblies on Glass and Mesoporous Silica Microbeads for Biotechnology" *Langmuir*, 19: 1654-1663.
Carmona-Ribeiro (2003) "Bilayer-forming synthetic lipids: drugs or carriers?" *Curr. Med. Chem.* 10: 2425-2446.
Cauda et al. (2010) "Colchicine-Loaded Lipid Bilayer-Coated 50 nm Mesoporous Nanoparticles Efficiently Induce Microtubule Depolymerization upon Cell Uptake" *Nano Letters* 10(7): 2484-2492.
Celano et al. (2004) "Cytotoxic effects of Gemcitabine-loaded liposomes in human anaplastic thyroid carcinoma cells," *BMC Cancer* 4(63):5 pages.
"CHEBI:53581—cetyttrimethylammonium chloride", Retrieved from the Internet: URL https://www.ebi.ac.uk/chebi/searchId.do?chebiId= CHEBI:53581, Sep. 11, 2013 (Sep. 11, 2013), Section "Synonyms".
Chemburu et al. (2010) "Biomimetic Silica Microspheres in Biosensing" *Molecules*, 15: 1932-1957.
Chen et al. (2009) "Co-delivery of Doxorubicin and Bcl-2 siRNA by Mesoporous Silica Nanoparticles Enhances the Efficacy of Chemotherapy in Multidrug Resistant Cancer Cells." *Small* 5(23):2673-2677.
Chen, et al. (2014) "Antitumor efficacy of irinotecan-loaded galactosyl modified lipid bilayer-coated mesoporous silica nanoparticles against hepatocellular carcinoma cells." *Acta Pharmaceutica Sinica*, 49(5): 718-725. [Article in Chinese with English abstract].
Cho et al. (2008) "Therapeutic nanoparticles for drug delivery in cancer." *Clin. Cancer Res.* 14(5):1310-1316.
Chou et al. (2003) "Effect of Composition on the stability of liposomal irinotecan prepared by a pH gradient method." *J Biosci Bioeng* 95(4):405-408.
Cosco et al. (2009) "In vivo activity of gemcitabine-loaded PEGylated small unilamellar liposomes against pancreatic cancer" *Cancer Chemother Pharmacol*, 64(5):1009-1020.
Davis et al. (2008) "Nanoparticle therapeutics: an emerging treatment modality for cancer." *Nature Reviews Discovery* 7:771-782.
Davis, M. E., (2009) "The first targeted delivery of siRNA in humans via a self-assembling, cyclodextrin polymer-based nanoparticle: from concept to clinic." *Molecular Pharmacuetics* 6(3):659-668.
Dengler et al. (2013) "Mesoporous Silica-Supported Lipid Bilayers (Protocells) for DNA Cargo Delivery to the Spinal Cord." *J.Controlled Release* 168: 209-224.
Dolainsky et al. (1993) "Transverse relaxation in supported and nonsupported phospholipid model membranes and the influence of ultraslow motions: A 31P-NMR study" *J. Chem. Phys.* 98: 1712-1720.
Drummond et al. (2006) "Development of a highly active nanoliposomal irinotecan using a novel intraliposomal stabilization strategy." *Cancer Research* 66(6):3271-3277.

Duncan et al. (2005) "Polymer-drug conjugates: towards a novel approach for the treatment of endrocine-related cancer." *Endocrine-Related Cancer* 12: S189-S199.
Eschwege et al. (1996) "Detection of bilayer phospholipid-binding antibodies using flow cytometry" *Clin. Exp. Immunol.* 103: 171-175.
Federico et al. (2012) "Gemcitabine-Loaded Liposomes: Rationale, Potentialities and Future Perspectives." *Int. J. Nanomed.* 7: 5423-5436.
Ferrari, M. (2005) "Cancer Nanotechnology: Opportunities and Challenges." *Nat. Rev. Cancer* 5: 161-171.
Frese et al. (2012) "Nab-Paclitaxel Potentiates Gemcitabine Activity by Reducing Cytidine Deaminase Levels in a Mouse Model of Pancreatic Cancer." *Cancer Discovery* 2: 260-269.
Fritze et al. (2006) "Remote loading of doxorubicin into liposomes driven by transmembrane phosphate gradient," *Biochimica Et Biophysica Acta (BBA)—Biomembranes*, Elsevier, Amsterdam, NL, 1758(10):1633-1640.
Fuchs et al. (2006) "Irinotecan in the treatment of colorectal cancer." *Cancer Treat. Rev.* 32:491-503.
Gahlyan et al. (2014) "Oral Controlled Release Drug Delivery System—A Review" *PharmaTutor* 2(8): 170-178.
Gilbert et al. (1992) "Specificity of phosphatidylserine-containing membrane binding sites for factor VIII. Studies with model membranes supported by glass microspheres (lipospheres)." *J. Biol. Chem.* 267: 15861-15868.
Gorelikov et al. (2008) "Single-step coating of mesoporous silica on cetyltrimethyl ammonium bromide-capped nanoparticles." *Nano Letters* 8(1):369-373.
Grün et al. (1997) "The Synthesis of Micrometer- and Submicrometer-Size Spheres of Ordered Mesoporous Oxide MCM-41." *Adv. Mater.* 9(3):254-257.
Guiotto et al. (2004) "Synthesis, Characterization, and Preliminary in Vivo Tests of New Poly(ethylene glycol) Conjugates of the Antitumor Agent 10-Amino-7-ethylcamptothecin." *J. Med. Chem.* 47(5):1280-1289 [Abstract—2pages].
Haran et al. (1993) "Transmembrane ammonium sulfate gradients in liposomes produce efficient and stable entrapment of amphipathic weak bases." *Biochim Biophys Acta Biomembr* 1151:201-215.
He et al. (2011) "In vivo biodistribution and urinary excretion of mesoporous silica nanoparticles: effects of particle size and PEGylation." *Small* 7:271-280.
Hetzer et al. (1998) "Asymmetric Molecular Friction in Supported Phospholipid Bilayers Revealed by NMR Measurements of Lipid Diffusion" *Langmuir*, 14: 982-984.
Jabr-Milane et al. (2008) "Multi-functional nanocarriers to overcome tumor drug resistance." *Cancer Treat. Rev.* 34:592-602.
Jin et al. (1996) "Lipobeads: a hydrogel anchored lipid vesicle system" *FEBS Lett.* 397: 70-74.
Junglas et al. (2003) "Molecular Order Parameter Profiles and Diffusion Coefficients of Cationic Lipid Bilayers on a Solid Support" *Langmuir*, 19: 1914-1917.
Kasbauer et al. (1999) "Effect of cationic lipids in the formation of asymmetries in supported bilayers." *Biophys. J.* 76: 2600-2605.
Katiyar et al. (2006) "Synthesis of ordered large pore SBA-15 spherical particles for adsorption of biomolecules." *J Chromatog* 1122(1-2):13-20.
Kiser et al. (1998) "A synthetic mimic of the secretory granule for drug delivery" *Nature*, 394: 459-62.
Kiser et al. (2000) "Lipid-coated microgels for the triggered release of doxorubicin" J. Control Release, 68: 9-22.
Kneuer et al. (2000) "A nonviral DNA delivery system based on surface modified silica-nanoparticles can efficiently transfect cells in vitro." *Bioconjugate Chem.* 11:926-932.
Kochy & Bayerl (1993) "Lateral diffusion coefficients of phospholipids in spherical bilayers on a solid support measured by resonance relaxation" *Phys. Rev. E.* 47: 2109-16.
Lammers et al. (2010) "Nanomedicine Formulations for Combination Therapies." *Nano Rev.*, 1: 5705 (4 pages) DOI: 10.3402/nano.vli0.5705.

(56) References Cited

OTHER PUBLICATIONS

Lee et al. (2008) "Synthesis and characterization of positive-charge functionalized mesoporous silica nanoparticles for oral drug delivery of an anti-inflammatory drug." *Advanced Functional Materials* 18:3283-3292.
Li et al. (2012) "Mesoporous silica nanoparticles in biomedical applications." *Chem Soc Rev* 41(7):2590-2605.
Li et al. (2013) "Preliminary study on pH-sensitive lipid bilayer-coated mesoporous silica nanoparticles as a novel drug carrier for antitumor drug." *Acta Pharmaceutica Sinica*, 48(2): 291-297. [Article in Chinese with English abstract].
Li et al. (2015) "Multiple Layer-by-Layer Lipid-Polymer Hybrid Nanoparticles for Improved FOLFIRINOX Chemotherapy in Pancreatic Tumor Models." *Adv Func Mat* 25(5):788-798.
Lin et al. (2009) "Synthesis and Characterization of Biocompatible and Size-Tunable Multifunctional Porous Silica Nanoparticles." *Chem. Mater.* 21:3979-3986.
Linseisen et al. (1996) "2H-NMR and DSC study of DPPC-DODAB mixtures" *Chem. Phys. Lipids*, 83: 9-23.
Linseisen et al. (1997) "Differences in the Physical Properties of Lipid Monolayers and Bilayers on a Spherical Solid Support." *Biophys. J.* 72: 1659-1667.
Liong et al. (2008) "Multifunctional inorganic nanoparticles for imaging, targeting and drug delivery." *ACS Nano* 2(5):889-896 [and supporting information attached].
Liong et al. (2009) "Mesostructured Multifunctional Nanoparticles for Imaging and Drug Delivery." *J. Mater. Chem.* 19(35):6251-6257 15 pages.
Liu et al. (2009) "Electrostatically Mediated Liposome Fusion and Lipid Exchange with a Nanoparticle-Supported Bilayer for Control of Surface Charge, Drug Containment, and Delivery." *J. Am. Chem. Soc.* 131: 7567-7569.
Liu et al. (2009) "Porous Nanoparticle Supported Lipid Bilayers (Protocells) as Delivery Vehicles," *Journal of the American Chemical Society* 131(4):1354-1355.
Liu et al. (2012) "Delivering hydrophilic and hydrophobic chemotherapeutics simultaneously by magnetic mesoporous silica nanoparticles to inhibit cancer cells" *International Journal of Nanomedicine* 7: 999-1013.
Liu et al. (2016) "Irinotecan delivery by lipid-coated mesoporous silica nanoparticles shows improved efficacy and safety over liposomes for pancreatic cancer." *ACS Nano* 10:2702-2715 [24 pages—with Supplementary Materials].
Liu et al. (2016) "Irinotecan delivery by lipid-coated mesoporous silica nanoparticles shows improved efficacy and safety over liposomes for pancreatic cancer." *ACS Nano* 10:2702-2715.
Loidl-Stahlhofen et al. (2001) "Multilamellar liposomes and solid-supported lipid membranes (TRANSIL): screening of lipid-water partitioning toward a high-throughput scale" *Pharm. Res.* 18: 1782-1788.
Loidl-Stahlhofen et al. (2001) "Solid-Supported Biomolecules on Modified Silica Surfaces—A Tool for Fast Physicochemical Characterization and High-Throughput Screening" *Advanced Materials* 13: 1829-1834.
Loidl-Stahlhofen et al. (2001) "Solid-supported lipid membranes as a tool for determination of membrane affinity: High-throughput screening of a physicochemical parameter." *J. Pharm. Sci.* 90: 599-606.
Loidl-Stahlhofen et al. (1996) "The thermodynamic control of protein binding to lipid bilayers for protein chromatography" *Nat. Biotechnol.* 14: 999-1002.
Lu et al. (2007) "Mesoporous silica nanoparticles as a delivery system for hydrophobic anticancer drugs." *Small* 3:1341-1346.
Ma et al. (2013) "Nanoparticles for Combination Drug Therapy." *ACS Nano* 7: 9518-9525.
Mackowiak et al. (2013) "Targeted Drug Delivery in Cancer Cells with Red-Light Photoactivated Mesoporous Silica Nanoparticles." *Nano Lett.* 13: 2576-2583.
Mai et al. (2013) "Mesoporous Silica Nanoparticles: A Multifunctional Nano Therapeutic System." *Integr. Biol.* 5: 19-28.
Mayer et al. (2007) "Optimizing Combination Chemotherapy by Controlling Drug Ratios." *Mol. Interventions* 7: 216-223.
Meng et al. (2006) "A Family of Highly Ordered Mesoporous Polymer Resin and Carbon Structures from Organic-Organic Self-Assembly." *Chem Mat* 6(18):4447-4464.
Meng et al. (2010) "Autonomous in Vitro Anticancer Drug Release from Mesoporous Silica Nanoparticles by pH-Sensitive Nanovalves." *J. Am. Chem. Soc.* 132:12690-12697.
Meng et al. (2010) "Engineered Design of Mesoporous Silica Nanoparticles to Deliver Doxorubicin and P-Glycoprotein siRNA to Overcome Drug Resistance in a Cancer Cell Line," *ACS Nano* 4(8):4539-4550.
Meng et al. (2010) "Potent Angiogenesis Inhibition by the Particulate Form of Fullerene Derivatives." *American Chemical Society* 4(5):2773-2783.
Meng et al. (2011) "Aspect Ratio Determines the Quantity of Mesoporous Silica Nanoparticle Uptake by a Small GTPase-Dependent Macropinocytosis Mechanism," *ACS Nano*, 5(6):4434-4447.
Meng et al. (2011) "Use of Size and a Copolymer Design Feature To Improve the Biodistribution and the Enhanced Permeability and Retention Effect of Doxorubicin Loaded Mesoporous Silica Nanoparticles in a Murine Xenograft Tumor Model," *ACS Nano* 5(5):4131-4144.
Meng et al. (2012) "Development of Pharmaceutically Adapted Mesoporous Silica Nanoparticles Platform." *J. Phys. Chem. Lett.* 3: 358-359.
Meng et al. (2013) "Codelivery of an Optimal Drug/siRNA Combination Using Mesoporous Silica Nano-particles To Overcome Drug Resistance in Breast Cancer in Vitro and in Vivo." *ACS Nano* 7: 994-1005.
Meng et al. (2013) "Two-Wave Nanotherapy to Target the Stroma and Optimize Gemcitabine Delivery to a Human Pancreatic Cancer Model in Mice," *ACS Nano* 7(11):10048-10065.
Meng et al. (2015) "Use of a Lipid-Coated Mesoporous Silica Nanoparticle Platform for Synergistic Gemcitabine and Paclitaxel Delivery to Human Pancreatic Cancer in Mice" *ACS Nano* 9(4): 3540-3557.
Messerer et al. (2004) "Liposomal Irinotecan: Formulation Development and Therapeutic Assessment in Murine Xenograft Models of Colorectal Cancer." *Clin Cancer Res* 10(19):6638-6649.
Miao et al. (2014) "Nanoparticles with Precise Ratiometric Co-loading and Co-delivery of Gemcitabine Monophosphate and Cisplatin for Treatment of Bladder Cancer." *Adv. Funct. Mater.* 24(42): 6601-6611. [NIH Public Access; Author Manuscript—24 pages].
Moore et al. (2007) "Erlotinib Plus Gemcitabine Compared with Gemcitabine Alone in Patients with Advanced Pancreatic Cancer: A Phase III Trial of the National Cancer Institute of Canada Clinical Trials Group." *J. Clin. Oncol.* 25(15): 1960-1966.
Mornet, et al. (2005) "The Formation of Supported Lipid Bilayers on Silica Nanoparticles Revealed by Cryoelectron Microscopy." *Nano Lett.*, 5(2): 281-285.
Moura & Carmona-Ribeiro (2003) "Cationic Bilayer Fragments on Silica at Low Ionic Strength: Competitive Adsorption and Colloid Stability" *Langmuir* 19: 6664-6667.
Moura & Carmona-Ribeiro (2005) "Biomimetic Particles: Optimization of Phospholipid Bilayer Coverage on Silica and Colloid Stabilization" *Langmuir* 21: 10160-10164.
Naumann et al. (1992) "Phase transition behavior of single phosphatidylcholine bilayers on a solid spherical support studied by DSC, NMR and FT-IR" *Biophys J.* 63: 1314-1319.
Ng et al. (2001) "One-Step Synthesis of a Fluorescent Phospholipid-Hydrogel Conjugate for Driving Self-Assembly of Supported Lipid Membranes" *Macromolecules* 34: 5759-5765.
Ng et al. (2004) "Properties of a Self-Assembled Phospholipid Membrane Supported on Lipobeads" *Biophys J.* 87: 323-331.
Nordlund et al. (2009) "Formation of supported lipid bilayers on silica particles studied using flow cytometry." *Langmuir* 25, 4601-4606.
Obringer et al.(1995) Antiphospholipid antibody binding to bilayer-coated glass microspheres *J Immunol Meth.* 185: 81-93.
Onishi et al. (2003) "Antitumor Properties of Irinotecan-Containing Nanoparticles Prepared Using Poly(DL-lactic acid) and Poly(eth-

(56) References Cited

OTHER PUBLICATIONS ylene glycol)-block-poly(propylene glycol)-block-poly(ethylene glycol)." *Biol. Pharmaceut Bull.* 26(1):116-119.
Onivyde (irinotecan liposome injection)—Highlights of Prescribing Information—Reference ID: 3836766; 18 pages [accessed Oct. 23, 2015]. Retrieved from the Internet, URL: https://www.accessdata.fda.gov/drugsatfda_docs/label/2015/207793 lbl.pdf.
Park et al. (2004) "Characterization of radioligand binding to a transmembrane receptor reconstituted into Lipobeads" *FEBS Lett* 567: 344-348.
Pasqua et al. (Published online Feb. 3, 2007) "Preparation of bifunctional hybrid mesoporous silica potentially useful for drug targeting." *Microporous and Mesoporous Materials* 103:166-173.
Patil et al. (2010) "Use of nanoparticle mediated gene silencing and drug delivery to overcome tumor drug resistance." Biomaterials 31:358-365.
Pearse et al. (1987) "Structure and assembly of coated vesicles." *Annu. Rev. Biophys. Biophys. Chem.* 16:49-68.
Peer, et al. (2007) "Nanocarriers as an Emerging Platform for Cancer Therapy." *Nat. Nanotechnol.*, 2: 751-760.
Piyasena et al. (2008) "Biosensors based on release of compounds upon disruption of lipid bilayers supported on porous microspheres." *Biointerphases* 3: 38-49.
Ramsay et al. (2008) "A novel liposomal irinotecan formulation with significant anti-tumour activity: Use of the divalent cation ionophore A23187 and copper-containing liposomes to improve drug retention." *Eur J Pharm Biopharm* 68(3):607-617.
Rapuano & Carmona-Ribeiro (1997) "Physical Adsorption of Bilayer Membranes on Silica" *J. Colloid Interface Sci.* 193: 104-111.
Rapuano & Carmona-Ribeiro (2000) "Supported Bilayers On Silica" *J. Colloid Interface Sci.* 226: 299-307.
Reinl & Bayerl (1993) "Interaction of myelin basic protein with single bilayers on a solid support: an NMR, DSC and polarized infrared ATR study" *Biochim Biophys Acta.* 1151: 127-136.
Reinl & Bayerl (1994) "Lipid Transfer between Small Unilamellar Vesicles and Single Bilayers on a Solid Support: Self-Assembly of Supported Bilayers with Asymmetric Lipid Distribution" *Biochemistry* 33: 14091-14099.
Roggers et al. (2012) "Chemically Reducible Lipid Bilayer Coated Mesoporous Silica Nano-particles Demonstrating Controlled Release and HeLa and Normal Mouse Liver Cell Biocompatibility and Cellular Internalization." *Mol. Pharmaceutics* 9: 2770-2777.
Roiter et al. (2008) "Interaction of Nanoparticles with Liquid Membrane." *Nano Lett.* 8:941-944.
Saad et al. (2008) "Co-delivery of siRNA and an anticancer drug for treatment of multi-drug resistant cancer." *Nanomedicine* 3:761-776.
Sachae et al. (2017) "Surfactant-Templating of Zeolites: From Design to Application" *Chem. Mater.*, 29(9): 3827-385, [Abstract only—2 pages].
Sackmann, E. (1996) "Supported Membranes: Scientific and Practical Applications." *Science*, 271(5245): 43-48.
Sadzuka et al. (1998) "Effect of liposomalization on the antitumor activity, side-effects and tissue distribution of CPT-11." *Cancer Lett.* 127(1):99-106.
Santos et al. (2009) "The Power of Ultrasound", *Ultrasound in Chemistry: Analytical Applications*, 16 pages.
Schmitt et al. (2001) "Polymer Cushions in Supported Phospholipid Bilayers Reduce Significantly the Frictional Drag between Bilayer and Solid Surface" *Langmuir* 17: 244-246.
Schmitz et al. (1999) "Interactions of Myristoylated Alanine-Rich C Kinase Substrate (MARCKS)-Related Protein with a Novel Solid-Supported Lipid Membrane System (TRANSIL)" *Anal. Biochem.* 268: 343-353.
Schuhmacher et al. (2004) "High-throughput determination of the free fraction of drugs strongly bound to plasma proteins." *J. Pharm. Sci.* 93: 816-830.
Sharma et al. (2004) "Bacteriorhodopsin conjugates as anchors for supported membranes." *Bioconjug. Chem.* 15: 942-947.
Shidhaye et al. (2008) "Nanogel Engineered Polymeric Micelles for Drug Delivery." *Current Drug Therapy* 3(3):209-217.
Singh et al. (2008) "Nanoengineering artificial lipid envelopes around adenovirus by self-assembly." *ACS Nano* 2: 1040-1050.
Slowing et al. (2008) "Mesoporous silica nanoparticles as controlled release drug delivery and gene transfection carriers." *Adv. Drug Deliv. Rev.* 60:1278-1288.
Sommerwerk et al. (2011) "Lipid Coated Chitosan Micro-particles as Protein Carriers." *Pulm. Pharmacol. Ther.* 8: 1978-1984.
Sugahara et al. (2010) "Coadministration of a tumor-penetrating peptiden enhances the efficacy fo cancer drugs." *Science* 328:1031-1035.
Szakacs et al. (2006) "Targeting multidrug resistance in cancer." *Nat. Rev. Drug Discov.* 5:219-234.
Tamanoi "Nanodelivery: Towards controlled release of anti-cancer drugs." Oral Presentation on Dec. 6, 2006 (see NanoBio-Tokyo 2006 Program), 7 pages. Abstract provided in Proceedings of UT Symposium on NanoBio Integration Program and Abstract provided.
Tang et al. (2012) "Mesoporous Silica Nanoparticles: Synthesis, Biocompatibility and Drug Delivery." *Adv Mat* 24(12):1504-1534.
Tardi et al. (2009) "In Vivo Maintenance of Synergistic Cytarabine: Daunorubicin Ratios Greatly Enhances Therapeutic Efficacy." *Leuk. Res.* 33: 129-139.
Tarn et al. (2013) "Mesoporous Silica Nanoparticle Nanocarriers: Biofunctionality and Biocompatibility." *Accounts of Chemical Research* 46(3):792-801.
Thorolfsson et al. (2002) "The binding of tyrosine hydroxylase to negatively charged lipid bilayers involves the N-terminal region of the enzyme." *FEBS Lett.* 519: 221-226.
Torney et al. (2007) "Mesoporous silica nanoparticles deliver DNA and chemicals into plants." *Nat. Nanotechnol.* 2:295-300.
Troutier & Lada Viere (2007) "An overview of lipid membrane supported by colloidal particles." *Adv. Colloid Interface Sci.* 133: 1-21.
Valencia et al. (2013) "Synergistic cytotoxicity of irinotecan and cisplatin in dual-drug targeted polymeric nanoparticles." *Nanomed* 8(5):687-698 [NIH Public Access—Author Manuscript—17pages].
Van Schooneveld et al. (2008) "Improved Biocompatibility and Pharmacokinetics of Silica Nanoparticles by Means of a Lipid Coating: A Multimodality Investigation." *Nano Lett.* 8(8): 2517-2525.
Van Vlerken et al. (2007) "Modulation of intracellular ceramide using polymeric nanoparticles to overcome multidrug resistance in cancer." *Cancer Res.* 67:4843-4850.
Von Hoff et al. (2011) "Gemcitabine Plus Nab-Paclitaxel Is an Active Regimen in Patients with Advanced Pancreatic Cancer: A Phase I/II Trial." *J. Clin. Oncol.* 29(34): 4548-4554.
Von Hoff et al. (2013) "Increased Survival in Pancreatic Cancer with Nab-Paclitaxel Plus Gemcitabine." *N. Engl. J. Med.* 369(18): 1691-1703.
Wu et al. (2007) "Reversal of multidrug resistance by transferrin-conjugated liposomes co-encapsulating doxorubicin and verapamil." *J Pharm. Pharmaceut. Sci.* 10:350-357.
Xia et al. (2009) "Polyethyleneimine Coating Enhances the Cellular Uptake of Mesoporous Silica Nanoparticles and Allows Safe Delivery of siRNA and DNA Constructs." *ACS Nano* 3(10):3273-3286.
Xu et al. (2013) "Biodistribution and Pharmacokinetics of EGFR-Targeted Thiolated Gelatin Nanoparticles Following Systemic Administration in Pancreatic Tumor-Bearing Mice." *Mol Pharmaceutics* 10:2031-2044.
Yang et al. (2010) "Lipid Coated Mesoporous Silica Nanoparticles as Photosensitive Drug Carriers." *Phys. Chem. Chem. Phys.* 12: 4418-4422.
Yezhelyev et al. (2008) "Proton-sponge coated quantum dots for siRNA delivery and intracellular imaging." *J. Am. Chem. Soc.* 130(28):9006-9012.
Zhang et al. (2011) "Synergistic Antitumor Activity of Gemcitabine and ABT-737 in Vitro and in Vivo through Disrupting the Interaction of USP9X and Mcl-1." *Mol. Cancer Ther.* 10: 1264-1275.
Zhang et al. (2013) "Facile Large-Scale Synthesis of Monodisperse Mesoporous Silica Nanospheres with Tunable Pore Structure" *J. Am. Chem. Soc.*, 135(7): 2427-2430.

(56) References Cited

OTHER PUBLICATIONS

Zhang et al. (2014) "Biofunctionalized polymer-lipid supported mesoporous silica nanoparticles for release of chemotherapeutics in multidrug resistant cancer cells." *Biomaterials* 35:3650-3665.
Zhu et al. (2004) "Poly(L-lysine)-modified silican nanoparticles for the delivery of anitsense oligonucleotides." *Biotechnol. Appl. Biochem.* 39:179-187.
Zucker et al. (2009) "Liposome drugs' loading efficiency: A working model based on loading conditions and drug's physicochemical properties." *J Control Release* 139(1):73-80.
US Notice of Allowance dated Jun. 22, 2020, issued in U.S. Appl. No. 14/772,740.
US Notice of Allowance dated May 6, 2020, issued in U.S. Appl. No. 16/164,030.
European 2nd Office Action dated May 26, 2020 issued in Application No. EP 14 760 467.2.
PCT International Preliminary Report on Patentability and Written Opinion dated Jul. 7, 2020 issued in PCT/US18/67970.
Chen, et al. (2014) "Antitumor efficacy of irinotecan-loaded galactosyl modified lipid bilayer-coated mesoporous silica nanoparticles against hepatocellular carcinoma cells." *Acta Pharmaceutica Sinica*, 49(5): 718-725. [English Translation of Chinese Article].
Li et al. (2013) "Preliminary study on pH-sensitive lipid bilayer-coated mesoporous silica nanoparticles as a novel drug carrier for antitumor drug." *Acta Pharmaceutica Sinica*, 48(2): 291-297. [English Translation of Chinese Article].
U.S. Appl. No. 16/947,539, filed Aug. 5, 2020, Nel et al.
U.S. Appl. No. 16/948,498, filed Sep. 21, 2020, Nel et al.
US Office Action dated Sep. 9, 2020, issued in U.S. Appl. No. 16/947,539.
US Notice of Allowance dated Apr. 21, 2021 issued in U.S. Appl. No. 16/947,539.
Australian Office Action dated Dec. 17, 2020 issued in AU 2017206077.
Chinese Office Action dated Aug. 14, 2020 issued in CN 201780010248.8.
Chinese 2nd Office Action dated May 17, 2021 issued in CN 201780010248.8.
Japanese Office Action dated Oct. 5, 2020 issued in JP 2018-535362.
Korean Office Action dated May 18, 2021 issued in KR 10-2018-7022622.
CN Office Action dated Jan. 30, 2022, in Application No. CN201780010248.8 with English translation.
Co-pending U.S. Appl. No. 17/384,214, filed Jul. 23, 2021.
Daqing Li., et al., "Critical Micelle Concentrations of Cetyltrimethylammonium Chloride and Their Influence on the Periodic Structure of Mesoporous Silica", Colloid Journal of The Russian Academy of Science—Kolloidnyyie Zhurnal, vol. 70, No. 6, Nov. 2008, pp. 747-752, XP0055244840.
EP Partial Supplemental Search Report dated Nov. 11, 2021 in EP Application No. 18897783.9.
European 3rd Office Action dated Sep. 2, 2021 issued in Application No. EP 14 760 467.2.
Extended European Search Report dated Mar. 15, 2022, in Application No. 18897783.9.
Japanese 2nd Office Action dated Aug. 2, 2021 issued in JP 2018-535362.
AU Office action dated May 22, 2023, in AU Application No. AU2022200881.
CA Office Action dated Oct. 24, 2023, in Application No. CA3010711.
EP Extended European Search Report dated Jul. 11, 2023, in Application No. 23158990.4.
JP Office Action dated Apr. 17, 2023 in Application No. JP2022-72344 with English translation.
JP Office Action dated Oct. 16, 2023 in Application No. JP2022-72344 with English translation.
KR Office Action dated Mar. 22, 2023 in Application No. KR10-2022-7019372 with English translation.
KR Office Action dated Sep. 25, 2023 in Application No. KR10-2022-7019372 with English translation.
U.S. Non-Final Office Action dated Aug. 22, 2023, in U.S. Appl. No. 16/948,498.
U.S. Non-Final Office Action dated Jul. 24, 2023, in U.S. Appl. No. 17/384,214.
U.S. Notice of Allowance dated Nov. 17, 2023 in U.S. Appl. No. 16/948,498.

B
Stirring speed effect
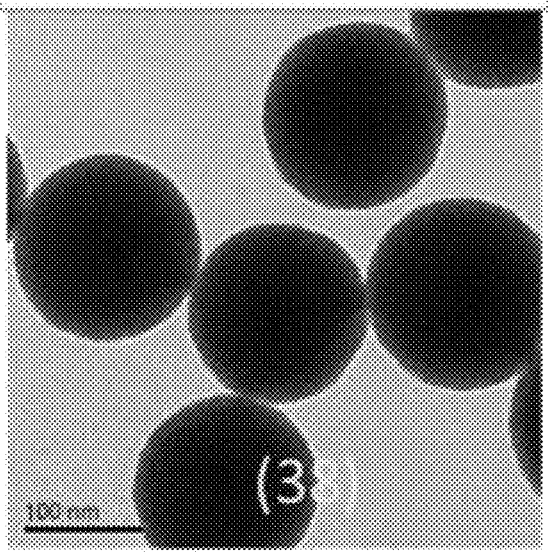 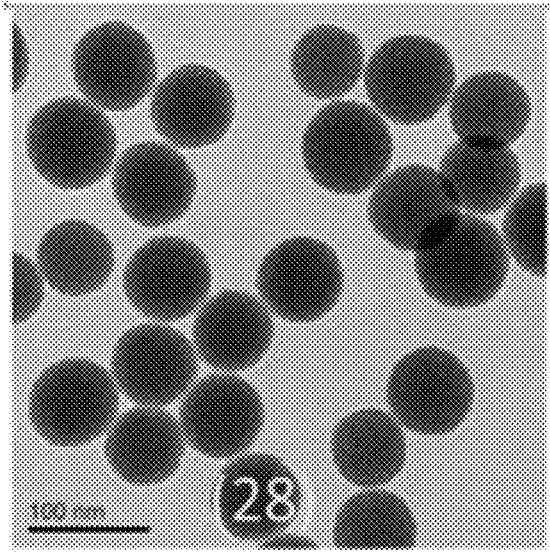
*Fig. 3, cont'd.*

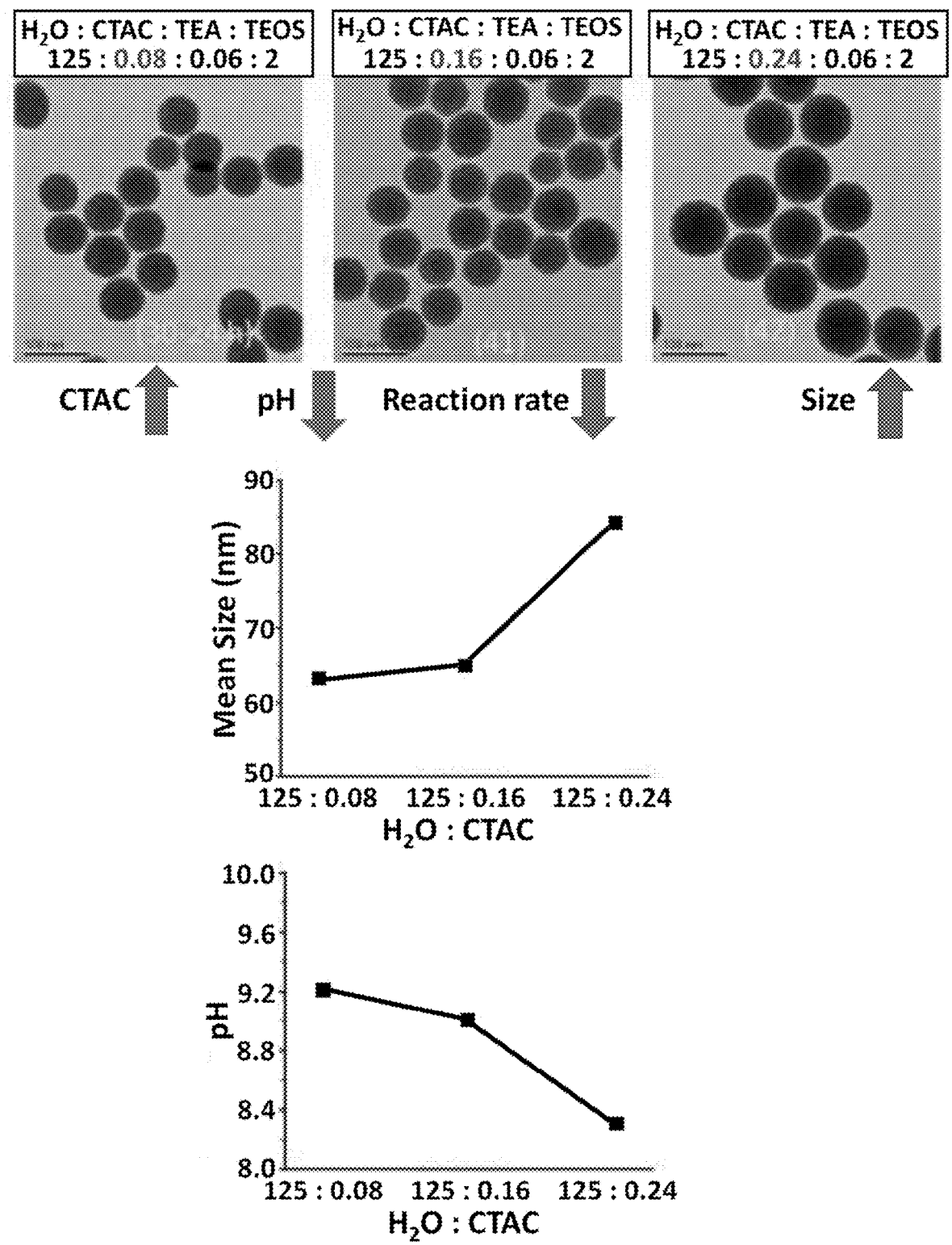
Fig. 3, cont'd.

(D) TEOS effect
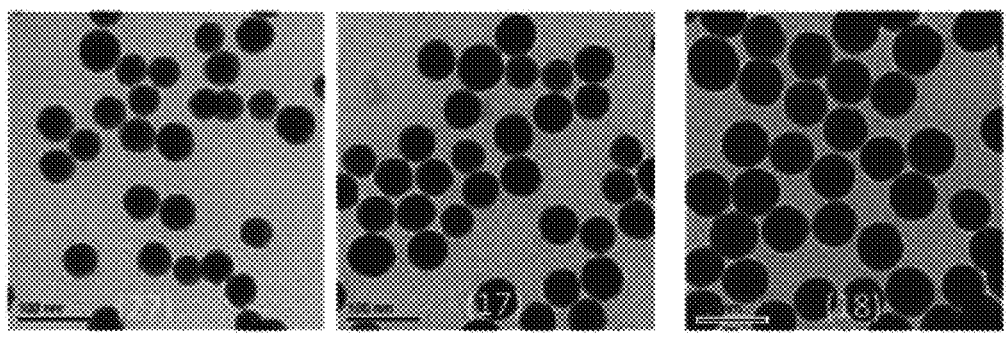
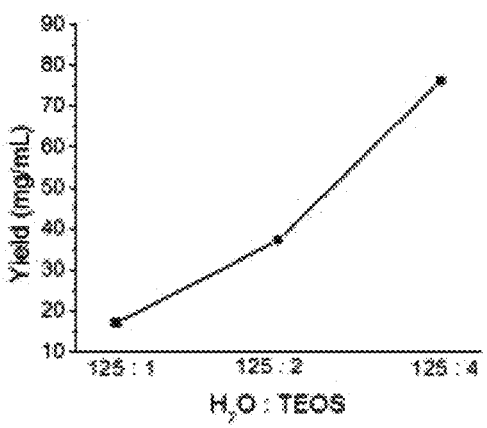
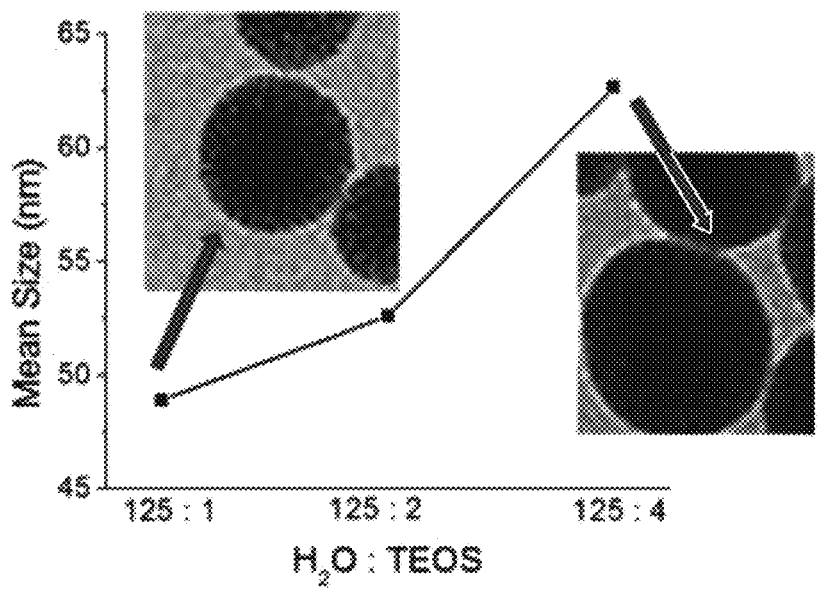
*Fig. 3, cont'd.*

(E)
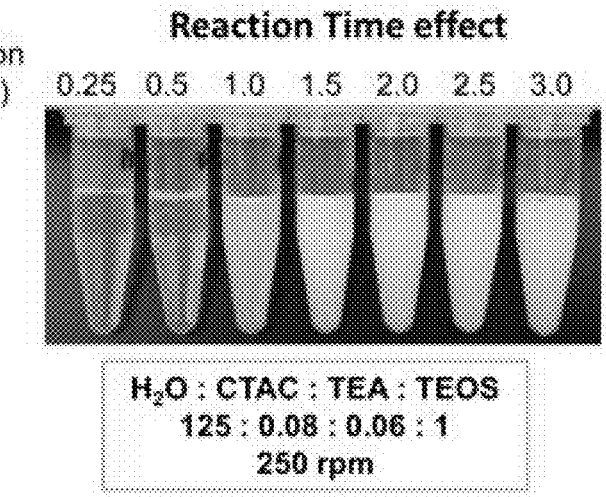
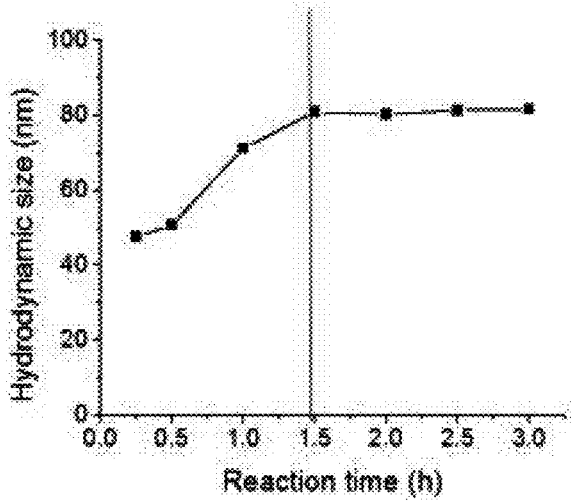
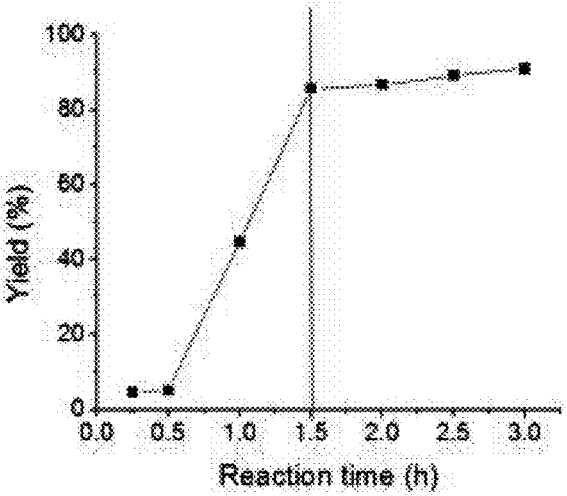
*Fig. 3, cont'd.*

(F)
Temperature Effect
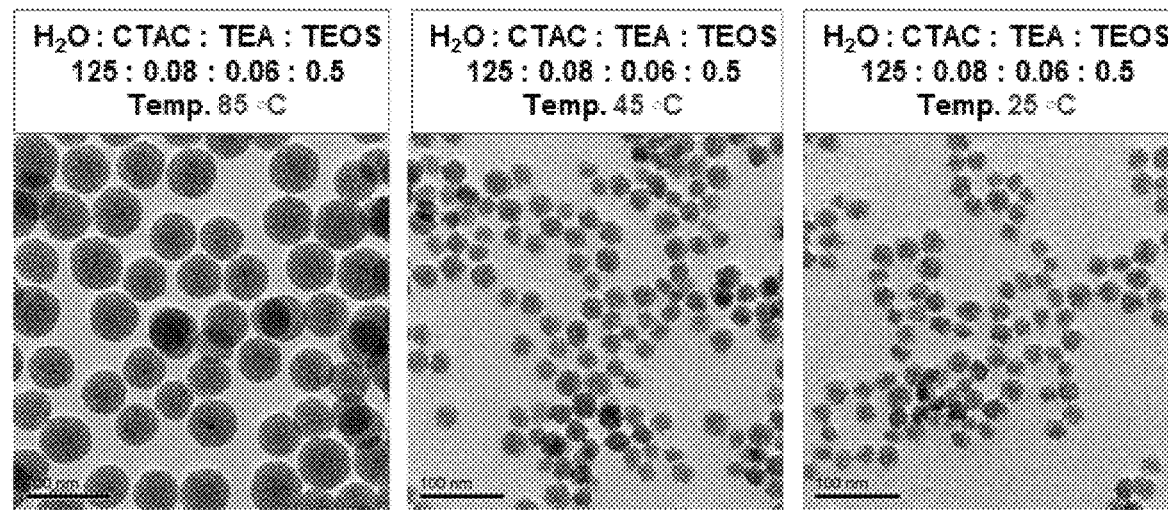
Low Temp favors nucleation rate to make small size, high temperature favors growth rate to make large size
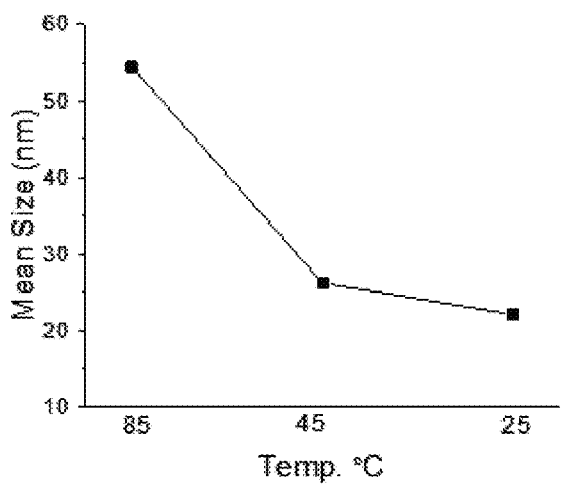
*Fig. 3, cont'd.*

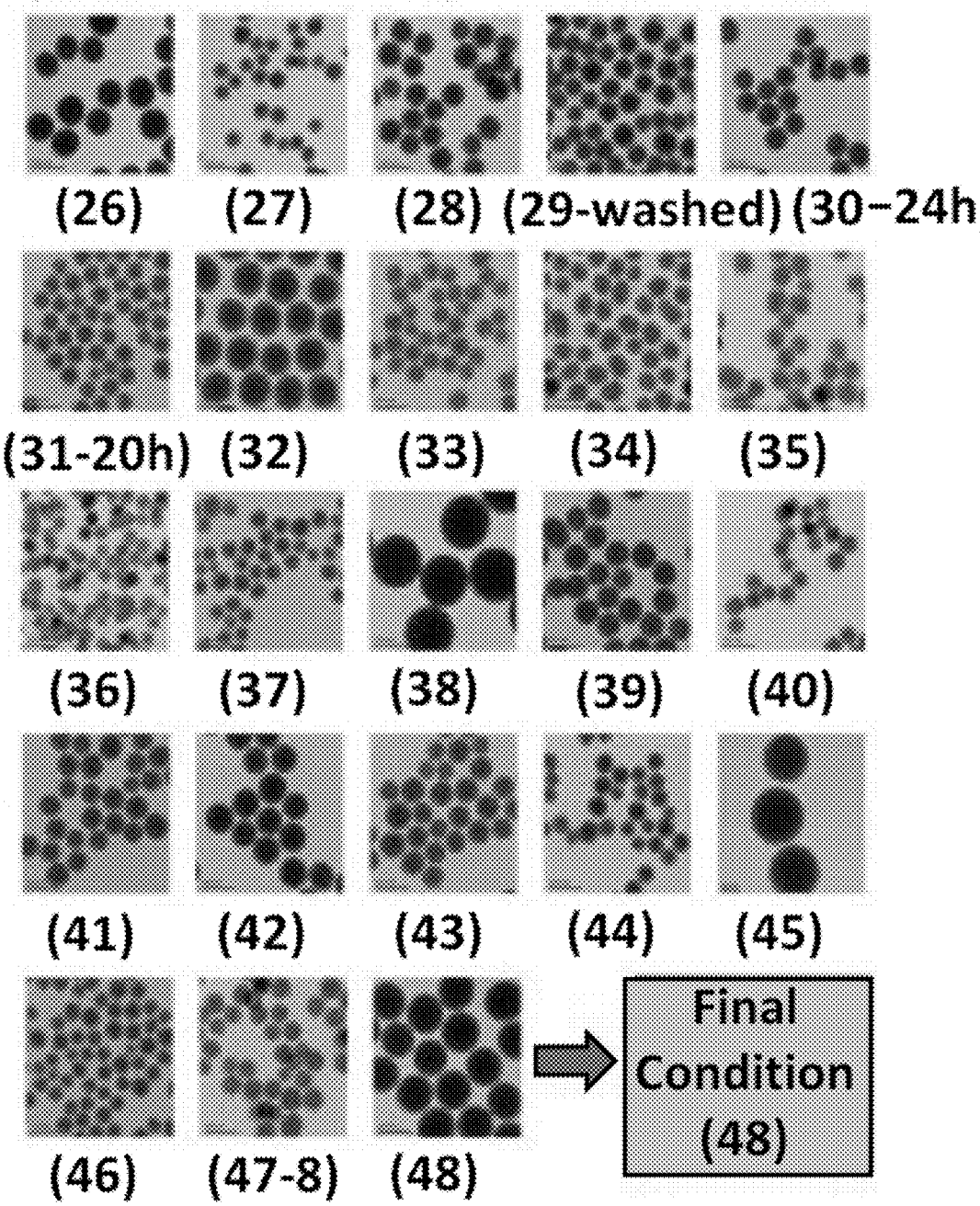
Fig. 4, cont'd.

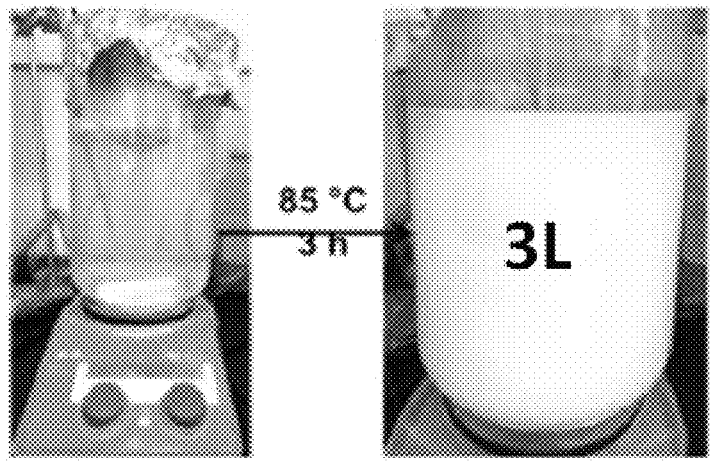
Fig. 4, cont'd.

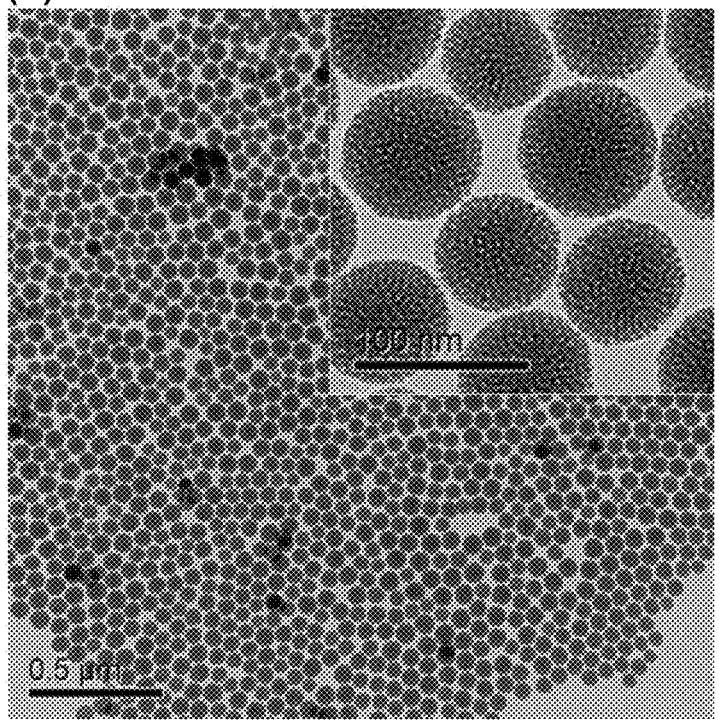
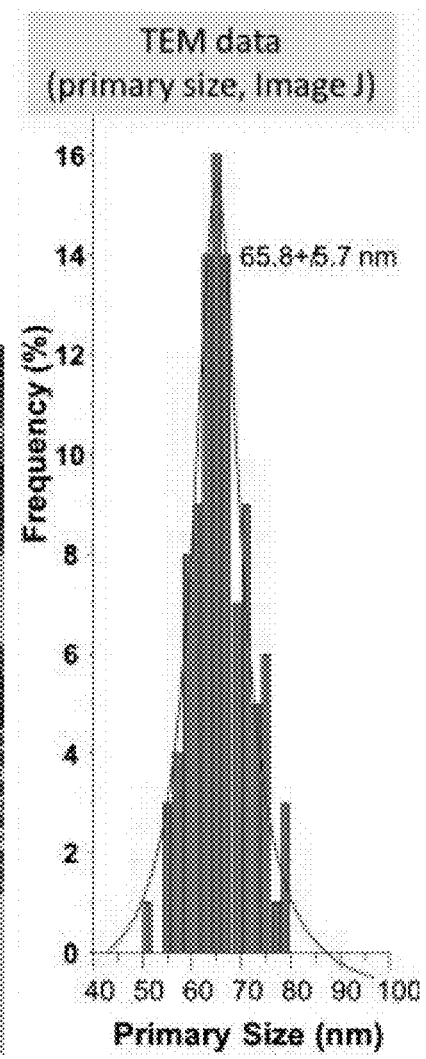
Fig. 4, cont'd.

(D)
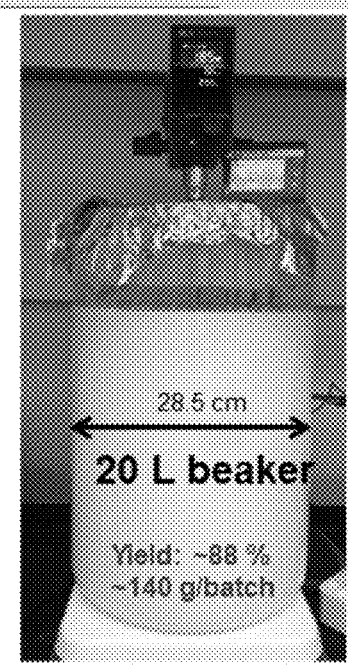
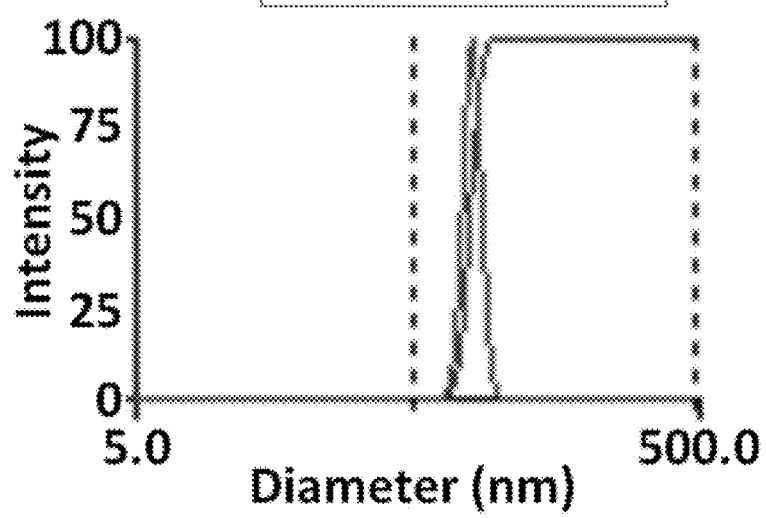
Fig. 4, cont'd.

(E)
TEM visualization of batch #71 MSNP (~140g batch)
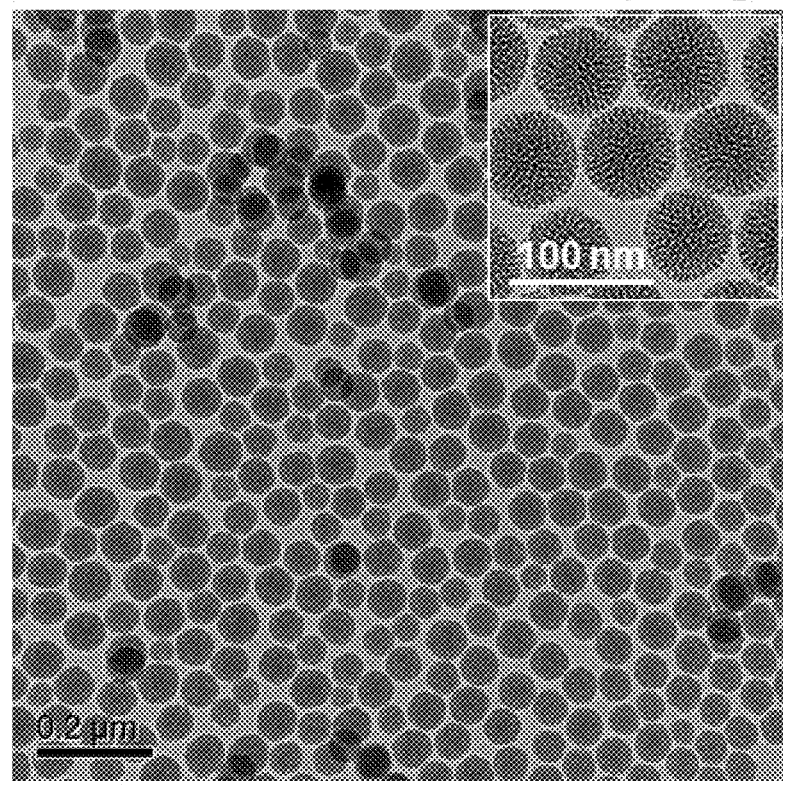
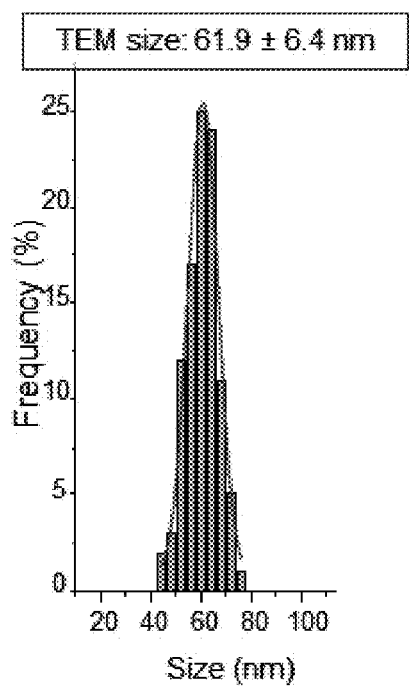
*Fig. 4, cont'd.*

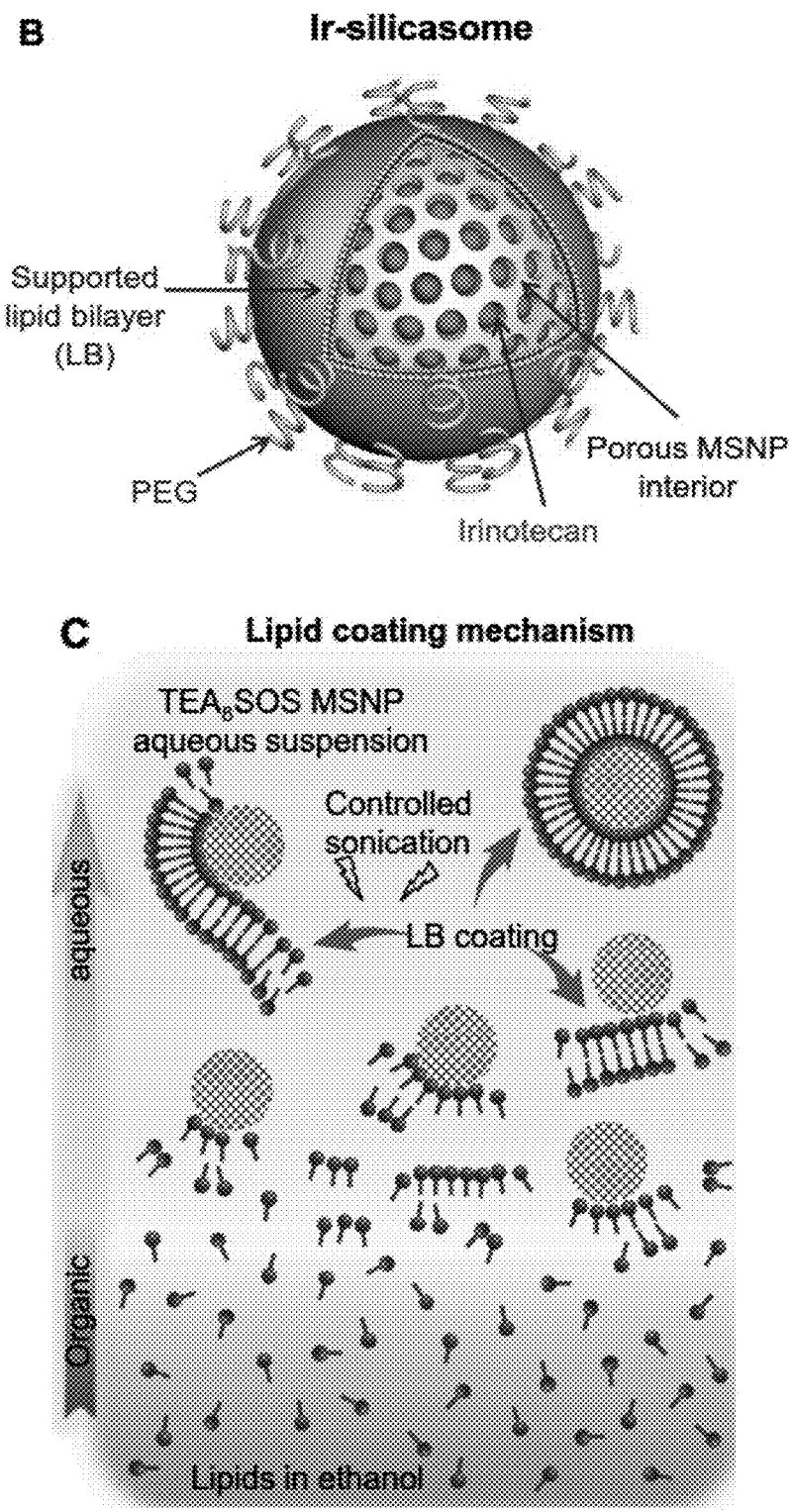
Fig. 9, cont'd

D
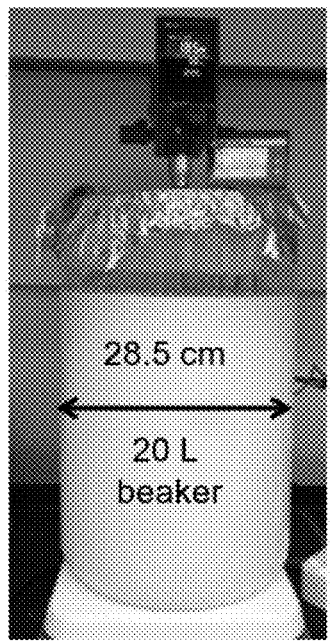
| Bare MSNP physicochemical properties | |
|---|---|
| Primary size | ~61.9 ± 6.4 nm |
| Hydrodynamic size (polydispersity index, PDI) | ~80 nm (PDI ~ 0.01) |
| MSNP surface area | ~837 m²/g |
| MSNP pore volume | ~0.977 cm³/g |
| MSNP pore size | ~3.1 nm |
| CTAC residue | <0.2% w/w (CTAC/MSNP) |
| Endotoxin level (at 10 mg/mL) | < 1 EU/ml |
*Fig. 9, cont'd*

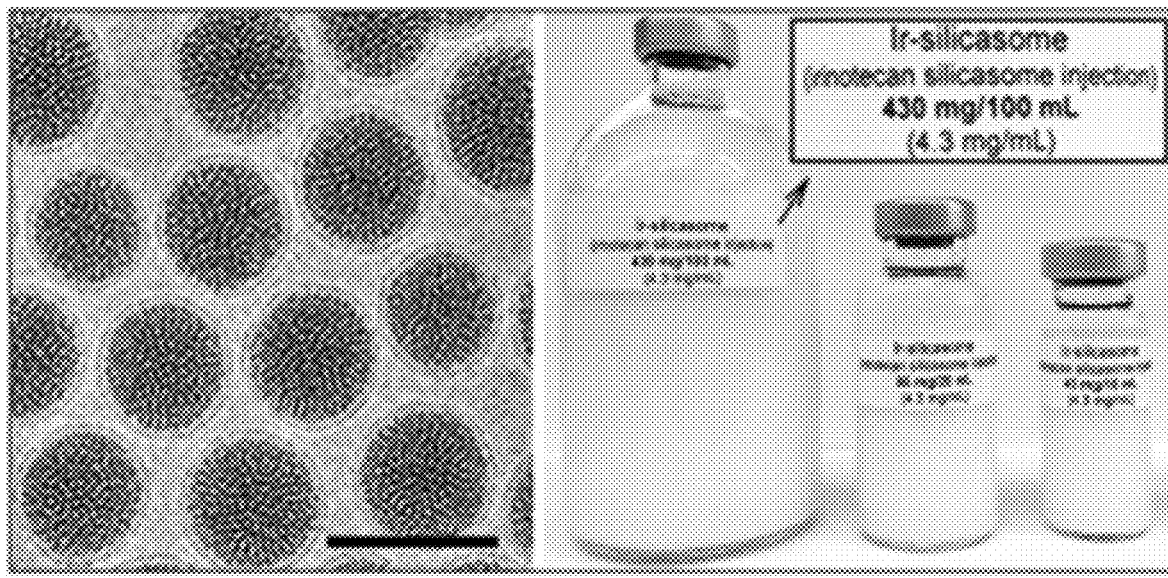
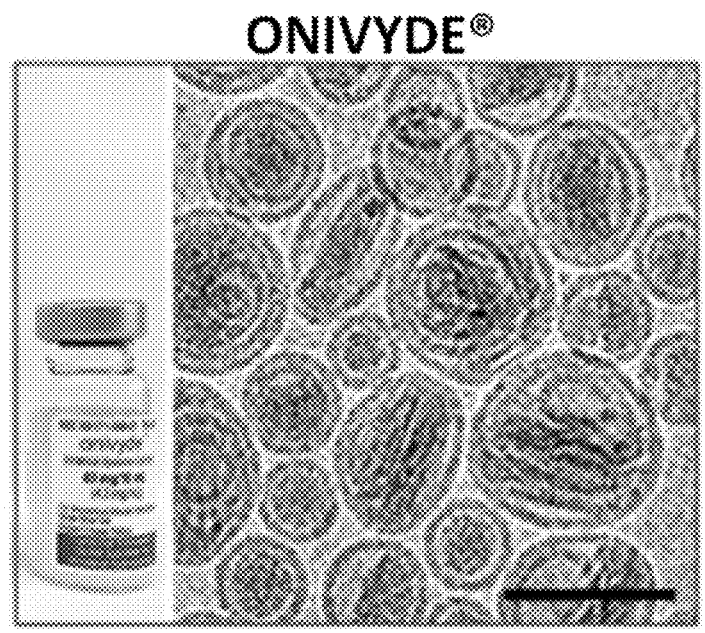
*Fig. 9, cont'd*

E, cont'd.

| Physicochemical characterization of the final product | | |
|---|---|---|
| | Ir-silicasome | ONIVYDE® |
| Primary size (cryo-EM) (coeff. variation, CV) | 78.0 ± 6.8 nm (8.7%) | 67.1 ± 19.7 nm (29.4%) |
| Hydrodynamic size (polydispersity index) | ~130 nm (PDI<0.1) | ~110 nm (PDI<0.1) |
| Zeta potential | ~ -11 mV | ~ -16 mV |
| API loading capacity | ~40% (w/w, drug/MSNP) | ~55% (w/w, drug/lipids) |
| pH | ~7.2 | ~7.2 |
| API concentration | 5 mg/mL | 5 mg/mL |
| Unencapsulated drug | <5% | <5% |
| Endotoxin level | <1EU/ml | <1EU/ml |
| Sterility testing | Sterile | Sterile |

*Fig. 9, cont'd.*

C
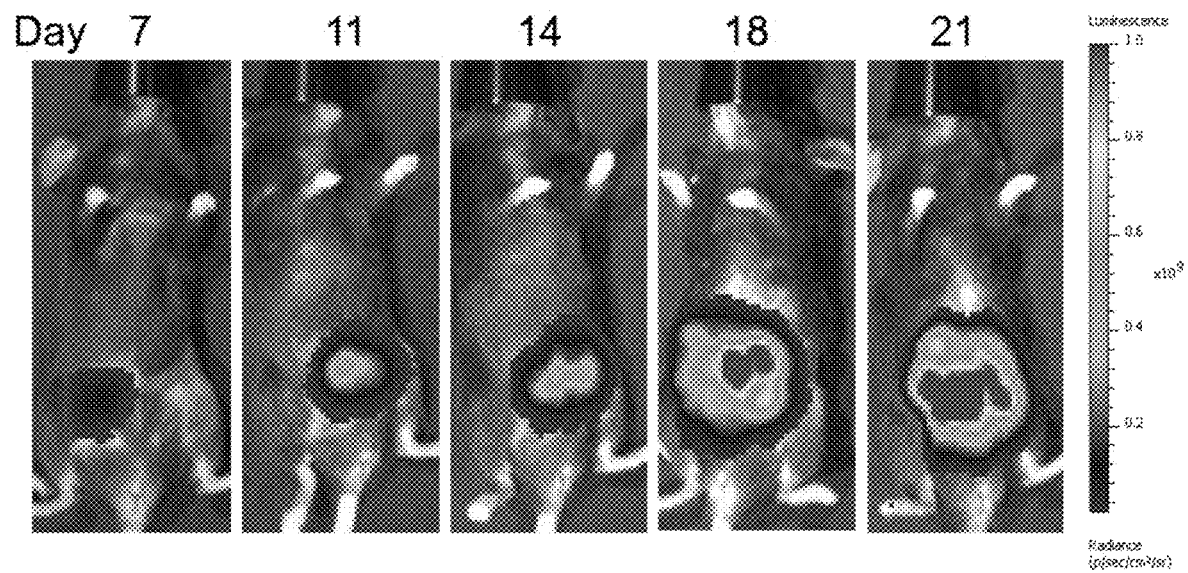
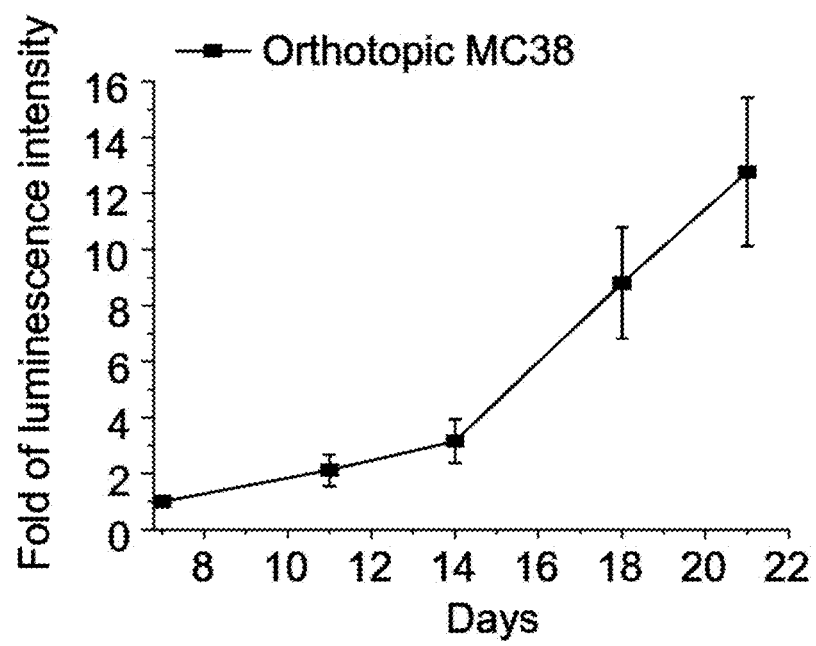
*Fig. 10, cont'd.*

D
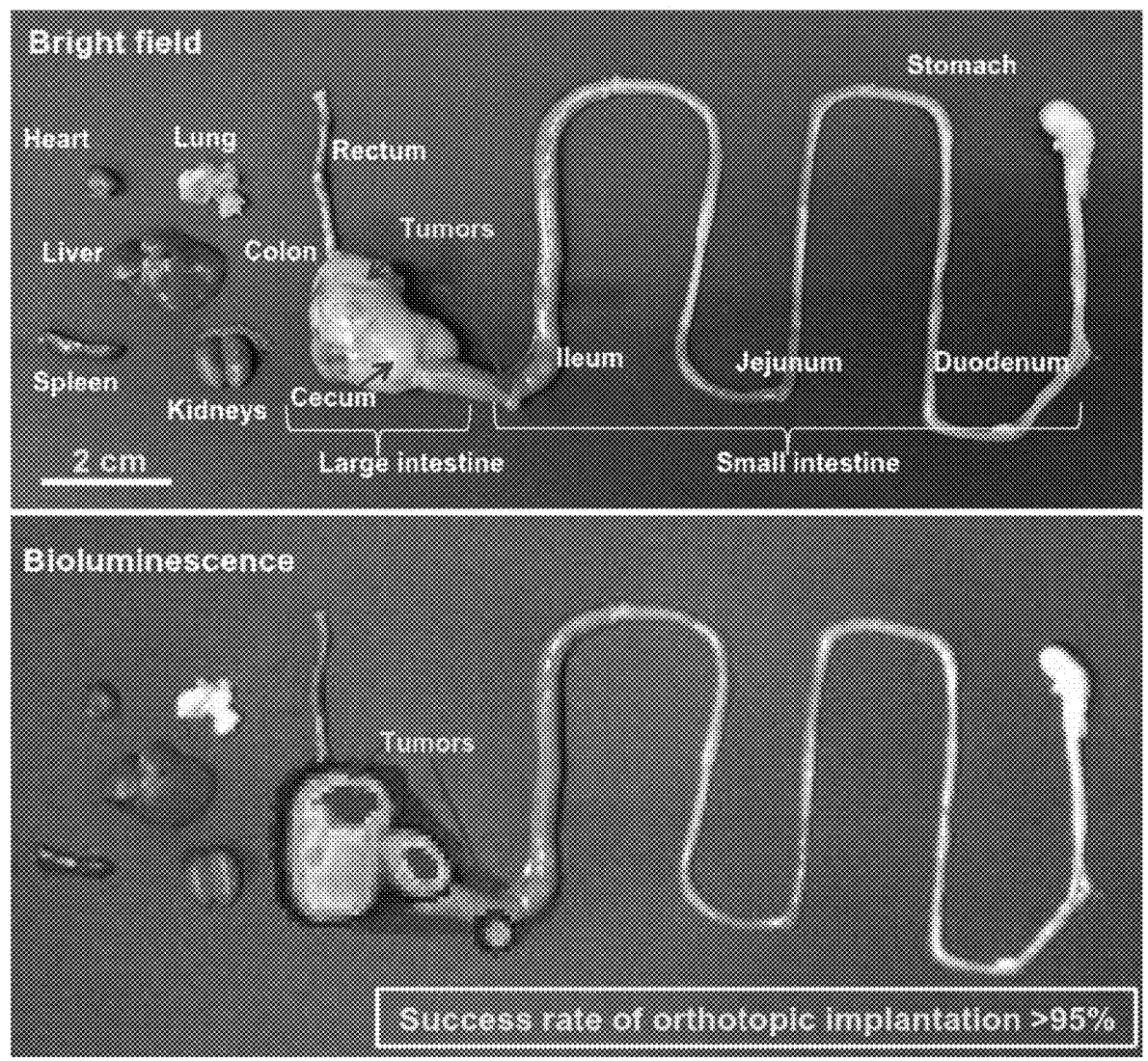
Fig. 10, cont'd.

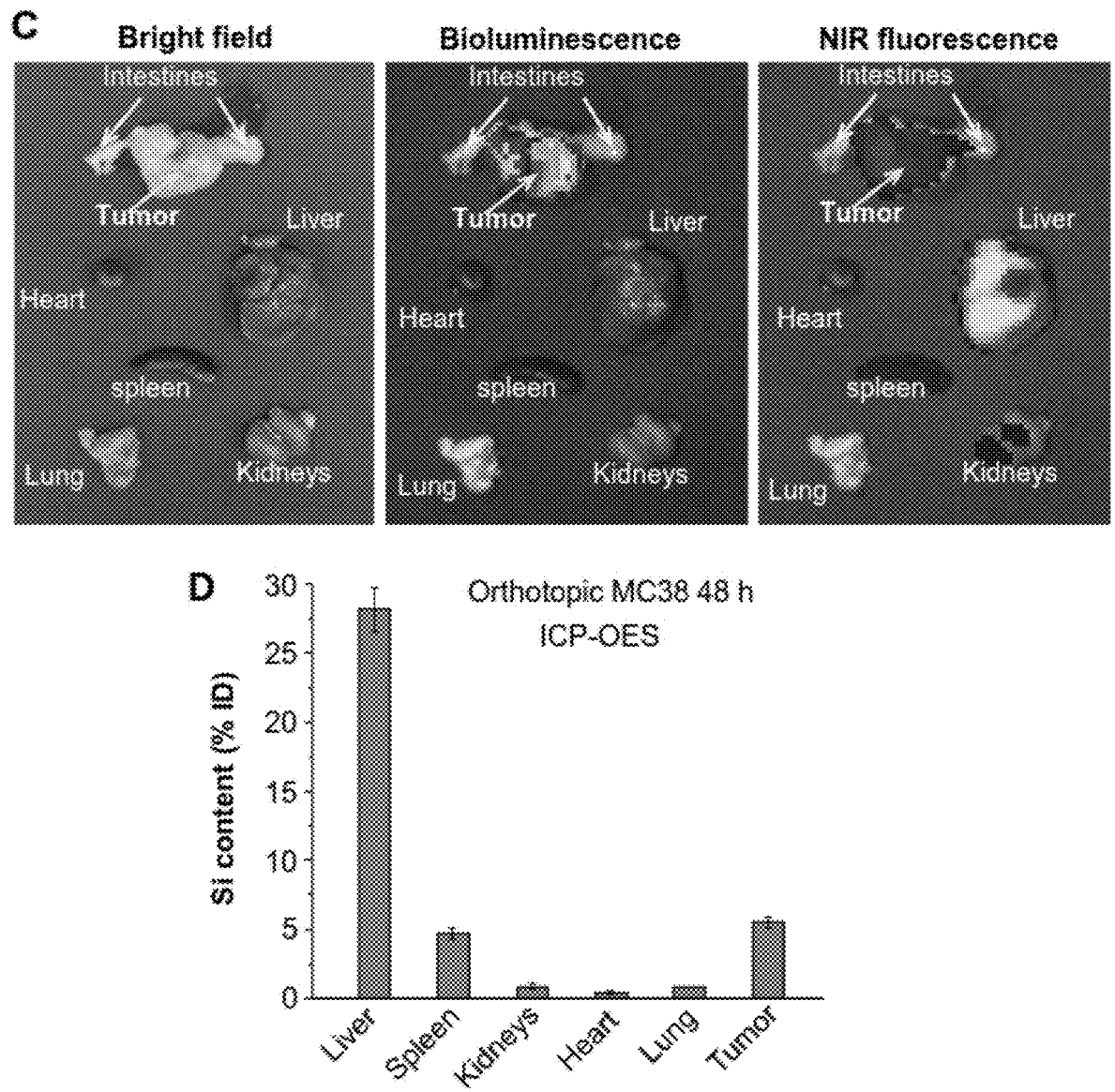
Fig. 11, cont'd.

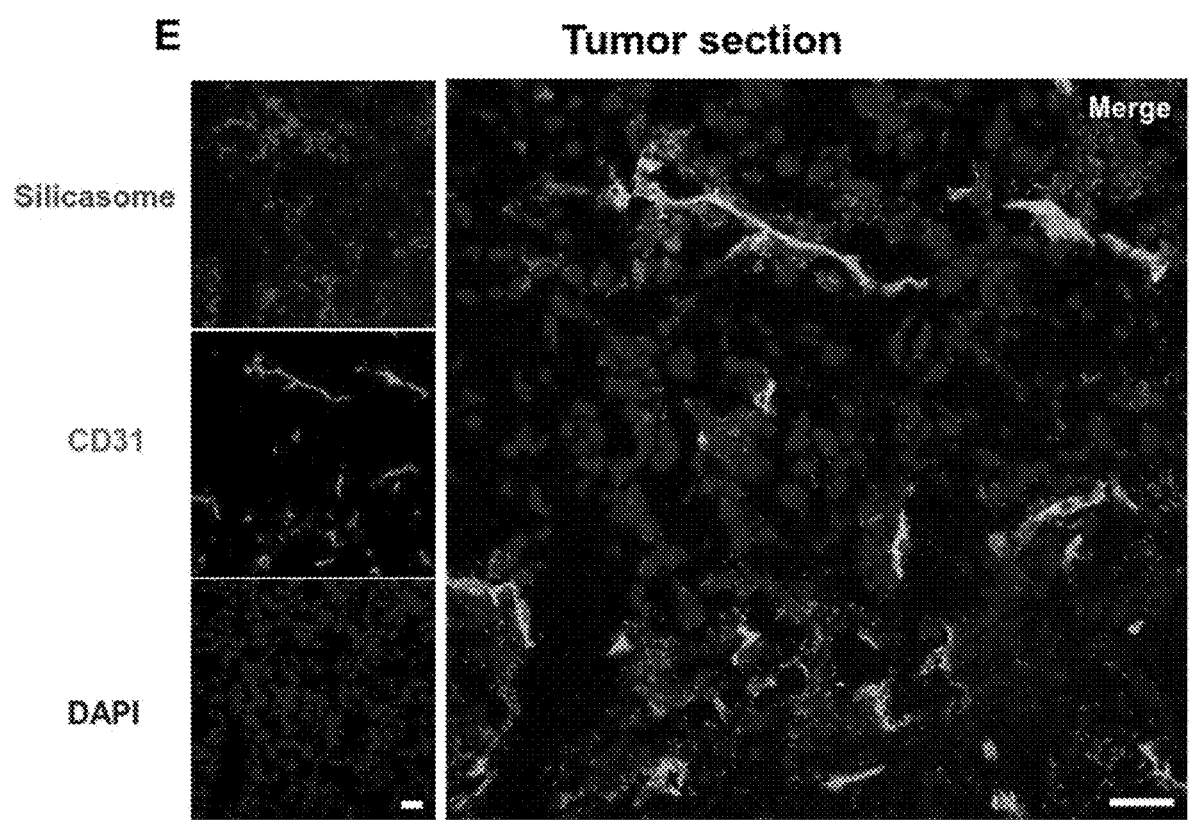
*Fig. 11, cont'd.*

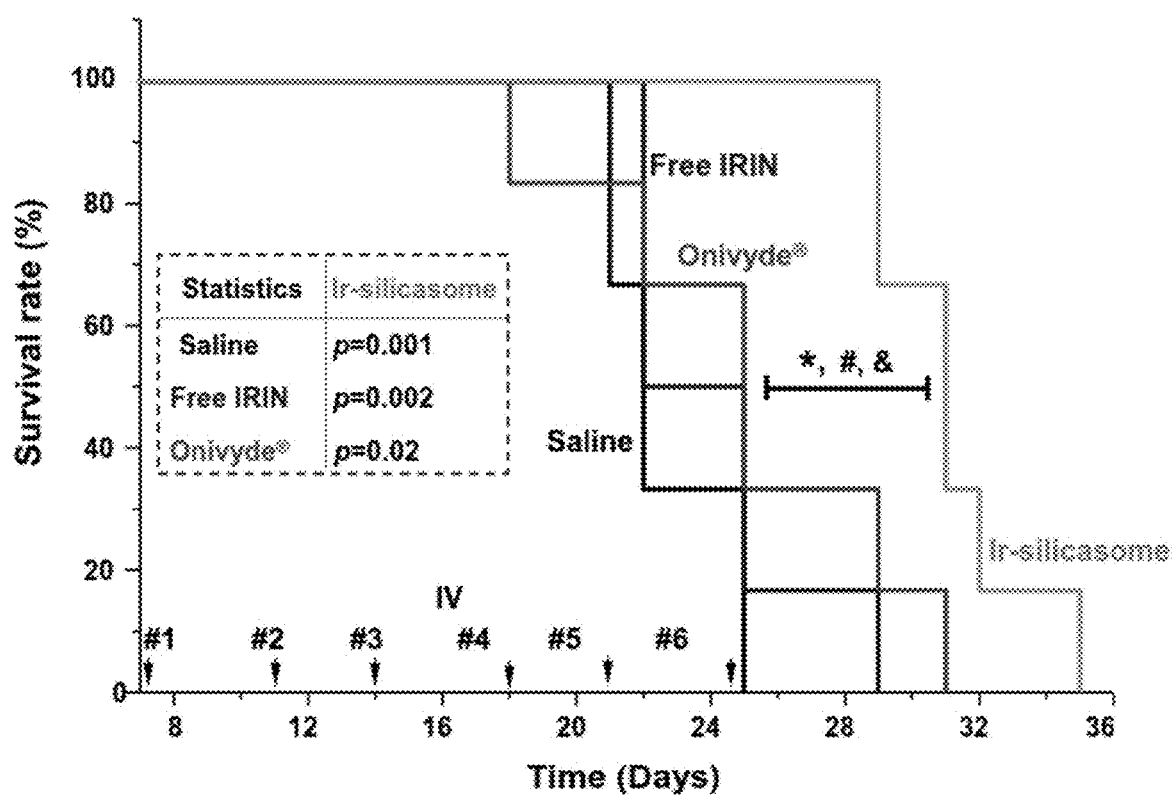
*Fig. 12, cont'd.*

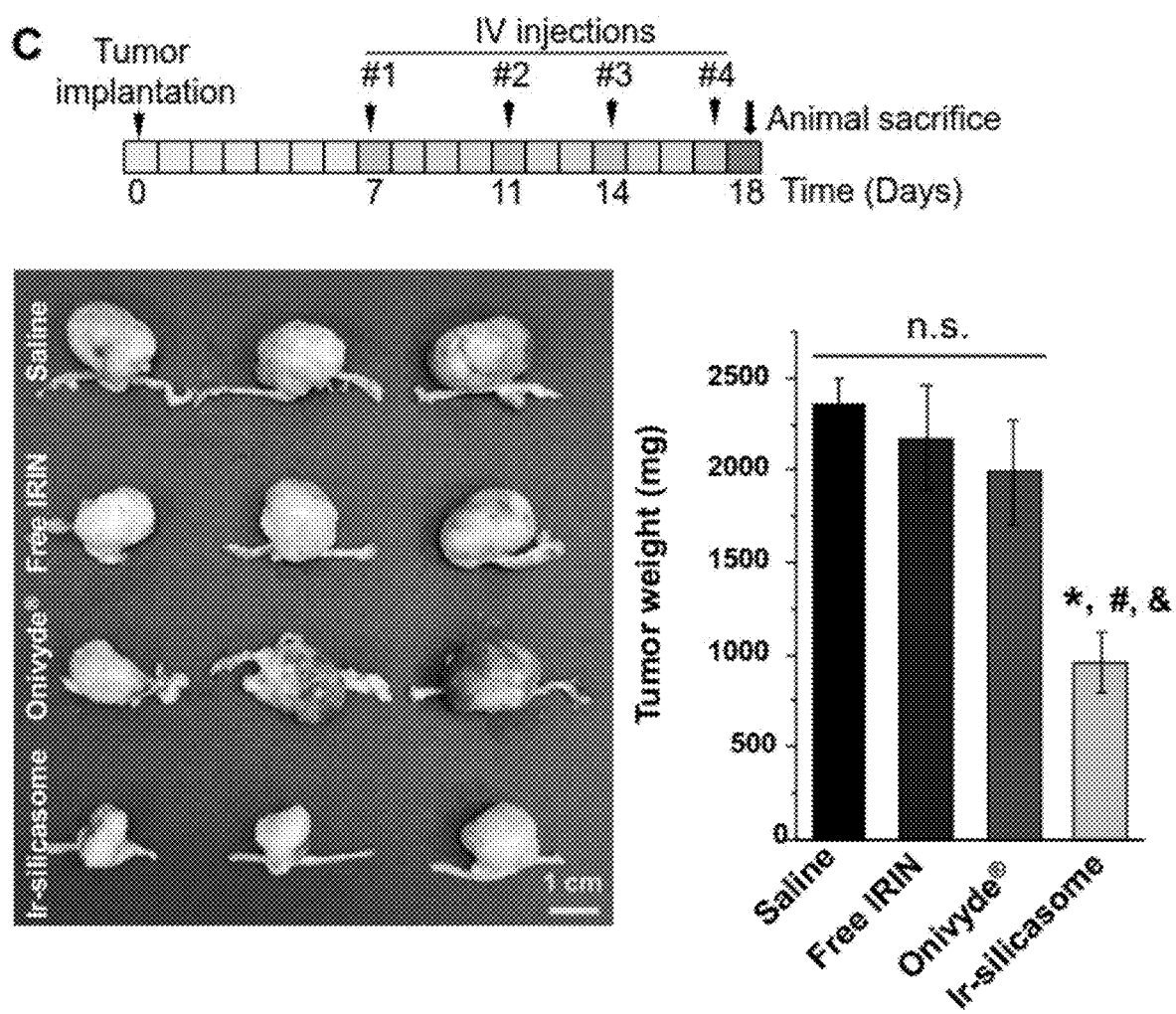
Fig. 12,cont'd.

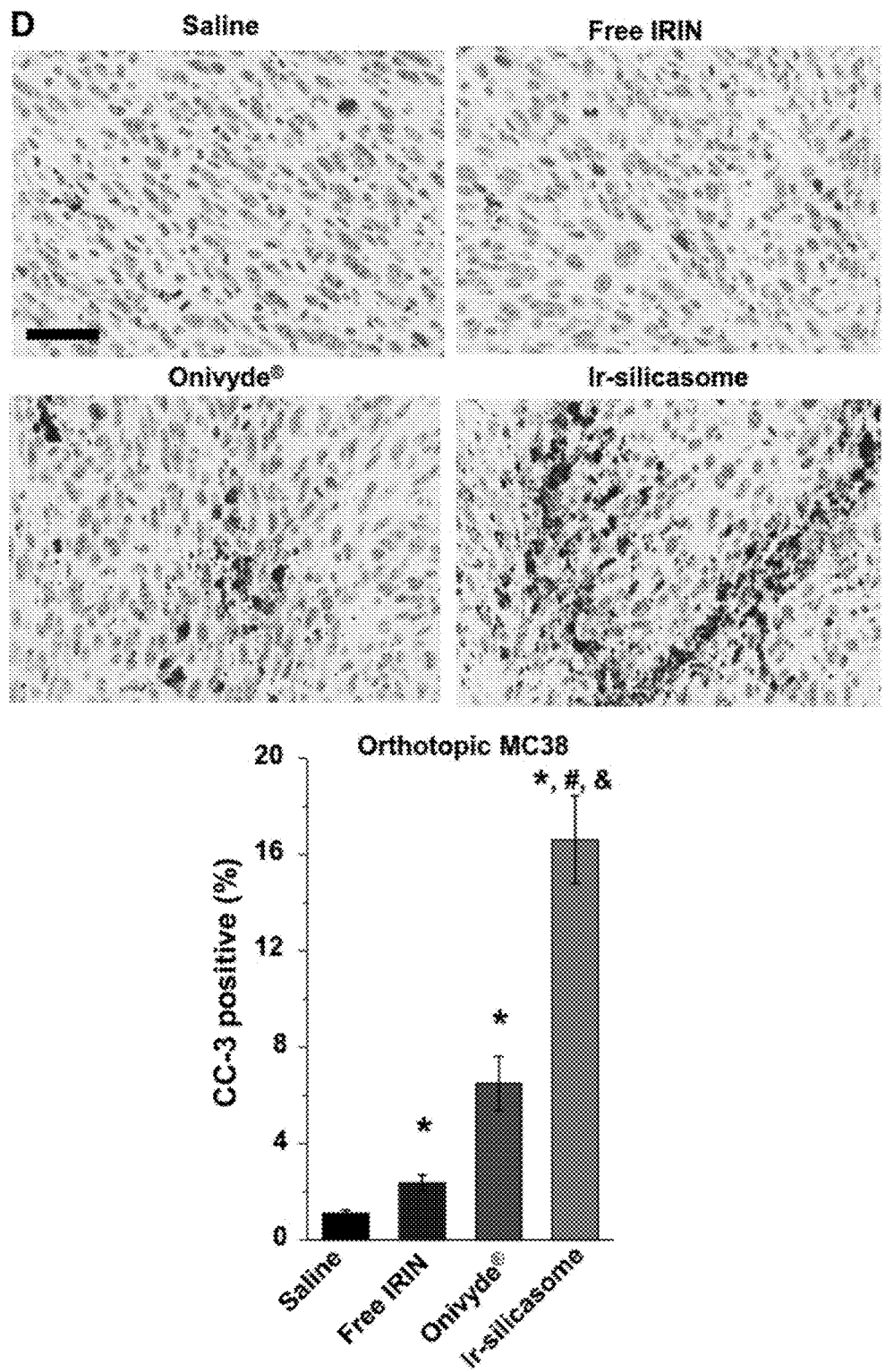
Fig. 12, cont'd.

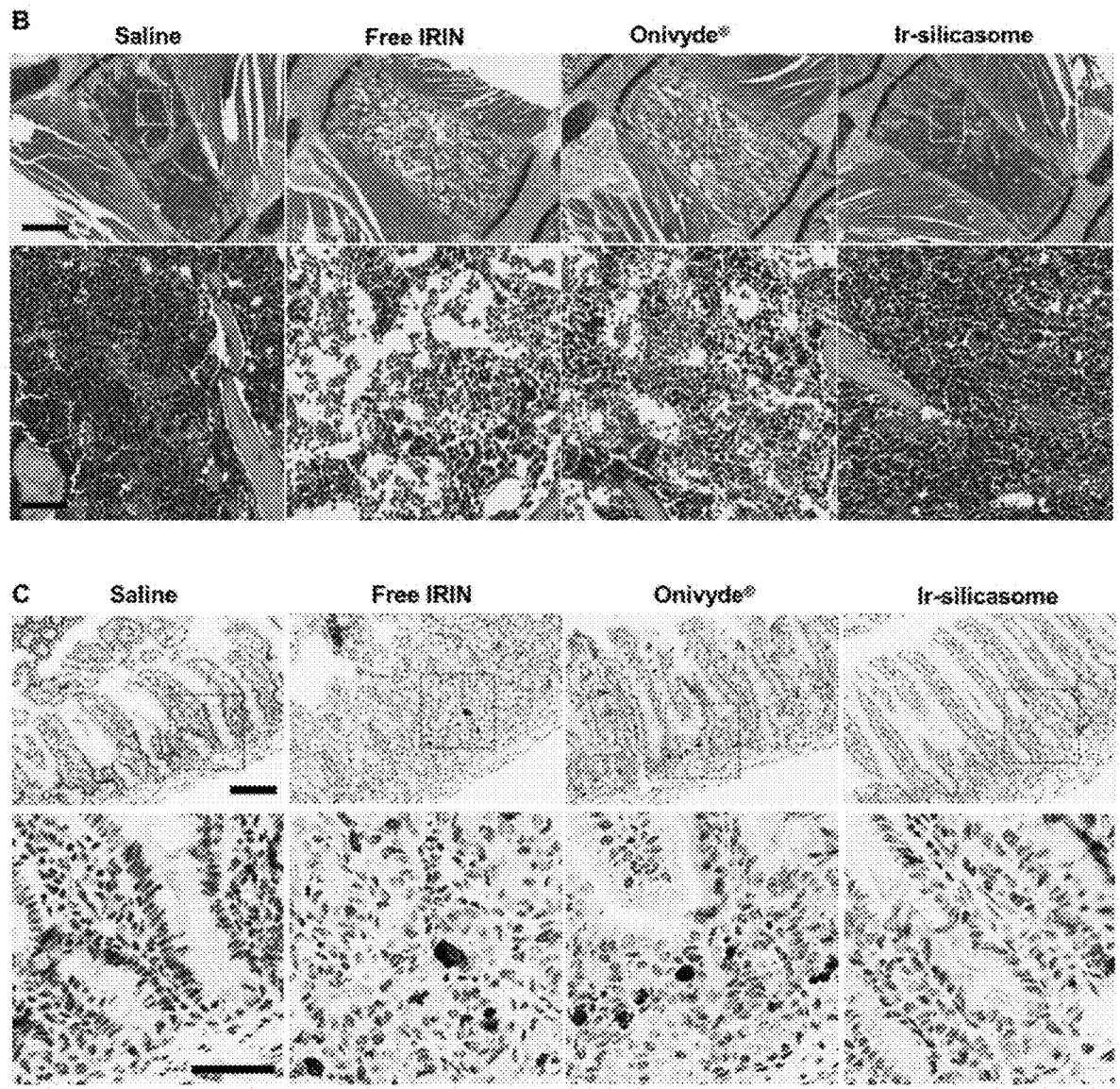
Fig. 13, cont'd.

Fig. 13, cont'd.

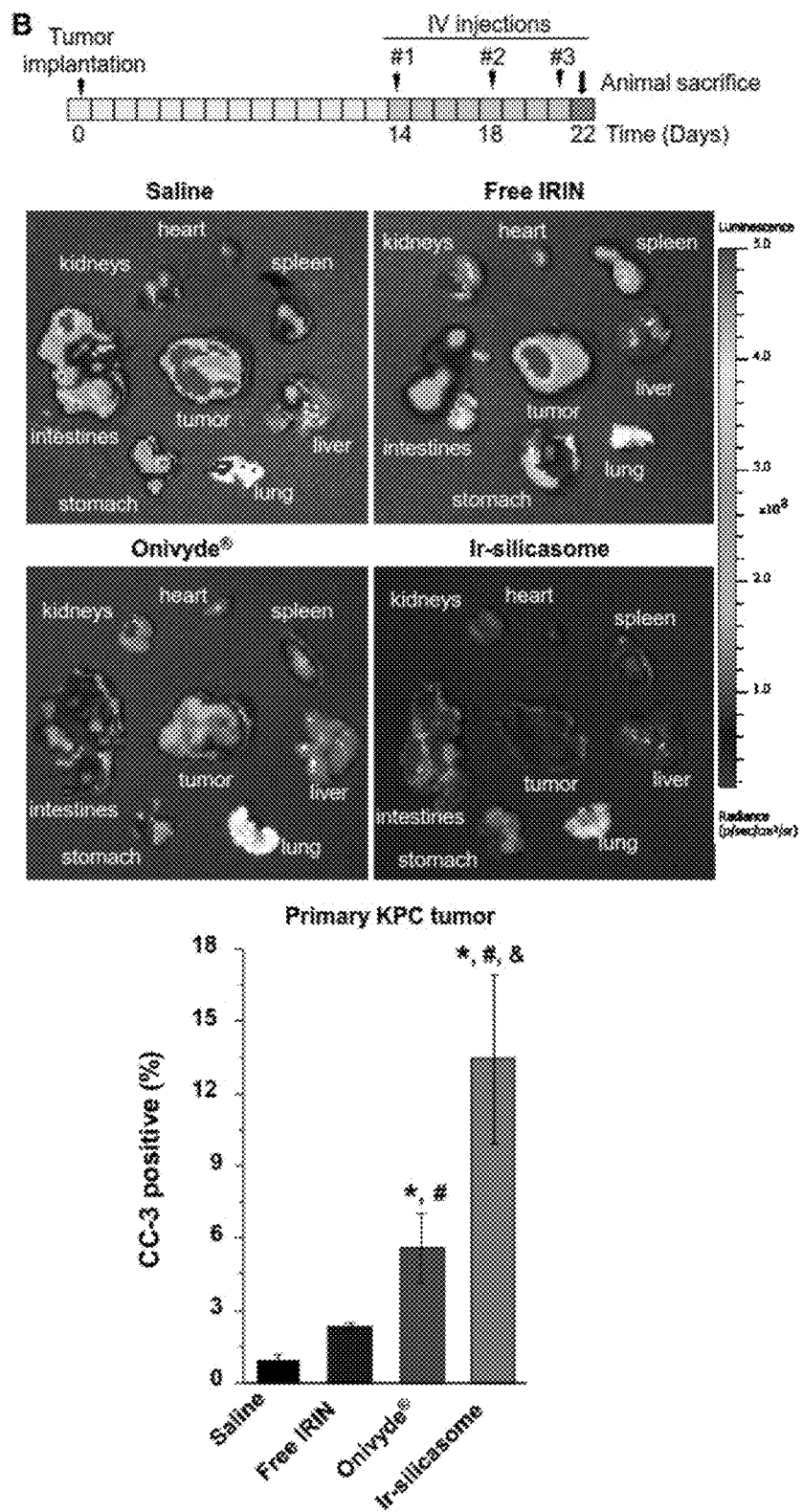
Fig. 14, cont'd.

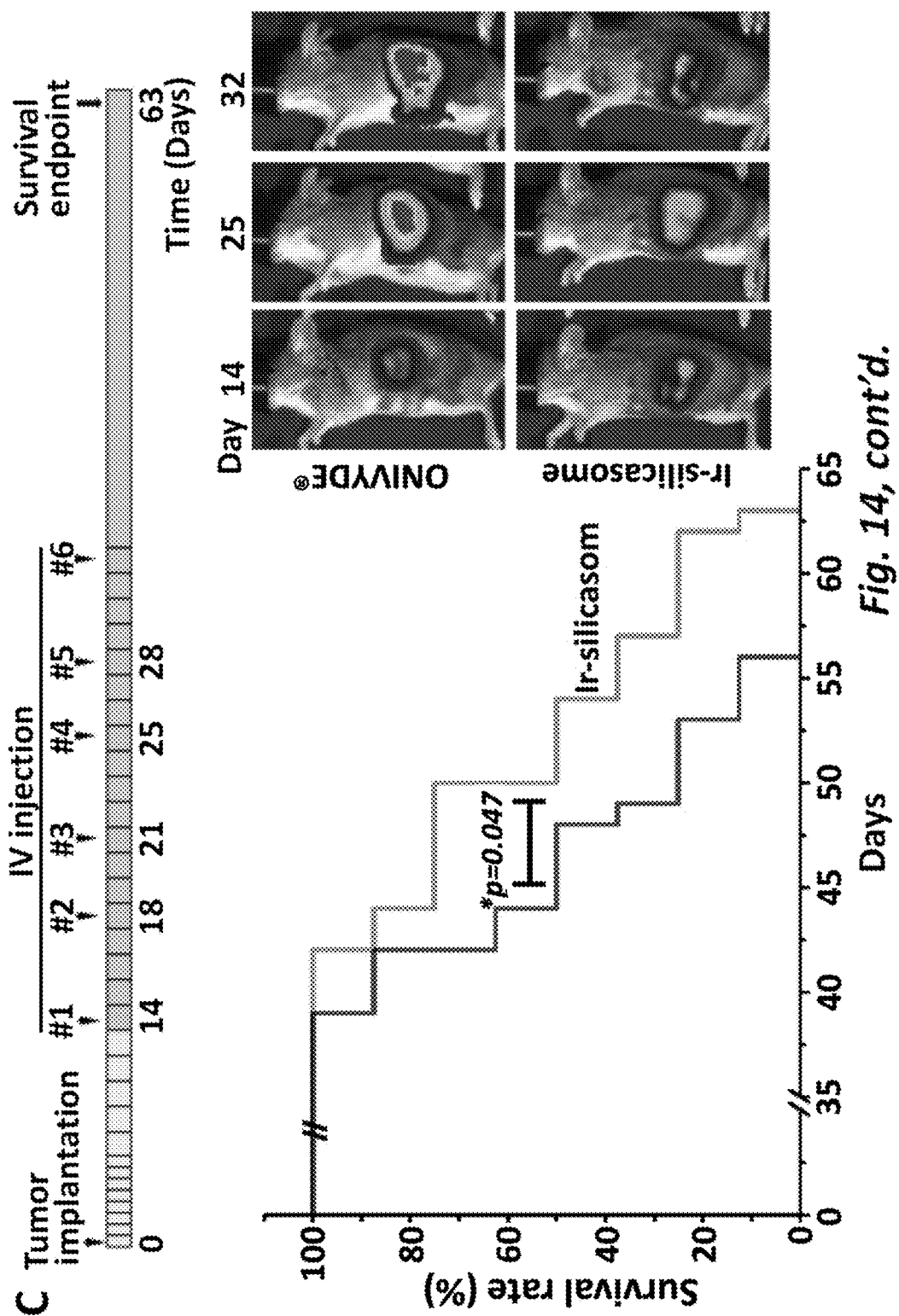
Fig. 14, cont'd.

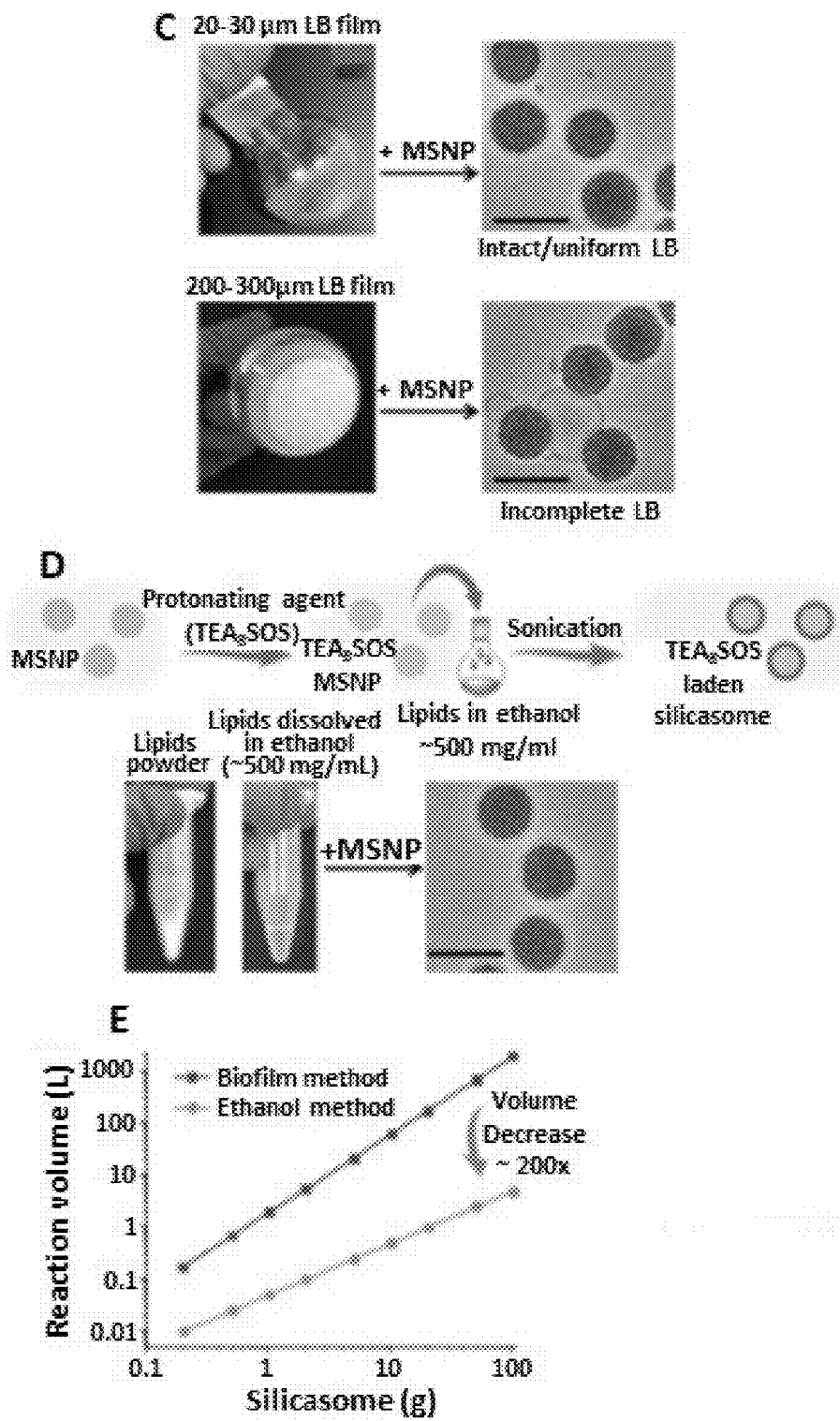
Fig. 15, cont'd.

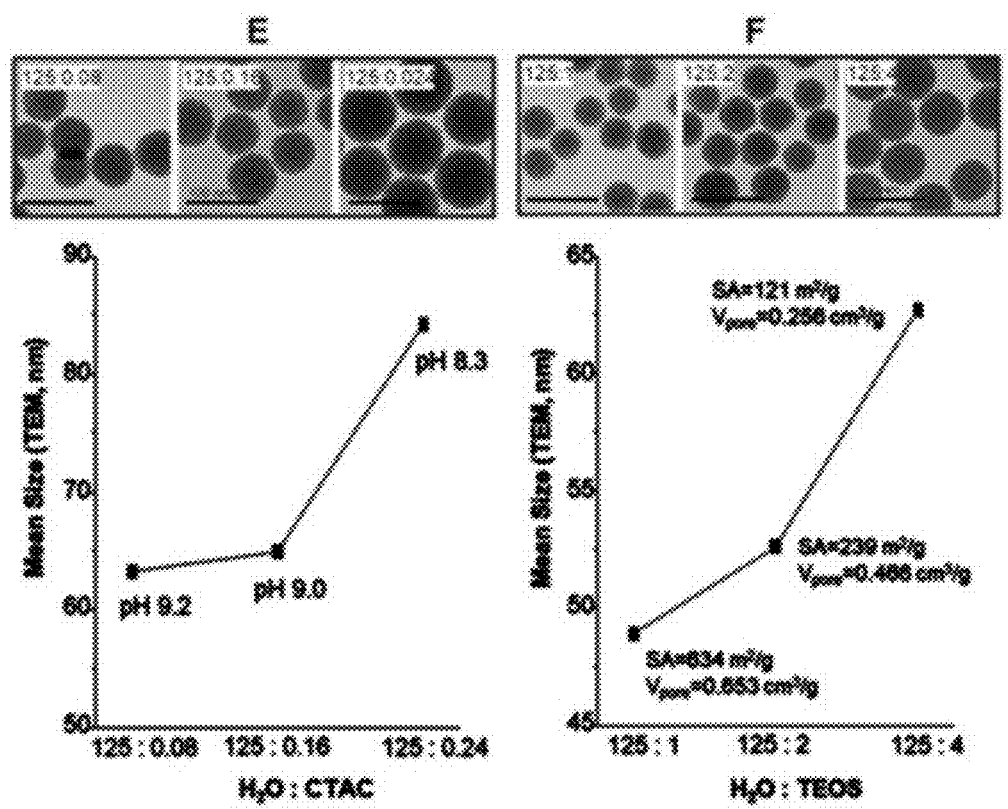
*Fig. 16, cont'd.*

```
                        SEQUENCE LISTING

<160> NUMBER OF SEQ ID NOS: 10

<210> SEQ ID NO 1
<211> LENGTH: 19
<212> TYPE: PRT
<213> ORGANISM: Artificial
<220> FEATURE:
<223> OTHER INFORMATION: Fusogenic peptide

<400> SEQUENCE: 1

Gly Leu Phe His Ala Ile Ala His Phe Ile His Gly Gly Trp His Gly
1               5                   10                  15

Leu Ile His

<210> SEQ ID NO 2
<211> LENGTH: 5
<212> TYPE: PRT
<213> ORGANISM: Artificial
<220> FEATURE:
<223> OTHER INFORMATION: Cyclic receptor binding peptide
<220> FEATURE:
<221> NAME/KEY: misc_feature
<222> LOCATION: (4)..(4)
<223> OTHER INFORMATION: Xaa is D-phenylalanine

<400> SEQUENCE: 2

Arg Gly Asp Xaa Lys
1               5

<210> SEQ ID NO 3
<211> LENGTH: 5
<212> TYPE: PRT
<213> ORGANISM: Artificial
<220> FEATURE:
<223> OTHER INFORMATION: Cyclic receptor binding peptide
<220> FEATURE:
<221> NAME/KEY: misc_feature
<222> LOCATION: (4)..(4)
<223> OTHER INFORMATION: Xaa is D-phenylalanine

<400> SEQUENCE: 3

Arg Gly Asp Xaa Cys
1               5

<210> SEQ ID NO 4
<211> LENGTH: 5
<212> TYPE: PRT
<213> ORGANISM: Artificial
<220> FEATURE:
<223> OTHER INFORMATION: Cyclic receptor binding peptide
<220> FEATURE:
```

```
<221> NAME/KEY: misc_feature
<222> LOCATION: (4)..(4)
<223> OTHER INFORMATION: Xaa is D-tyrosine

<400> SEQUENCE: 4

Arg Gly Asp Xaa Cys
1               5

<210> SEQ ID NO 5
<211> LENGTH: 12
<212> TYPE: PRT
<213> ORGANISM: Artificial
<220> FEATURE:
<223> OTHER INFORMATION: Receptor binding peptide

<400> SEQUENCE: 5

Tyr His Trp Tyr Gly Tyr Thr Pro Gln Asn Val Ile
1               5                   10

<210> SEQ ID NO 6
<211> LENGTH: 9
<212> TYPE: PRT
<213> ORGANISM: Artificial
<220> FEATURE:
<223> OTHER INFORMATION: Receptor binding peptide

<400> SEQUENCE: 6

Gly Ser Gly Lys Cys Cys Tyr Ser Leu
1               5

<210> SEQ ID NO 7
<211> LENGTH: 8
<212> TYPE: PRT
<213> ORGANISM: Artificial
<220> FEATURE:
<223> OTHER INFORMATION: Receptor binding peptide

<400> SEQUENCE: 7

Gln Trp Ala Val Gly His Met Leu
1               5

<210> SEQ ID NO 8
<211> LENGTH: 8
<212> TYPE: PRT
<213> ORGANISM: Artificial
<220> FEATURE:
<223> OTHER INFORMATION: Receptor binding peptide

<400> SEQUENCE: 8

Asp Tyr Met Gly Trp Met Asp Phe
1               5

<210> SEQ ID NO 9
<211> LENGTH: 6
<212> TYPE: PRT
<213> ORGANISM: Artificial
<220> FEATURE:
<223> OTHER INFORMATION: Receptor binding peptide

<400> SEQUENCE: 9

Arg Arg Pro Tyr Ile Leu
1               5

<210> SEQ ID NO 10
<211> LENGTH: 19
<212> TYPE: PRT
<213> ORGANISM: Artificial
```

```
<220> FEATURE:
<223> OTHER INFORMATION: Receptor binding peptide

<400> SEQUENCE: 10

Arg Arg Pro Tyr Ile Leu Gln Leu Tyr Glu Asn Lys Pro Arg Arg Pro
1               5                   10                  15

Tyr Ile Leu
```

SCALE UP SYNTHESIS OF SILICASOME NANOCARRIERS

CROSS-REFERENCE TO RELATED APPLICATIONS

This application claims benefit of and priority to U.S. Ser. No. 62/612,671, filed on Jan. 1, 2018, which is incorporated herein by reference in its entirety for all purposes.

INCORPORATION BY REFERENCE OF SEQUENCE LISTING PROVIDED AS A TEXT FILE

A Sequence Listing is provided herewith as a text file, "UCLA-P195US ST25.txt" created on Mar. 15, 2019 and having a size of 2,564 bytes. The contents of the text file are incorporated by reference herein in their entirety.

STATEMENT OF GOVERNMENTAL SUPPORT

This invention was made with government support under Grant Number CA198846, awarded by the National Institutes of Health. The Government has certain rights in the invention.

BACKGROUND

Mesoporous silica nanoparticles (MSNPs) can provide more efficacious, safe and well-tolerated chemotherapy for cancer treatment. However, there is a lack of effective methods for scaled up synthesis of these MSNPs.

SUMMARY

In order to facilitate the approval and commercialization of silicasome drug delivery systems (e.g. irinotecan silicasomes) it is necessary to scale up the synthesis of the drug-loaded silicasomes, in a manner that also takes into consideration the stringency of therapeutic nanocarrier performance. In this regard, it was discovered that the synthesis protocols used for laboratory synthesis of drug-loaded silicasomes (e.g., 500 mg/batch) do not linearly scale to large scale silicasome production, because the resulting nanoparticle carriers were too heterogeneous or of incorrect size for use as pharmaceuticals. Accordingly, new methods are provided herein that effectively afford the large-scale production of mesoporous silica nanoparticles (MSNPs) and lipid bilayer coated MSNPs (silicasomes). These methods were developed by multi-parameter design since it is not possible to achieve large batch sizes using linear increases of compositional ingredients and reaction conditions, which had to be novel designed to meet the criteria and manufacturing requirements for pharmaceutical quality nanocarriers.

Various embodiments contemplated herein may include, but need not be limited to, one or more of the following:

Embodiment 1

A method for the large-scale preparation of mesoporous silica nanoparticles suitable use in pharmaceuticals, said method comprising:
providing a surfactant in water at a concentration greater than the CTAC critical micellar concentration (CMC) of said surfactant to form a mixture comprising surfactant;
adding to said mixture triethanolamine (TEA);
adding to said mixture tetraethylorthosilicate (TEOS);
where the molar ratio of $H_2O$:TEOS ranges from about 100:0.1 to about 100:1, the molar ratio of $H_2O$:CTAC ranges from about 100:0.04 to about 100:0.4, and the molar ratio of $H_2O$:TEA ranges from about 100:0.02 to about 100:0.2; and
stirring (or agitating) said mixture to allow said CTAC micelles, TEA, and TEOS to react to form a population of mesoporous silica nanoparticles (MSNPs).

Embodiment 2

The method of embodiment 1, wherein said surfactant comprises a cationic surfactant.

Embodiment 3

The method of embodiment 2, wherein said surfactant comprises a surfactant selected from the group consisting of a tetradecyl-trimethyl-ammonium salt (e.g., tetradecyl-trimethyl-ammonium bromide (C14TAB; CTAB) or tetradecyl-trimethyl-ammonium chloride (CTAC), a hexadecyltrimethylammonium salt (e.g., hexadecyltrimethylammonium bromide (C16; CTAB)), an octadecyltrimethylammonium salt (e.g., octadecyltrimethylammonium bromide (C18; OTAB)), a dodecylethyldimethylammonium salt (e.g., dodecylethyldimethylammonium bromide), a cetylpyridinium salt (e.g., cetylpyridinium chloride (CPC)), polyethoxylated tallow amine (POEA), hexadecyl trimethylammonium p-toluenesulfonate, a benzalkonium salt (e.g., benzalkonium chloride (BAC)), or a benzethonium salt (e.g., benzethonium chloride (BZT)) and mixtures thereof.

Embodiment 4

The method of embodiment 2, wherein said surfactant comprises cetyltrimethylammonium chloride (CTAC) or cetyltrimethylammonium bromide (CTAB).

Embodiment 5

The method of embodiment 2, wherein said surfactant comprises cetyltrimethylammonium chloride (CTAC).

Embodiment 6

The method according to any one of embodiments 1-5, wherein said method produces at least 30 g or greater, or 40 g or greater, or 50 g or greater, or 60 g or greater, or 80 g or greater, or 1 kg or greater MSNPs in a single batch.

Embodiment 7

The method according to any one of embodiments 1-6, wherein the molar ratio of $H_2O$:CTAC:TEA:TEOS ranges from about 100 to about 150 water: about 0.06 to about 0.10 CTAC:about 0.04 to about 0.08 TEA:about 0.8 to about 1.2 TEOS.

Embodiment 8

The method according to any one of embodiments 1-7, wherein the molar ratio of $H_2O$:CTAC:TEA:TEOS is about 125:0.08:0.06:1.

Embodiment 9

The method of embodiment 8, wherein said method produces about 60 g to about 70 g of MSNPs.

Embodiment 10

The method according to any one of embodiments 1-7, wherein the molar ratio of $H_2O$:CTAC:TEA:TEOS is about 125:0.08:0.06:0.33.

Embodiment 11

The method of embodiment 10, wherein said method produces about 120 g to about 140 g of MSNPs.

Embodiment 12

The method according to any one of embodiments 1-7, wherein said method comprises combining about 3,000 mL water, about 36.3 g CTAC, about 12 g TEA and about 280 g TEOS.

Embodiment 13

The method according to any one of embodiments 1-12, wherein said method is performed at a temperature ranging from about 25° C. up to about 99° C., or from about 75° C. to about 90° C.

Embodiment 14

The method of embodiment 13, wherein said method is performed at a temperature of about 85° C.

Embodiment 15

The method according to any one of embodiments 1-14, wherein said stirring or agitating comprises stirring at a speed ranging from about 150 rpm, or from about 200 rpm, or from about 250 rpm up to about 800 rpm, or up to about 600 rpm, or up to about 400 rpm, or up to about 300 rpm.

Embodiment 16

The method of embodiment 15, wherein said stirring or agitating comprises stirring at about 250 rpm.

Embodiment 17

The method according to any one of embodiments 1-16, wherein said reaction proceeds until the hydrodynamic size of the MSNPs is substantially constant and/or where the yield of MSNPs is substantially constant.

Embodiment 18

The method of embodiment 17, wherein said reaction proceeds for a time period ranging from about 0.5 hours, or from about 1 hour, up to about 5 hours, or up to about 4 hours.

Embodiment 19

The method of embodiment 18, wherein said reaction proceeds for about 2 hours.

Embodiment 20

The method of embodiment 19, wherein said reaction produces about 60-70 g of MSNPs.

Embodiment 21

The method of embodiment 18, wherein said reaction proceeds for about 4 hours.

Embodiment 22

The method according to any one of embodiments 1-21, wherein said reaction produces about 120-140 g of MSNPs.

Embodiment 23

The method according to any one of embodiments 1-22, wherein said method has a yield of greater than about 80%.

Embodiment 24

The method according to any one of embodiments 1-23, wherein said method produces MSNPs having a substantially monotonic size distribution.

Embodiment 25

The method of embodiment 24, wherein said method produces MSNPs whose size distribution has a coefficient of variation of less than about 0.10.

Embodiment 26

The method according to any one of embodiments 1-25, wherein said method produces MSNPs having an average diameter ranging from about 40 nm up to about 100 nm.

Embodiment 27

The method of embodiment 26, wherein said method produces MSNPs having an average diameter of about 60-70 nm.

Embodiment 28

The method according to any one of embodiments 1-27, wherein said method produces MSNPs having an average pore size ranging from about 2.2 to about 3.4 nm, or from about 2.3 to about 3.2 nm.

Embodiment 29

The method of embodiment 28, wherein said method produces MSNPs having an average pore size ranging from about 2.2-3.4 nm.

Embodiment 30

The method according to any one of embodiments 1-29, wherein said synthesis is performed in a reaction vessel.

Embodiment 31

The method according to any one of embodiments 1-29, wherein said synthesis is performed in a microfluidic reactor.

Embodiment 32

The method according to any one of embodiments 1-31, wherein said method comprises removing the CTAC surfactant by a wash procedure.

Embodiment 33

The method of embodiment 32, wash procedure comprises washing said MSNPs with an alcohol and/or an acid.

Embodiment 34

The method of embodiment 33, wherein said wash procedure comprises washing said MSNPs with an alcohol/acid mixture.

Embodiment 35

The method of embodiment 34, wherein said alcohol/acid mixture comprises a methanol/HCl mixture.

Embodiment 36

The method of embodiment 34, wherein said alcohol/acid mixture comprises an ethanol/HCl mixture.

Embodiment 37

The method according to any one of embodiments 35-36, wherein said alcohol/acid mixture comprises alcohol/HCL at 500:19 v/v and said washing is at room temperature.

Embodiment 38

The method according to any one of embodiments 1-37, wherein said method further comprises centrifuging and/or washing said MSNPs.

Embodiment 39

The method according to any one of embodiments 1-38, wherein said method further comprises filtering using a non-dead end filtration system with a nm or less cut off pore size.

Embodiment 40

A population of MSNPs produced by a method according to any one of embodiments 1-39.

Embodiment 41

A method for the large-scale synthesis of silicasomes, said method comprising:
providing a population of mesoporous silica nanoparticles (MSNPs);
providing a plurality of lipids dispersed in a polar solvent forming a lipid/solvent dispersion;
introducing said population of MSNPs into said lipid/solvent dispersion; and
sonicating/homogenizing said lipid/solvent dispersion containing said MSNPs to provide a population of MSNPs encased in a lipid bilayer.

Embodiment 42

The method of embodiment 41, wherein said sonicating comprises direct sonication.

Embodiment 43

The method of embodiment 42, wherein said sonicating comprises use of a probe sonicator.

Embodiment 44

The method of embodiment 42, wherein said sonicating comprises use of a static sonicator.

Embodiment 45

The method of embodiment 42, wherein said sonicating comprises use of a probe flow through sonicator/homogenizer.

Embodiment 46

The method of embodiment 41, wherein said sonicating comprises indirect sonication.

Embodiment 47

The method according to any one of embodiments 41-46, wherein said population of MSNPs is prepared according to the method of any one of embodiments 1-39.

Embodiment 48

The method according to any one of embodiments 41-47, wherein said polar solvent comprises a solvent selected from the group consisting of ethanol, methanol, ethanol containing an aqueous solvent with the organic phase greater than 30%, methanol containing an aqueous solvent with the organic phase greater than 30%, pure acetone, and acetone aqueous solution with acetone concentration of 50% or greater.

Embodiment 49

The method of embodiment 48, wherein said polar solvent comprises absolute ethanol.

Embodiment 50

The method according to any one of embodiments 41-49, wherein the ratio of MSNP to lipid ranges from about 1:0.5 to about 1:5 (w/w).

Embodiment 51

The method of embodiment 50, wherein the ratio of MSNP to lipid is about 1:1.1 (wt/wt).

Embodiment 52

The method according to any one of embodiments 41-51, wherein said reaction is performed at a temperature ranging from about 40° C., or from about 50° C., or from about 60° C., to about 80° C., or to about 75° C., or to about 70° C.

Embodiment 53

The method of embodiment 51 wherein said reaction is performed at a temperature of about 65° C.

Embodiment 54

The method according to any one of embodiments 41-53, wherein said sonication proceeds at an energy and duration sufficient to provide a substantially clear suspension of silicasomes.

Embodiment 55

The method according to any one of embodiments 41-54, wherein said plurality of lipids comprise a phospholipid, cholesterol (CHOL), and an mPEG phospholipid and the lipid bilayer encapsulating said MNSPs comprise said phospholipid, cholesterol (CHOL), and an mPEG phospholipid.

Embodiment 56

The method of embodiment 55, wherein said phospholipid comprises a saturated fatty acid with a C14-C20 carbon chain, and/or an unsaturated fatty acid with a C14-C20 carbon chain, and/or a natural lipid comprising a mixture of fatty acids with C12-C20 carbon chains.

Embodiment 57

The method of embodiment 56, wherein said phospholipid comprises a saturated fatty acid selected from the group consisting of phosphatidylcholine (DPPC), dimyristoylphosphatidylcholine (DMPC), distearoylphosphatidylcholine (DSPC), and diactylphosphatidylcholine (DAPC).

Embodiment 58

The method of embodiment 56, wherein said phospholipid comprises a natural lipid selected from the group consisting of egg phosphatidylcholine (egg PC), and soy phosphatidylcholine (soy PC).

Embodiment 59

The method of embodiment 56, wherein said phospholipid comprises an unsaturated fatty acid selected from the group consisting of 1,2-dimyristoleoyl-sn-glycero-3-phosphocholine, 1,2-dipalmitoleoyl-sn-glycero-3-phosphocholine, 1,2-dioleoyl-sn-glycero-3-phosphocholine (DOPC), and 1,2-dieicosenoyl-sn-glycero-3-phosphocholine.

Embodiment 60

The method according to any one of embodiments 55-59, wherein said lipid bilayer comprises an mPEG phospholipid with a phospholipid C14-C18 carbon chain, and a PEG molecular weight ranging from about 350 Da to 5000 Da.

Embodiment 61

The method of embodiment 60, wherein said lipid bilayer comprises 1,2-distearoyl-sn-glycero-3-phosphoethanolamine-PEG (DSPE-PEG).

Embodiment 62

The method of embodiment 55, wherein said lipid bilayer comprises DPPC/Chol/DSPE-PEG or DSPC/Chol/DSPE-PEG.

Embodiment 63

The method of embodiment 62, wherein said lipid bilayer comprises DSPC/Chol/DSPE-PEG.

Embodiment 64

The method of embodiment 63, wherein said lipid bilayer comprises D SPC/Chol/D SPE-PEG2000.

Embodiment 65

The method according to any one of embodiments 55-64, wherein said lipid bilayer comprises a phospholipid, cholesterol, and mPEG phospholipid at a ratio of 50-90 mol % phospholipid:10-50 mol % CHOL:1-10 mol % mPEG phospholipid.

Embodiment 66

The method of embodiment 63, wherein said lipid bilayer comprises DSPC/Chol/DSPE-PEG in a molar ratio of about 3:2:0.15.

Embodiment 67

The method according to any one of embodiments 41-66, wherein said lipid bilayer forms a substantially continuous bilayer encompassing the entire nanoparticle.

Embodiment 68

The method according to any one of embodiments 41-67, wherein said lipid bilayer forms a substantially uniform and intact bilayer encompassing the entire nanoparticle.

Embodiment 69

The method according to any one of embodiments 41-68, wherein said providing a population of mesoporous silica nanoparticles (MSNPs) comprises providing a population of MSNPs loaded with a protonating agent and the silicasomes formed by said method contain said protonating agent.

Embodiment 70

The method of embodiment 69, wherein said MSNPs are loaded with a protonating agent by soaking said MSNPs in a protonating mixture.

Embodiment 71

The method of embodiment 70, wherein said method comprises isolating and washing the MSNPs loaded with said protonating agent.

Embodiment 72

The method according to any one of embodiments 69-71, wherein said protonating agent is selected from the group consisting of $TEA_8SOS$, proton-generating dissociable salts (e.g. $(NH_4)_2SO_4$), an ammonium salt (e.g., ammonium sulfate, ammonium sucrose octasulfate, ammonium α-cyclodextrin sulfate, ammonium β-cyclodextrin sulfate, ammonium γ-cyclodextrin sulfate, ammonium phosphate, ammonium α-cyclodextrin phosphate, ammonium β-cyclodextrin phosphate, ammonium γ-cyclodextrin phosphate, ammonium citrate, ammonium acetate, and the like), a trimethylammonium salt (e.g., trimethylammonium sulfate, trimethylammonium sucrose octasulfate, trimethylammonium α-cyclodextrin sulfate, trimethylammonium 3-cyclodextrin sulfate, trimethylammonium γ-cyclodextrin sulfate, trimethylammonium phosphate, trimethylammonium α-cyclodextrin phosphate, trimethylammonium 3-cyclodextrin phosphate, trimethylammonium γ-cyclodextrin phosphate, trimethylammonium citrate, trimethylammonium acetate, and the like), a triethylammonium salt (e.g., triethylammonium sulfate, triethylammonium sucrose octasulfate, triethylammonium α-cyclodextrin sulfate, triethylammonium 3-cyclodextrin sulfate, triethylammonium γ-cyclodextrin sulfate, triethylammonium phosphate, triethylammonium α-cyclodextrin phosphate, triethylammonium 3-cyclodextrin phosphate, triethylammonium γ-cyclodextrin phosphate, triethylammonium citrate, triethylammonium acetate, and the like), an acidic buffer (e.g., citrate), a metal salt (e.g. A23187 and $MnSO_4$), and calcium acetate.

Embodiment 73

The method according to any one of embodiments 69-71, wherein said protonating agent is selected from the group consisting of triethylammonium sucrose octasulfate ($TEA_8SOS$), $(NH_4)_2SO_4$, an ammonium salt, a trimethylammonium salt, and a triethylammonium salt.

Embodiment 74

The method of embodiment 72, wherein said protonating agent before reaction with said drug comprises triethylammonium sucrose octasulfate ($TEA_8SOS$).

Embodiment 75

The method of embodiment 74, wherein, when a drug is loaded into said MSNPs, the drug is protonated and trapped in said pores as a gel-like precipitate in association of $SOS^{8-}$.

Embodiment 76

The method according to any one of embodiments 69-75, wherein said method comprises remote loading the silicasomes with a drug by incubating the silicasomes containing a protonating agent with one or more drugs comprising at least one weakly basic group capable of being protonated.

Embodiment 77

The method of embodiment 76, wherein: said drug comprises at least one weakly basic group capable of being protonated, and the protonating agent comprises at least one anionic group; and/or said drug is selected to have a pKa greater than 7 and less than 11; and/or said drug comprises a primary, secondary, or tertiary amine; and/or said drug is selected to have a water solubility index of about 2 to about 25 mg/mL; and/or said drug is selected to have an octanol/water partition coefficient or log P value of about −3.0 to about 3.0; and/or said drug is smaller than the average or median size of the pores of the silica nanoparticle.

Embodiment 78

The nanoparticle drug of embodiment 77, wherein said drug comprises an anti-cancer drug.

Embodiment 79

The method of embodiment 78, wherein said drug comprises irinotecan.

Embodiment 80

The method of embodiment 78, wherein said irinotecan comprises a substantially pure D isomer of irinotecan.

Embodiment 81

The method of embodiment 78, wherein said irinotecan comprises a substantially pure L isomer of irinotecan.

Embodiment 82

The method of embodiment 78, wherein said silicasome is loaded with one or more drugs independently selected from the group consisting of a topoisomerase inhibitor, an antitumor anthracycline antibiotic, a mitotic inhibitor, an alkaloid, an alkaline alkylating agent, a purine or pyrimidine derivative, and a protein kinase inhibitor.

Embodiment 83

The method of embodiment 82, wherein said silicasome is loaded with a drug selected from the group consisting of topotecan, 10-hydroxycamptothecin, belotecan, rubitecan, vinorelbine, LAQ824, doxorubicin, mtoxantrone, vinblastine, vinorelbine, cyclophosphamide, mechlorethamine, temozolomide, 5-fluorouracil, 5'-deoxy-5-fluorouridine, gemcitabine, imatinib, osimertinib and sunitinib pazopanib, enzastaurin, vandetanib, erlotinib, dasatinib, nilotinib, abemaciclib, palbociclib, and ribociclib.

Embodiment 84

The method according to any one of embodiments 41-83, wherein said silicasome is conjugated to a moiety selected from the group consisting of a targeting moiety, a fusogenic peptide, and a transport peptide.

Embodiment 85

The method of embodiment 84, wherein said silicasome is conjugated to a peptide that binds a receptor on a cancer cell or tumor blood vessel.

Embodiment 86

The method of embodiment 85, wherein said silicasome is conjugated to an iRGD peptide.

Embodiment 87

The method of embodiment 85, wherein said silicasome is conjugated to a targeting peptide shown in Table 3.

Embodiment 88

The method according to any one of embodiments 84-87, wherein said silicasome is conjugated to transferrin, and/or ApoE, and/or folate.

Embodiment 89

The method according to any one of embodiments 84-88, wherein said silicasome is conjugated to a targeting moiety that comprises an antibody that binds to a cancer marker.

Embodiment 90

The method of embodiment 89, wherein said silicasome is conjugated to a targeting moiety that comprises an antibody that binds a cancer marker shown in Table 2.

Embodiment 91

The method of embodiment 77, wherein said drug comprises an antibiotic, an antiviral agent, or an antifungal agent.

Embodiment 92

The method of embodiment 91, wherein: said drug comprises an antibiotic selected from the group consisting of ciprofloxacin, and levofloxacin; and/or said drug comprises an antiviral selected from the group consisting of tenofovir, disoproxil, and fumarate; and/or said drug comprises an antifungal agent selected from the group consisting of Amphotericin B, Anidulafungin, Caspofungin, Fluconazole, Flucytosine, Isavuconazole, Itraconazole, Micafungin, Posaconazole, and Voriconazole.

Embodiment 93

The method according to any one of embodiments 76-92, wherein said silicasome has a drug loading capacity of at least about 5% w/w, or at least about 10% w/w, or at least about 20% w/w, or at least about 30% w/w, or greater than about 40% w/w, or greater than about 50% w/w, or greater than about 60% w/w, or greater than about 70% w/w, or greater than about 80% w/w.

Embodiment 94

The method according to any one of embodiments 76-92, wherein said silicasome has a drug loading capacity of up to 80% w/w.

Embodiment 95

The method according to any one of embodiments 41-94, wherein the lipid bilayer comprises a hydrophobic drug that is introduced into said lipid before encapsulation of the MSNPs.

Embodiment 96

The method of embodiment 95, wherein the lipid bilayer comprises a hydrophobic drug selected from the group consisting of paclitaxel, ellipticine, camptothecan, SN-38, and a lipid prodrug (e.g., acyclovir diphosphate dimyristoylglycerol, doxorubicin conjugated phospholipid prodrug, phospholipid derivatives of nucleoside analogs, phospholipid linked chlorambucil, and the like).

Embodiment 97

The method of embodiment 95, wherein the lipid bilayer comprises paclitaxel.

Embodiment 98

The method according to any one of embodiments 41-96, wherein said silicasomes in suspension are stable for at least 1 month, or at least 2 months, or at least 3 months, or at least 4 months, or at least 5 months, or at least 6 months when stored at 4° C.

Embodiment 99

The method according to any one of embodiments 41-98, wherein said method produces a population of said silicasomes in suspension that: shows a size distribution ranging in width (full width half maximum) of less than about 30 nm, or less than about 20 nm, or less than about 10 nm, or less than about 5 nm, or less than about 3 nm, or less than about 2 nm; and/or shows a substantially unimodal size distribution; and/or shows a PDI less than about 0.2, or less than about 0.1; and/or shows a coefficient of variation in size less than about 0.1 or less than about 0.05, or less than about 1.7/120.

Embodiment 100

A population of silicasomes prepared by a method according to any one of embodiments 41-99.

Embodiment 101

The population of silicasomes of embodiment 100, wherein said silicasomes form a stable suspension on rehydration after lyophilization.

Embodiment 102

The population of silicasomes according to any one of embodiments 100-101, wherein said silicasomes, when loaded with an anti-cancer drug, provide more effective cancer cell killing than free drug, or liposomes containing said drug, in an orthotopic PDAC model.

Embodiment 103

The population of silicasomes according to any one of embodiments 100-102, wherein said silicasomes, when loaded with an anti-cancer drug, show reduced drug toxicity as compared to free drug and/or drug in liposomes.

Embodiment 104

The population of silicasomes according to any one of embodiments 100-103, wherein said silicasome has colloidal stability in physiological fluids with pH 7.4 and remains monodisperse to allow systemic biodistribution and is capable of entering a disease site by vascular leakage (EPR effect) or transcytosis.

Embodiment 105

A pharmaceutical formulation said formulation comprising:
  a population of silicasomes according to any one of embodiments 100-104; and
  a pharmaceutically acceptable carrier.

Embodiment 106

The formulation of embodiment 105, wherein said formulation is formulated for administration via a route selected from the group consisting of intravenous administration, intraarterial administration, intracerebral administration, intrathecal administration, oral administration, aerosol administration, administration via inhalation (including intranasal and intratracheal delivery, intracranial administration via a cannula, and subcutaneous or intramuscular depot deposition.

Embodiment 107

The formulation according to any one of embodiments 105-106, wherein said formulation is a sterile injectable.

Embodiment 108

The formulation according to any one of embodiments 105-107, wherein said formulation is a unit dosage formulation.

Embodiment 109

A method of treating a cancer in a subject, said method comprising:
administering to a subject in need thereof an effective amount of a silicasome fabricated according to the method of any one of embodiments 41-90, where the drug in said silicasome comprises an anti-cancer drug.

Embodiment 110

The method of embodiment 109, wherein said drug comprises irinotecan.

Embodiment 111

The method of embodiment 110, wherein said drug comprise a substantially pure D isomer of irinotecan.

Embodiment 112

The method of embodiment 110, wherein said drug comprise a substantially pure L isomer of irinotecan.

Embodiment 113

The method according to any one of embodiments 109-112, wherein said silicasome comprises a primary therapy in a chemotherapeutic regimen.

Embodiment 114

The method according to any one of embodiments 109-112, wherein said silicasome comprises a component in a multi-drug chemotherapeutic regimen.

Embodiment 115

The method of embodiment 114, wherein said multi-drug chemotherapeutic regimen comprises at least two drugs, or at least three drugs, or at least 4 drugs selected from the group consisting of irinotecan (IRIN), oxaliplatin (OX), 5-fluorouracil (5-FU), and leucovorin (LV).

Embodiment 116

The method according to any one of embodiments 109-115, wherein said cancer is pancreatic ductal adenocarcinoma (PDAC).

Embodiment 117

The method according to any one of embodiments 109-115, wherein said cancer is a cancer selected from the group consisting of acute lymphoblastic leukemia (ALL), acute myeloid leukemia (AML), Adrenocortical carcinoma, AIDS-related cancers (e.g., Kaposi sarcoma, lymphoma), anal cancer, appendix cancer, astrocytomas, atypical teratoid/rhabdoid tumor, bile duct cancer, extrahepatic cancer, bladder cancer, bone cancer (e.g., Ewing sarcoma, osteosarcoma, malignant fibrous histiocytoma), brain stem glioma, brain tumors (e.g., astrocytomas, brain and spinal cord tumors, brain stem glioma, central nervous system atypical teratoid/rhabdoid tumor, central nervous system embryonal tumors, central nervous system germ cell tumors, craniopharyngioma, ependymoma, breast cancer, bronchial tumors, burkitt lymphoma, carcinoid tumors (e.g., childhood, gastrointestinal), cardiac tumors, cervical cancer, chordoma, chronic lymphocytic leukemia (CLL), chronic myelogenous leukemia (CML), chronic myeloproliferative disorders, colon cancer, colorectal cancer, craniopharyngioma, cutaneous t-cell lymphoma, duct cancers e.g. (bile, extrahepatic), ductal carcinoma in situ (DCIS), embryonal tumors, endometrial cancer, ependymoma, esophageal cancer, esthesioneuroblastoma, extracranial germ cell tumor, extragonadal germ cell tumor, extrahepatic bile duct cancer, eye cancer (e.g., intraocular melanoma, retinoblastoma), fibrous histiocytoma of bone, malignant, and osteosarcoma, gallbladder cancer, gastric (stomach) cancer, gastrointestinal carcinoid tumor, gastrointestinal stromal tumors (GIST), germ cell tumors (e.g., ovarian cancer, testicular cancer, extracranial cancers, extragonadal cancers, central nervous system), gestational trophoblastic tumor, brain stem cancer, hairy cell leukemia, head and neck cancer, heart cancer, hepatocellular (liver) cancer, histiocytosis, langerhans cell cancer, Hodgkin lymphoma, hypopharyngeal cancer, intraocular melanoma, islet cell tumors, pancreatic neuroendocrine tumors, kaposi sarcoma, kidney cancer (e.g., renal cell, Wilm's tumor, and other kidney tumors), langerhans cell histiocytosis, laryngeal cancer, leukemia, acute lymphoblastic (ALL), acute myeloid (AML), chronic lymphocytic (CLL), chronic myelogenous (CML), hairy cell, lip and oral cavity cancer, liver cancer (primary), lobular carcinoma in situ (LCIS), lung cancer (e.g., childhood, non-small cell, small cell), lymphoma (e.g., AIDS-related, Burkitt (e.g., non-Hodgkin lymphoma), cutaneous T-Cell (e.g., mycosis fungoides, Sezary syndrome), Hodgkin, non-Hodgkin, primary central nervous system (CNS)), macroglobulinemia, Waldenström, male breast cancer, malignant fibrous histiocytoma of bone and osteosarcoma, melanoma (e.g., childhood, intraocular (eye)), merkel cell carcinoma, mesothelioma, metastatic squamous neck cancer, midline tract carcinoma, mouth cancer, multiple endocrine neoplasia syndromes, multiple myeloma/plasma cell neoplasm, mycosis fungoides, myelodysplastic syndromes, Myelogenous Leukemia, Chronic (CML), multiple myeloma, nasal cavity and paranasal sinus cancer, nasopharyngeal cancer, neuroblastoma, oral cavity cancer, lip and oropharyngeal cancer, osteosarcoma, ovarian cancer, pancreatic cancer, pancreatic neuroendocrine tumors (islet cell tumors), papillomatosis, paraganglioma, paranasal sinus and nasal cavity cancer, parathyroid cancer, penile cancer, pharyngeal cancer, pheochromocytoma, pituitary tumor, plasma cell neoplasm, pleuropulmonary blastoma, primary central nervous system (CNS) lymphoma, prostate cancer, rectal cancer, renal cell (kidney) cancer, renal pelvis and ureter, transitional cell cancer, rhabdomyosarcoma, salivary gland cancer, sarcoma (e.g., Ewing, Kaposi, osteosarcoma, rhadomyosarcoma, soft tissue, uterine), Sezary syndrome, skin cancer (e.g., melanoma, merkel cell carcinoma, basal cell carcinoma, non-melanoma), small intestine cancer, squamous cell carcinoma, squamous neck cancer with occult primary, stomach (gastric) cancer, testicular cancer, throat cancer, thymoma and thymic carcinoma, thyroid cancer, trophoblastic tumor, ureter and renal pelvis cancer, urethral cancer, uterine cancer, endometrial cancer, uterine sarcoma, vaginal cancer, vulvar cancer, Waldenström macroglobulinemia, and Wilm's tumor.

Embodiment 118

The method according to any one of embodiments 109-117, wherein said silicasome is not conjugated to an iRGD peptide and the silicasome is administered in conjunction with an iRGD peptide.

Embodiment 119

The method according to any one of embodiments 109-118, wherein said subject is a human.

Embodiment 120

The method according to any one of embodiments 109-118, wherein said subject is a non-human mammal.

Embodiment 121

A kit comprising a container containing: a population of silicasomes according to any one of embodiments 100-104; and/or a pharmaceutical formulation according to any one of embodiments 105-108.

Embodiment 122

The kit of embodiment 121, wherein silicasomes comprising said population of silicasomes and/or silicasomes comprising said pharmaceutical formulation contain a drug.

Embodiment 123

The kit of according to any one of embodiments 121-122, wherein said kit further comprises instructional materials teaching the use of said population of silicasomes or said pharmaceutical formulation for administration of a drug to a subject.

Definitions

The terms "subject," "individual," and "patient" may be used interchangeably and refer to humans, as well as non-human mammals (e.g., non-human primates, canines, equines, felines, porcines, bovines, ungulates, lagomorphs, and the like). In various embodiments, the subject can be a human (e.g., adult male, adult female, adolescent male, adolescent female, male child, female child) under the care of a physician or other health worker in a hospital, as an outpatient, or other clinical context. In certain embodiments, the subject may not be under the care or prescription of a physician or other health worker.

As used herein, the phrase "a subject in need thereof" refers to a subject, as described infra, that suffers from, or is at risk for a pathology to which the nanoparticle drug carriers described herein (silicasomes) are directed. Thus, for example, in certain embodiments the subject is a subject with a cancer (e.g., pancreatic ductal adenocarcinoma (PDAC), breast cancer (e.g., drug-resistant or triple negative breast cancer), colon cancer, brain cancer, and the like). In certain embodiments the subject is a subject with a microbial infection including, but not limited to drug-resistant microbial infections.

The term "treat" when used with reference to treating, e.g., a pathology or disease refers to the mitigation and/or elimination of one or more symptoms of that pathology or disease, and/or a delay in the progression and/or a reduction in the rate of onset or severity of one or more symptoms of that pathology or disease, and/or the prevention of that pathology or disease. The term treat can refer to prophylactic treatment which includes a delay in the onset or the prevention of the onset of a pathology or disease.

The terms "coadministration" or "administration in conjunction with" or "cotreatment" when used in reference to the coadministration of a first compound (e.g., a silicasome containing irinotecan) and a second compound (e.g., an iRGD peptide) indicates that the first compound and the second compound are administered so that there is at least some chronological overlap in the biological activity of first compound and the second compound in the organism to which they are administered. Coadministration can include simultaneous administration or sequential administration. In sequential administration there may even be some substantial delay (e.g., minutes or even hours) between administration of the first compound and the second compound as long as their biological activities overlap. In certain embodiments the coadminstration is over a time frame that permits the first compound and second compound to produce an enhanced therapeutic or prophylactic effect on the organism. In certain embodiments the enhanced effect is a synergistic effect.

The terms "nanocarrier" and "nanoparticle drug carrier" and "silicasome" are used interchangeably and refer to a nanostructure having a porous particle core, which is interchangeable with the term "porous nanoparticle" as used herein, and a lipid bilayer encasing (or surrounding or enveloping) the porous particle core. In certain embodiments the silica nanoparticle is a porous silica nanoparticle (e.g., mesoporous silica nanoparticle (MSNP)). Typically, the lipid bilayer fully encapsulates the MSNP.

As used herein, the term "lipid" refers to conventional lipids, phospholipids, cholesterol, chemically functionalized lipids for attachment of PEG and ligands, etc.

As used herein, the terms "lipid bilayer" or "LB" refers to any double layer of oriented amphipathic lipid molecules in which the hydrocarbon tails face inward to form a continuous non-polar phase.

As used herein, the term "liposome" refers to an aqueous compartment enclosed by a lipid bilayer, as being conventionally defined (see, e.g., Stryer (1981) *Biochemistry*, 2d Edition, W. H. Freeman & Co., p. 213).

Compared with the lipid bilayer defined in a silicasome, the lipid bilayer in a liposome can be referred to as an "unsupported lipid bilayer" and the liposome itself (when unloaded) can be referred to as an "empty liposome". The lipid bilayer in a silicasome can be referred to as a "supported lipid bilayer" because the lipid bilayer in a silicasome is located on the surface and supported by a porous particle core. In certain embodiments, the lipid bilayer can have a thickness ranging from about 5 nm to about 7 nm which includes a 3-4 nm thickness of the hydrophobic core, plus the hydrated hydrophilic head group layers (each about 0.9 nm) plus two partially hydrated regions of about 0.3 nm each.

As used herein, the term "selective targeting" or "specific binding" refers to use of targeting ligands on the surface of silicasomes (empty or loaded), in particular, on the surface of the lipid bilayer of the silicasomes, wherein the ligands interact specifically/selectively with receptors or other biomolecular components expressed on the target, e.g., a cell surface of interest. The targeting ligands can include such molecules and/or materials as peptides, antibodies, aptamers, targeting peptides, polysaccharides, and the like.

A silicasome having targeting ligands can be referred to as a "targeted silicasome".

The term "silicasome" refers to a drug containing (drug delivery) silica nanoparticle in which the silica nanoparticle is fully covered with a lipid bilayer (e.g., a phospholipid bilayer). In certain embodiments the silica nanoparticle is a porous silica nanoparticle (e.g., mesoporous silica nanoparticle).

The term "about" or "approximately" as used herein refers to being within an acceptable error range for the particular value as determined by one of ordinary skill in the art, which will depend in part on how the value is measured or determined, i.e. the limitations of the measurement system, i.e. the degree of precision required for a particular purpose, such as a pharmaceutical formulation. For example, "about" can mean within 1 or more than 1 standard deviation, per the practice in the art. Alternatively, "about" can mean a range of up to 20%, preferably up to 10%, more preferably up to 5% and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated, the term "about" meaning within an acceptable error range for the particular value should be assumed.

The term "drug" as used herein refers to a chemical entity of varying molecular size, small and large, naturally occurring or synthetic, that exhibits a therapeutic effect in animals and humans. A drug may include, but is not limited to, an organic molecule (e.g., a small organic molecule), a therapeutic protein, peptide, antigen, or other biomolecule, an oligonucleotide, an siRNA, a construct encoding CRISPR Cas9 components and, optionally one or more guide RNAs, and the like.

A "pharmaceutically acceptable carrier" as used herein is defined as any of the standard pharmaceutically acceptable carriers. The pharmaceutical compositions of the subject invention can be formulated according to known methods for preparing pharmaceutically useful compositions. The pharmaceutically acceptable carrier can include diluents, adjuvants, and vehicles, as well as carriers, and inert, non-toxic solid or liquid fillers, diluents, or encapsulating material that does not react with the active ingredients of the invention. Examples include, but are not limited to, phosphate buffered saline, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. Formulations are described in a number of sources that are well known and readily available to those skilled in the art. For example, Remington's Pharmaceutical Sciences (Martin E W Easton Pa., Mack Publishing Company, 19th ed.) describes formulations which can be used in connection with the silicasomes described herein.

As used herein, an "antibody" refers to a protein consisting of one or more polypeptides substantially encoded by immunoglobulin genes or fragments of immunoglobulin genes or derived therefrom that is capable of binding (e.g., specifically binding) to a target (e.g., to a target polypeptide). The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist as intact immunoglobulins or as a number of well characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region thereby converting the (Fab')$_2$ dimer into a Fab' monomer. The Fab' monomer is essentially a Fab with part of the hinge region (see, *Fundamental Immunology*, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Certain preferred antibodies include single chain antibodies (antibodies that exist as a single polypeptide chain), more preferably single chain Fv antibodies (sFv or scFv) in which a variable heavy and a variable light chain are joined together (directly or through a peptide linker) to form a continuous polypeptide. The single chain Fv antibody is a covalently linked $V_H$-$V_L$ heterodimer which may be expressed from a nucleic acid including $V_H$- and $V_L$-encoding sequences either joined directly or joined by a peptide-encoding linker. Huston, et al. (1988) *Proc. Nat. Acad. Sci. USA*, 85: 5879-5883. While the $V_H$ and $V_L$ are connected to each as a single polypeptide chain, the $V_H$ and $V_L$ domains associate non-covalently. The first functional antibody molecules to be expressed on the surface of filamentous phage were single-chain Fv's (scFv), however, alternative expression strategies have also been successful. For example, Fab molecules can be displayed on a phage if one of the chains (heavy or light) is fused to g3 capsid protein and the complementary chain exported to the periplasm as a soluble molecule. The two chains can be encoded on the same or on different replicons; the important point is that the two antibody chains in each Fab molecule assemble post-translationally and the dimer is incorporated into the phage particle via linkage of one of the chains to, e.g., g3p (see, e.g., U.S. Pat. No. 5,733,743). The scFv antibodies and a number of other structures converting the naturally aggregated, but chemically separated light and heavy polypeptide chains from an antibody V region into a molecule that folds into a three-dimensional structure substantially similar to the structure of an antigen-binding site are known to those of skill in the art (see e.g., U.S. Pat. Nos. 5,091,513, 5,132,405, and 4,956,778). In certain embodiments antibodies should include all that have been displayed on phage (e.g., scFv, Fv, Fab and disulfide linked Fv (see, e.g, Reiter et al. (1995) *Protein Eng.* 8: 1323-1331) as well as affibodies, unibodies, and the like.

The term "specifically binds", as used herein, when referring to a biomolecule (e.g., protein, nucleic acid, antibody, etc.), refers to a binding reaction that is determinative of the presence of a biomolecule in heterogeneous population of molecules (e.g., proteins and other biologics). Thus, under designated conditions (e.g. immunoassay conditions in the case of an antibody or stringent hybridization conditions in the case of a nucleic acid), the specified ligand or antibody binds to its particular "target" molecule and does not bind in a significant amount to other molecules present in the sample.

The term "substantially pure isomer" refers to a formulation or composition wherein among various isomers of a compound a single isomer is present at 70%, or greater or at 80% or greater, or at 90% or greater, or at 95% or greater, or at 98% or greater, or at 99% or greater, or said compound or composition comprises only a single isomer of the compound The terms "pharmaceutical grade" or "suitable for use in pharmaceuticals", or "suitable for use in the manufacture of pharmaceuticals" when used in reference to a population (e.g., a plurality) of nanoparticles (e.g., mesoporous silica nanoparticles (MSNPs)) indicates that the population of particles possesses sufficient homogeneity with respect to physical, chemical, and biological properties that it can be utilized in the manufacture of a therapeutic. With respect to nanoparticle delivery systems, illustrative parameters for a population of nanoparticles (e.g., MSNPs and/or silicasomes) include, but need not be limited to a monodisperse size population preferably with a coefficient of variation (sd/mean) of about 0.1 or less, or about 0.08 or less, or about 0.05 or less, and/or a polydispersity index (PDI) less than about 0.3, or less than about 0.2, or less than about 0.1, a loading capacity of 5% or greater w/w (drug/MSNP), or 10%, or greater, or 15%, or greater, or 20% or greater, or about 30% or greater, or about 40% or greater w/w (drug/MSNP), 20% or less pre-mature release in pure human serum or plasma when incubated at 24° C. for 24 hours, endotoxin free, bacteria free and comprises biocompatible materials. In certain embodiments the MSNPs comprises an optimal pore size of about 2 nm up to about 5 nm, or from about 2 nm up to about 3 nm.

The terms "large-scale preparation" and "large-scale synthesis" are used interchangeably and refer to the preparation of large quantities of MSNPs and/or silicasomes such as about greater than 20 g, or about 30 g or greater, or about 40 g or greater, or about 50 g or greater, or about 60 g or greater, or about 80 g or greater, or about 100 g or greater, or about 200 g or greater, or about 300 g or greater, or about 400 g or greater, or about 500 g or greater, or about 600 g or greater, or about 700 g or greater, or about 800 g or greater, or about 900 g or greater, or about 1 kg or greater, or about 2 kg or greater, or about 3 kg or greater, or about 4 kg or greater, or about 5 kg or greater in a single batch.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
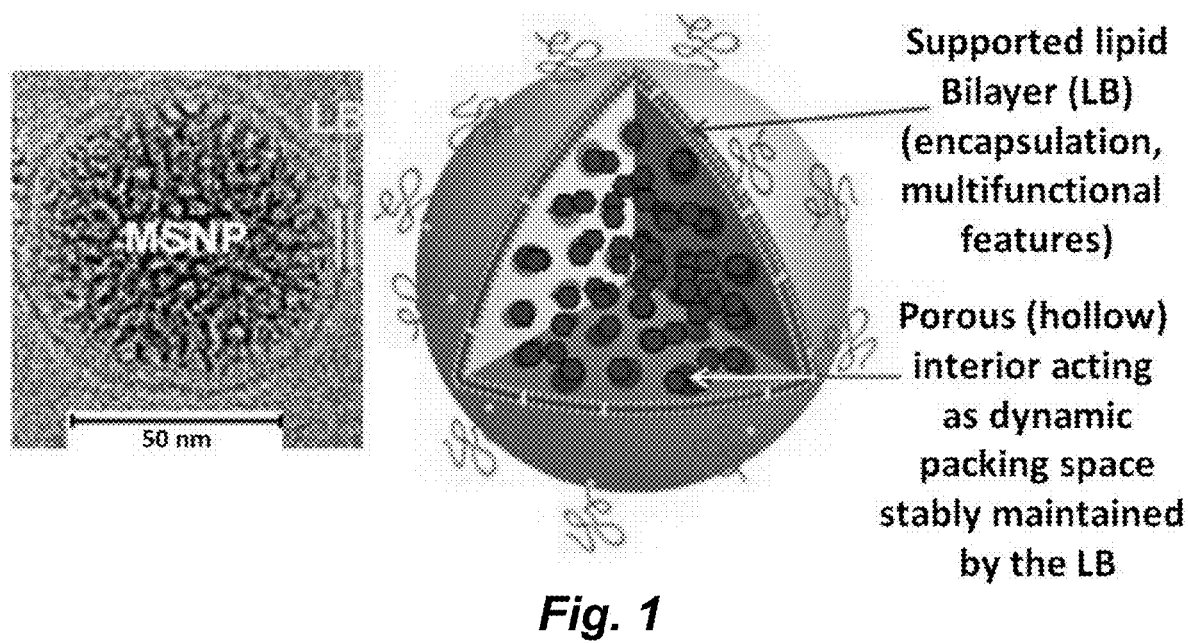
FIG. 1 illustrates the structure of one embodiment of a silicasome. Silicasomes provide dramatically improved stability, drug loading capacity, efficacy and toxicity-reduction options for cancer therapy compared to the classic liposomal formulation, introducing a new generation of lipid bilayer encapsulated nanocarriers as a treatment platform for pancreatic and other forms of cancer. cyroEM picture shows a ~80 nm silicasome.

In order to facilitate the FDA approval and commercialization of silicasome technology, one of the key tasks becomes the scale up synthesis of pharmaceutical grade silicasome that is suitable for, inter alia, a late stage clinical trial and/or commercial production. Previously we have made 500 mg/batches of irinotecan silicasomes for research purposes using a laboratory protocol, e.g., as described in PCT Pub. No: PCT/US2017/012625 (WO 2017/120537)). While it is possible to synthesize a ~20 g batch of the silicasomes (enough for Phase 1 study that involves 10-15 human subjects) by linear scale up of the processes based on the 500 mg/batch protocol (Id.), this approach is not be suitable for a Phase 2 or 3 trial that may require 100 g to Kg quantities. Problems incurred in scaling the laboratory protocol include, inter alia, impractical high reaction volumes, difficulty controlling particle quality (e.g., size, porosity, size distribution, zeta potential, etc.), purification difficulties, and cost concerns.

In order to fulfill the task of Kg batch synthesis, we needed to first establish the scale-up synthesis, initial process development and physicochemical characterization of large batch silicasome (e.g., irinotecan-silicasome) production under non-GMP conditions to facilitate subsequent GMP manufacturing. Having established scaled up synthesis protocols GMP manufacturing of the drug product can readily proceed, including drug substance manufacturing, drug substance characterization, drug product manufacturing, drug product characterization, stability testing, documentation, certification and label design in the GFP facility.

As explained below, synthesis protocols for the large-scale synthesis (e.g., 30 g or greater/batch) of MSNPs and silicasomes are provided herein. The methods are not simply a linear scale-up of laboratory methods, but rather required tuning of a large number of parameters where the effect of each parameter on the resulting product could not be predicted absent the relevant experimentation. Moreover, as explained below, the various parameters interact with each other in a non-linear, non-additive manner that again required actual preparation of the MSNPs and/or silicasomes to evaluate the effects of various changes in protocol.

These MSNPs, which structurally resemble a hollow glass bubble, have a huge interior packaging space for loading drugs against the walls of the pores. This leads to a substantial increase in loading capacity and stable retention until the nanoparticles enter the tumor site to deliver their payload.

There can be a lipid bilayer (LB) coating disposed on these nanoparticles and forming a supported LB, that facilitates stable drug encapsulation by the LB coating that resembles a cell membrane. The LB-coated MSNPs have been named "silicasomes" to distinguish them from liposomes, which comprise (a non-supported) LB that encapsulates a fluid space and its content (drug).

A key finding we achieved is the demonstration of the versatility of this platform that allows us to individually deliver drugs (e.g., cancer drugs), or to co-deliver multiple drugs (e.g., cancer drugs). Four distinct methods have been established to load nanoparticles, depending on the drug (and particles) chemical structure. These include: 1) encapsulation of a drug (e.g., a hydrophilic drug or a hydrophobic drug) into porous space in the carrier; 2) incorporation of a hydrophobic drug into the lipid bilayer (LB) of the liposome or silicasome; 3) ratiometric incorporation and co-delivery of hydrophobic (in the LB of the silicasome) and hydrophilic drug (in the pores of the silicasome); and 4) remote loading of weak base drug (e.g., cancer drugs).

As one example of a silicasome using method #4, we constructed a nanocarrier that provides high irinotecan loading by a remote loading technique. This begins by encapsulating a protonating agent in MSNP pores, which subsequently allows the irinotecan to be imported across the LB by a proton gradient that converts the drug to a compound that is incapable of escaping from the pores. When comparing the performance of the irinotecan-silicasome against a liposomal equivalent of the FDA-approved irinotecan carrier, ONIVYDE®, we observed increased drug delivery and a ~3× increase in efficacy in a rigorous KPC-derived orthotopic model (see, e.g., PCT Pub. No: PCT/US2017/012625 (WO 2017/120537)). We have also demonstrated increased stability of the silicasome over the liposome, leading to less irinotecan leakage and a major reduction in GIT, bone marrow and the liver toxicity compared to the ONIVYDE® equivalent (Id.). Because ONIVYDE® received a black box warning as a result of severe toxicity at certain target sites in humans, it is reserved as a $2^{nd}$ line treatment.

Unlike ONIVYDE®, it is believed that the irinotecan silicasomes described herein can be used as a first-line treatment for, inter alia, pancreatic cancer (Id.). However, there is a need for an effective large-scale synthesis of such MSNPs. Accordingly, described herein are methods for scaled up synthesis of MSNPs. Scale Up Synthesis of Mesoporous Silica Nanoparticle Cores (MSNPs)

Figure 2:
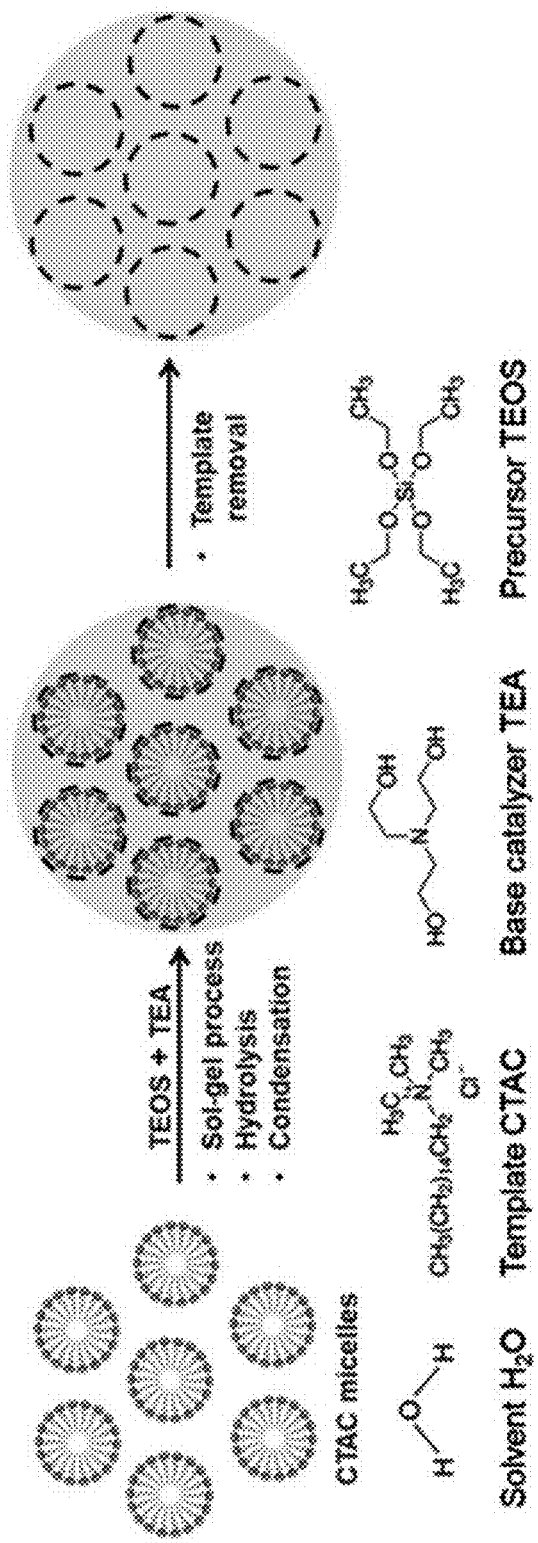
FIG. 2 illustrates the sol/gel synthesis of MSNP cores. Figure. Upper panel: Schematic to show the steps of MSNP synthesis through a sol-gel synthesis process. Lower panel: Summary of the major parameters required to be controlled for changing the production volume of the sol-gel procedure.

MSNP cores can be synthesized using a laboratory protocol described, inter alia, by Liu et al. (2016) ACS Nano, 10(2): 2702-2715. Generally, MSNP cores were synthesized by a sol/gel procedure (see, e.g., FIG. 2). Using this laboratory procedure, to synthesize a batch ~500 mg MSNP, 50 mL of CTAC (cetyltrimethylammonium chloride) was mixed with 150 mL of $H_2O$ in a 500 mL conical flask, followed by stirring at 350 rpm for 15 min at 85° C. This was followed by the addition of 8 mL of 10% triethanolamine (TEA) for 30 min at the same temperature. Then, 7.5 mL of the silica precursor, tetraethyl orthosilicate (TEOS), was added dropwise at a rate of 1 mL/min using a peristaltic pump. The solution was stirred at 350 rpm at 85° C. for 20 min, leading to the formation particles with a primary size of ~65 nm. The surfactant was removed by washing the particles with a mixture of methanol/HCl (500:19 v/v) at room temperature for 24 h. The particles were centrifuged at 10,000 rpm for 60 min and washed three times in methanol.

While, as described above, in various embodiments, the surfactant CTAC was used, in certain other embodiments any of a number of surfactants including, but not limited to anionic surfactants or cationic surfactants can be used. Illustrative, but non-limiting examples of anionic surfactants include a dodecylsulfate salt (e.g., sodium dodecylsulfate or lithium dodecylsulfate (SDS)), and illustrative, but non-limiting examples of cationic surfactants include, but are not limited to, a tetradecyl-trimethyl-ammonium salt (e.g., tetradecyl-trimethyl-ammonium bromide (C14TAB; CTAB) or tetradecyl-trimethyl-ammonium chloride (CTAC), a hexadecyltrimethylammonium salt (e.g., hexadecyltrimethylammonium bromide (C16; CTAB)), an octadecyltrimethylammonium salt (e.g., octadecylt rimethylammonium bromide (C18; OTAB)), a dodecylethyldimethylammonium salt (e.g., dodecylethyldimethylammonium bromide), a cetylpyridinium salt (e.g., cetylpyridinium chloride (CPC)), polyethoxylated tallow amine (POEA), hexadecyl trimethylammonium p-toluenesulfonate, a benzalkonium salt (e.g., benzalkonium chloride (BAC)), or a benzethonium salt (e.g., benzethonium chloride (BZT)) and mixtures thereof. In certain embodiments the use of cationic surfactants (e.g., CTAC) is preferred.

Based on the small batch protocol, we identified the major parameters that can impact the yield and characteristics of MSNPs (see, e.g., Table 1).'

TABLE 1

Major parameters that impact the yield and characteristics of MSNPs.

| Parameters | Roles |
| --- | --- |
| Precursor TEOS | Introducing Si source |
| Organic base TEA | Catalyzer to facilitate the reaction |
| Templating agent (CTAC) | Leads to the formation of porous structure |
| Stirring speed | Determine reaction rate and particle uniformity |
| Reaction time | Determine particle size and yield |
| Temperature | Determine rate of reaction |

In order to determine the impact of each of these parameters when scaling up MSNP synthesis to large batches, which was not a priori evident, we systemically varied the amount of silica precursor TEOS, the amount of organic base catalyzer TEA, the templating agent CTAC, stirring speed and reaction time. For convenience, the temperature was initially fixed to 85° C. (FIG. 3, panels A-E).

Figure 3:
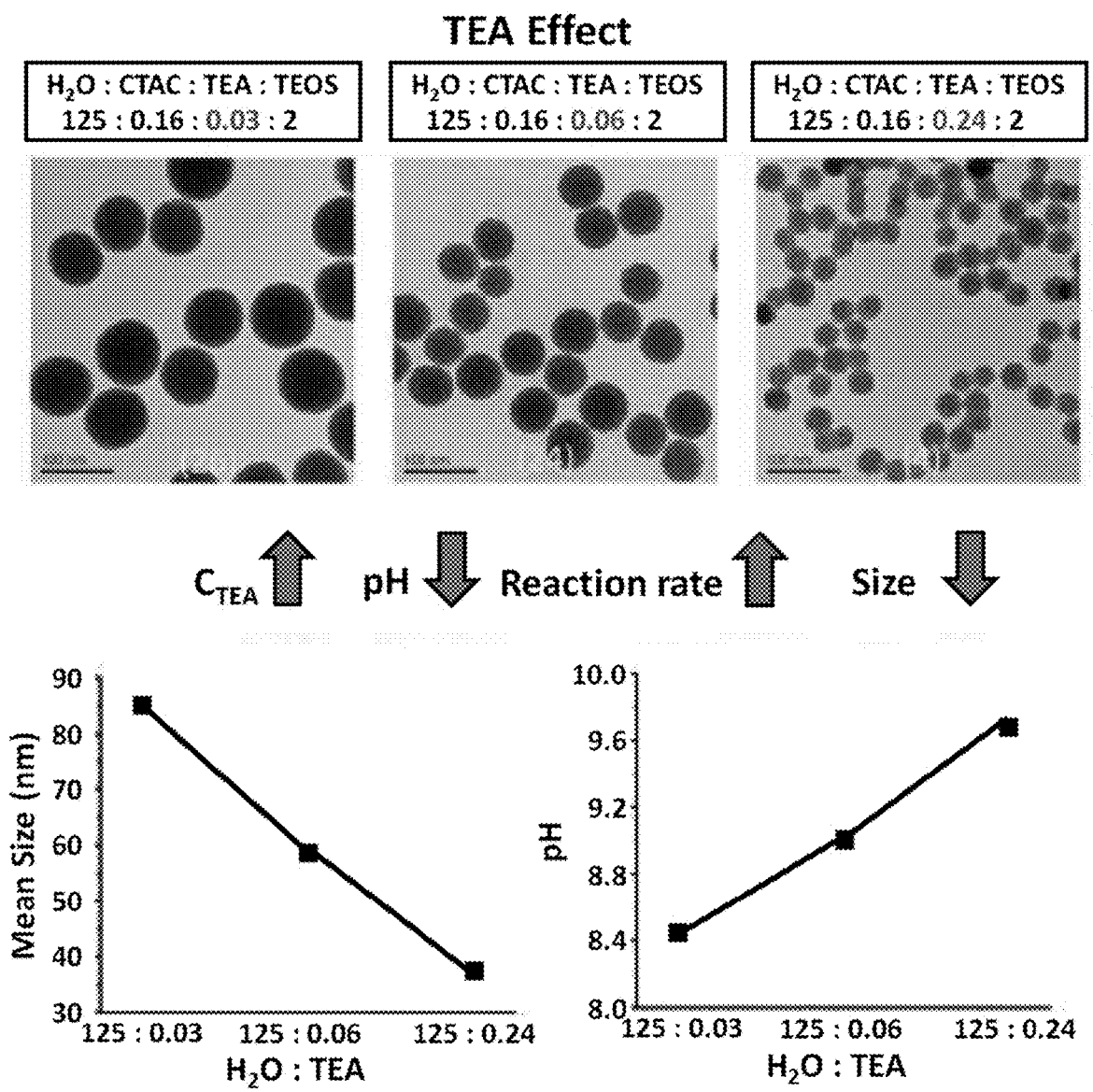
FIG. 3, panels A-F, illustrates scale up MSNP synthesis by systemically varying amount of silica precursor TEOS, amount of organic base catalyzer TEA, templating agent CTAC, stirring speed and reaction time. Panel A) TEA, serving as a catalyzer, speeds up the reaction rate. Due to the rapid nucleation process, the primary MSNP size decreased when TEA concentration was increased. Panel B) Increased stirring speed from 250 rpm to 800 rpm significantly decreased the particle primary size. Panel C) While CTAC concentration did not alter the particle pore size as long as it was greater than CMC concentration, we showed that high CTAC concentration reduced the reaction rate via a pH mediated mechanism. This is because CTAC is a strong acid-weak base salt (functionally similar to acid). It is also possible that the formation of micelles may encapsulate basic TEA in the solution, leading to lowered pH. Panel D) TEOS effect. While the yield of MSNP concentration per mL can be elevated using higher TEOS concentration, it was important to monitor particle porosity because the high TEOS content may increase the MSNP wall thickness. Panel E) Reaction time effect. At early time points, the larger particles were formed when we increased the reaction time. However, at certain time point, i.e. 1.5 hr in the demonstrated case, the particle size increase reached plateau. Panel F) Reaction temperature effect. Decreased reaction temperature from 85° C. to 25° C. significantly decreased the particle primary size. Understanding the quantitative role of these parameters allowed us to find the optimal condition to make large batches.

As shown in FIG. 3 TEA acts as a catalyzer and speeds up the reaction rate. Due to the rapid nucleation process, the primary MSNP size decreased when TEA concentration was increased (FIG. 3, panel A). Importantly, increased stirring speed from 250 rpm to 800 rpm significantly decreased the particle primary size (FIG. 3, panel B), while CTAC concentration did not alter the particle pore size as long as it was greater than CMC concentration (FIG. 3, panel C). Without being bound to a particular theory, high CTAC concentration reduced the reaction rate (presumably by a pH mediated mechanism) and therefor countered the one effect of the TEA catalyzer. While the yield of MSNP concentration per mL could be elevated using higher TEOS concentration, it was difficult to monitor particle porosity because the high TEOS content appeared to increase the MSNP wall thickness (FIG. 3, panel D). It was also discovered that at early time points, larger particles were formed when the reaction time was increased (FIG. 3, panel E). However, at a certain time point, i.e. 1.5 hr in the demonstrated case, the particle size increase reached a plateau. In a study of reaction temperature effect, it was observed that decreased reaction temperature from 85° C. to 25° C. significantly decreased the particle primary size (see, e.g., FIG. 3, panel E). Understanding the quantitative role of these parameters allowed us to find the desired condition to make large batches.

Figure 4:
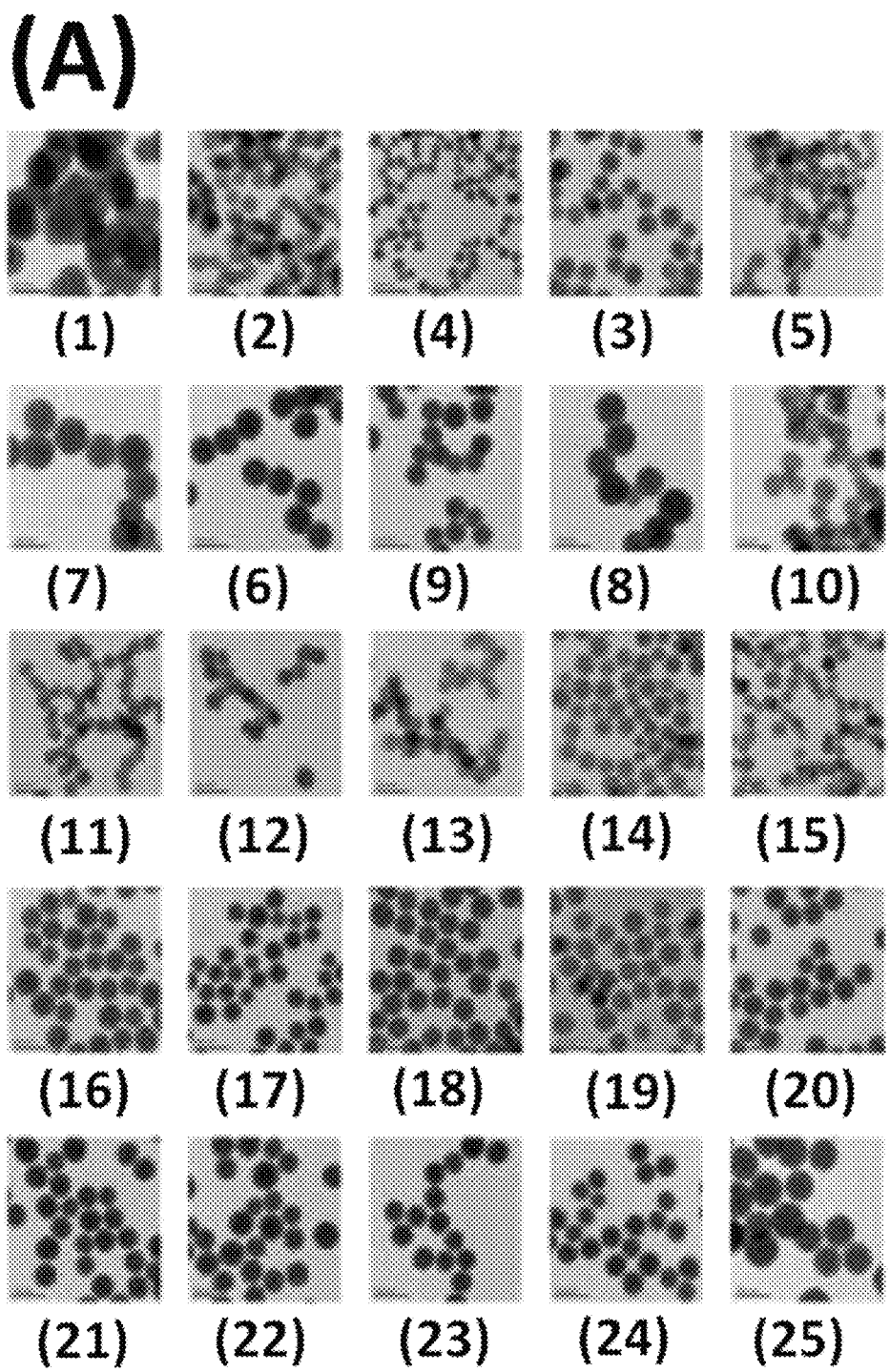
FIG. 4, panels A-E, illustrates determination of an optimal conditions for MSNP scale up. The establishment of the best MSNP scale up condition was not a priori obvious as the effects of the various parameters could not be predicted, and the parameters interacted with each other. Determination of desirable conditions for large-scale synthesis required the full elucidation of the sol-gel reaction, followed by fine-tuning and iterative condition testing. Panel A) TEM visualization of 48 batches of MSNP that we synthesized. Panel B) shows identified conditional #49 as one of the optimal scale up conditions in a 3 L system. Panel C) TEM visualization of batch #49 MSNP. Panel D) shows #71, which is another optimal scale up condition in a 18 L reaction system. Panel E) TEM visualization of batch #71 MSNP. While the synthetic condition may require minor modification in different equipment/facility, these representative optimal parameters exhibit the ballpark conditions for the large scale bare MSNP synthesis with desired size and porosity, which are suitable for silicasome manufacture.

To date, we have evaluated more than 70 synthesis protocols to integrate the parameters described above into synthesis protocols that provide therapeutically useful MSNPs, particularly at large batch size (see, e.g., FIG. 4, panel A). The establishment of the best MSNP scale up condition was not a priori obvious as the effects of the various parameters could not be predicted, without a multi-parameter design process that takes into consideration the interdependence of the parameters. Determination of desirable conditions for large-scale synthesis required the full elucidation of the sol-gel reaction, followed by fine-tuning and iterative condition testing. FIG. 4, panel A) shows a TEM visualization of 48 batches of MSNP that were synthesized. The synthesis conditions depicted in batch 49 (see, e.g., FIG. 4, panels B, C) provided an integrated set of synthesis parameters that permit effective scale-up synthesis of therapeutic MSNPs. The synthesis conditions shown in batch 71 (see, e.g., FIG. 4, panels D, and E) provided other representative optimal conditions in a 20 L reaction system. It is believed these parameters (with some variation) are effective for large scale synthesis of a substantially homogenous population of MSNPs having the desired size and porosity.

Accordingly, in certain embodiments, methods for the large-scale (e.g., about 20 g, or greater, or about 30 g or greater, or about 40 g or greater, or about 50 g or greater, or about 60 g or greater, or about 80 g or greater, or about 1 kg or greater in a single batch) preparation of mesoporous silica nanoparticles suitable use in pharmaceuticals are provided where the methods involve providing cetyltrimethylammonium chloride (CTAC) in water at a concentration greater than the CTAC critical micellar concentration (CMC) to form a mixture comprising CTAC micelles; adding to the mixture triethanolamine (TEA); adding to the mixture tetraethylorthosilicate (TEOS) where the molar ratio of $H_2O$:CTAC:TEA:TEOS ranges from about 100 to about 150 water:about 0.06 to about 0.10 CTAC:about 0.04 to about 0.08 TEA:about 0.8 to about 1.2 TEOS; and stirring (or agitating) the mixture to allow the CTAC micelles, TEA, and TEOS to react to form a population of mesoporous silica nanoparticles (MSNPs). In certain embodiments the method produces at least 20 g or greater, or 40 g or greater, or 50 g or greater, or 60 g or greater, or 80 g or greater, or 1 kg or greater MSNPs in a single batch. In certain embodiments the ratio of $H_2O$:CTAC:TEA:TEOS molar ratio is about 125:0.08:0.06:1 and, in certain embodiments, ranges from about 100 to about 150 water:about 0.06 to about 0.10 CTAC:about 0.04 to about 0.08 TEA:about 0.8 to about 1.2 TEOS. In certain embodiments the method comprises combining about 3,000 mL water, about 36.3 g CTAC, about 12 g TEA and about 280 g TEOS.

In some embodiments, the molar ratio of $H_2O$ (water):CTAC:TEA:TEOS is about 100 to about 110 water, about 110 to about 120 water, about 120 to about 130 water, about 130 to about 140 water, about 140 to about 150 water, about 100 to about 120 water, about 110 to about 130 water, about 120 to about 140 water, or about 130 to about 150 water:about 0.06 to about 0.07 CTAC, about 0.07 to about 0.08 CTAC, about 0.08 to about 0.09 CTAC, about 0.09 to about 0.10 CTAC, about 0.06 to about 0.08 CTAC, about 0.07 to about 0.09 CTAC, or about 0.08 to about 0.10 CTAC:about 0.04 to about 0.05 TEA, about 0.05 to about 0.06 TEA, about 0.06 to about 0.07 TEA, about 0.07 to about 0.08 TEA, about 0.04 to about 0.06 TEA, about 0.05 to about 0.07 TEA, or about 0.06 to about 0.08 TEA:about 0.8 to about 0.9 TEOS, about 0.9 to about 1.0 TEOS, about 1.0 to about 1.1 TEOS, about 1.1 to about 1.2 TEOS, about 0.8 to about 1.0 TEOS, about 0.9 to about 1.1 TEOS, or about 1.0 to about 1.2 TEOS. In addition to CTAC, these molar ratios are also contemplated for other surfactants described herein such as, for example, C14TAB, CTAB, OTAB, CPC, POEA, BAC, BZT, other suitable surfactants, and mixtures thereof.

In certain embodiments the method is performed at a temperature ranging from about 75° C. to about 90° C. (e.g., at about 85° C.). In some embodiments, the method is performed at a reaction temperature of about 70° C. to about 95° C. In some embodiments, the method is performed at a reaction temperature of about 70° C. to about 75° C., about 70° C. to about 80° C., about 70° C. to about 85° C., about 70° C. to about 90° C., about 70° C. to about 95° C., about 75° C. to about 80° C., about 75° C. to about 85° C., about 75° C. to about 90° C., about 75° C. to about 95° C., about 80° C. to about 85° C., about 80° C. to about 90° C., about 80° C. to about 95° C., about 85° C. to about 90° C., about 85° C. to about 95° C., or about 90° C. to about 95° C. In some embodiments, the method is performed at a reaction temperature of about 70° C., about 75° C., about 80° C., about 85° C., about 90° C., or about 95° C. In some embodiments, the method is performed at a reaction temperature of at least about 70° C., about 75° C., about 80° C., about 85° C., or about 90° C. In some embodiments, the method is performed at a reaction temperature of at most about 75° C., about 80° C., about 85° C., about 90° C., or about 95° C. In some embodiments, the method is performed at a reaction volume of about 1 L to about 50 L. In some embodiments, the method is performed at a reaction volume of about 1 L to about 5 L, about 1 L to about 10 L, about 1 L to about 15 L, about 1 L to about 18 L, about 1 L to about 20 L, about 1 L to about 25 L, about 1 L to about 30 L, about 1 L to about 40 L, about 1 L to about 50 L, about 5 L to about 10 L, about 5 L to about 15 L, about 5 L to about 18 L, about 5 L to about 20 L, about 5 L to about 25 L, about 5 L to about 30 L, about 5 L to about 40 L, about 5 L to about 50 L, about 10 L to about 15 L, about 10 L to about 18 L, about 10 L to about 20 L, about 10 L to about 25 L, about 10 L to about 30 L, about 10 L to about 40 L, about 10 L to about 50 L, about 15 L to about 18 L, about 15 L to about 20 L, about 15 L to about 25 L, about 15 L to about 30 L, about 15 L to about 40 L, about 15 L to about 50 L, about 18 L to about 20 L, about 18 L to about 25 L, about 18 L to about 30 L, about 18 L to about 40 L, about 18 L to about 50 L, about 20 L to about 25 L, about 20 L to about 30 L, about 20 L to about 40 L, about 20 L to about 50 L, about 25 L to about 30 L, about 25 L to about 40 L, about 25 L to about 50 L, about 30 L to about 40 L, about 30 L to about 50 L, or about 40 L to about 50 L. In some embodiments, the method is performed at a reaction volume of about 1 L, about 5 L, about 10 L, about 15 L, about 18 L, about 20 L, about 25 L, about 30 L, about 40 L, or about 50 L. In some embodiments, the method is performed at a reaction volume of at least about 1 L, about 5 L, about 10 L, about 15 L, about 18 L, about 20 L, about 25 L, about 30 L, or about 40 L. In some embodiments, the method is performed at a reaction volume of at most about 5 L, about 10 L, about 15 L, about 18 L, about 20 L, about 25 L, about 30 L, about 40 L, or about 50 L.

In certain embodiments, e.g., to make about 60 g to about 70 g bare MSNP, the molar ratio of $H_2O$:CTAC:TEA:TEOS is about 125:0.08:0.06:1 and the temperature is at about 85° C. for about 2 hrs, in a reaction volume of about 3 L. After reaction, the system can be naturally cooled to room temperature. While CTAC is used in various embodiments, other surfactants are also contemplated such as, for example, C14TAB, CTAB, OTAB, CPC, POEA, BAC, BZT, other suitable surfactants, and mixtures thereof.

In certain embodiments, e.g., to make about 120 g to about 140 g bare MSNP, the molar ratio of $H_2O$:CTAC:TEA:TEOS is about 125:0.08:0.06:0.33, and the temperature is at about 85° C. for about 4 hrs in a reaction volume of about 18 L. After reaction, the system can be naturally cooled to room temperature.

In certain embodiments the stirring or agitating comprises stirring at a speed ranging from about 150 rpm, or from about 200 rpm, or from about 250 rpm up to about 800 rpm, or up to about 600 rpm, or up to about 400 rpm, or up to about 300 rpm. In certain embodiments the stirring or agitating comprises stirring at about 250 rpm. In certain embodiments the reaction proceeds until the hydrodynamic size of the MSNPs is substantially constant and/or where the yield of MSNPs is substantially constant.

In certain embodiments the stirring or agitating comprises stirring at a speed of about 150 rpm to about 800 rpm. In certain embodiments the stirring or agitating comprises stirring at a speed of about 150 rpm to about 200 rpm, about 150 rpm to about 300 rpm, about 150 rpm to about 400 rpm, about 150 rpm to about 500 rpm, about 150 rpm to about 600 rpm, about 150 rpm to about 700 rpm, about 150 rpm to about 800 rpm, about 200 rpm to about 300 rpm, about 200 rpm to about 400 rpm, about 200 rpm to about 500 rpm, about 200 rpm to about 600 rpm, about 200 rpm to about 700 rpm, about 200 rpm to about 800 rpm, about 300 rpm to about 400 rpm, about 300 rpm to about 500 rpm, about 300 rpm to about 600 rpm, about 300 rpm to about 700 rpm, about 300 rpm to about 800 rpm, about 400 rpm to about 500 rpm, about 400 rpm to about 600 rpm, about 400 rpm to about 700 rpm, about 400 rpm to about 800 rpm, about 500 rpm to about 600 rpm, about 500 rpm to about 700 rpm, about 500 rpm to about 800 rpm, about 600 rpm to about 700 rpm, about 600 rpm to about 800 rpm, or about 700 rpm to about 800 rpm. In certain embodiments the stirring or agitating comprises stirring at a speed of about 150 rpm, about 200 rpm, about 300 rpm, about 400 rpm, about 500 rpm, about 600 rpm, about 700 rpm, or about 800 rpm. In certain embodiments the stirring or agitating comprises stirring at a speed of at least about 150 rpm, about 200 rpm, about 300 rpm, about 400 rpm, about 500 rpm, about 600 rpm, or about 700 rpm. In certain embodiments the stirring or agitating comprises stirring at a speed of at most about 200 rpm, about 300 rpm, about 400 rpm, about 500 rpm, about 600 rpm, about 700 rpm, or about 800 rpm.

In certain embodiments the reaction proceeds for a time period of about 1.5 hours, and in certain embodiments, the time period ranges from about 0.5 hr, or from about 1 hour, up to about 5 hours or up to about 4 hours, or up to about 3 hours, or up to about 2 hours. In some embodiments, the reaction proceeds for a time period of about 0.5 hours to about 5 hours. In some embodiments, the reaction proceeds for a time period of about 0.5 hours to about 1 hour, about 0.5 hours to about 1.5 hours, about 0.5 hours to about 2 hours, about 0.5 hours to about 3 hours, about 0.5 hours to about 4 hours, about 0.5 hours to about 5 hours, about 1 hour to about 1.5 hours, about 1 hour to about 2 hours, about 1 hour to about 3 hours, about 1 hour to about 4 hours, about 1 hour to about 5 hours, about 1.5 hours to about 2 hours, about 1.5 hours to about 3 hours, about 1.5 hours to about 4 hours, about 1.5 hours to about 5 hours, about 2 hours to about 3 hours, about 2 hours to about 4 hours, about 2 hours to about 5 hours, about 3 hours to about 4 hours, about 3 hours to about 5 hours, or about 4 hours to about hours. In some embodiments, the reaction proceeds for a time period of about 0.5 hours, about 1 hour, about 1.5 hours, about 2 hours, about 3 hours, about 4 hours, or about 5 hours. In some embodiments, the reaction proceeds for a time period of at least about 0.5 hours, about 1 hour, about 1.5 hours, about 2 hours, about 3 hours, or about 4 hours. In some embodiments, the reaction proceeds for a time period of at most about 1 hour, about 1.5 hours, about 2 hours, about 3 hours, about 4 hours, or about 5 hours.

In certain embodiments the method has a yield of greater than about 80%. In certain embodiments the method produces MSNPs having a substantially monotonic size distribution. In certain embodiments the method produces MSNPs whose size distribution has a coefficient of variation of less than about 0.10. In certain embodiments the method produces MSNPs having an average diameter ranging from about 60 nm up to about 70 nm (e.g., an average diameter of about 65-66 nm). In certain embodiments the method produces MSNPs having an average pore size ranging from about 2.2 to about 2.7 nm, or from about 2.3 to about 2.6 nm, or ranging from about 2.4-2.5 nm. In certain embodiments the synthesis is performed in a reaction vessel or in a microfluidic reactor.

In some embodiments, the method produces MSNPs whose size distribution has a coefficient of variation of about 0.01 to about 0.3. In some embodiments, the method produces MSNPs whose size distribution has a coefficient of variation of about 0.01 to about 0.05, about 0.01 to about 0.1, about 0.01 to about 0.15, about 0.01 to about 0.2, about 0.01 to about 0.25, about 0.01 to about 0.3, about 0.05 to about 0.1, about 0.05 to about 0.15, about 0.05 to about 0.2, about 0.05 to about 0.25, about 0.05 to about 0.3, about 0.1 to about 0.15, about 0.1 to about 0.2, about 0.1 to about 0.25, about 0.1 to about 0.3, about 0.15 to about 0.2, about 0.15 to about 0.25, about 0.15 to about 0.3, about 0.2 to about 0.25, about 0.2 to about 0.3, or about 0.25 to about 0.3. In some embodiments, the method produces MSNPs whose size distribution has a coefficient of variation of about 0.01, about 0.05, about 0.1, about 0.15, about 0.2, about 0.25, or about 0.3. In some embodiments, the method produces MSNPs whose size distribution has a coefficient of variation of at least about 0.01, about 0.05, about 0.1, about 0.15, about 0.2, or about 0.25. In some embodiments, the method produces MSNPs whose size distribution has a coefficient of variation of at most about 0.05, about 0.1, about 0.15, about 0.2, about 0.25, or about 0.3.

In some embodiments, the method produces MSNPs having an average diameter of about 30 nm to about 300 nm.

In some embodiments, the method produces MSNPs having an average diameter of about 30 nm to about 40 nm, about 30 nm to about 50 nm, about nm to about 60 nm, about 30 nm to about 70 nm, about 30 nm to about 80 nm, about 30 nm to about 90 nm, about 30 nm to about 100 nm, about 30 nm to about 150 nm, about 30 nm to about 200 nm, about 30 nm to about 250 nm, about 30 nm to about 300 nm, about 40 nm to about 50 nm, about 40 nm to about 60 nm, about 40 nm to about 70 nm, about 40 nm to about 80 nm, about 40 nm to about 90 nm, about 40 nm to about 100 nm, about 40 nm to about 150 nm, about 40 nm to about 200 nm, about 40 nm to about 250 nm, about 40 nm to about 300 nm, about 50 nm to about 60 nm, about 50 nm to about 70 nm, about 50 nm to about 80 nm, about 50 nm to about 90 nm, about 50 nm to about 100 nm, about 50 nm to about 150 nm, about 50 nm to about 200 nm, about 50 nm to about 250 nm, about 50 nm to about 300 nm, about 60 nm to about 70 nm, about 60 nm to about 80 nm, about 60 nm to about 90 nm, about 60 nm to about 100 nm, about 60 nm to about 150 nm, about 60 nm to about 200 nm, about 60 nm to about 250 nm, about 60 nm to about 300 nm, about 70 nm to about 80 nm, about 70 nm to about 90 nm, about 70 nm to about 100 nm, about 70 nm to about 150 nm, about 70 nm to about 200 nm, about 70 nm to about 250 nm, about 70 nm to about 300 nm, about 80 nm to about 90 nm, about 80 nm to about 100 nm, about 80 nm to about 150 nm, about 80 nm to about 200 nm, about 80 nm to about 250 nm, about 80 nm to about 300 nm, about 90 nm to about 100 nm, about 90 nm to about 150 nm, about 90 nm to about 200 nm, about 90 nm to about 250 nm, about 90 nm to about 300 nm, about 100 nm to about 150 nm, about 100 nm to about 200 nm, about 100 nm to about 250 nm, about 100 nm to about 300 nm, about 150 nm to about 200 nm, about 150 nm to about 250 nm, about 150 nm to about 300 nm, about 200 nm to about 250 nm, about 200 nm to about 300 nm, or about 250 nm to about 300 nm. In some embodiments, the method produces MSNPs having an average diameter of about 30 nm, about nm, about 50 nm, about 60 nm, about 70 nm, about 80 nm, about 90 nm, about 100 nm, about 150 nm, about 200 nm, about 250 nm, or about 300 nm. In some embodiments, the method produces MSNPs having an average diameter of at least about 30 nm, about 40 nm, about 50 nm, about 60 nm, about 70 nm, about 80 nm, about 90 nm, about 100 nm, about 150 nm, about 200 nm, or about 250 nm. In some embodiments, the method produces MSNPs having an average diameter of at most about 40 nm, about 50 nm, about 60 nm, about 70 nm, about 80 nm, about 90 nm, about 100 nm, about 150 nm, about 200 nm, about 250 nm, or about 300 nm.

In some embodiments, the method produces MSNPs having an average pore size of about 2 nm to about 4 nm. In some embodiments, the method produces MSNPs having an average pore size of about 2 nm to about 2.2 nm, about 2 nm to about 2.4 nm, about 2 nm to about 2.6 nm, about 2 nm to about 2.8 nm, about 2 nm to about 3 nm, about 2 nm to about 3.2 nm, about 2 nm to about 3.4 nm, about 2 nm to about 3.6 nm, about 2 nm to about 3.8 nm, about 2 nm to about 4 nm, about 2.2 nm to about 2.4 nm, about 2.2 nm to about 2.6 nm, about 2.2 nm to about 2.8 nm, about 2.2 nm to about 3 nm, about 2.2 nm to about 3.2 nm, about 2.2 nm to about 3.4 nm, about 2.2 nm to about 3.6 nm, about 2.2 nm to about 3.8 nm, about 2.2 nm to about 4 nm, about 2.4 nm to about 2.6 nm, about 2.4 nm to about 2.8 nm, about 2.4 nm to about 3 nm, about 2.4 nm to about 3.2 nm, about 2.4 nm to about 3.4 nm, about 2.4 nm to about 3.6 nm, about 2.4 nm to about 4 nm, about 2.6 nm to about 2.8 nm, about 2.6 nm to about 3 nm, about 2.6 nm to about 3.2 nm, about 2.6 nm to about 3.4 nm, about 2.6 nm to about 3.6 nm, about 2.6 nm to about 3.8 nm, about 2.6 nm to about 4 nm, about 2.8 nm to about 3 nm, about 2.8 nm to about 3.2 nm, about 2.8 nm to about 3.4 nm, about 2.8 nm to about 3.6 nm, about 2.8 nm to about 3.8 nm, about 2.8 nm to about 4 nm, about 3 nm to about 3.2 nm, about 3 nm to about 3.4 nm, about 3 nm to about 3.6 nm, about 3 nm to about 3.8 nm, about 3 nm to about 4 nm, about 3.2 nm to about 3.4 nm, about 3.2 nm to about 3.6 nm, about 3.2 nm to about 3.8 nm, about 3.2 nm to about 4 nm, about 3.4 nm to about 3.6 nm, about 3.4 nm to about 3.8 nm, about 3.4 nm to about 4 nm, about 3.6 nm to about 3.8 nm, about 3.6 nm to about 4 nm, or about 3.8 nm to about 4 nm. In some embodiments, the method produces MSNPs having an average pore size of about 2 nm, about 2.2 nm, about 2.4 nm, about 2.6 nm, about 2.8 nm, about 3 nm, about 3.2 nm, about 3.4 nm, about 3.6 nm, about 3.8 nm, or about 4 nm. In some embodiments, the method produces MSNPs having an average pore size of at least about 2 nm, about 2.2 nm, about 2.4 nm, about 2.6 nm, about 2.8 nm, about 3 nm, about 3.2 nm, about 3.4 nm, about 3.6 nm, or about 3.8 nm. In some embodiments, the method produces MSNPs having an average pore size of at most about 2.2 nm, about 2.4 nm, about 2.6 nm, about 2.8 nm, about 3 nm, about 3.2 nm, about 3.4 nm, about 3.6 nm, about 3.8 nm, or about 4 nm.

In certain embodiments the method comprises removing the CTAC surfactant by a wash procedure (e.g., washing the MSNPs with an alcohol and/or an acid). In certain embodiments the wash procedure comprises washing the MSNPs with an alcohol/acid mixture. In certain embodiments the alcohol/acid mixture comprises a methanol/HCl mixture (e.g., methanol/HCL at 500:19 v/v) and the washing is, optionally, at room temperature. In certain embodiments the method further comprises centrifuging and/or washing the MSNPs.

Scale-Up of Lipid Bilayer (LB) Formation on the MSNPs

To make small (e.g., a few hundred mg) batches of silicasomes, we used a one-step biofilm encapsulation method which holds significant advances over other methods of MSNP bilayer coating, such as the liposome fusion approach (see, e.g., Brinker J et al. (2009) *J. Am. Chem. Soc.,* 131: 7567-7569). The biofilm approach involved creation of a biofilm and then application of MSNPs to the film and sonication. Without being bound to a particular theory, it is believed that, using this method, van der Waals forces contribute to the rapid and complete coating of the MSNP surface. Our published protocol (Liu et al. (2016) *ACS Nano,* 10(2): 2702-2715) showed that 220 mg lipid mixture can make biofilm at ~75 cm$^2$ with a thickness of about 24 μm in a 150 mL flask, which is enough to coat about 200 mg MSNPs.

Figure 5:
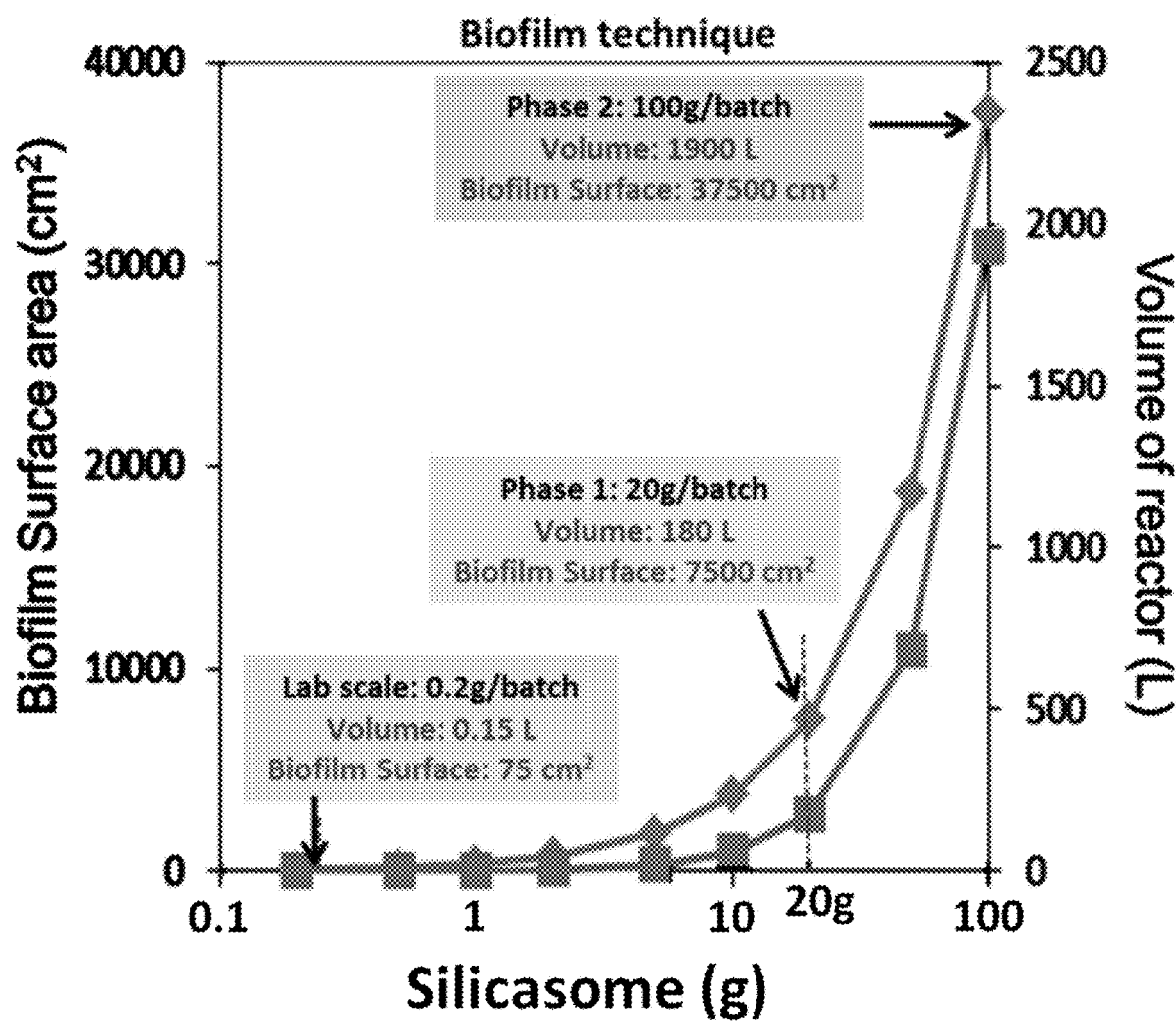
FIG. 5 shows that the biofilm pore sealing method does not scale up effectively for a large-scale synthesis of silicasomes. A theoretical calculation of rehydration volume based on the biofilm pore sealing protocol is illustrated.

However, it was determined that the lipid-bilayer approach is unsuitable for scale-up to large scale silicasome synthesis. Based on LB surface area, it is possible to calculate the rehydration reaction volume for different silicasome batch sizes (see, e.g., FIG. 5). For example, to make 100 g/batch silicasome for, e.g., a phase 2 study, we need to generate about 37,500 cm$^2$ biofilm, which requires about a 1,900 L rehydration reactor. This is impractical because of the huge reaction volume, difficulty of particle quality control, significant sample purification burden and cost concerns. Accordingly, we sought to develop alternative methodologies for MSNP pore sealing (LB formation on MSNPs) with a view to, inter alia, reducing reaction volume. In other words, we sought to provide uniform and intact MSNP pore sealing (LB formation on MSNPs) in a concentrated system.

Figure 6:
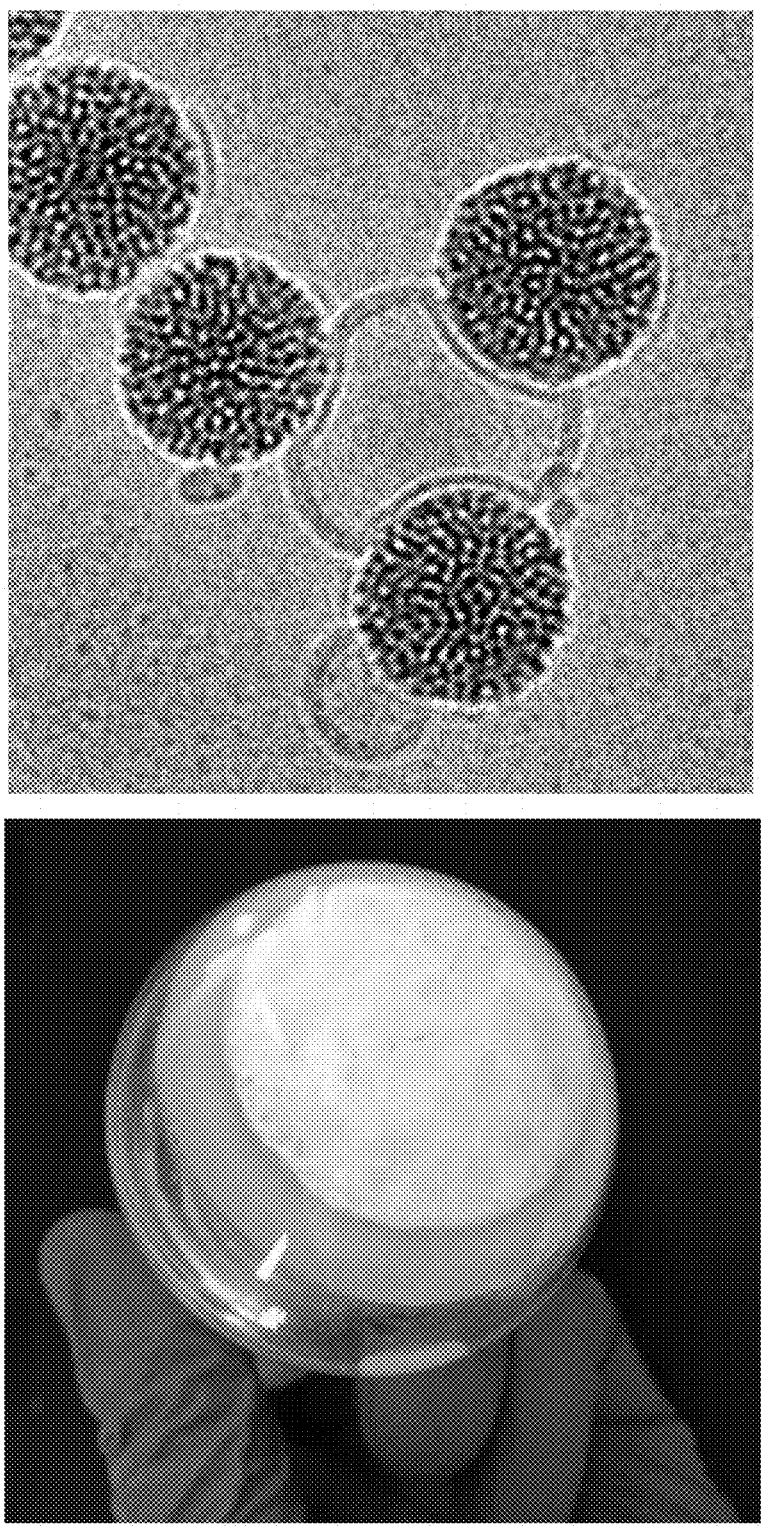
FIG. 6 shows a representative image of a thicker (~300 m) but non-uniform biofilm (left panel). Use of such biofilm for MSNP pore sealing is inefficient, similar to the liposome fusion approach. A representative cryoEM picture of MSNP with incomplete lipid coat was provided (right panel).

In order to reduce the reaction volume, our initial attempt was to make thicker LB. The resulting biofilm was non-uniform. The coating was inefficient for MSNP pore sealing, and essentially downgraded the effective thin biofilm approach to the ineffective liposome fusion method (see, e.g., FIG. 6).

In order to establish an effective method of lipid bilayer (LB) encapsulation of MSNPs (MSNP pore sealing) for large batches, we developed a novel a novel solvent precipitation method (e.g., a "lipid ethanol solution" method). Unlike previous lipid coating procedures (see, e.g., the liposome fusion method described in Brinker et al. (2009) *Am. Chem. Soc.* 131: 7567-7569, and the biofilm encapsulation methods described by Meng et al. (2015) *ACS Nano*, 9(4): 3540-3557), the "solvent precipitation" allows utilization of much more concentrated lipid or particle solutions/suspensions, which makes possible the large-scale synthesis of silicasomes.

Figure 7:
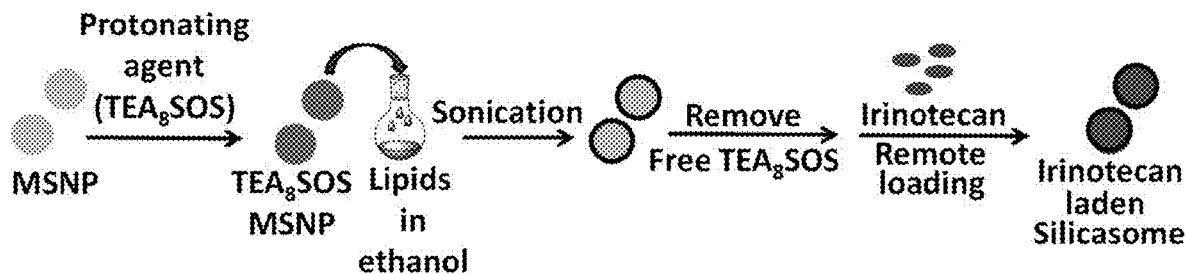
FIG. 7 illustrates the use of a lipid ethanol solution method for silicasome synthesis.

The new "solvent precipitation" method is illustrated in FIG. 7 which illustrates one embodiment of a synthesis protocol that produces an irinotecan loaded silicasome. Instead of making lipid biofilm, we introduced trapping agent (e.g., protonating agent) soaked MSNP into a highly concentrated lipids ethanol solution at appropriate temperature, which was 65° C. in the illustrated embodiment. In some embodiments, the appropriate temperature is about 55° C. to about 75° C. In some embodiments, the appropriate temperature is about 55° C. to about 60° C., about 55° C. to about 65° C., about 55° C. to about 70° C., about 55° C. to about 75° C., about 60° C. to about 65° C., about 60° C. to about 70° C., about 60° C. to about 75° C., about 65° C. to about 70° C., about 65° C. to about 75° C., or about 70° C. to about 75° C. In some embodiments, the appropriate temperature is about 55° C., about 60° C., about 65° C., about 70° C., or about 75° C. In some embodiments, the appropriate temperature is at least about 55° C., about 60° C., about 65° C., or about 70° C. In some embodiments, the appropriate temperature is at most about 60° C., about 65° C., about 70° C., or about 75° C.

While various parameters, including, but not limited to aqueous solution/ethanol volume ratio and sonication conditions, effective large scale synthesis was accomplished using the parameters for lipid concentration, temperature, MSNP:lipid ratio, etc. as described below. The illustrated protocol permitted the provision of large-scale (large batch) effective, uniform, and intact LB coating of MSNPs.

In the illustrated solvent precipitation approach which utilized a lipid ethanol solution, x mg MSNPs were soaked in a x/40 mL TEA$_8$SOS trapping agent (80 mM) solution, which was added to a mixture of lipids in x/400 mL ethanol at 65° C., comprised of a x:1.1 mg mixture of DSPC/Chol/DSPE-PEG2000 (molar ratio 3:2:0.15). This equals to a MSNP concentration of 40 mg/mL, MSNP:Lipid ratio of 1:1.1 w/w, and a lipid concentration of ~440 mg/mL. In certain embodiments the alcohol (e.g., ethanol) is a 100% absolute alcohol (e.g., absolute ethanol), while in other embodiments the alcohol is a 97% alcohol, or in certain embodiments a 95% alcohol.

The mixture was then sonicated using a probe sonicator with a 15/15 s on/off working cycle and a power output of 52 W to obtain a clear suspension. Free TEA$_8$SOS was removed by size exclusion chromatography over a Sepharose CL-4B column. In certain embodiments alternatives to a probe sonicator can be used. Such alternatives include, but are not limited to a static sonicator (homogenizer), or a dynamic flow system (homogenizer/sonicator) with an energy input function, both of which provide energy control for effective lipid coating without unwanted damage that may lead to overheating or raw material degradation. One illustrative, but non-limiting example is the SONOLATOR® (Sonic Corp.).

In general, any device that provides substantial and controllable intensity of ultrasound and high ultrasonic vibration amplitudes. Such devices include, but are not limited to "direct sonication" equipment, which usually refers to the ultrasound that is directly coupled into the processing liquid. Examples include, but are not limited to probe-type ultrasonicators. The coating can also be achieved by the use of "indirect sonication" equipment, which means the coupling of the ultrasound waves via ultrasonic bath through a container's wall into the sample liquid, e.g. VialTweeter, CupHorn, and the like.

In one illustrative, but non-limiting embodiment a probe flow through sonicator is used because this is one of the most popular setups used in pharmaceutical preparation.

The optimal sonication conditions can be determined using routine methods. IN one illustrative, but non-limiting embodiment, probe sonication is used to coat 20 g silicasome at a power of 200 W, using a 15 s/5 s on/off cycle for 2 hr. This can also be achieved using flow sonication system using continuous power input of 400 W at flow rate of 10 mL/min. For the flow sonication, the total time for making 20 g silicasome is about ~100 min.

Figure 8:
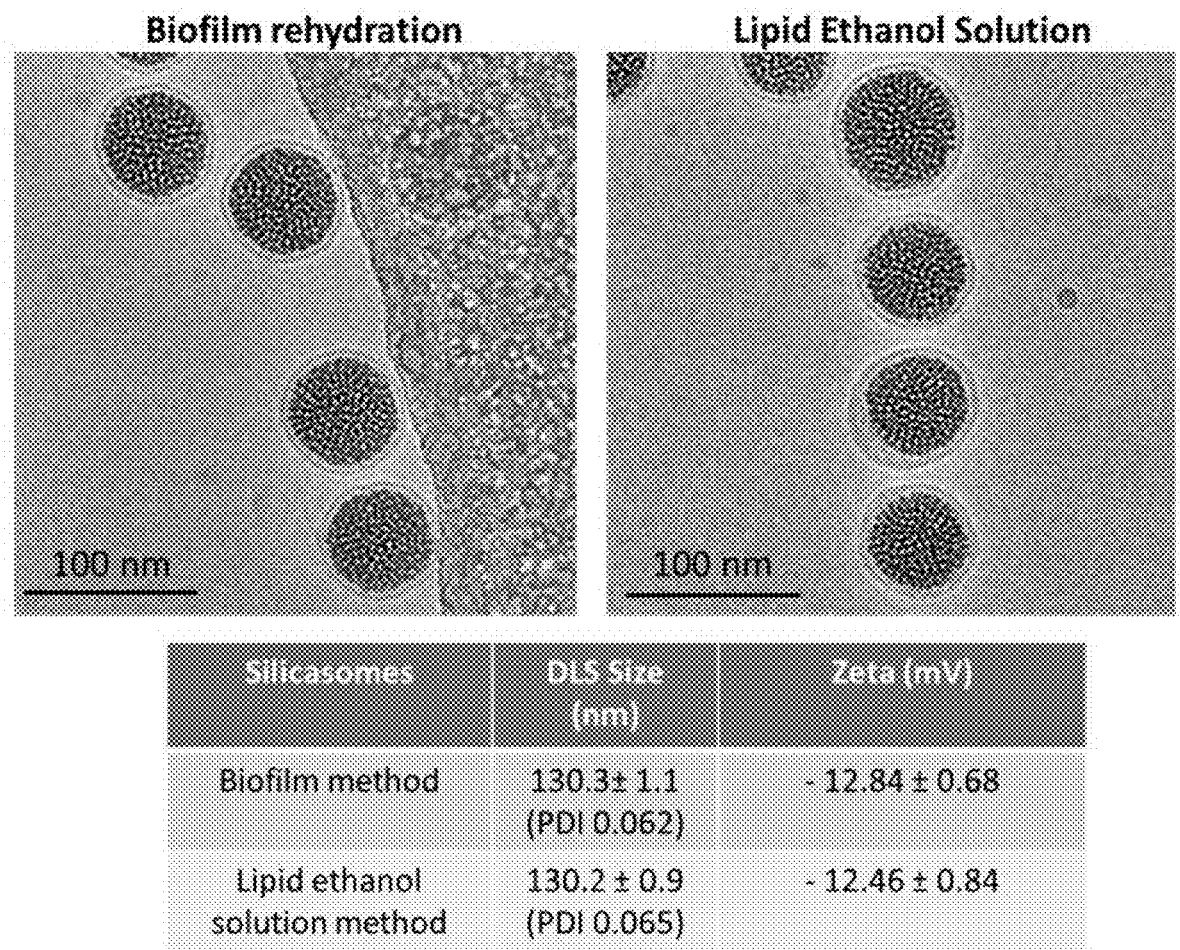
FIG. 8 shows a preliminary comparative characterization of silicasome samples synthesized using biofilm technique (left) versus ethanol solution method (right).

The TEA$_8$SOS loaded silicasomes were incubated in a 10 mg/mL irinotecan solution for drug loading in a water bath at 65° C. The loading was stopped after 30 min by quenching in and ice water bath, following which the drug-loaded silicasomes were washed 3 times by centrifugation and re-suspended in PBS (FIG. 7). Our preliminary comparative analysis showed that both methods (lipid bilayer fusion method and presently described solvent precipitation method) led to similar silicasomes in terms of size, morphology, zeta potential, and PDI (FIG. 8). The drug loading analysis showed similar loading capacity, i.e. 40-80% wt, when same amount free irinotecan was added during remote loading.

While the solvent-precipitation of lipid bilayer formation on MSNPs described above utilized an ethanol solution, a TEA$_8$SOS trapping agent (protonating agent), and particular composition lipids, in certain embodiments, other solvents can be used, other trapping agents can be used, and different lipid bilayer compositions can be utilized.

Accordingly, in certain embodiments, the solvent comprises a polar solvent selected from the group consisting of ethanol, methanol, or an ethanol or methanol containing aqueous solvent with the organic phase greater than 95% w/w. In certain embodiments the ratio of MSNP to lipid ranges from about 1:3 to about 1:1, or from about 1:2 to about 1:15, or from about 1:2 to about 1:1 (w/w), while as illustrated above, in certain embodiments the ratio of MSNP to lipid is about 1:1.1 (wt/wt). In some embodiments, the ratio of MSNP to lipid is at least about 1:1 (w/w), at least about 1:1.1, at least about 1:1.2, at least about 1:1.3, at least about 1:1.4, at least about 1:1.5, at least about 1:2, at least about 1:3, at least about 1:4, at least about 1:5, at least about 1:6, at least about 1:7, at least about 1:8, at least about 1:9, at least about 1:10, at least about 1:11, at least about 1:12, at least about 1:13, at least about 1:14, or at least about 1:15 or more. In some embodiments, the ratio of MSNP to lipid is no more than about 1:1 (w/w), no more than about 1:1.1, no more than about 1:1.2, no more than about 1:1.3, no more than about 1:1.4, no more than about 1:1.5, no more than about 1:2, no more than about 1:3, no more than about 1:4, no more than about 1:5, no more than about 1:6, no more than about 1:7, no more than about 1:8, no more than about 1:9, no more than about 1:10, no more than about 1:11, no more than about 1:12, no more than about 1:13, no more than about 1:14, or no more than about 1:15 or more.

In typical embodiments, the temperature is greater than the liquid transition temperature for each component. In certain embodiments the reaction is performed at a temperature ranging from about 40° C., or from about 50° C., or from about 60° C., to about 80° C., or to about 75° C., or to about 70° C. In certain embodiments the reaction is performed at a temperature of about 65° C. In certain embodiments the sonication proceeds at an energy and duration sufficient to provide a substantially clear suspension of silicasomes.

Various lipid formulations for the lipid bilayer, trapping agents, and silicasome features are described below.

Lipid Bilayer

In various embodiments the bilayer composition utilized in the silicasomes synthesized using the large-scale synthesis methods described herein is optimized to provide a rapid and uniform particle coating, to provide colloidal and circulatory stability, and to provide effective cargo retention, while also permitting a desirable cargo release profile.

In certain embodiments the lipid bilayer comprises a combination of a phospholipid, cholesterol, and in certain embodiments, a pegylated lipid (e.g., DSPE-PEG$_{2000}$), or a factionalized pegylated lipid (e.g., DSPE-PEG$_{2000}$-maleimide) to facilitate conjugation with targeting or other moieties.

In certain embodiments the lipids used comprise DSPC/Chol/DSPE-PEG$_{2000}$ (molar ratio 3:2:0.15). The ratio of "3:2:0.15" equals to "58.3 mol %:38.8 mol %:3.9 mol %" if one uses mol % to present the ratio. This provides a particle:lipid ratio of ~1:1.1. After sonication to accomplish particle wrapping and coating with a LB, free trapping agent (e.g., TEA$_8$SOS) can be removed by any of a number of methods known to one of skill in the art. In the illustrated protocol, TEA$_8$SOS was removed by size exclusion chromatography over a Sepharose CL-4B column.

The lipid bilayer formulation(s) described above are illustrative and non-limiting. Depending on the drug(s) being loaded into the silicasome and the desired release provide, in various embodiments different lipid bilayer formulations can be used and an optimal formulation can be determined.

Accordingly, in certain embodiments the lipid bilayer can comprise: 1) one or more saturated fatty acids with C14-C20 carbon chain, such as dimyristoylphosphatidylcholine (DMPC), dipalmitoylphosphatidylcholine (DPPC), distearoylphosphatidylcholine (DSPC), and diactylphosphatidylcholine (DAPC); and/or 2) One or more unsaturated fatty acids with a C14-C20 carbon chain, such as 1,2-dimyristoleoyl-sn-glycero-3-phosphocholine, 1,2-dipalmitoleoyl-sn-glycero-3-phosphocholine, 1,2-dioleoyl-sn-glycero-3-phosphocholine (DOPC), 1,2-dieicosenoyl-sn-glycero-3-phosphocholine; and/or 3) Natural lipids comprising a mixture of fatty acids with C12-C20 carbon chain, such as Egg PC, and Soy PC, sphingomyelin, and the like. These lipids are illustrative but non-limiting and numerous other lipids are known and can be incorporated into a lipid bilayer for formation of a silicasome.

In certain embodiments the silicasome contains a lipid (e.g., a phospholipid), cholesterol, and a PEG functionalized lipid (e.g., a mPEG phospholipid). In certain embodiments the mPEG phospholipids comprise a C14-C18 phospholipid carbon chain from, and a PEG molecular weight from 350-5000 (e.g., MPEG 5000, MPEG 3000, MPEG 2000, MPEG 1000, MPEG 750, MPEG 550, MPEG 350, and the like). In certain embodiments the mPEG phospholipid comprises DSPE-PEG5000, DSPE-PEG3000, DSPE-PEG2000, DSPE-PEG1000, DSPE-PEG750, DSPE-PEG550, or DSPE-PEG350. MPEGs are commercially available (see, e.g., //avantilipids.com/product-category/products/polymers-polymerizable-lipids/mpeg-phospholipids/).

In certain embodiments the ratio of phospholipid:CHOL:PEG, is about phospholipid (50-90 mol %):CHOL (10-50 mol %):PEG (1-10 mol %).

The protocols provided above are illustrative. As noted, in certain embodiments the trapping agent can be altered, the lipid composition and molar ratios can be altered, and the drug or drugs can be altered to identify other silicasomes optimized for their particular cargo(s).

It is noted, for example, that an effective lipid formulation for a gemcitabine-containing silicasome comprises DPPC/cholesterol/DSPE-PEG at a molar ratio of 77.5:20:2.5, while an effective lipid formulation for an irinotecan containing silicasome comprises DSPC/Chol/DSPE-PEG$_{2000}$ (molar ratio 3:2:0.15, which equals 58.3 mol %:38.8 mol %:3.9 mol %).

In some embodiments, a lipid bilayer comprises a phospholipid, cholesterol, and mPEG phospholipid at a ratio of:50-90 mol %, 50-60 mol %, 60-70 mol %, 70-80 mol %, 80-90 mol %, 50-70 mol %, 60-80 mol %, or 70-90 mol % phospholipid:10-50 mol %, 10-20 mol %, 20-30 mol %, 30-40 mol %, 40-50 mol %, 10-30 mol %, 20-40 mol %, or 30-50 mol % CHOL:1-mol %, 1-3 mol %, 3-6 mol %, 6-10 mol %, 1-5 mol %, 5-10 mol %, 2-8 mol %, 3-7 mol %, or 4-6 mol % mPEG phospholipid.

In some embodiments, the lipid bilayer comprises the phospholipid at a mole percentage of about 50 mol % to about 90 mol %. In some embodiments, the lipid bilayer comprises the phospholipid at a mole percentage of about 50 mol % to about 60 mol %, about 50 mol % to about 70 mol %, about 50 mol % to about 80 mol %, about 50 mol % to about 90 mol %, about 60 mol % to about 70 mol %, about 60 mol % to about 80 mol %, about 60 mol % to about 90 mol %, about 70 mol % to about 80 mol %, about 70 mol % to about 90 mol %, or about 80 mol % to about 90 mol %. In some embodiments, the lipid bilayer comprises the phospholipid at a mole percentage of about 50 mol %, about 60 mol %, about 70 mol %, about 80 mol %, or about 90 mol %. In some embodiments, the lipid bilayer comprises the phospholipid at a mole percentage of at least about 50 mol %, about 60 mol %, about 70 mol %, or about 80 mol %. In some embodiments, the lipid bilayer comprises the phospholipid at a mole percentage of at most about 60 mol %, about 70 mol %, about 80 mol %, or about 90 mol %.

In some embodiments, the lipid bilayer comprises the cholesterol at a mole percentage of about 10 mol % to about 50 mol %. In some embodiments, the lipid bilayer comprises the cholesterol at a mole percentage of about 10 mol % to about 20 mol %, about 10 mol % to about 30 mol %, about 10 mol % to about 40 mol %, about 10 mol % to about 50 mol %, about 20 mol % to about 30 mol %, about 20 mol % to about 40 mol %, about 20 mol % to about 50 mol %, about 30 mol % to about 40 mol %, about 30 mol % to about 50 mol %, or about 40 mol % to about 50 mol %. In some embodiments, the lipid bilayer comprises the cholesterol at a mole percentage of about 10 mol %, about 20 mol %, about 30 mol %, about 40 mol %, or about 50 mol %. In some embodiments, the lipid bilayer comprises the cholesterol at a mole percentage of at least about 10 mol %, about 20 mol %, about 30 mol %, or about 40 mol %. In some embodiments, the lipid bilayer comprises the cholesterol at a mole percentage of at most about 20 mol %, about 30 mol %, about 40 mol %, or about 50 mol %.

In some embodiments, the lipid bilayer comprises the mPEG phospholipid at a mole percentage of about 1 mol % to about 10 mol %. In some embodiments, the lipid bilayer comprises the mPEG phospholipid at a mole percentage of about 1 mol % to about 2 mol %, about 1 mol % to about 4 mol %, about 1 mol % to about 5 mol %, about 1 mol % to about 6 mol %, about 1 mol % to about 8 mol %, about 1 mol % to about 10 mol %, about 2 mol % to about 4 mol %, about 2 mol % to about 5 mol %, about 2 mol % to about 6 mol %, about 2 mol % to about 8 mol %, about 2 mol % to about 10 mol %, about 4 mol % to about 5 mol %, about 4 mol % to about 6 mol %, about 4 mol % to about 8 mol %, about 4 mol % to about 10 mol %, about 5 mol % to about 6 mol %, about 5 mol % to about 8 mol %, about 5 mol % to about 10 mol %, about 6 mol % to about 8 mol %, about 6 mol % to about 10 mol %, or about 8 mol % to about 10 mol %. In some embodiments, the lipid bilayer comprises the mPEG phospholipid at a mole percentage of about 1 mol %, about 2 mol %, about 4 mol %, about 5 mol %, about 6 mol %, about 8 mol %, or about 10 mol %. In some embodiments, the lipid bilayer comprises the mPEG phospholipid at a mole percentage of at least about 1 mol %, about 2 mol %, about 4 mol %, about 5 mol %, about 6 mol %, or about 8 mol %. In some embodiments, the lipid bilayer comprises the mPEG phospholipid at a mole percentage of at most about 2 mol %, about 4 mol %, about 5 mol %, about 6 mol %, about 8 mol %, or about 10 mol %.

In certain embodiments these methods can be varied to improve drug-loading capacity (weight of drug/total weight of carrier). In certain embodiments the drug loading capacity is at least about 20%, at least about 30%, or at least about 40%, at least about 50%, at least about 55%, at least about 60%, at least about 65%, at least about 70%, at least about 75%, or at least 80% w/w. In certain embodiments drug loading is greater than 40% w/w, or greater than 45% w/w, or greater than 50% w/w, or greater than 55% w/w, or greater than 60% w/w, or greater than 65% w/w, or greater than 70% w/w, %, or greater than 75% w/w, or greater than 80% w/w.

The large-scale synthesis methods described herein provide large populations of silicasomes (in a single bath) where the silicasomes outperform nanocarriers made by the liposomal method of coating by fusion and also outperform liposome compositions. Protonating agents (a.k.a. Trapping agents).

The trapping agent (e.g., protonating agent) can be selected to interact with a desired drug, for example to facilitate remote loading and/or retention within the nanoparticle(s) comprising the silicasome(s). While typically the interaction can be a protonation reaction, in certain embodiments, and ionic reaction as well as other modes of interaction are contemplated. The protonating agent can have one or more ionic sites, i.e., can be mono-ionic or poly-ionic. The ionic moiety can be cationic, anionic, or in some cases, the protonating agent can include both cationic and anionic moieties. The ionic sites can be in equilibrium with corresponding uncharged forms; for example, an anionic carboxylate (—COO⁻) can be in equilibrium with its corresponding carboxylic acid (—COOH); or in another example, an amine (—NH$_2$) can be in equilibrium with its corresponding protonated ammonium form (—NH$_3^+$). These equilibriums are influenced by the pH of the local environment.

Likewise, in certain embodiments, the drug can include one or more ionic sites. The protonating agent and drug can be selected to interact inside the silicasome (e.g., inside the mesoporous silica nanoparticle). This interaction can help retain the drug within the nanoparticle until release of the drug is desired. In some embodiments, the drug can exist in a pH-dependent equilibrium between non-ionic and ionic forms. The non-ionic form can diffuse across the lipid bilayer and enter pores of the MSNP. There, the protonating agent (e.g., a polyionic protonating agent) can interact with the ionic form of the drug and thereby retain the drug within the nanocarrier, e.g., within pores of the MSNP (provided the ionic forms of the drug and protonating agent have opposite charges). The interaction can be an ionic interaction, and can include formation of a precipitate. Trapping of drug within the nanocarrier can provide higher levels of drug loading compared to similar systems, e.g., nanocarriers that omit the protonating agent, or liposomes that do include a trapping agent. Release of the drug can be achieved by an appropriate change in pH to disrupt the interaction between the drug and protonating agent, for example, by returning the drug to its non-ionic state which can more readily diffuse across the lipid bilayer. In one embodiment, the drug is irinotecan and the protonating agent is TEA$_8$SOS.

The protonating agent need not be limited to TEA8SOS. In certain embodiments the protonating (drug trapping) agent comprises small molecules like (NH$_4$)$_2$SO$_4$, and the like. Other protonating agents include, but are not limited to, ammonium salts (e.g., ammonium sulfate, ammonium sucrose octasulfate, ammonium α-cyclodextrin sulfate, ammonium β-cyclodextrin sulfate, ammonium γ-cyclodextrin sulfate, ammonium phosphate, ammonium α-cyclodextrin phosphate, ammonium β-cyclodextrin phosphate, ammonium γ-cyclodextrin phosphate, ammonium citrate, ammonium acetate, and the like), trimethylammonium salts (e.g., trimethylammonium sulfate, trimethylammonium sucrose octasulfate, trimethylammonium α-cyclodextrin sulfate, trimethylammonium β-cyclodextrin sulfate, trimethylammonium γ-cyclodextrin sulfate, trimethylammonium phosphate, trimethylammonium α-cyclodextrin phosphate, trimethylammonium β-cyclodextrin phosphate, trimethylammonium γ-cyclodextrin phosphate, trimethylammonium citrate, trimethylammonium acetate, and the like), triethylammonium salts (e.g., triethylammonium sulfate, triethylammonium sucrose octasulfate, triethylammonium α-cyclodextrin sulfate, triethylammonium β-cyclodextrin sulfate, triethylammonium α-cyclodextrin sulfate, triethylammonium phosphate, triethylammonium α-cyclodextrin phosphate, triethylammonium β-cyclodextrin phosphate, triethylammonium γ-cyclodextrin phosphate, triethylammonium citrate, triethylammonium acetate, and the like).

It is also worth pointing out that, in addition to TEA$_8$SOS, transmembrane pH gradients can also be generated by acidic buffers (e.g. citrate) (Chou et al. (2003) *J. Biosci. Bioengineer.*, 95(4): 405-408; Nichols et al. (1976) *Biochimica et Biophysica Acta (BBA)-Biomembranes*, 455(1): 269-271), proton-generating dissociable salts (e.g. (NH$_4$)$_2$SO$_4$) (Haran et al. (1993) *Biochimica et Biophysica Acta (BBA)-Biomembranes*, 1151(2): 201-215; Maurer-Spurej et al. (1999) *Biochimica et Biophysica Acta (BBA)-Biomembranes*, 1416 (1): 1-10; Fritze et al. (2006) *Biochimica et Biophysica Acta (BBA)-Biomembranes*, 1758(10): 1633-1640), or ionophore-mediated ion gradients from metal salts (e.g. A23187 and MnSO$_4$) (Messerer et al. (2004) *Clinical Cancer Res.* 10(19): 663 8-6649; Ramsay et al. (2008) *Eur. J. Pharmaceut. Biopharmaceut.* 68(3): 607-617; Fenske et al. (1998) *Biochimica et Biophysica Acta (BBA)-Biomembranes*, 1414 (1): 188-204). Moreover, it is possible to generate reverse pH gradients for drug loading, such as use a calcium acetate gradient to improve amphiphilic weak acid loading in LB-MSNP, a strategy that has been utilized in liposomes (Avnir et al. (2008) *Arthritis & Rheumatism*, 58(1): 119-129).

Drugs to be Loaded into Silicasomes.

In certain embodiments, silicasomes made according to the large-scale synthesis methods described herein are loaded with one or more drugs (e.g., using a remote loading method as described above, or in certain embodiments, using other loading methods). In certain embodiments the drug comprises an organic compound that includes at least one primary amine group, or at least one secondary amine group, or at least one tertiary amine group, or at least one quaternary amine group, or any combination thereof, capable of being protonated. We have also identified a comprehensive list of weak basic drugs that can be loaded into LB-MSNPs through a proton gradient. In certain embodiments the general characteristics of these drug molecules include the following chemical properties:

(i) organic molecular compounds that include primary, secondary, tertiary or amine(s);

(ii) a pKa <11 to allow protonation and entrapment behind the LB (see, e.g., Zucker et al. (2009) *J. Control. Release*, 139(1): 73-80; Cern et al. (2012) *J. Control. Release*, 160(2): 147-157; Xu et al. (2014) *Pharmaceut. Res.* 31(10): 2583-2592);

(iii) a water solubility index of 5-25 mg/mL and amphipathic characteristics that allow diffusion across the LB;

(iv) an octanol/water partition coefficient or log P value of −3.0 to 3.0 (see, e.g., Zucker et al. (2009) *J. Control. Release*, 139(1): 73-80; Cern et al. (2012) *J. Control. Release*, 160(2): 147-157);

(v) suitable molecular weight with a geometric size less than MSNP pore size (2-8 nm), to allow entry into the MSNP pores (see, e.g., Li et al. (2012) *Chem. Soc. Rev.* 41(7): 2590-2605; Tang et al. (2012) *Adv. Mat.* 24(12): 1504-1534; Tarn et al. (2013) *Acc. Chem. Res.* 46(3): 792-801).

It is noted that for a drug that is a weak base with low water solubility (e.g., <2 mg/mL) but with a solubility in DMSO >5 mg/mL, one can use DMSO containing solution to prepare the drug bath. In certain embodiments the ratio of DMSO to $H_2O$ is about 1% to 10% v/v.

Without being all-inclusive, in various embodiments a list of potential chemotherapy agents can include irinotecan, and irinotecan derivatives and metabolites such as SN38, as well as various alkaloids (e.g. topotecan, 10-hydroxycamptothecin, belotecan, rubitecan, vinorelbine, LAQ824, vinblastine, vincristine, homoharringtonine, trabectedin), anthracyclines (e.g. doxorubicin, epirubicin, pirarubicin, daunorubicin, rubidomycin, valrubicin, amrubicin), alkaline anthracenediones (e.g. mitoxantrone), alkaline alkylating agents (e.g. cyclophosphamide, mechlorethamine, temozolomide), purine or pyrimidine derivatives (e.g. 5-fluorouracil, 5'-deoxy-5-fluorouridine, gemcitabine, capecitabine), and protein kinase inhibitors (e.g. pazopanib, enzastaurin, vandetanib erlotinib, dasatinib, nilotinib, sunitinib).

In certain embodiments the drug is irinotecan. In certain embodiments the drug comprises a substantially pure D isomer of irinotecan, while in other embodiments, the drug comprises a substantially pure L isomer of irinotecan.

The ability to package and deliver one or a combination of the above agents enhances the wider utility of the multifunctional silicasome platform described herein including, for example, treatment of additional cancer types such as colon, breast, lung, liver, glioma, melanoma, etc.

It is also possible to co-package drug combinations in the above list into a single carrier. For example, based on the success that we achieved with our GEM/PTX co-delivery platform (see, e.g. Meng et al. (2015) *ACS Nano*, 9(4): 3540-3557), it is possible to consider combining drugs in the FOLFIRINOX regimen (e.g., oxaliplatin with irinotecan) for synergistic and ratiometric delivery using the silicasomes described herein. Moreover, drug loading by the silicasomes described herein can be used for non-cancerous applications, such as encapsulating antibiotics for infectious disease applications, e.g., ciprofloxacin, levofloxacin or HIV antiretrovirals (e.g., tenofovir disoproxil fumarate).

In addition to the above-mentioned cancer drugs, as long as the drug molecules are basic as described above, the trapping reagent facilitated silicasome platform is useful in efficient drug loading and delivery. For non-basic drug molecules, while the trapping reagent will provide limited help, silicasomes synthesized using the large-scale synthesis methods described herein can be used for a large spectrum of drug molecules, such as anticancer drugs, anti-viral drugs, antifungal drugs, and antibiotics.

For example, in certain embodiments, silicasomes synthesized using the large-scale synthesis methods described herein can be loaded with various drugs including, but is not limited to, everolimus, trabectedin, paclitaxel, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhibitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatinib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR1 KRX-0402, lucanthone, LY 317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES (diethylstilbestrol), estradiol, estrogen, conjugated estrogen, bevacizumab, IMC-1C11, CHIR-258,); 3-[5-(methylsulfonylpiperadinemethyl)-indolylj-quinolone, vatalanib, AG-013736, AVE-0005, the acetate salt of [D-Ser(But) 6, Azgly 10] (pyro-Glu-His-Trp-Ser-Tyr-D-Ser(But)-Leu-Arg-Pro-Azgly-$NH_2$ acetate [C59H84N180i4-($C_2H_4O_2$)X where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, lonafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, amsacrine, anagrelide, L-asparaginase, *Bacillus* Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine, gleevac, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779, 450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, and darbepoetin alfa, boceprevir, daclatasvir, asunapavir, INX-189, FV-100, NM 283, VX-950 (telaprevir), SCH 50304, TMC435, VX-500, BX-813, SCH503034, R1626, ITMN-191 (R7227), R7128, PF-868554, TT033, CGH-759, GI 5005, MK-7009, SIRNA-034, MK-0608, A-837093, GS 9190, GS 9256, GS 9451, GS 5885, GS 6620, GS 9620, GS9669, ACH-1095, ACH-2928, GSK625433, TG4040 (MVA-HCV), A-831, F351, NS5A, NS4B, ANA598, A-689, GNI-104, IDX102, ADX184, ALS-2200, ALS-2158, BI 201335, BI 207127, BIT-225, BIT-8020, GL59728, GL60667, PSI-938, PSI-7977, PSI-7851, SCY-635, ribavirin, pegylated interferon, PHX1766, SP-30, or a mixture thereof.

In certain embodiments the drug(s) loaded into the silicasomes synthesized using the large-scale synthesis methods described herein comprise an antifungal agent. Illustrative antifungal agents include, but are not limited to Amphotericin B (e.g., for Most fungal infections except Pseudallescheria sp., and the like), Anidulafungin (e.g., for candidiasis, including candidemia, and the like), Caspofungin (e.g., for aspergillosis, candidiasis, including candidemia, and the like), Fluconazole (e.g., for mucosal and systemic candidiasis, cryptococcal meningitis, coccidioidal meningitis, and the like), Flucytosine (e.g., for Candidiasis (systemic), Cryptococcosis, and the like), Isavuconazole (e.g., for Aspergillosis, Mucormycosis, and the like), Itraconazole (e.g., for Dermatomycosis, Histoplasmosis, blastomycosis, coccidioidomycosis, sporotrichosis, and the like), Micafungin (e.g., for Candidiasis, including candidemia), Posaconazole (e.g., for prophylaxis for invasive aspergillosis and candidiasis, oral candidiasis, oral candidiasis refractory to itraconazole, and the like), Voriconazole (e.g., for Invasive aspergillosis, Fusariosis, Scedosporiosis, and the like), and so forth.

Dual Therapeutic Silicasomes.

It will be recognized that in certain embodiments, the silicasomes synthesized using the large-scale synthesis methods described herein can comprise two or more therapeutic agents. Thus, for example, in certain embodiments the pores in the silicasome can be loaded with two, or with three, or with four, or more different therapeutic agents. This can, in certain embodiments, permit ratiometric delivery of these therapeutic agents. By way of non-limiting illustration, numerous multi-agent therapeutic regimens are known for the treatment of cancer. These include, but are not limited to COMP (methotrexate, prednisone), $LSA_2-L_2$ (cyclophosphamide, vincristine, prednisone, daunomycin, methotrexate, cytarabine, thioguanine, asparaginase, and carmustine), FOLFIRINOX (irinotecan, oxaliplatin, 5-fluorouracil, leucovorin), and the like. In certain embodiments two or more agents that meet the requirements described herein for drugs to be loaded into silicasomes using the methods described herein can be provided in the silicasomes.

In certain embodiments hydrophobic (e.g., lipophilic) drugs, and other agents) can be provided in the lipid bilayer component of the silicasome. Such hydrophobic drugs include, but are not limited to paclitaxel, ellipticine, camptothecan, L-asparaginase, doxorubicin, SN-38 and the like. In certain embodiments the lipid bilayer component of the silicasome can contain one or more phospholipid prodrugs (e.g., drugs conjugated to a lipid). Illustrative lipid prodrugs include, but are not limited to acyclovir diphosphate dimyristoylglycerol (see, e.g., Hostetler, et al. (1993) *Proc. Natl. Acad. Sci. USA,* 90(24): 11835-11839), doxorubicin conjugated phospholipid prodrugs (see, e.g., Wang et al. (2015) *J. Mater. Chem. B.,* 3: 3297-3305), Phospholipid Derivatives of Nucleoside Analogs (e.g., 5'-diphosphate-L-1,2-dipalmitin derivatives of 1-β-D-arabinofuranosylcytosine (ara-C), 9-β-D-arabinofuranosyladenine (ara-A), tubercidin, and the like (see, e.g., Matsushita et al. (1981) *Cancer Res.,* 41: 2707-2713)), phospholipid linked chlorambucil (see, e.g., Pederson et al. (2010) *J. Med. Chem.,* 53: 3782-3792), and the like.

The foregoing multi-agent silicasomes are illustrative and non-limiting. Using the teachings provided herein numerous combinations of therapeutic agents for incorporation in (or on) the silicasomes described herein will be available to one of skill in the art.

Targeting Ligands and Immunoconjugates

In certain embodiments the silicasomes synthesized using the large-scale synthesis methods described herein can be conjugated to one or more targeting ligands, e.g., to facilitate specific delivery in endothelial cells, to cancer cells, to fusogenic ligands, e.g., to facilitate endosomal escape, ligands to promote transport across the blood-brain barrier, and the like.

In one illustrative, but non-limiting embodiments, the silicasome is conjugated to a fusogenic peptides such as histidine-rich H5WYG ($H_2N$-GLFHAIAHFIHGGWHG- LIHGWYG-COOH, (SEQ ID NO: 1)) (see, e.g., Midoux et al., (1998) *Bioconjug. Chem.* 9: 260-267).

In certain embodiments the silicasome is conjugated to targeting ligands which include antibodies as well as targeting peptides. Targeting antibodies include, but are not limited to intact immunoglobulins, immunoglobulin fragments (e.g., F(ab)'$_2$, Fab, etc.) single chain antibodies, diabodies, affibodies, unibodies, nanobodies, and the like. In certain embodiments antibodies will be used that specifically bind a cancer marker (e.g., a tumor associated antigen). A wide variety of cancer markers are known to those of skill in the art. The markers need not be unique to cancer cells, but can also be effective where the expression of the marker is elevated in a cancer cell (as compared to normal healthy cells) or where the marker is not present at comparable levels in surrounding tissues (especially where the chimeric moiety is delivered locally).

Illustrative cancer markers include, for example, the tumor marker recognized by the ND4 monoclonal antibody. This marker is found on poorly differentiated colorectal cancer, as well as gastrointestinal neuroendocrine tumors (see, e.g., Tobi et al. (1998) *Cancer Detection and Prevention,* 22(2): 147-152). Other important targets for cancer immunotherapy are membrane bound complement regulatory glycoproteins CD46, CD55 and CD59, which have been found to be expressed on most tumor cells in vivo and in vitro. Human mucins (e.g. MUC1) are known tumor markers as are gpl00, tyrosinase, and MAGE, which are found in melanoma. Wild-type Wilms' tumor gene WT1 is expressed at high levels not only in most of acute myelocytic, acute lymphocytic, and chronic myelocytic leukemia, but also in various types of solid tumors including lung cancer.

Acute lymphocytic leukemia has been characterized by the TAAs HLA-Dr, CD1, CD2, CD5, CD7, CD19, and CD20. Acute myelogenous leukemia has been characterized by the TAAs HLA-Dr, CD7, CD13, CD14, CD15, CD33, and CD34. Breast cancer has been characterized by the markers EGFR, HER2, MUC1, and Tag-72. Various carcinomas have been characterized by the markers MUC1, TAG-72, and CEA. Chronic lymphocytic leukemia has been characterized by the markers CD3, CD19, CD20, CD21, CD25, and HLA-DR. Hairy cell leukemia has been characterized by the markers CD19, CD20, CD21, and CD25. Hodgkin's disease has been characterized by the Leu-M1 marker. Various melanomas have been characterized by the HMB 45 marker. Non-hodgkins lymphomas have been characterized by the CD20, CD19, and Ia marker. And various prostate cancers have been characterized by the PSMA and SE10 markers.

In addition, many kinds of tumor cells display unusual antigens that are either inappropriate for the cell type and/or its environment, or are only normally present during the organisms' development (e.g., fetal antigens). Examples of such antigens include the glycosphingolipid GD2, a disialoganglioside that is normally only expressed at a significant level on the outer surface membranes of neuronal cells, where its exposure to the immune system is limited by the blood-brain barrier. GD2 is expressed on the surfaces of a wide range of tumor cells including neuroblastoma, medulloblastomas, astrocytomas, melanomas, small-cell lung cancer, osteosarcomas and other soft tissue sarcomas. GD2 is thus a convenient tumor-specific target for immunotherapies.

Other kinds of tumor cells display cell surface receptors that are rare or absent on the surfaces of healthy cells, and which are responsible for activating cellular signaling pathways that cause the unregulated growth and division of the tumor cell. Examples include (ErbB2) HER2/neu, a constitutively active cell surface receptor that is produced at abnormally high levels on the surface of breast cancer tumor cells.

Other useful targets include, but are not limited to CD20, CD52, CD33, epidermal growth factor receptor and the like.

An illustrative, but not limiting list of suitable tumor markers is provided in Table 2. Antibodies to these and other cancer markers are known to those of skill in the art and can be obtained commercially or readily produced, e.g. using phage-display technology. Such antibodies can readily be conjugated to the silicasomes described herein, e.g., in the same manner that iRGD peptide is conjugated in Example 3.

TABLE 2

Illustrative cancer markers and associated references, all of which are incorporated herein by reference for the purpose of identifying the referenced tumor markers.

| Marker | Reference |
|---|---|
| 5 alpha reductase | Délos et al. (1998) *Int J Cancer,* 75: 6 840-846 |
| α-fetoprotein | Esteban et al. (1996) *Tumour Biol.,* 17(5): 299-305 |
| AM-1 | Harada et al. (1996) *Tohoku J Exp Med.,* 180(3): 273-288 |
| APC | Dihlmannet al. (1997) *Oncol Res.,* 9(3) 119-127 |
| APRIL | Sordat et al. ('998) *J Exp Med.,* 188(6): 1185-1190 |
| BAGE | Böel et al. (1995) *Immunity,* 2: 167-175. |
| β-catenin | Hugh et al. (1999) *Int J Cancer,* 82(4): 504-11 |
| Bcl2 | Koty et al. (1999) *Lung Cancer,* 23(2): 115-127 |
| bcr-abl (b3a2) | Verfaillie et al.('996) *Blood,* 87(11): 4770-4779 |
| CA-125 | Bast et al. ('998) *Int J Biol Markers,* 13(4): 179-187 |
| CASP-8/FLICE | Mandruzzato et al. (1997) *J Exp Med.,* 186(5): 785-793. |
| Cathepsins | Thomssen et al.(1995) *Clin Cancer Res.,* 1(7): 741-746 |
| CD19 | Scheuermann et al. (1995) *Leuk Lymphoma,* 18(5-6): 385-397 |
| CD20 | Knox et al. (1996) *Clin Cancer Res.,* 2(3): 457-470 |
| CD21, CD23 | Shubinsky et al. (1997) *Leuk Lymphoma,* 25(5-6): 521-530 |
| CD22, CD38 | French et al. (1995) *Br J Cancer,* 71(5): 986-994 |
| CD33 | Nakase et al. (1996) *Am J Clin Pathol.,* 105(6): 761-768 |
| CD35 | Yamakawa et al. *Cancer,* 73(11): 2808-2817 |
| CD44 | Naot et al. (1997) *Adv Cancer Res.,* 71: 241-319 |
| CD45 | Buzzi et al. (1992) *Cancer Res.,* 52(14): 4027-4035 |
| CD46 | Yamakawa et al. (1994) *Cancer,* 73(11): 2808-2817 |
| CD5 | Stein et al. (1991) *Clin Exp Immunol.,* 85(3): 418-423 |
| CD52 | Ginaldi et al. (1998) *Leuk Res.,* 22(2): 185-191 |
| CD55 | Spendlove et al. (1999) *Cancer Res.,* 59: 2282-2286. |

TABLE 2-continued

Illustrative cancer markers and associated references, all of which are incorporated herein by reference for the purpose of identifying the referenced tumor markers.

| Marker | Reference |
| --- | --- |
| CD59 (791Tgp72) | Jarvis et al. (1997) *Int J Cancer*, 71(6): 1049-1055 |
| CDC27 | Wang et al. (1999) *Science*, 284(5418): 1351-1354 |
| CDK4 | Wölfel et al. (1995) *Science*, 269(5228): 1281-1284 |
| CEA | Kass et al. (1999) *Cancer Res.*, 59(3): 676-683 |
| c-myc | Watson et al. (1991) *Cancer Res.*, 51(15): 3996-4000 |
| Cox-2 | Tsujii et al. (1998) *Cell*, 93: 705-716 |
| DCC | Gotley et al. (1996) *Oncogene*, 13(4): 787-795 |
| DcR3 | Pitti et al. (1998) *Nature*, 396: 699-703 |
| E6/E7 | Steller et al. (1996) *Cancer Res.*, 56(21): 5087-5091 |
| EGFR | Yang et al. (1999) *Cancer Res.*, 59(6): 1236-1243. |
| EMBP | Shiina et al. (1996) *Prostate*, 29(3): 169-176. |
| Ena78 | Arenberg et al. (1998) *J. Clin. Invest.*, 102: 465-472. |
| FGF8b and FGF8a | Dorkin et al. (1999) *Oncogene*, 18(17): 2755-2761 |
| FLK-1/KDR | Annie and Fong (1999) *Cancer Res.*, 59: 99-106 |
| Folic Acid Receptor | Dixon et al. (1992) *J Biol Chem.*, 267(33): 24140-72414 |
| G250 | Divgi et al. (1998) *Clin Cancer Res.*, 4(11): 2729-2739 |
| GAGE-Family | De Backer et al. (1999) *Cancer Res.*, 59(13): 3157-3165 |
| gastrin 17 | Watson et al. (1995) *Int J Cancer*, 61(2): 233-240 |
| Gastrin-releasing hormone (bombesin) | Wang et al. (1996) *Int J Cancer*, 68(4): 528-534 |
| GD2/GD3/GM2 | Wiesner and Sweeley (1995) *Int J Cancer*, 60(3): 294-299 |
| GnRH | Bahk et al.(1998) *Urol Res.*, 26(4): 259-264 |
| GnTV | Hengstler et al. (1998) *Recent Results Cancer Res.*, 154: 47-85 |
| gp100/Pmel17 | Wagner et al. (1997) *Cancer Immunol Immunother.*, 44(4): 239-247 |
| gp-100-in4 | Kirkin et al. (1998) *APMIS*, 106(7): 665-679 |
| gp15 | Maeurer et al.(1996) *Melanoma Res.*, 6(1): 11-24 |
| gp75/TRP-1 | Lewis et al.(1995) *Semin Cancer Biol.*, 6(6): 321-327 |
| hCG | Hoermann et al. (1992) *Cancer Res.*, 52(6): 1520-1524 |
| Heparanase | Vlodavsky et al. (1999) *Nat Med.*, 5(7): 793-802 |
| Her2/neu | Lewis et al. (1995) *Semin Cancer Biol.*, 6(6): 321-327 |
| Her3 | |
| HMTV | Kahl et al.(1991) *Br J Cancer*, 63(4): 534-540 |
| Hsp70 | Jaattela et al. (1998) *EMBO J.*, 17(21): 6124-6134 |
| hTERT (telomerase) | Vonderheide et al. (1999) *Immunity*, 10: 673-679. 1999. |
| IGFR1 | Ellis et al. (1998) *Breast Cancer Res. Treat.*, 52: 175-184 |
| IL-13R | Murata et al. (1997) *Biochem Biophys Res Commun.*, 238(1): 90-94 |
| iNOS | Klotz et al. (1998) *Cancer*, 82(10): 1897-1903 |
| Ki 67 | Gerdes et al. (1983) *Int J Cancer*, 31: 13-20 |
| KIAA0205 | Guéguen et al. (1998) *J Immunol.*, 160(12): 6188-6194 |
| K-ras, H-ras, N-ras | Abrams et al. (1996) *Semin Oncol.*, 23(1): 118-134 |
| KSA (CO17-1A) | Zhang et al. (1998) *Clin Cancer Res.*, 4(2): 295-302 |
| LDLR-FUT | Caruso et al. (1998) *Oncol Rep.*, 5(4): 927-930 |
| MAGE Family (MAGE1, MAGE3, etc.) | Marchand et al. (1999) *Int J Cancer*, 80(2): 219-230 |
| Mammaglobin | Watson et al. (1999) *Cancer Res.*, 59: 13 3028-3031 |
| MAP17 | Kocher et al. (1996) *Am J Pathol.*, 149(2): 493-500 |
| Melan-A/MART-1 | Lewis and Houghton (1995) *Semin Cancer Biol.*, 6(6): 321-327 |
| mesothelin | Chang et al. (1996) *Proc. Natl. Acad. Sci., USA*, 93(1): 136-140 |
| MIC A/B | Groh et al.(1998) *Science*, 279: 1737-1740 |
| MT-MMP's, such as MMP2, MMP3, MMP7, MMP9 | Sato and Seiki (1996) *J Biochem (Tokyo)*, 119(2): 209-215 |
| Mox1 | Candia et al. (1992) *Development*, 116(4): 1123-1136 |
| Mucin, such as MUC-1, MUC-2, MUC-3, and MUC-4 | Lewis and Houghton (1995) *Semin Cancer Biol.*, 6(6): 321-327 |
| MUM-1 | Kirkin et al. (1998) *APMIS*, 106(7): 665-679 |
| NY-ESO-1 | Jager et al. (1998) *J. Exp. Med.*, 187: 265-270 |
| Osteonectin | Graham et al. (1997) *Eur J Cancer*, 33(10): 1654-1660 |
| p15 | Yoshida et al. (1995) *Cancer Res.*, 55(13): 2756-2760 |
| P170/MDR1 | Trock et al. (1997) *J Natl Cancer Inst.*, 89(13): 917-931 |
| p53 | Roth et al. (1996) *Proc. Natl. Acad. Sci., USA*, 93(10): 4781-4786. |
| p97/melanotransferrin | Furukawa et al. (1989) *J Exp Med.*, 169(2): 585-590 |
| PAI-1 | Grøndahl-Hansen et al. (1993) *Cancer Res.*, 53(11): 2513-2521 |
| PDGF | Vassbotn et al. (1993) *Mol Cell Biol.*, 13(7): 4066-4076 |
| Plasminogen (uPA) | Naitoh et al. (1995) *Jpn J Cancer Res.*, 86(1): 48-56 |
| PRAME | Kirkin et al. (1998) *APMIS*, 106(7): 665-679 |
| Probasin | Matuo et al. (1985) *Biochem Biophys Res Commun.*, 130(1): 293-300 |
| Progenipoietin | — |
| PSA | Sanda et al. (1999) *Urology*, 53(2): 260-266. |
| PSM | Kawakami et al.(1997) *Cancer Res.*, 57(12): 2321-2324 |
| RAGE-1 | Gaugler et al.(1996) *Immunogenetics*, 44(5): 323-330 |
| Rb | Dosaka-Akita et al. (1997) *Cancer*, 79(7): 1329-1337 |
| RCAS1 | Sonoda et al.(1996) *Cancer*, 77(8): 1501-1509. |

TABLE 2-continued

Illustrative cancer markers and associated references, all of which are incorporated herein by reference for the purpose of identifying the referenced tumor markers.

| Marker | Reference |
| --- | --- |
| SART-1 | Kikuchi et al.(1999(*Int J Cancer*, 81(3): 459-466 |
| SSX gene Family | Gure et al. (1997) *Int J Cancer*, 72(6): 965-971 |
| STAT3 | Bromberg et al. (1999) *Cell*, 98(3): 295-303 |
| STn (mucin assoc.) | Sandmaier et al. (1999) *J Immunother.*, 22(1): 54-66 |
| TAG-72 | Kuroki et al. (1990)*Cancer Res.*, 50(16): 4872-4879 |
| TGF-α | Imanishi et al. (1989) *Br J Cancer*, 59(5): 761-765 |
| TGF-β | Picon et al. (1998) *Cancer Epidemiol Biomarkers Prev*, 7(6): 497-504 |
| Thymosin β 15 | Bao et al. (1996) *Nature Medicine.* 2(12), 1322-1328 |
| IFN-α | Moradi et al. (1993) *Cancer*, 72(8): 2433-2440 |
| TPA | Maulard et al. (1994) *Cancer*, 73(2): 394-398 |
| TPI | Nishida et al.(1984) *Cancer Res* 44(8): 3324-9 |
| TRP-2 | Parkhurst et al. (1998) *Cancer Res.*, 58(21) 4895-4901 |
| Tyrosinase | Kirkin et al. (1998) *APMIS*, 106(7): 665-679 |
| VEGF | Hyodo et al. (1998) *Eur J Cancer*, 34(13): 2041-2045 |
| ZAG | Sanchez et al. (1999) *Science*, 283(5409): 1914-1919 |
| p16INK4 | Quelle et al. (1995) *Oncogene* Aug. 17, 1995; 11(4): 635-645 |
| Glutathione S-transferase | Hengstler (1998) et al. *Recent Results Cancer Res.*, 154: 47-85 |

Any of the foregoing markers can be used as targets for the targeting moieties comprising the silicasome constructs described herein. In certain embodiments the target markers include, but are not limited to members of the epidermal growth factor family (e.g., HER2, HER3, EGF, HER4), CD1, CD2, CD3, CD5, CD7, CD13, CD14, CD15, CD19, CD20, CD21, CD23, CD25, CD33, CD34, CD38, 5E10, CEA, HLA-DR, HM 1.24, HMB 45, 1a, Leu-M1, MUC1, PMSA, TAG-72, phosphatidyl serine antigen, and the like.

The foregoing markers are intended to be illustrative and not limiting. Other tumor associated antigens will be known to those of skill in the art.

Where the tumor marker is a cell surface receptor, ligand to that receptor can function as targeting moieties. Similarly, mimetics of such ligands can also be used as targeting moieties. Thus, in certain embodiments peptide ligands can be used in addition to or in place of various antibodies. An illustrative, but non-limiting list of suitable targeting peptides is shown in Table 3. In certain embodiments any one or more of these peptides can be conjugated to a silicasome described herein.

TABLE 3

Illustrative, but non-limiting peptides that target membrane receptors expressed or overexpressed by various cancer cells.

| Target Membrane Receptor | Targeting Peptide | SEQ ID NO |
| --- | --- | --- |
| Integrin receptor $A_v\beta_3$ | c(RGDfK) | 2 |
| | c(RGDfC) | 3 |
| | c(RGDyC) | 4 |
| | RGD | |
| GFR | GE11 (YHWYGYTPQNVI) | 5 |
| GFR | GSG-KCCYSL | 6 |
| SSTR2 | Ostreotide | |
| GRP | QWAVGHML | 7 |
| CCK | DYMGWMDF | 8 |
| NT | RRPYIL | 9 |
| | RRPYILQLYENKPRRPYIL | 10 |
| LHRH | Gondaorelin | |
| GPRC family members | Antagonist G | | c() indicates cyclopeptide. Lower case indicates "D" amino acid.

In certain embodiments the silicasomes synthesized using the large-scale synthesis methods described herein can be conjugated to moieties that facilitate stability in circulation and/or that hide the silicasome from the reticuloendothelial system (REC) and/or that facilitate transport across a barrier (e.g., a stromal barrier, the blood brain barrier, etc.), and/or into a tissue. In certain embodiments the silicasomes are conjugated to transferrin or ApoE to facilitate transport across the blood brain barrier. In certain embodiments the silicasomes are conjugated to folate.

Methods of coupling the silicasomes to targeting (or other) agents are well known to those of skill in the art. Examples include, but are not limited to the use of biotin and avidin or streptavidin (see, e.g., U.S. Pat. No. 4,885,172 A), by traditional chemical reactions using, for example, bifunctional coupling agents such as glutaraldehyde, diimide esters, aromatic and aliphatic diisocyanates, bis-p-nitrophenyl esters of dicarboxylic acids, aromatic disulfonyl chlorides and bifunctional arylhalides such as 1,5-difluoro-2,4-dinitrobenzene; p,p'-difluoro m,m'-dinitrodiphenyl sulfone, sulfhydryl-reactive maleimides, and the like. Appropriate reactions which may be applied to such couplings are described in Williams et al. Methods in Immunology and Immunochemistry Vol. 1, Academic Press, New York 1967. In one illustrative but non-limiting approach described in Example 3 a peptide (in this example iRGD) is coupled to the silicasome by substituting DSPE-PEG$_{2000}$ with DSPE-PEG$_{2000}$-maleimide (see methods section in Example 3), allowing thiol-maleimide coupling to the cysteine-modified peptide. It will also be recognized that in certain embodiments the targeting (and other) moieties can be conjugated to a lipid comprising the lipid bilayer.

The former conjugates and coupling methods are illustrative and non-limiting. Using the teachings provided herein, numerous other moieties can be conjugated to the silicasomes described herein by any of a variety of methods. Pharmaceutical Formulations, Administration and Therapy Pharmaceutical Formulations.

In some embodiments, the silicasomes synthesized using the large-scale synthesis methods described herein are administered alone or in a mixture with a physiologically-acceptable carrier (such as physiological saline or phosphate buffer) selected in accordance with the route of administration and standard pharmaceutical practice. For example, when used as an injectable, the silicasomes can be formulated as a sterile suspension, dispersion, or emulsion with a pharmaceutically acceptable carrier. In certain embodiments normal saline can be employed as the pharmaceutically acceptable carrier. Other suitable carriers include, e.g., water, buffered water, 0.4% saline, 0.3% glycine, and the like, including glycoproteins for enhanced stability, such as albumin, lipoprotein, globulin, etc. In compositions comprising saline or other salt-containing carriers, the carrier is preferably added following silicasome formation. Thus, after the silicasome is formed and loaded with suitable drug(s), the silicasome can be diluted into pharmaceutically acceptable carriers such as normal saline. These compositions may be sterilized by conventional, well-known sterilization techniques. The resulting aqueous solutions, suspensions, dispersions, emulsions, etc., may be packaged for use or filtered under aseptic conditions. In certain embodiments the silicasomes are lyophilized, the lyophilized preparation being combined with a sterile aqueous solution prior to administration. The compositions may also contain pharmaceutically acceptable auxiliary substances as required to approximate physiological conditions, such as pH-adjusting and buffering agents, tonicity adjusting agents and the like, for example, sodium acetate, sodium lactate, sodium chloride, potassium chloride, calcium chloride, etc.

Additionally, in certain embodiments, the pharmaceutical formulation may include lipid-protective agents that protect lipids against free-radical and lipid-peroxidative damages on storage. Lipophilic free-radical quenchers, such as alpha-tocopherol and water-soluble iron-specific chelators, such as ferrioxamine, are suitable.

The concentration of silicasomes in the pharmaceutical formulations can vary widely, e.g., from less than approximately 0.05%, usually at least approximately 2 to 5% to as much as 10 to 50%, or to 40%, or to 30% by weight and are selected primarily by fluid volumes, viscosities, etc., in accordance with the particular mode of administration selected. For example, the concentration may be increased to lower the fluid load associated with treatment. This may be particularly desirable in patients having atherosclerosis-associated congestive heart failure or severe hypertension. Alternatively, silicasomes composed of irritating lipids may be diluted to low concentrations to lessen inflammation at the site of administration. The amount of silicasomes administered will depend upon the particular drug used, the disease state being treated and the judgment of the clinician but will generally be between approximately 0.01 and approximately 50 mg per kilogram of body weight, preferably between approximately 0.1 and approximately 5 mg per kg of body weight.

In some embodiments, e.g., it is desirable to include polyethylene glycol (PEG)-modified phospholipids in the silicasomes. Alternatively, or additionally, in certain embodiments, PEG-ceramide, or ganglioside $G_M$-modified lipids can be incorporated in the silicasomes. Addition of such components helps prevent silicasome aggregation and provides for increasing circulation lifetime and increasing the delivery of the loaded silicasomes to the target tissues. In certain embodiments the concentration of the PEG-modified phospholipids, PEG-ceramide, or $G_M$-modified lipids in the silicasome will be approximately 1 to 15%. In certain embodiments the concentration of the PEG-modified phospholipids, PEG-ceramide, or GMI-modified lipids in the silicasome is about 1% to about 15%. In certain embodiments the concentration of the PEG-modified phospholipids, PEG-ceramide, or GMI-modified lipids in the silicasome is about 1% to about 5%, about 1% to about 10%, about 1% to about 15%, about 5% to about 10%, about 5% to about 15%, or about 10% to about 15%. In certain embodiments the concentration of the PEG-modified phospholipids, PEG-ceramide, or GMI-modified lipids in the silicasome is about 1%, about 5%, about 10%, or about 15%. In certain embodiments the concentration of the PEG-modified phospholipids, PEG-ceramide, or GMI-modified lipids in the silicasome is at least about 1%, about 5%, or about 10%. In certain embodiments the concentration of the PEG-modified phospholipids, PEG-ceramide, or GMI-modified lipids in the silicasome is at most about 5%, about 10%, or about 15%.

In some embodiments, overall silicasome charge is an important determinant in silicasome clearance from the blood. It is believed that charged silicasomes will be typically taken up more rapidly by the reticuloendothelial system (see, e.g., Juliano (1975) *Biochem. Biophys. Res. Commun.* 63: 651-658 discussing liposome clearance by the RES) and thus have shorter half-lives in the bloodstream. Silicasomes with prolonged circulation half-lives are typically desirable for therapeutic uses. For instance, in certain embodiments, silicasomes that are maintained from 8 hours, or 12 hours, or 24 hours, or greater are desirable. In some embodiments, the silicasomes have a half-life of about 4 h to about 24 h. In some embodiments, the silicasomes have a half-life of about 4 h to about 5 h, about 4 h to about 6 h, about 4 h to about 7 h, about 4 h to about 8 h, about 4 h to about 9 h, about 4 h to about 10 h, about 4 h to about 11 h, about 4 h to about 12 h, about 4 h to about 15 h, about 4 h to about 20 h, about 4 h to about 24 h, about 5 h to about 6 h, about 5 h to about 7 h, about 5 h to about 8 h, about 5 h to about 9 h, about 5 h to about 10 h, about 5 h to about 11 h, about 5 h to about 12 h, about 5 h to about 15 h, about 5 h to about 20 h, about 5 h to about 24 h, about 6 h to about 7 h, about 6 h to about 8 h, about 6 h to about 9 h, about 6 h to about 10 h, about 6 h to about 11 h, about 6 h to about 12 h, about 6 h to about 15 h, about 6 h to about 20 h, about 6 h to about 24 h, about 7 h to about 8 h, about 7 h to about 9 h, about 7 h to about 10 h, about 7 h to about 11 h, about 7 h to about 12 h, about 7 h to about 15 h, about 7 h to about 20 h, about 7 h to about 24 h, about 8 h to about 9 h, about 8 h to about 10 h, about 8 h to about 11 h, about 8 h to about 12 h, about 8 h to about 15 h, about 8 h to about 20 h, about 8 h to about 24 h, about 9 h to about 10 h, about 9 h to about 11 h, about 9 h to about 12 h, about 9 h to about 15 h, about 9 h to about 20 h, about 9 h to about 24 h, about 10 h to about 11 h, about 10 h to about 12 h, about 10 h to about 15 h, about 10 h to about 20 h, about 10 h to about 24 h, about 11 h to about 12 h, about 11 h to about 15 h, about 11 h to about 20 h, about 11 h to about 24 h, about 12 h to about 15 h, about 12 h to about 20 h, about 12 h to about 24 h, about 15 h to about 20 h, about 15 h to about 24 h, or about 20 h to about 24 h. In some embodiments, the silicasomes have a half-life of about 4 h, about 5 h, about 6 h, about 7 h, about 8 h, about 9 h, about 10 h, about 11 h, about 12 h, about 15 h, about 20 h, or about 24 h. In some embodiments, the silicasomes have a half-life of at least about 4 h, about 5 h, about 6 h, about 7 h, about 8 h, about 9 h, about 10 h, about 11 h, about 12 h, about 15 h, or about 20 h. In some embodiments, the silicasomes have a half-life of at most about 5 h, about 6 h, about 7 h, about 8 h, about 9 h, about 10 h, about 11 h, about 12 h, about 15 h, about 20 h, or about 24 h.

In another example of their use, drug-loaded silicasomes synthesized using the large-scale synthesis methods described herein can be incorporated into a broad range of topical dosage forms including but not limited to gels, oils, emulsions, and the like, e.g., for the treatment of a topical cancer. For instance, in some embodiments the suspension containing the drug-loaded silicasomes is formulated and administered as a topical cream, paste, ointment, gel, lotion, and the like.

In some embodiments, pharmaceutical formulations comprising silicasomes synthesized using the large-scale synthesis methods described herein additionally incorporate a buffering agent. The buffering agent may be any pharmaceutically acceptable buffering agent. Buffer systems include, but are not limited to citrate buffers, acetate buffers, borate buffers, and phosphate buffers. Examples of buffers include, but are not limited to citric acid, sodium citrate, sodium acetate, acetic acid, sodium phosphate and phosphoric acid, sodium ascorbate, tartaric acid, maleic acid, glycine, sodium lactate, lactic acid, ascorbic acid, imidazole, sodium bicarbonate and carbonic acid, sodium succinate and succinic acid, histidine, and sodium benzoate, benzoic acid, and the like.

In some embodiments, pharmaceutical formulations comprising silicasomes synthesized using the large-scale synthesis methods described herein additionally incorporate a chelating agent. The chelating agent may be any pharmaceutically acceptable chelating agent. Chelating agents include, but are not limited to ethylene diaminetetraacetic acid (also synonymous with EDTA, edetic acid, versene acid, and sequestrene), and EDTA derivatives, such as dipotassium edetate, disodium edetate, edetate calcium disodium, sodium edetate, trisodium edetate, and potassium edetate. Other chelating agents include citric acid (e.g., citric acid monohydrate) and derivatives thereof. Derivatives of citric acid include anhydrous citric acid, trisodiumcitratedihydrate, and the like. Still other chelating agents include, but are not limited to, niacinamide and derivatives thereof and sodium deoxycholate and derivatives thereof.

In some embodiments, pharmaceutical formulations comprising silicasomes synthesized using the large-scale synthesis methods described herein additionally incorporate a bioactive agent contain an antioxidant. The antioxidant may be any pharmaceutically acceptable antioxidant. Antioxidants are well known to those of ordinary skill in the art and include, but are not limited to, materials such as ascorbic acid, ascorbic acid derivatives (e.g., ascorbylpalmitate, ascorbylstearate, sodium ascorbate, calcium ascorbate, etc.), butylated hydroxy anisole, buylated hydroxy toluene, alkylgallate, sodium meta-bisulfate, sodium bisulfate, sodium dithionite, sodium thioglycollic acid, sodium formaldehyde sulfoxylate, tocopherol and derivatives thereof, (d-alpha tocopherol, d-alpha tocopherol acetate, dl-alpha tocopherol acetate, d-alpha tocopherol succinate, beta tocopherol, delta tocopherol, gamma tocopherol, and d-alpha tocopherol polyoxyethylene glycol 1000 succinate) monothioglycerol, sodium sulfite and N-acetyl cysteine. In certain embodiments such materials, when present, are typically added in ranges from 0.01 to 2.0%.

In some embodiments, pharmaceutical formulations comprising silicasomes synthesized using the large-scale synthesis methods described herein are formulated with a cryoprotectant. The cryoprotecting agent may be any pharmaceutically acceptable cryoprotecting agent. Common cryoprotecting agents include, but are not limited to, histidine, polyethylene glycol, polyvinyl pyrrolidine, lactose, sucrose, mannitol, polyols, and the like.

In some embodiments, pharmaceutical formulations comprising silicasomes synthesized using the large-scale synthesis methods described herein are formulated with an isotonic agent. The isotonic agent can be any pharmaceutically acceptable isotonic agent. This term is used in the art interchangeably with iso-osmotic agent, and is known as a compound that is added to the pharmaceutical preparation to increase the osmotic pressure, e.g., in some embodiments to that of 0.9% sodium chloride solution, which is iso-osmotic with human extracellular fluids, such as plasma. Illustrative isotonicity agents include, but are not limited to, sodium chloride, mannitol, sorbitol, lactose, dextrose and glycerol.

In certain embodiments pharmaceutical formulations of the silicasomes are synthesized using the large-scale synthesis methods that optionally comprise a preservative. Common preservatives include, but are not limited to, those selected from the group consisting of chlorobutanol, parabens, thimerosol, benzyl alcohol, and phenol. Suitable preservatives include but are not limited to: chlorobutanol (e.g., 0.3-0.9% w/v), parabens (e.g., 0.01-5.0%), thimerosal (e.g., 0.004-0.2%), benzyl alcohol (e.g., 0.5-5%), phenol (e.g., 0.1-1.0%), and the like.

In some embodiments, pharmaceutical formulations comprising silicasomes synthesized using the large-scale synthesis methods are formulated with a humectant, e.g., to provide a pleasant mouth-feel in oral applications. Humectants known in the art include, but are not limited to, cholesterol, fatty acids, glycerin, lauric acid, magnesium stearate, pentaerythritol, and propylene glycol.

In some embodiments, an emulsifying agent is included in the formulations, for example, to ensure complete dissolution of all excipients, especially hydrophobic components such as benzyl alcohol. Many emulsifiers are known in the art, e.g., polysorbate 60.

For some embodiments related to oral administration, it may be desirable to add a pharmaceutically acceptable flavoring agent and/or sweetener. Compounds such as saccharin, glycerin, simple syrup, and sorbitol are useful as sweeteners.

Administration and Therapy

The silicasomes synthesized using the large-scale synthesis methods described herein, particularly when loaded with one or more drugs, can be can be administered to a subject (e.g., patient) by any of a variety of techniques to deliver those drug(s).

In certain embodiments the silicasomes synthesized using the large-scale synthesis methods described herein, or pharmaceutical formulations thereof, are administered parenterally, e.g., intraarticularly, intravenously, intraperitoneally, subcutaneously, or intramuscularly. In some embodiments, the silicasomes, or pharmaceutical formulations thereof, are administered intravenously, intraarterially, or intraperitoneally by a bolus injection (see, e.g., U.S. Pat. Nos. 3,993,754; 4,145,410; 4,235,871; 4,224,179; 4,522,803; and 4,588,578 describing administration of liposomes). Particular excipients for use in pharmaceutical formulations suitable for this administration are found in *Remington's Pharmaceutical Sciences*, Mack Publishing Company, Philadelphia, Pa., 17th ed. (1985). Typically, the formulations comprise a solution of the silicasomes synthesized using the large-scale synthesis methods described herein suspended in an acceptable carrier, preferably an aqueous carrier. As noted above, suitable aqueous solutions include, but are not limited to physiologically compatible buffers such as Hanks solution, Ringer's solution, or physiological (e.g., 0.9% isotonic) saline buffer and/or in certain emulsion formulations. In various embodiments, the solution(s) can contain formulatory agents such as suspending, stabilizing and/or dispersing agents. In certain embodiments the silicasomes synthesized using the large-scale synthesis methods described herein can be provided in powder form for constitution with a suitable vehicle, e.g., sterile pyrogen-free water, before use. For transmucosal administration, and/or for blood/brain barrier passage, penetrants appropriate to the barrier to be permeated can be used in the formulation. These compositions may be sterilized by conventional, well-known sterilization techniques, or may be sterile filtered. The resulting aqueous solutions may be packaged for use as is, or lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc., e.g., as described above.

In certain embodiments, the pharmaceutical formulations containing silicasomes synthesized using the large-scale synthesis methods described herein may be contacted with the target tissue by direct application of the preparation to the tissue. The application may be made by topical, "open" or "closed" procedures. By "topical" it is meant the direct application of the pharmaceutical preparation to a tissue exposed to the environment, such as the skin, oropharynx, external auditory canal, and the like. Open procedures are those procedures that include incising the skin of a patient and directly visualizing the underlying tissue to which the silicasomes, or pharmaceutical formulations thereof, are applied. This is generally accomplished by a surgical procedure, such as a thoracotomy to access the lungs, abdominal laparotomy to access abdominal viscera, or other direct surgical approaches to the target tissue. Closed procedures are invasive procedures in which the internal target tissues are not directly visualized, but accessed via inserting instruments through small wounds in the skin. For example, the preparations may be administered to the peritoneum by needle lavage. Likewise, the silicasomes synthesized using the large-scale synthesis methods described herein, or pharmaceutical formulations thereof, may be administered to the meninges or spinal cord by infusion during a lumbar puncture followed by appropriate positioning of the patient as commonly practiced for spinal anesthesia or metrizamide imaging of the spinal cord. Alternatively, the silicasomes, or pharmaceutical formulations thereof, may be administered through endoscopic devices. In certain embodiments the silicasomes synthesized using the large-scale synthesis methods described herein, or pharmaceutical formulations thereof, are introduced via a cannula.

In certain embodiments the silicasomes synthesized using the large-scale synthesis methods described herein, or pharmaceutical formulations thereof, are administered via inhalation (e.g., as an aerosol). Inhalation can be a particularly effective delivery rout for administration to the lungs and/or to the brain. In certain embodiments, for administration by inhalation, the silicasomes can be conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g. gelatin for use in an inhaler or insufflator may be formulated containing a powder mix of the silicasomes and a suitable powder base such as lactose or starch.

In certain embodiments, the silicasomes synthesized using the large-scale synthesis methods described herein are formulated for oral administration. For oral administration, suitable formulations can be readily prepared by combining the silicasome(s) with pharmaceutically acceptable carriers suitable for oral delivery well known in the art. Such carriers enable the silicasomes synthesized using the large-scale synthesis methods described herein to be formulated as tablets, pills, dragees, caplets, lozenges, gelcaps, capsules, liquids, gels, syrups, slurries, suspensions and the like, for oral ingestion by a patient to be treated. For oral solid formulations such as, for example, powders, capsules and tablets, suitable excipients can include fillers such as sugars (e.g., lactose, sucrose, mannitol and sorbitol), cellulose preparations (e.g., maize starch, wheat starch, rice starch, potato starch, gelatin, gum tragacanth, methyl cellulose, hydroxypropylmethyl-cellulose, sodium carboxymethylcellulose), synthetic polymers (e.g., polyvinylpyrrolidone (PVP)), granulating agents; and binding agents. If desired, disintegrating agents may be added, such as the cross-linked polyvinylpyrrolidone, agar, or alginic acid or a salt thereof such as sodium alginate. If desired, solid dosage forms may be sugar-coated or enteric-coated using standard techniques. The preparation of enteric-coated particles is disclosed for example in U.S. Pat. Nos. 4,786,505 and 4,853,230.

In various embodiments the silicasomes synthesized using the large-scale synthesis methods described herein can be formulated in rectal or vaginal compositions such as suppositories or retention enemas, e.g., containing conventional suppository bases such as cocoa butter or other glycerides. Methods of formulating active agents for rectal or vaginal delivery are well known to those of skill in the art (see, e.g., Allen (2007) *Suppositories*, Pharmaceutical Press) and typically involve combining the active agents with a suitable base (e.g., hydrophilic (PEG), lipophilic materials such as cocoa butter or Witepsol W45), amphiphilic materials such as Suppocire AP and polyglycolized glyceride, and the like). The base is selected and compounded for a desired melting/delivery profile.

The route of delivery of silicasomes can also affect their distribution in the body. Passive delivery of silicasomes involves the use of various routes of administration e.g., parenterally, although other effective administration forms, such as intraarticular injection, inhalant mists, orally active formulations, transdermal iontophoresis, or suppositories are also envisioned. Each route produces differences in localization of the silicasomes.

Because dosage regimens for pharmaceutical agents are well known to medical practitioners, the amount of the silicasomes synthesized using the large-scale synthesis methods described herein, or pharmaceutical formulations thereof, that is effective or therapeutic for the treatment of a disease or condition in mammals and particularly in humans will be apparent to those skilled in the art. The optimal quantity and spacing of individual dosages of the formulations herein will be determined by the nature and extent of the condition being treated, the form, route and site of administration, and the particular subject being treated, and such optima can be determined by conventional techniques. It will also be appreciated by one of skill in the art that the optimal course of treatment, e.g., the number of doses given per day for a defined number of days, can be ascertained by those skilled in the art using conventional course of treatment determination tests.

In certain embodiments the silicasomes synthesized using the large-scale synthesis methods described herein, and/or pharmaceutical formations thereof, can be used therapeutically in animals (including man) in the treatment of various cancers, or various infections, and the like including, but not limited to, conditions that require: (1) repeated administrations, (2) the sustained delivery of the drug in its bioactive form, or (3) the decreased toxicity with suitable efficacy compared with the free drug in question. In various embodiments the silicasomes, and/or pharmaceutical formations thereof, are administered in a therapeutically effective dose. The term "therapeutically effective" as it pertains to the silicasomes described herein and formulations thereof means that a biologically active substance present or and/or in the silicasome provided/released in a manner sufficient to achieve a particular medical effect for which the biologically active substance (therapeutic agent) is intended. Examples, without limitation of desirable medical effects that can be attained are chemotherapy, antibiotic therapy, and regulation of metabolism. Thus, for example, a therapeutically effective dose for cancer chemotherapy may be a dose (and/or dosage regimen) effective to slow the growth and/or proliferation of cancer cells, and/or to slow, stop the growth of a solid tumor or shrink or eliminate a solid tumor, and/or slow, stop the proliferation of metastatic cells, and the like. A therapeutically effective dose for treating an infection can be a dose (and/or dosage regimen) sufficient to inhibit the growth and/or proliferation of a pathogen, and/or to kill a pathogen, and/or to mitigate one or more symptoms produced by the pathogen.

Exact dosages will vary depending upon such factors as the particular therapeutic agent (drug) and desirable medical effect, as well as patient factors such as age, sex, general condition, and the like. Those of skill in the art can readily take these factors into account and use them to establish effective therapeutic concentrations without resort to undue experimentation.

For administration to humans (or to non-human mammals) in the curative, remissive, retardive, or prophylactic treatment of diseases the prescribing physician will ultimately determine the appropriate dosage of the drug for a given human (or non-human) subject, and this can be expected to vary according to the age, weight, and response of the individual as well as the nature and severity of the patient's disease. In certain embodiments the dosage of the drug provided by the silicasome(s) can be approximately equal to that employed for the free drug. However as noted above, the silicasomes described herein can significantly reduce the toxicity of the drug(s) administered thereby and significantly increase a therapeutic window. Accordingly, in some cases dosages in excess of those prescribed for the free drug will be utilized.

In certain embodiments, the dose of the drug encapsulated in the silicasomes synthesized using the large-scale synthesis methods described herein, administered at a particular time point will be in the range from about 1 to about 1,000 mg/m$^2$/day, or to about 800 mg/m$^2$/day, or to about 600 mg/m$^2$/day, or to about 400 mg/m$^2$/day. For example, in certain embodiments a dosage (dosage regiment) is utilized that provides a range from about 1 to about 350 mg/m$^2$/day, 1 to about 300 mg/m$^2$/day, 1 to about 250 mg/m$^2$/day, 1 to about 200 mg/m$^2$/day, 1 to about 150 mg/m$^2$/day, 1 to about 100 mg/m$^2$/day, from about 5 to about 80 mg/m$^2$/day, from about 5 to about 70 mg/m$^2$/day, from about 5 to about 60 mg/m$^2$/day, from about 5 to about 50 mg/m$^2$/day, from about 5 to about 40 mg/m$^2$/day, from about 5 to about 20 mg/m$^2$/day, from about 10 to about 80 mg/m$^2$/day, from about 10 to about 70 mg/m$^2$/day, from about 10 to about 60 mg/m$^2$/day, from about 10 to about 50 mg/m$^2$/day, from about 10 to about 40 mg/m$^2$/day, from about 10 to about 20 mg/m$^2$/day, from about 20 to about 40 mg/m$^2$/day, from about 20 to about 50 mg/m$^2$/day, from about 20 to about 90 mg/m$^2$/day, from about 30 to about 80 mg/m$^2$/day, from about 40 to about 90 mg/m$^2$/day, from about 40 to about 100 mg/m$^2$/day, from about 80 to about 150 mg/m$^2$/day, from about 80 to about 140 mg/m$^2$/day, from about 80 to about 135 mg/m$^2$/day, from about 80 to about 130 mg/m$^2$/day, from about 80 to about 120 mg/m$^2$/day, from about 85 to about 140 mg/m$^2$/day, from about 85 to about 135 mg/m$^2$/day, from about 85 to about 135 mg/m$^2$/day, from about 85 to about 130 mg/m$^2$/day, or from about 85 to about 120 mg/m$^2$/day. In certain embodiments the does administered at a particular time point may also be about 130 mg/m$^2$/day, about 120 mg/m$^2$/day, about 100 mg/m$^2$/day, about 90 mg/m$^2$/day, about 85 mg/m$^2$/day, about 80 mg/m$^2$/day, about 70 mg/m$^2$/day, about 60 mg/m$^2$/day, about 50 mg/m$^2$/day, about 40 mg/m$^2$/day, about 30 mg/m$^2$/day, about 20 mg/m$^2$/day, about 15 mg/m$^2$/day, or about 10 mg/m$^2$/day.

Dosages may also be estimated using in vivo animal models, as will be appreciated by those skill in the art. In this regard, with respect to the irinotecan-loaded silicasomes described herein, it is noted that the effective therapeutic dose of the Ir-silicasome in a KPC-derived orthotopic animal model is about 40 mg/kg, which is equivalent to 120 mg/m$^2$ in a 70 Kg human subject (Liu, et al. (2016) *ACS Nano*, 10: 2702-2715). Fibonacci analysis indicates this dose can be achieved by starting and intermediary doses of 40 and 80 mg/m$^2$.

The dose administered may be higher or lower than the dose ranges described herein, depending upon, among other factors, the bioavailability of the composition, the tolerance of the individual to adverse side effects, the mode of administration and various factors discussed above. Dosage amount and interval may be adjusted individually to provide plasma levels of the composition that are sufficient to maintain therapeutic effect, according to the judgment of the prescribing physician. Skilled artisans will be able to optimize effective local dosages without undue experimentation in view of the teaching provided herein.

Multiple doses (e.g., continuous or bolus) of the compositions as described herein may also be administered to individuals in need thereof of the course of hours, days, weeks, or months. For example, but not limited to, 1, 2, 3, 4, 5, or 6 times daily, every other day, every 10 days, weekly, monthly, twice weekly, three times a week, twice monthly, three times a month, four times a month, five times a month, every other month, every third month, every fourth month, etc.

Methods of Treatment.

In various embodiments methods of treatment using the silicasomes synthesized using the large-scale synthesis methods described herein, and/or pharmaceutical formulation(s) thereof, are provided. In certain embodiments the method(s) comprise a method of treating a cancer. In certain embodiments the method can comprise administering to a subject in need thereof an effective amount of a silicasome, and/or a pharmaceutical formulation comprising a silicasome as described herein, where the drug in the silicasome, and/or pharmaceutical formulation, comprises an anti-cancer drug. In certain embodiments the silicasome and/or pharmaceutical formulation is a primary therapy in a chemotherapeutic regimen. In certain embodiments the silicasome and/or pharmaceutical formulation thereof, is a component in a multi-drug chemotherapeutic regimen. In certain embodiments the multi-drug chemotherapeutic regimen comprises at least two drugs selected from the group consisting of irinotecan (IRIN), oxaliplatin (OX), 5-fluorouracil (5-FU), and leucovorin (LV). In certain embodiments the multi-drug chemotherapeutic regimen comprises at least three drugs selected from the group consisting of irinotecan (IRIN), oxaliplatin (OX), 5-fluorouracil (5-FU), and leucovorin (LV). In certain embodiments the multi-drug chemotherapeutic regimen comprises at least irinotecan (IRIN), oxaliplatin (OX), 5-fluorouracil (5-FU), and leucovorin (LV).

In various embodiments the silicasomes synthesized using the large-scale synthesis methods described herein, and/or pharmaceutical formulation(s) thereof, are effective for treating any of a variety of cancers. In certain embodiments the cancer is pancreatic ductal adenocarcinoma (PDAC). In certain embodiments the cancer is a cancer selected from the group consisting of acute lymphoblastic leukemia (ALL), acute myeloid leukemia (AML), adrenocortical carcinoma, AIDS-related cancers (e.g., Kaposi sarcoma, lymphoma), anal cancer, appendix cancer, astrocytomas, atypical teratoid/rhabdoid tumor, bile duct cancer, extrahepatic cancer, bladder cancer, bone cancer (e.g., Ewing sarcoma, osteosarcoma, malignant fibrous histiocytoma), brain stem glioma, brain tumors (e.g., astrocytomas, glioblastoma, brain and spinal cord tumors, brain stem glioma, central nervous system atypical teratoid/rhabdoid tumor, central nervous system embryonal tumors, central nervous system germ cell tumors, craniopharyngioma, ependymoma, breast cancer, bronchial tumors, burkitt lymphoma, carcinoid tumors (e.g., childhood, gastrointestinal), cardiac tumors, cervical cancer, chordoma, chronic lymphocytic leukemia (CLL), chronic myelogenous leukemia (CML), chronic myeloproliferative disorders, colon cancer, colorectal cancer, craniopharyngioma, cutaneous t-cell lymphoma, duct cancers e.g. (bile, extrahepatic), ductal carcinoma in situ (DCIS), embryonal tumors, endometrial cancer, ependymoma, esophageal cancer, esthesioneuroblastoma, extracranial germ cell tumor, extragonadal germ cell tumor, extrahepatic bile duct cancer, eye cancer (e.g., intraocular melanoma, retinoblastoma), fibrous histiocytoma of bone, malignant, and osteosarcoma, gallbladder cancer, gastric (stomach) cancer, gastrointestinal carcinoid tumor, gastrointestinal stromal tumors (GIST), germ cell tumors (e.g., ovarian cancer, testicular cancer, extracranial cancers, extragonadal cancers, central nervous system), gestational trophoblastic tumor, brain stem cancer, hairy cell leukemia, head and neck cancer, heart cancer, hepatocellular (liver) cancer, histiocytosis, langerhans cell cancer, Hodgkin lymphoma, hypopharyngeal cancer, intraocular melanoma, islet cell tumors, pancreatic neuroendocrine tumors, kaposi sarcoma, kidney cancer (e.g., renal cell, Wilm's tumor, and other kidney tumors), langerhans cell histiocytosis, laryngeal cancer, leukemia, acute lymphoblastic (ALL), acute myeloid (AML), chronic lymphocytic (CLL), chronic myelogenous (CML), hairy cell, lip and oral cavity cancer, liver cancer (primary), lobular carcinoma in situ (LCIS), lung cancer (e.g., childhood, non-small cell, small cell), lymphoma (e.g., AIDS-related, Burkitt (e.g., non-Hodgkin lymphoma), cutaneous T-Cell (e.g., mycosis fungoides, Sezary syndrome), Hodgkin, non-Hodgkin, primary central nervous system (CNS)), macroglobulinemia, Waldenström, male breast cancer, malignant fibrous histiocytoma of bone and osteosarcoma, melanoma (e.g., childhood, intraocular (eye)), merkel cell carcinoma, mesothelioma, metastatic squamous neck cancer, midline tract carcinoma, mouth cancer, multiple endocrine neoplasia syndromes, multiple myeloma/plasma cell neoplasm, mycosis fungoides, myelodysplastic syndromes, chronic myeloid leukemia (CML), multiple myeloma, nasal cavity and paranasal sinus cancer, nasopharyngeal cancer, neuroblastoma, oral cavity cancer, lip and oropharyngeal cancer, osteosarcoma, ovarian cancer, pancreatic cancer, pancreatic neuroendocrine tumors (islet cell tumors), papillomatosis, paraganglioma, paranasal sinus and nasal cavity cancer, parathyroid cancer, penile cancer, pharyngeal cancer, pheochromocytoma, pituitary tumor, plasma cell neoplasm, pleuropulmonary blastoma, primary central nervous system (CNS) lymphoma, prostate cancer, rectal cancer, renal cell (kidney) cancer, renal pelvis and ureter, transitional cell cancer, rhabdomyosarcoma, salivary gland cancer, sarcoma (e.g., Ewing, Kaposi, osteosarcoma, rhadomyosarcoma, soft tissue, uterine), Sezary syndrome, skin cancer (e.g., melanoma, merkel cell carcinoma, basal cell carcinoma, nonmelanoma), small intestine cancer, squamous cell carcinoma, squamous neck cancer with occult primary, stomach (gastric) cancer, testicular cancer, throat cancer, thymoma and thymic carcinoma, thyroid cancer, trophoblastic tumor, ureter and renal pelvis cancer, urethral cancer, uterine cancer, endometrial cancer, uterine sarcoma, vaginal cancer, vulvar cancer, Waldenström macroglobulinemia, and Wilm's tumor.

In certain embodiments, particularly for the treatment of pancreatic ductal adenocarcinoma (PDAC) the silicasomes synthesized using the large-scale synthesis methods described herein, are loaded with irinotecan. In certain embodiments the irinotecan comprises a racemic mixture of D and L forms of irinotecan. In certain embodiments the irinotecan comprises a substantially pure D isomer and in other embodiments the irinotecan comprises a substantially pure L isomer.

In certain embodiments the silicasome is not conjugated to an iRGD peptide and the silicasome is administered in conjunction with an iRGD peptide (e.g., the silicasome and the iRGD peptide are co-administered as separate formulations).

In certain embodiments the method(s) comprise a method of treating an infection. In certain embodiments the method can comprise administering to a subject in need thereof an effective amount of a the silicasomes synthesized using the large-scale synthesis methods described herein, and/or a pharmaceutical formulation thereof, as described herein, where the drug in said silicasome and/or the pharmaceutical formulation comprises an anti-microbial or anti-viral agent. In certain embodiments the infection comprises a nosocomial infection. In certain embodiments the infection is caused by viral, bacterial, or fungal pathogens. In certain embodiments the infection comprises a bloodstream infection (BSI), pneumonia (e.g., ventilator-associated pneumonia (VAP)), a gastrointestinal infection, a urinary tract infection (UTI), a surgical site infection (SSI), or a skin infection. In certain embodiments the infection is caused by a pathogen such as *Staphylococcus aureus* (e.g., blood infection), *Escherichia coli* (e.g., UTI), Enterococci (e.g., blood, UTI, wound), *Pseudomonas aeruginosa* (e.g., kidney or respiratory infection), *Mycobacterium tuberculosis* (e.g., lung), and the like. In certain embodiments the infection is a viral infection (e.g., HIV, hepatitis B, hepatitis C, etc.).

In certain embodiments the infection is caused by a drug-resistant pathogen. Illustrative drug-resistant pathogens include, but are not limited to methicillin-resistant *Staphylococcus aureus* (MRSA), vancomycin-resistant *Enterococcus* (VRE) and multi-drug-resistant *Mycobacterium tuberculosis* (MDR-TB), and *Klebsiella pneumoniae* carbapenemase-producing bacteria (KPC).

In various embodiments of these treatment methods, the silicasomes synthesized using the large-scale synthesis methods described herein and/or pharmaceutical formulation(s) thereof, are administered via a route selected from the group consisting of intravenous administration, intraarterial administration, intracerebral administration, intrathecal administration, oral administration, aerosol administration, administration via inhalation (including intranasal and intratracheal delivery, intracranial administration via a cannula, and subcutaneous or intramuscular depot deposition. In certain embodiments the silicasome and/or pharmaceutical formulation is administered as an injection, from an IV drip bag, or via a drug-delivery cannula. In various embodiments the subject is a human and in other embodiments the subject is a non-human mammal.

Kits.

In certain embodiments, kits are provided containing the silicasomes produced using the large-scale methods described herein and/or pharmaceutical formulations thereof. In certain embodiments the silicasomes are loaded with a drug and are suitable for the treatment of a pathology (e.g., a cancer, a microbial infection, a viral infection, etc.). The kits typically comprise a drug-loaded silicasome as described herein and/or an immunoconjugate comprising a drug-loaded silicasome described herein. In certain embodiments the silicasome contains irinotecan (e.g., a racemic mixture thereof, or a substantially pure D isomer or a substantially pure L isomer). In certain embodiments the silicasome has attached thereto an iRGD peptide while in other embodiments the kit contains a separate iRGD peptide formulated for coadministration with the drug (e.g., irinotecan) loaded silicasome or silicasome immunoconjugate.

Additionally, in certain embodiments, the kits can include instructional materials disclosing means of use of the drug-loaded silicasome or silicasome immunoconjugate (e.g. as a therapeutic for a pancreatic cancer, gastric cancer, cervical cancer, ovarian cancer, etc.).

In addition, the kits optionally include labeling and/or instructional materials providing directions (e.g., protocols) for the use of the silicasomes described herein, e.g., alone or in combination for the treatment of various cancers. Instructional materials can also include recommended dosages, description(s) of counterindications, and the like.

While the instructional materials in the various kits typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

Improved Efficacy and Reduced Toxicity Using a Custom-Designed Irinotecan-Delivering Silicasome for Orthotopic Colon Cancer Irinotecan is a key chemotherapeutic agent for the treatment of colorectal (CRC) and pancreatic (PDAC) cancer. Because of a high incidence of bone marrow and gastrointestinal (GI) toxicity, ONIVYDE® (a liposome) was introduced to provide encapsulated irinotecan (Ir) delivery in PDAC patients. While there is an ongoing clinical trial (NCT02551991) to investigate the use of ONIVYDE® as a $1^{st}$-line option to replace irinotecan in FOLFIRINOX, the liposomal formulation is currently prescribed as a $2^{nd}$-line treatment option (in combination with 5-fluorouracil and leucovorin) for patients with metastatic PDAC who failed gemcitabine therapy. However, the toxicity of ONIVYDE® remains a concern that needs to be addressed for use in CRC as well. Our goal was to custom design a mesoporous silica nanoparticle (MSNP) carrier for encapsulated irinotecan delivery in a robust CRC model. This was achieved by developing an orthotopic tumor chunk model in immunocompetent mice. With a view to increase the production volume and to expand the disease applications, the carrier design was improved by using an ethanol exchange method for coating of a supported lipid bilayer (LB) that entraps a protonating agent. The encapsulated protonating agent was subsequently used for remote loading of irinotecan. The excellent irinotecan loading capacity and stability of the LB-coated MSNP carrier, also known as a "silicasome", previously showed improved efficacy and reduced toxicity when compared to an in-house liposomal carrier in a PDAC model. Intravenous injection of the silicasomes in a well-developed orthotopic colon cancer model in mice demonstrated improved pharmacokinetics (PK) and tumor drug content over free drug and ONIVYDE®. Moreover, improved drug delivery was accompanied by substantially improved efficacy, increased survival and reduced bone marrow and GI toxicity compared to the free drug and ONIVYDE®. We also confirmed that the custom-designed irinotecan silicasomes outperform ONIVYDE® in an orthotopic PDAC model. In summary, the Ir-silicasome appears to be promising as a treatment option for CRC in humans based on improved efficacy and the carrier's favorable safety profile.

Details.

Irinotecan, a topoisomerase I inhibitor, is frequently used for chemotherapy in gastrointestinal (GI) cancers, including colorectal cancer (CRC) and pancreatic ductal adenocarcinoma (PDAC) (Bleiberg (1999) *Eur. J. Cancer,* 35: 371-379; Cunningham et al. (1998) *The Lancet,* 352, 1413-1418; Rougier et al. (1998) *The Lancet,* 352: 1407-1412; Saltz et al. (2000) *N. Engl. J. Med.* 343: 905-914; Fuchs et al. (2006) *Cancer Treat. Rev.* 32: 491-503; Conroy et al. (2011) *N. Engl. J. Med.* 364: 1817-1825). Most commonly, irinotecan is used in combination with infusion fluorouracil (5-FU) and leucovorin (LV) as a $1^{st}$-line treatment option for metastatic CRC (Saltz et al. (2000) *N. Engl. J. Med.* 343: 905-914; Fuchs et al. (2006) *Cancer Treat. Rev.* 32: 491-503). It was also suggested that irinotecan can serve as a monotherapy for CRC patients who are unable to tolerate 5-FU (Fuchs et al. (2006) *Cancer Treat. Rev.* 32: 491-503; Ychou et al. (2002) *Cancer Chemother. Pharmacol.* 50: 383-391). In spite of its efficacy, irinotecan use is hindered by high drug toxicity, with especially severe impact on the bone marrow (e.g., neutropenia) and the GI tract (e.g., diarrhea) (Hecht (1998) *Oncology,* 12: 72-78; Mathijssen et al. (2001) *Clin. Cancer Res.* 7: 2182-2194). As a result, irinotecan-based chemotherapy is generally conserved for patients with good performance status who tolerate the side effects. This restricts its use in poor performance status patients, who are often in need of cytotoxic therapy.

The high rate of irinotecan toxicity has prompted the development of alternative treatment strategies to reduce the drug's serious side effects. This includes the use of encapsulated drug delivery by various nanocarriers, including liposomes (e.g., FDA approved MM-398 for PDAC and IHL-305 in a phase I clinical trial for advanced solid tumors), polymeric nano-conjugates (e.g., NKTR102 in phase III for metastatic breast cancer) and hyaluronic acid nano-complexes (HyACT™ in phase II for colorectal cancer) (Drummond et al. (2006) *Cancer Res.* 66: 3271-3277; Khalid et al. (2017) *Expert Opin. Drug Deliv.* 14: 865-877; Li et al. (2015) *Funct. Mater.* 25: 788-798; Li et al. (2016) *Theranostics,* 6: 1393-1402; Liu et al. (2016) *ACS Nano,* 10: 2702-2715; Luo et al. (2015) *Nanomedical Engineering: Shaping Future Nanomedicines: Nanomedical Engineering.* Wiley Interdiscip. Rev. Nanomed. Nanobiotechnol. 2015, 7, 169-188; Pelaz et al. (2017) *ACS Nano,* 11: 2313-2381; Wang et al. (2012) *Annu. Rev. Med.* 63: 185-198; Han et al. (2017) *ACS Nano,* 11: 1281-1291). The liposomal carrier, ONIVYDE® (also known as MM-398 or PEP02), was approved in 2015 for combination with 5-FU/LV as a 2nd-line therapeutic option for patients with metastatic PDAC who progressed after gemcitabine monotherapy, based on an overall survival improvement of ~2 months (Chiang et al. (2016) *Expert Opin. Pharmacother.* 17: 1413-1420; Passero et al. (2016) *Anticancer Ther.* 16: 697-703; Wang-Gillam et al. (2016) *The Lancet,* 387: 545-557). However, this approval was accompanied by a "black box" safety warning from the Food and Drug Administration (FDA), citing the possibility of severe and life-threatening neutropenia (grades 3-4, 27%) and severe diarrhea (grades 3-4, 13%) (Wang-Gillam et al. (2016) *The Lancet,* 387: 545-557). Although ONIVYDE® also demonstrated antitumor efficacy and improved safety in a subcutaneous CRC model in nude mice (Drummond et al. (2006) *Cancer Res.* 66: 3271-3277), the advantages of encapsulated drug delivery could not be demonstrated in CRC patients in a phase II clinical trial, and the effort was abandoned (Chibaudel et al. (2016) *Cancer Med.* 5: 676-683). Nonetheless, ONIVYDE® is currently being tested in variety of solid tumor types, including lung and breast cancer (Zhang (2016) *Onco Targets Ther.* 20: 3001-3007; Wu et al. (2017) *Int. J. Nanomedicine,* 12:5879-5892).

We have recently demonstrated the utility of a first-generation mesoporous silica nanoparticle (MSNP) drug carrier for irinotecan delivery in an orthotopic PDAC model, with improved efficacy and reduced toxicity compared to an in-house liposome (Liu et al. (2016) *ACS Nano,* 10: 2702-2715). MSNPs are excellent carriers due to high biocompatibility, large surface area, tunable particle/pore sizes and tunable surface functionalization (Liu et al. (2016) *ACS Nano,* 10: 2702-2715; Trewyn et al. (2007) *Acc. Chem. Res.* 40: 846-853; Slowing et al. (20080 *Adv. Drug Deliv. Rev.* 60: 1278-1288; Liu et al. (2009) *J. Am. Chem. Soc.* 131:1354-1355; Cauda et al. (2010) *Nano Lett.* 10: 2484-2492; Ashley et al. (2011) *Nat. Mater.* 10: 389-397; He et al. (2011) *Biomaterials,* 32: 7711-7720; He et al. (2011) *J. Mater. Chem.* 21: 5845; Tang et al. (2012) *Adv. Mater.* 24: 1504-1534; Argyo et al. (2014) *Chem. Mater.* 26: 435-451; Zhang et al. (2014) *Adv. Funct. Mater.* 24: 2450-2461; Meng et al. (2015) *ACS Nano,* 9: 3540-3557; Alvarez-Berríos et al. (2016) *J. Chem.* 2016: 1-15; Singh et al. (2017) *ACSAppl. Mater. Interfaces,* 9: 10309-10337). It was also demonstrated that the MSNPs are biodegradable to silicic acid that is eliminated via urinary and fecal secretion in mice (Lu et al. (20100 *Small,* 6: 1794-1805; Huang et al. (2011) *ACS Nano,* 5: 5390-5399; Liu et al. (2011) *Biomaterials,* 32: 1657-1668). Since the improved efficacy of our lipid bilayer (LB)-coated MSNP carrier, a.k.a. silicasome, has been ascribed to improved drug loading capacity and LB stability over the liposome (Liu et al. (2016) *ACS Nano,* 10: 2702-2715), we were interested in testing a next-generation silicasome carrier in a murine orthotopic colon cancer model. The design improvement was necessitated by the demand for an increased production volume for a possible clinical trial as well as expanding the use of the carrier for other disease applications. In addition to redesigning the synthesis of the bare MSNPs by a multi-parametric approach, it was also necessary to develop an ethanol exchange method for coating, the surface of the MSNPs with a LB in light of the logistical limitations of using a biofilm encapsulating method. In order to perform the study in a reproducible preclinical CRC model, we also developed a rigorous and reproducible orthotopic tumor chunk model in mice. Our data will show that the improved pharmacokinetics (PK) and tumor irinotecan levels of the silicasome is accompanied by increased efficacy compared to free drug or ONIVYDE®. We will also show that the silicasome substantially reduces bone marrow and GI toxicity compared to other treatment modalities. We further confirmed that the next generation silicasomes outperforms ONIVYDE® in an orthotopic PDAC model.

Results

Customized Design of the Irinotecan Silicasome for Comparative Studies

In order to streamline silicasome production for a comprehensive series of comparative studies in orthotopic animal models other than PDAC, it was necessary to scale up the synthesis of the particles by eliminating the use of a lipid biofilm method to coat the particles (Liu et al. (2016) *ACS Nano,* 10: 2702-2715; Meng et al. (2015) *ACS Nano,* 9: 3540-3557). Since the surface area of the lipid biofilm is a limiting factor for synthesizing large particle batches (as explained in supplementary data and FIG. 15, panels A-C), it was necessary to substitute this procedure by a custom-designed approach that uses an ethanol exchange procedure as described in FIG. 9 (Id.).

Figure 9:
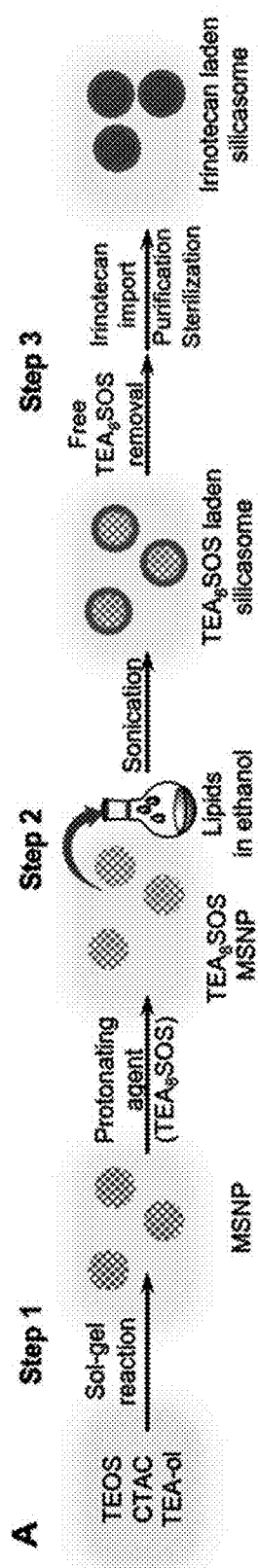
FIG. 9, panels A-E, illustrates development of a custom-designed irinotecan silicasome nanocarrier. Panel A) Schematic to show the different steps for developing the irinotecan nanocarrier, namely: (1) bare mesoporous silica nanoparticle (MSNP) synthesis and purification, (2) lipid coating of the particles containing the soaked-in trapping agent, triethylammmonium sucrose octasulfate ($TEA_8SOS$); and (3) remote loading of irinotecan by a proton gradient (generated by the trapping agent), followed by purification and sterilization. Panel B) The final product, the Ir-silicasome, is comprised of a MSNP core that contains a large packaging space for irinotecan, which is stably entrapped by a lipid bilayer (LB). The LB contains a PEG attachment to improve colloidal stability and circulatory half-life. Panel C) Schematic to show the custom-designed procedure for surface coating by an alcohol-exchange method. Lipids are dissolved in ethanol as described in the online data section FIG. 15. This ethanol suspension is rapidly mixed with TEA8SOS laden particles and sonicated, which leads to the lipids assembling on the particle surface, and rapid sealing of the pores. Panel D) The integrated synthesis process, with precise control of temperature, stirring speed, and addition of the precursor materials at optimal ratios, is capable of producing 18 L batches that contain ~100 g of particles, as described online. The table shows the physicochemical properties of the purified bare MSNPs. Panel E) CryoEM visualization of the Ir-silicasome and ONIVYDE®. The final Ir-silicasome product contains an irinotecan (free base) concentration of 4.3 mg/mL, which was dispensed in smaller volumes in glass containers. The table summarizes the comparative physicochemical properties.
Figure 15:
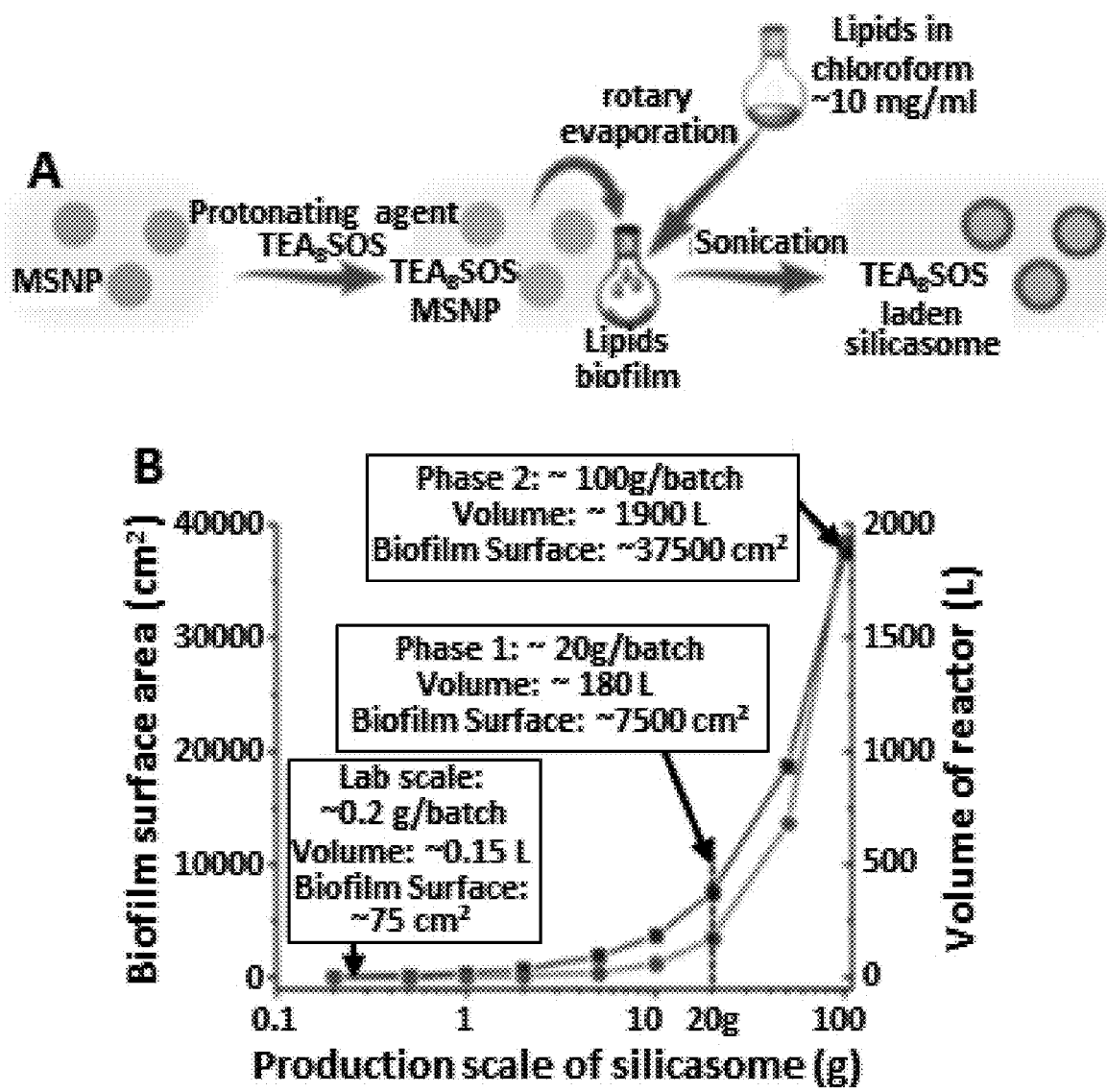
FIG. 15, panels A-E, illustrates customized development of the Ir-silicasome, allowing larger batch production by using an ethanol-exchange method for the lipid bilayer (LB) coating. Panels A and B) Our previous approach of rapid sealing of MSNP pores through sonication of a biofilm becomes a limiting factor when synthesizing larger particle batches.[1] The biofilm protocol, which utilizes lipid suspension in chloroform at −10 mg/mL, forms a −3 mg/cm2 lipid film with a 20-30 m thickness (Meng et al. (2015) *ACS Nano*, 9: 3540-3557). The blue line and red lines in the graphic show the theoretical calculation of the required biofilm surface area and reactor volume for making incremental silicasome batch sizes. For instance, if linearly scaled, this would require, a ~37,500 cm2 lipid biofilm surface area to coat 100 g MSNP in a 1,900 L flask container. Panel C) Making use of a more concentrated lipid suspension is also challenging because it results in the formation of a biofilm that is too thick and heterogeneous for the task at hand. This leads to incomplete lipid coating of the MSNP surface, as shown in the cryoEM picture. Panel D) Bein et al. have previously shown, the use of a solvent-exchange method containing ethanol for coating of silica particle surfaces at a low particle working concentration (~1.25 mg/mL) (Cauda et al. (2010) *Nano Lett*. 10: 2484-2492). We developed an improved alcohol-exchange method for coating the MSNP surfaces with a simplified process that can work at particle concentrations up to 40 mg/mL. This approach involves the direct introduction of an aqueous suspension of MSNP particles into a concentrated lipid solution in ethanol, followed by controlled energy input through probe sonication. The proposed mechanism of coating is the assembly of the suspended lipid monomers onto on the surfaces of the MSNPs as they are being introduced as an aqueous suspension into the solution (FIG. 9, panel D) (Hohner (2010) *Biointerphases*, 5: 1-8). This approach is advantageous from the perspective that: (i) cryoEM visualization shows complete surface coating of the MSNP by the LB lipid coating (similar to the biofilm approach) (Liu et al. (2016) *ACS Nano*, 10: 2702-2715), (ii) the ethanol exchange method avoids the use of highly toxic chloroform, and (iii) the lipid coating procedure can be used with either conventional probe sonication approach or through the use of a flow cell sonication approach. Panel E) Collectively, the newly developed alcohol-exchange method dramatically reduced the production volume by ~200 fold compared to the biofilm method. It allowed us to apply lipid coating to incremental batch sizes, ranging from a few hundred mg up to a size of 100 g.
Figure 16:
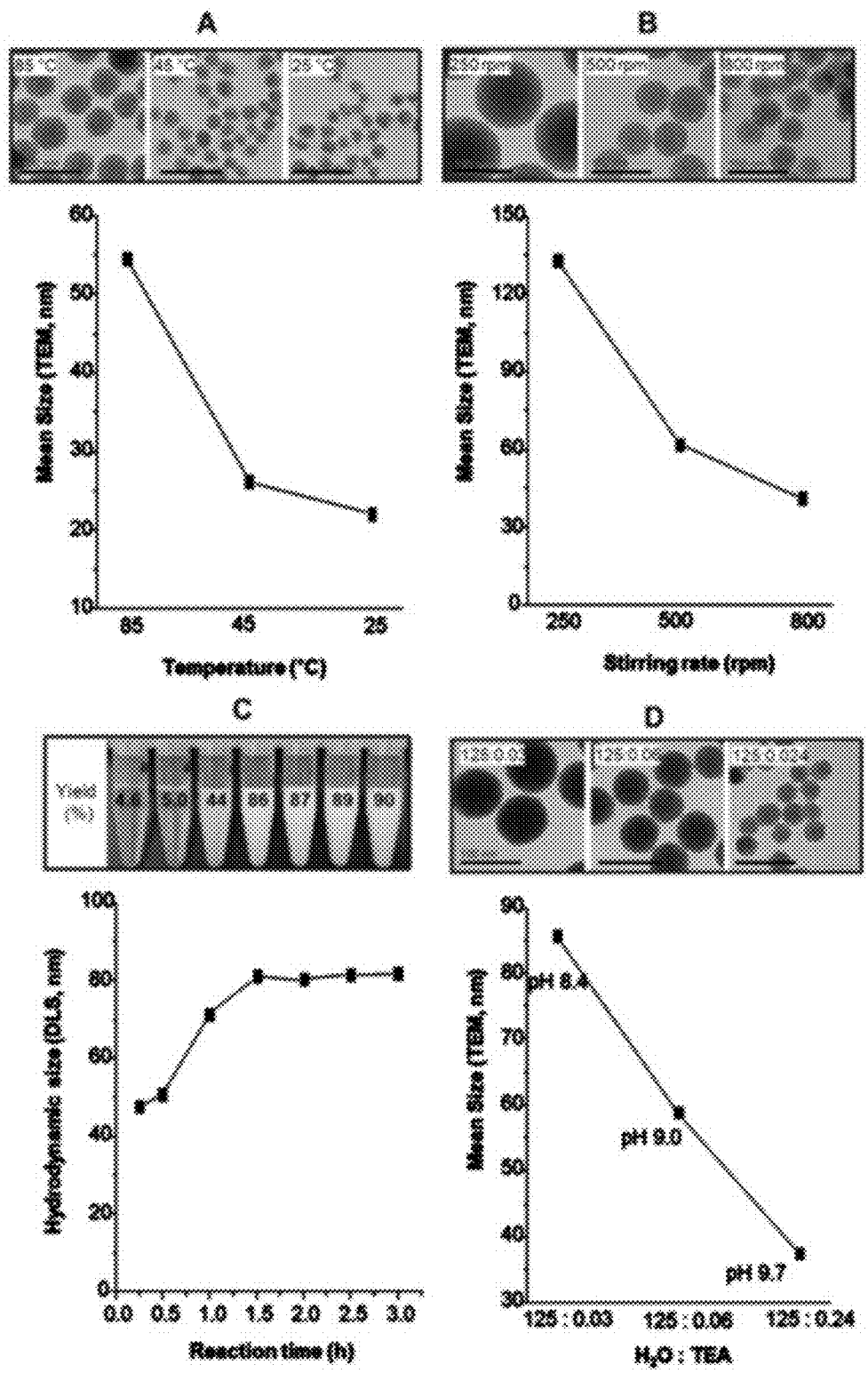
FIG. 16, panels A-F, shows examples of adjusting the sol-gel parameters to optimize the large-scale MSNP synthesis by controlling: temperature (panel A), stirring speed (panel B), reaction time (panel C), concentration of the base catalyzer triethanolamine (TEA) (panel D), concentration of the templating agent cetyltrimethylammonium chloride (CTAC) (panel E), and amount of silica precursor tetraethyl orthosilicate (TEOS) in the sol-gel synthesis (panel F). The integrated use of these tunable parameters provided a means of optimizing large scale synthesis of MSNPs.
Figure 17:
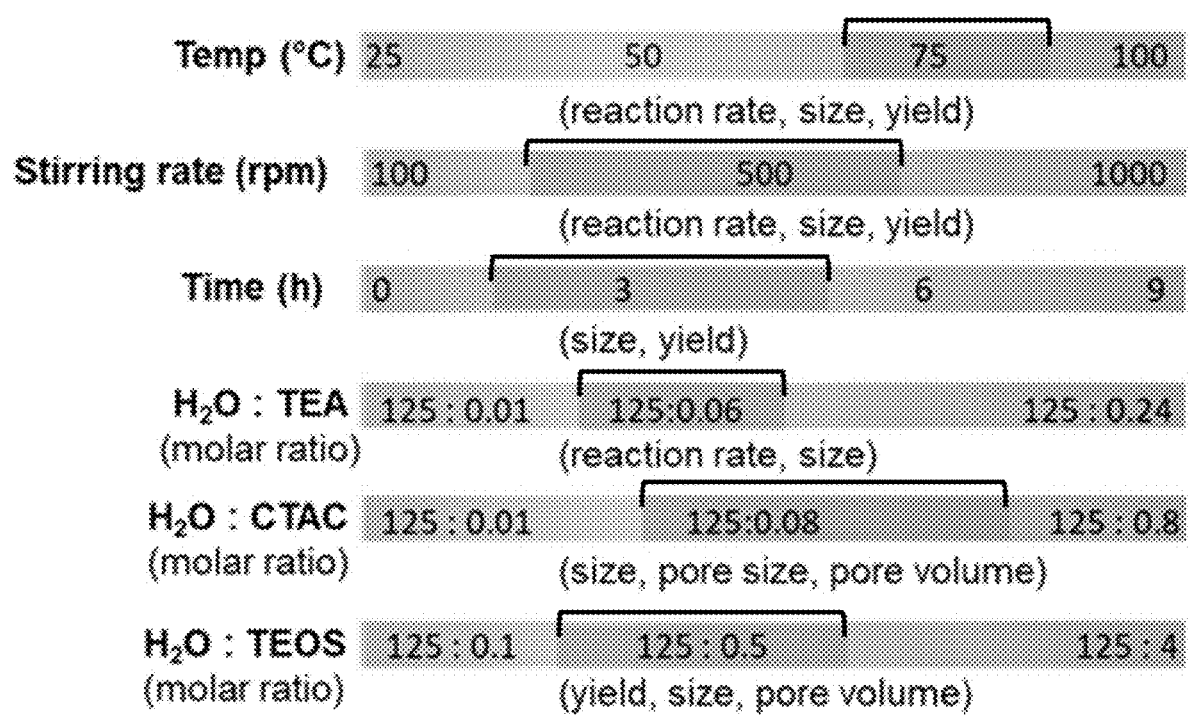
FIG. 17. Utilizing ~70 rounds to optimize MSNP synthesis through a multi-parameter approach, we arrived at a preferred range for each parameter (see brackets) in the synthesis of an ~100 g per batch of bare MSNP in a reaction volume of 18 L. This provides a guideline for the integrated use of multiple MSNP synthesis parameters in tuning the desired MSNP properties, e.g., particle size, morphology, uniformity, pore structure, surface area, pore volume and yield.
Figure 18:
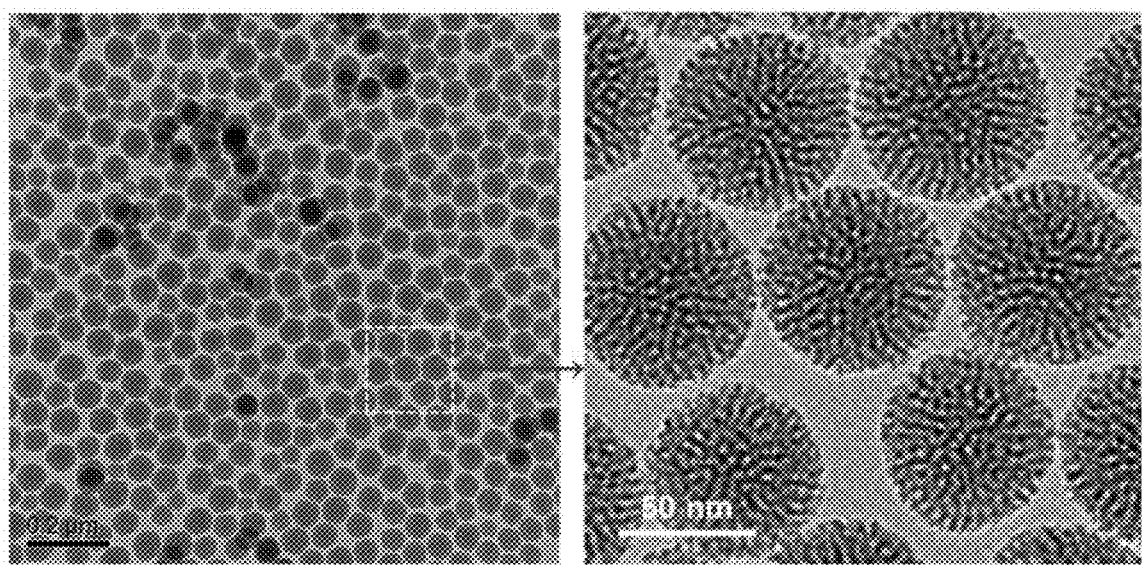
FIG. 18 shows TEM images of bare MSNP sample synthesized in an ~100 g batch. This batch was prepared in a ~18 L reaction volume as shown in FIG. 9, panel D.
Figure 19:
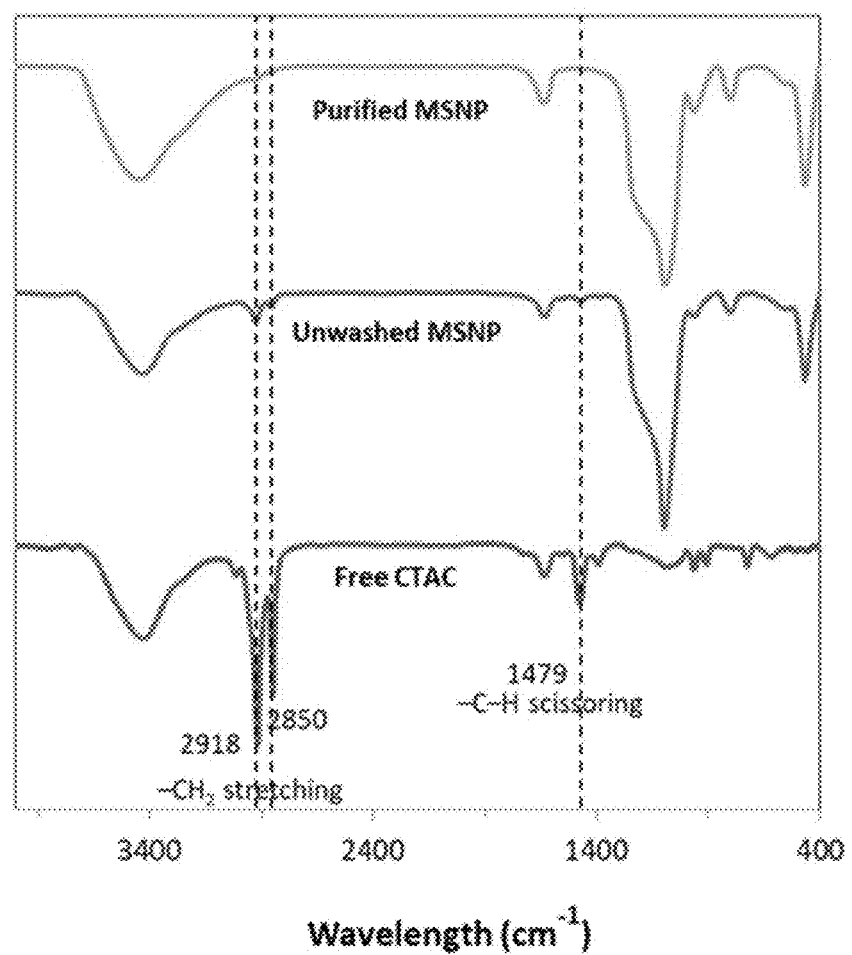
FIG. 19. Besides HPLC quantification, FTIR spectra were used to confirm the effective removal of surfactant (CTAC) before (middle line) and after the use of a series of repetitive washing steps (top line). Free CTAC (bottom line) was used as a control. The major peaks representing CTAC, i.e. the peak for —$CH_2$ stretching (2918 cm-1) and the peak for —C—H scissoring (1479 cm-1), are highlighted by dotted lines.
Figure 20:
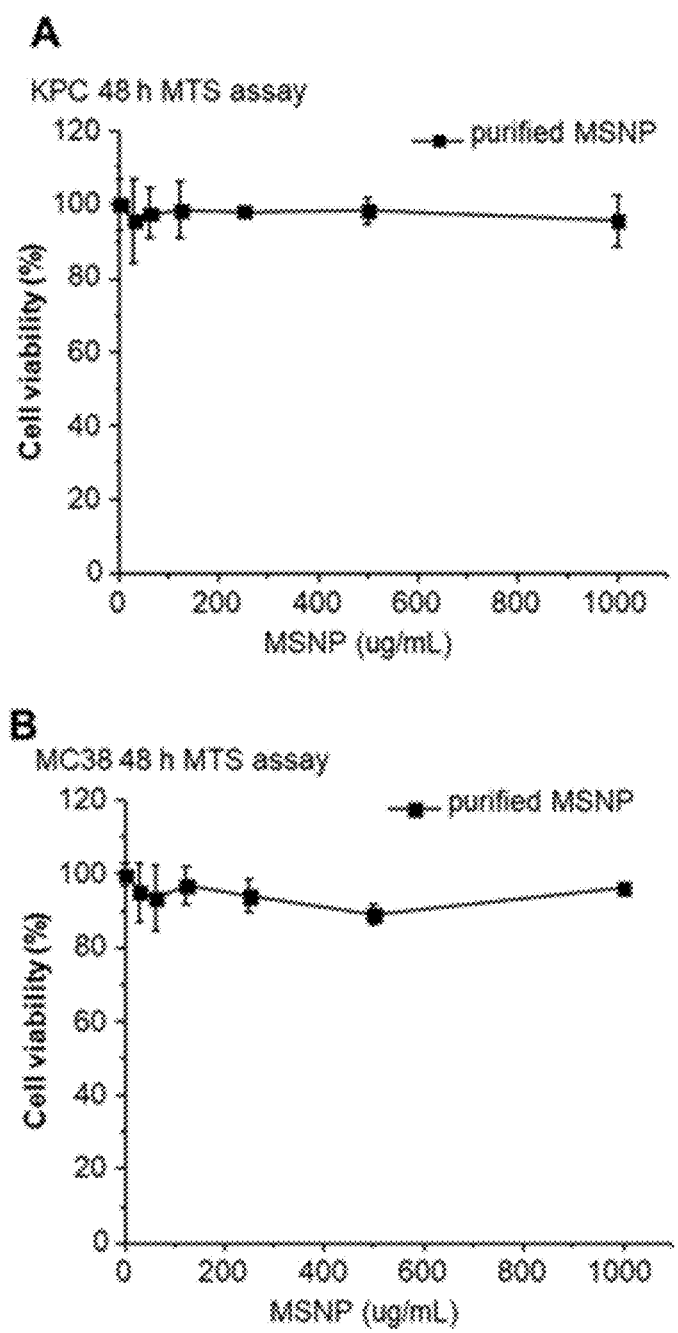
FIG. 20, panels A and B, illustrate cell viability testing, using an MTS assay, to demonstrate the absence of toxicity in KPC (panel A) and MC38 (panel B) cell lines, exposed to the purified bare MSNPs at concentrations up to 1,000 μg/mL for 48 h (n=3, data represent mean±SD).
Figure 21:
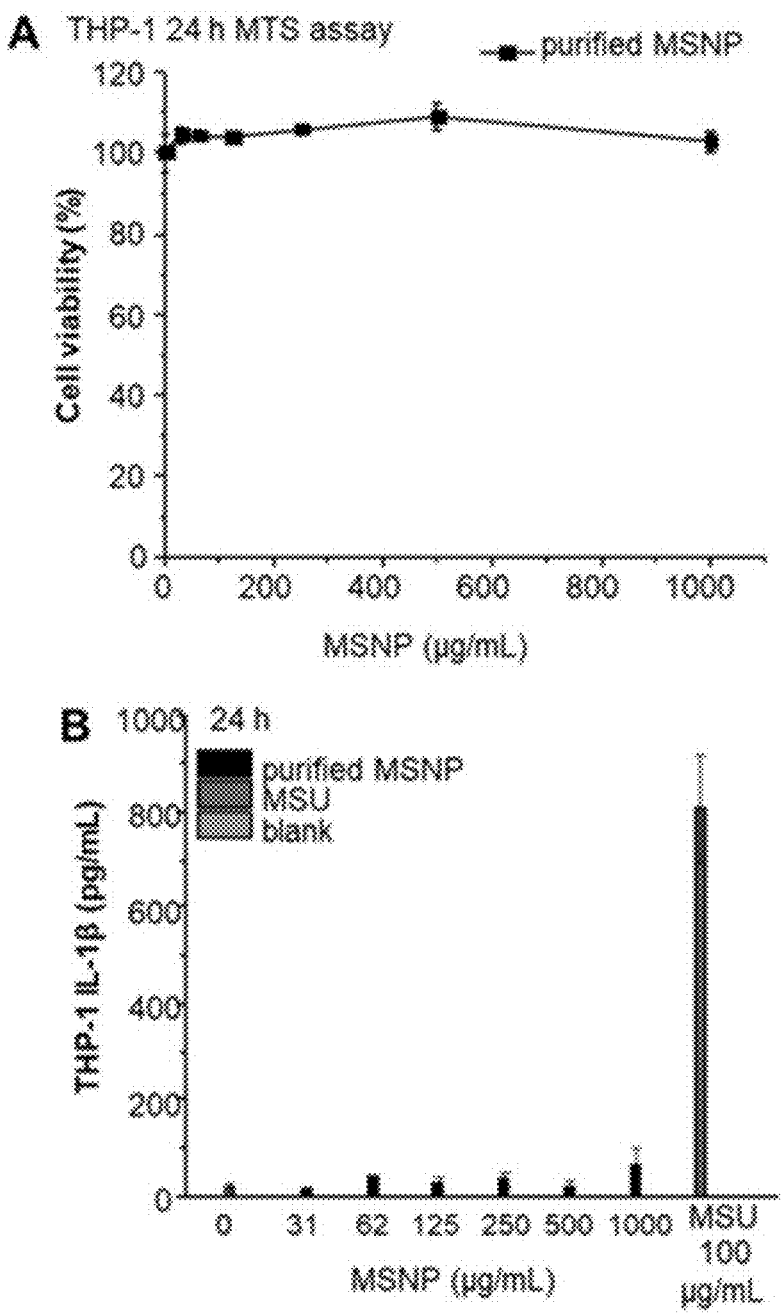
FIG. 21. Panel A) MTS assay, demonstrating the lack of cytotoxicity of purified bare MSNP, using a concentration up to 1,000 μg/mL over 24 h in THP-1 cells. THP-1 cells are useful for studying IL-13 production, which can be triggered by CTAC (information provided by the NCL at NCI). Panel B) ELISA assay, demonstrating a lack of release of IL-113 cytokine from THP-1 cells over the same concentration range as in panel A. 100 μg/mL monosodium urate (MSU) was used as a positive control. n=3, data represent mean±SD. It is also important note that previous testing demonstrated that the coated MSNPs are devoid of biohazard, as determined by elaborate in vivo studies for biocompatibility, biodegradability, and bio-elimination of degraded silica (Singh et al. (2017) *ACS Appl. Mater. Interfaces*, 9: 10309-10337; Slowing et al. (2008) *Adv. Drug Deliv. Rev.* 60: 1278-1288; Tang et al. (2012) *Adv. Mater.* 24: 1504-1534). We have also previously demonstrated that MSNP synthesis under low temperature conditions do not lead to the formation of highly energetic and strained 3-member siloxane rings that serves as the basis for biopersistent fumed silica toxicity (Hecht (1998) *Oncology,* 12: 72-78).

The ethanol exchange method involved the direct introduction of the bare MSNP, suspended in an aqueous solution, into a concentrated ethanol-dissolved lipid solution, followed by sonication (FIGS. 9, panel C and 15, panels D-E) (Cauda et al. (2010) *Nano Lett.* 10: 2484-2492; Hohner et al. (2010) *Biointerphases,* 5: 1-8). This approach allowed us to increase the LB coated batch size from a few hundred milligrams up to ~100 g batch sizes (FIG. 15, panel E). Increased batch sizes also demanded optimization of the sol-gel reaction parameters for MSNP synthesis, as described in FIGS. 2, 16, and 17. This involved a multi-parameter design process in which the reaction temperature, reaction time, stirring speed and the ratio of silica precursor (tetraethyl orthosilicate, TEOS) vs. the organic base (triethanolamine, TEA-ol) and templating agent (cetyltrimethylammonium chloride, CTAC) were varied in a combinatorial fashion. After experimenting with ~70 reaction conditions in an iterative design process, it was possible to accomplish ~100 g batch sizes in ~18 L reaction volume (FIG. 9, panel D). The particles were of the desired particle size, pore structure and size, surface area and pore volume as shown in FIGS. 9, panel D, and 18. We demonstrated that extensive washing in ethanol/HCl and pure ethanol can effectively remove the CTAC, which is capable of exerting cytotoxic effects and activation of pro-inflammatory responses (FIGS. 9, panel D and 19). The absence of cytotoxicity and pro-inflammatory effects of the bare particles were demonstrated in vitro in a variety of cell lines, using particle doses up to 1,000 µg/mL (FIGS. 20 and 21).

Figure 22:
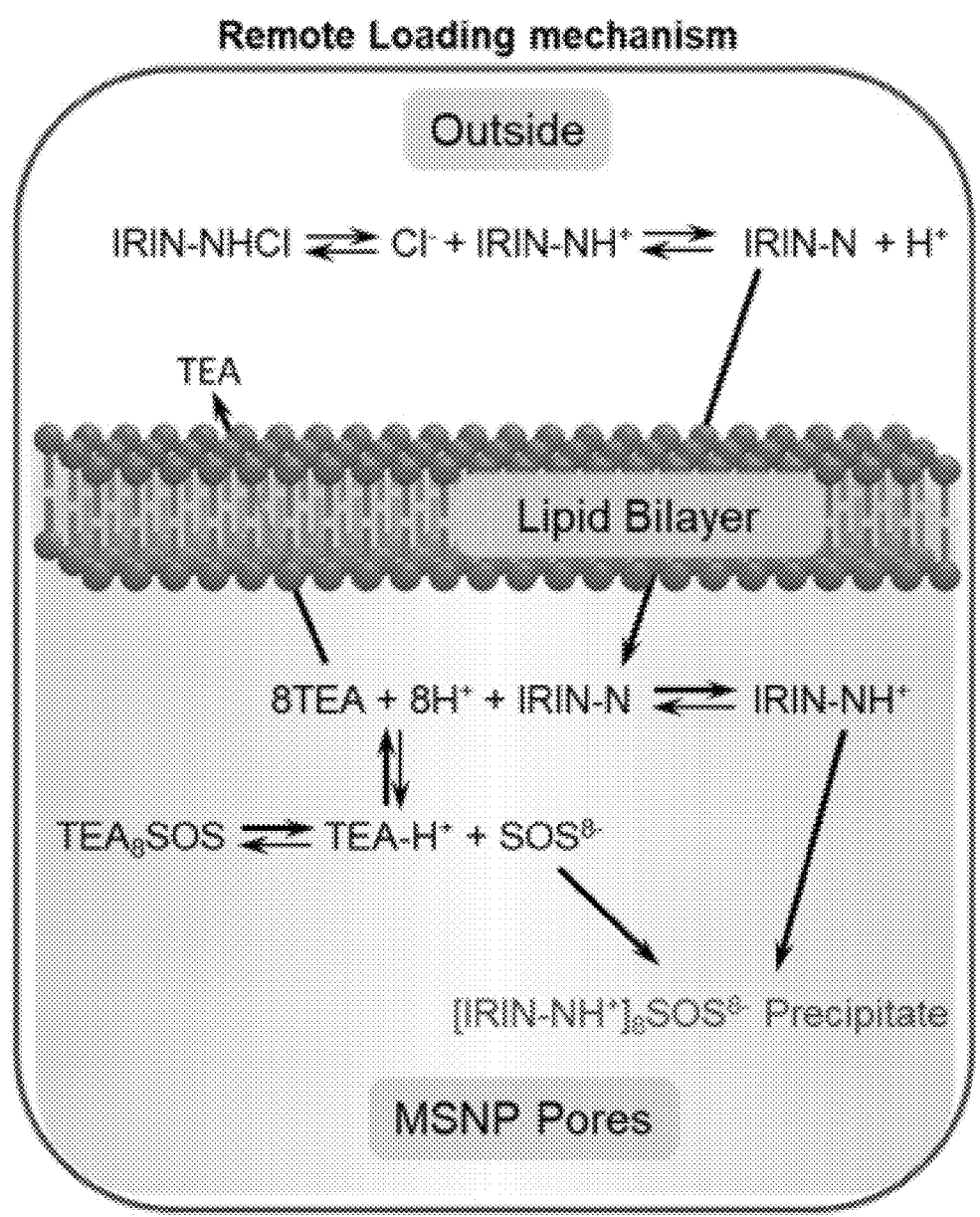
FIG. 22 shows a schematic illustration of the mechanism of irinotecan remote loading. The silicasome trapping agent, TEA8SOS, was incubated in an irinotecan solution, allowing the amphipathic drug to diffuse across the LB. Proton release from the trapping agent converted the encapsulated irinotecan to a hydrophilic derivative that cannot diffuse across the LB. The protonated drug interacts with SOSs- to form a drug precipitate. We have previously identified a comprehensive list of weak basic drugs that can be loaded into silicasome using the proton gradient loading mechanism (Liu et al. (2016)*ACS Nano,* 10: 2702-2715). The general characteristics of these cargo molecules include properties such as: (i) organic molecular compounds that include primary, secondary, tertiary, or quaternary amine(s); (ii) a pKa <11 to allow protonation and entrapment behind the LB; (iii) water solubility ranging from 5 to 25 mg/mL and amphipathic characteristics that allow diffusion across the LB; (iv) an octanol/water partition coefficient or log P value of −3.0 to 3.0; (v) a molecular weight that is compatible with the geometric size of the MSNP pore size (2-8 nm).

To prepare a 20 g batch of silicasomes for the performance of experimentation in this communication, we followed the steps outlined in FIG. 9, panel A. Briefly, MSNP (40 mg/mL) was incubated in a solution containing the trapping agent triethylammmonium sucrose octasulfate (TEA$_8$SOS), and then mixed with 500 mg/mL lipid ethanol solution at the ratio of 1:10 (v/v, ethanol: H$_2$O). The remaining steps for making the drug-laden particles included the removal of the free TEA$_8$SOS, remote irinotecan loading, purification and sterilization as described in the methods section (FIG. 9, panel A). A schematic depicting the principles for remote drug loading is shown in FIG. 22. The final product was referred as the "Ir-silicasome". Physicochemical characteristics of Ir-silicasome vs ONIVYDE® are summarized in FIG. 9, panel E. This includes the hydrodynamic size measurement by DLS, which demonstrated a hydrodynamic size of ~110 nm and ~130 nm for Ir-silicasome and ONIVYDE®, respectively. The Ir-silicasome sample was also visualized by CryoEM, and compared to the morphology of ONIVYDE® (FIG. 9, panel E). This allowed us to obtain primary particle sizes and standard deviation by viewing at least 100 randomly selected particles in each of the Ir-silicasome and ONIVYDE® formulations. CryoEM data showed primary sizes of 78.0±6.8 nm for the silicasome and 67.1±19.7 nm for ONIVYDE®, respectively. CryoEM also revealed that although the silicasome particles were of uniform size (FIG. 9, panel E), ONIVYDE® contained a mixture of large and small liposomal vesicles of uni- or multi-lamellar composition. This is reflected by the coefficient of variation index (CV %) of 29.4% for ONIVYDE® vs. 8.7% for the Ir-silicasome (Rice et al. (2013) *Metrologia*, 50: 663-678). Other physicochemical characteristics, including loading capacity, hydrodynamic size, zeta potential, endotoxin level and sterility, are shown in FIG. 9, panel E.

Figure 23:
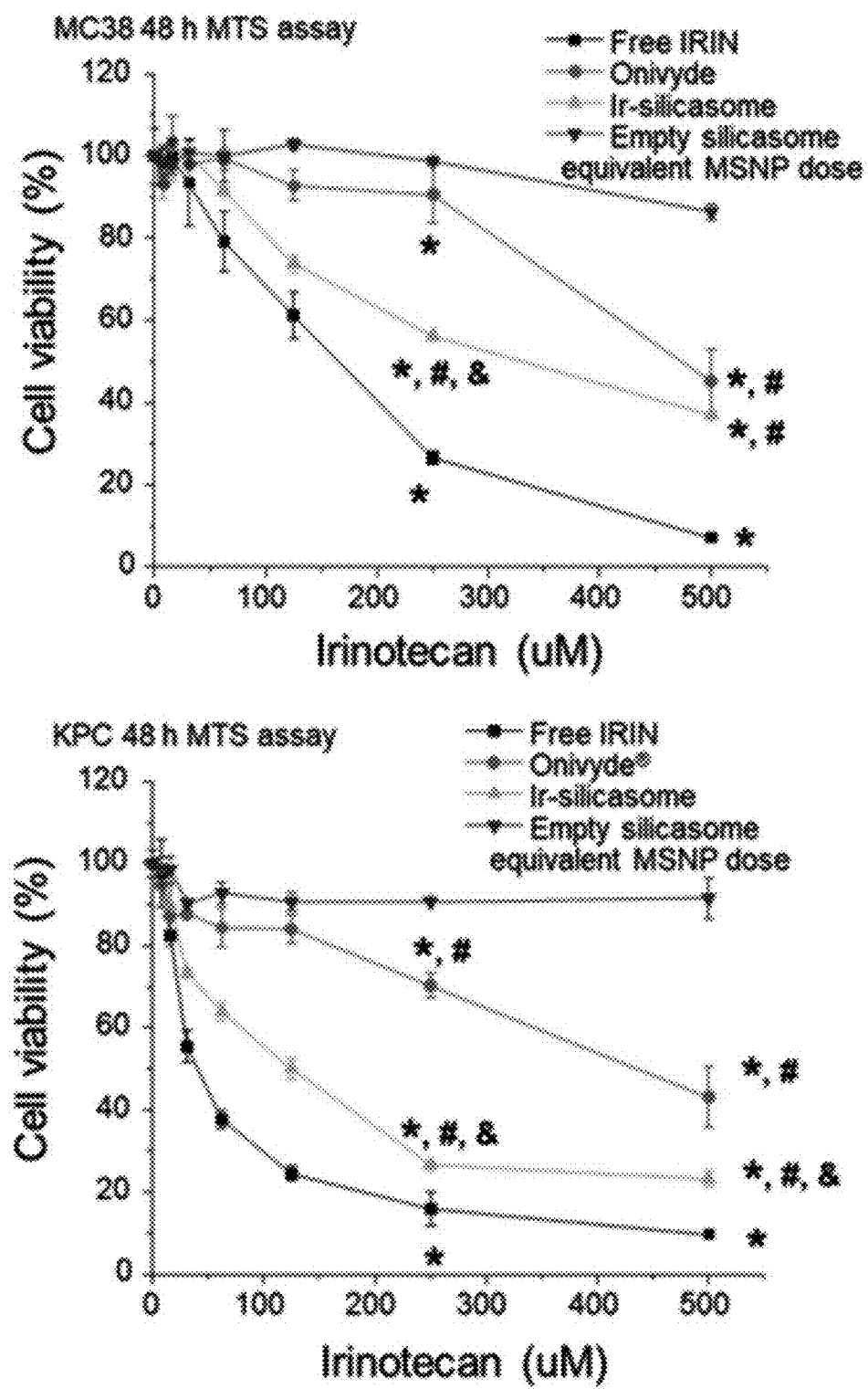
FIG. 23. The in vitro killing effects of different irinotecan formulations were evaluated by an MTS assay in both colon cancer MC38 (top left) and pancreatic cancer KPC (bottom right) cell lines, exposed to the indicated irinotecan concentrations. The empty silicasome did not show obvious cytotoxicity. n=3, data represent mean±SD. $*p<0.05$ compared to empty silicasome; $\#p<0.05$ compared to free IRIN; $\&p<0.05$ compared to ONIVYDE® (1-way ANOVA followed by a Tukey's test). The free drug exhibited the most robust killing effect, a finding that is frequently seen in comparative analyses of free vs encapsulated chemotherapy agents in vitro (Eliaz et al. (2001) *Cancer Res.* 61: 2592-2601; Alyane et al. (2016) *Saudi Pharm. J.* 24: 165-175).

The cytotoxic potential of the newly synthesized Ir-silicasome was tested by an MTS assay in a variety of cancer cells. The demonstrated that the silicasome could provide increased MC38 and KPC cell killing compared to the liposomal irinotecan carrier (FIG. 23). The free drug exhibited the most robust killing effect, a finding that is frequently seen in comparative analyses of free vs encapsulated chemotherapy agents in vitro (Eliaz et al. (2001) *Cancer Res.* 61: 2592-2601; Alyane et al. (2016) *Saudi Pharm. J.* 24: 165-175). One explanation is that the free drug is more rapidly taken up into the cytosol while the encapsulated drug carriers need to be internalized, followed by more gradual drug release to the cytosol and the nucleus.

Establishing a Robust Orthotopic Model for Colon Cancer

Figure 10:
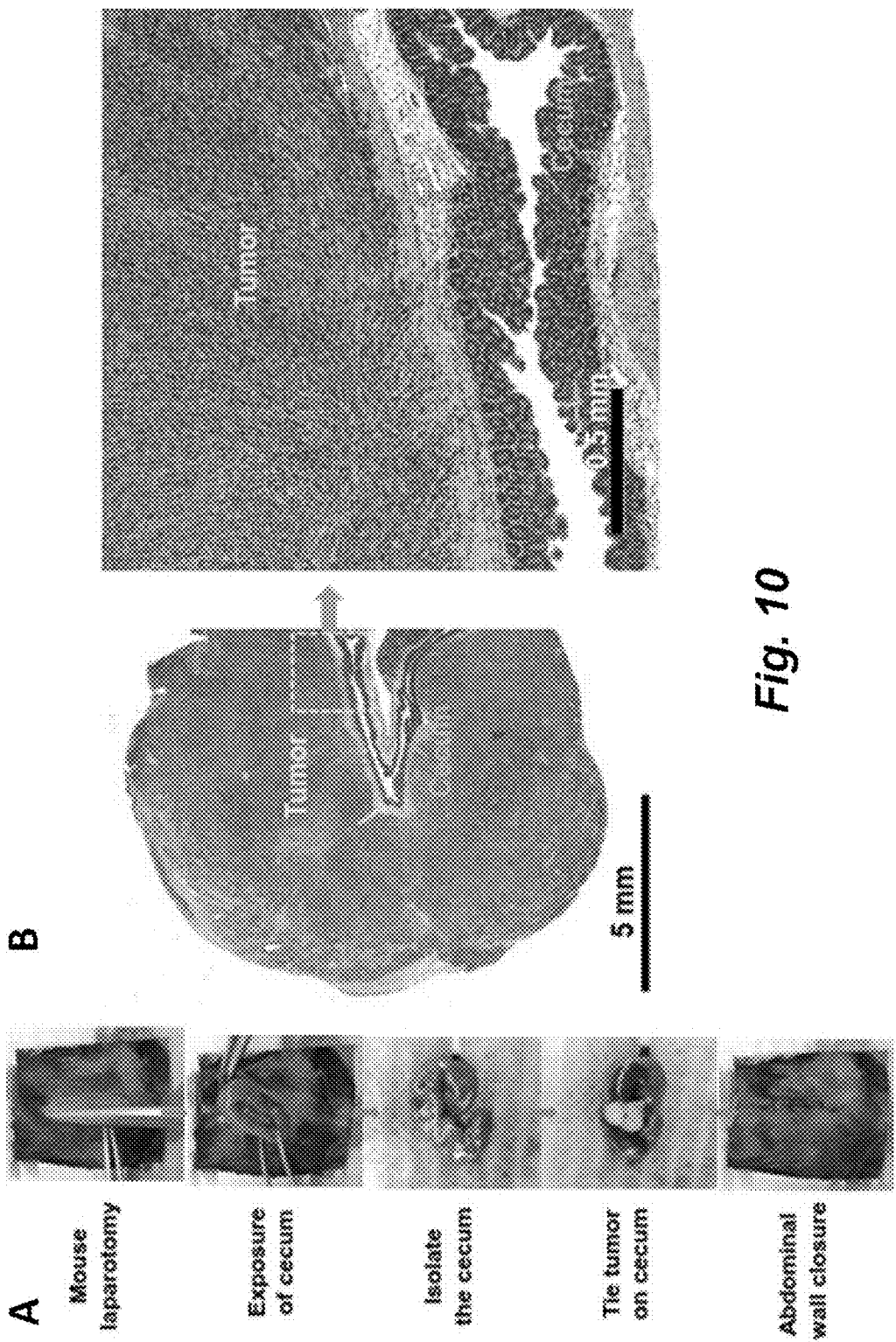
FIG. 10, panels A-D, shows establishment of an orthotopic MC38-luc tumor chuck model in C57BL/6 mice. Panel A) The orthotopic implantation involves minor surgery to place the MC38 tumor chunks on the cecum wall of C57BL/6 mice. Briefly, the tumor chunks were obtained from subcutaneous growing tumors established in C57BL/6 mice. Once the tumor reached ~1 cm in size, the tumor mass was aseptically harvested and cut up into 2-4 $mm^3$ chunks. These tumor chunks were tied onto the cecum wall by absorbable surgical sutures. Panel B) H&E staining to show the growth of the orthotopic tumor in relation to the adjacent normal tissue. Panel C) Live-animal IVIS imaging to monitor the orthotopic tumor growth. The bioluminescence intensity was quantified at the region of interest (ROI) by IVIS Living Image software. Panel D) Example ex vivo IVIS image of the complete gastrointestinal tract of an animal, sacrificed ~3 weeks post tumor chunk implantation. More than 95% of operated mice developed primary tumors, which metastasized to adjacent intestinal tissues and the peritoneum.
Figure 24:
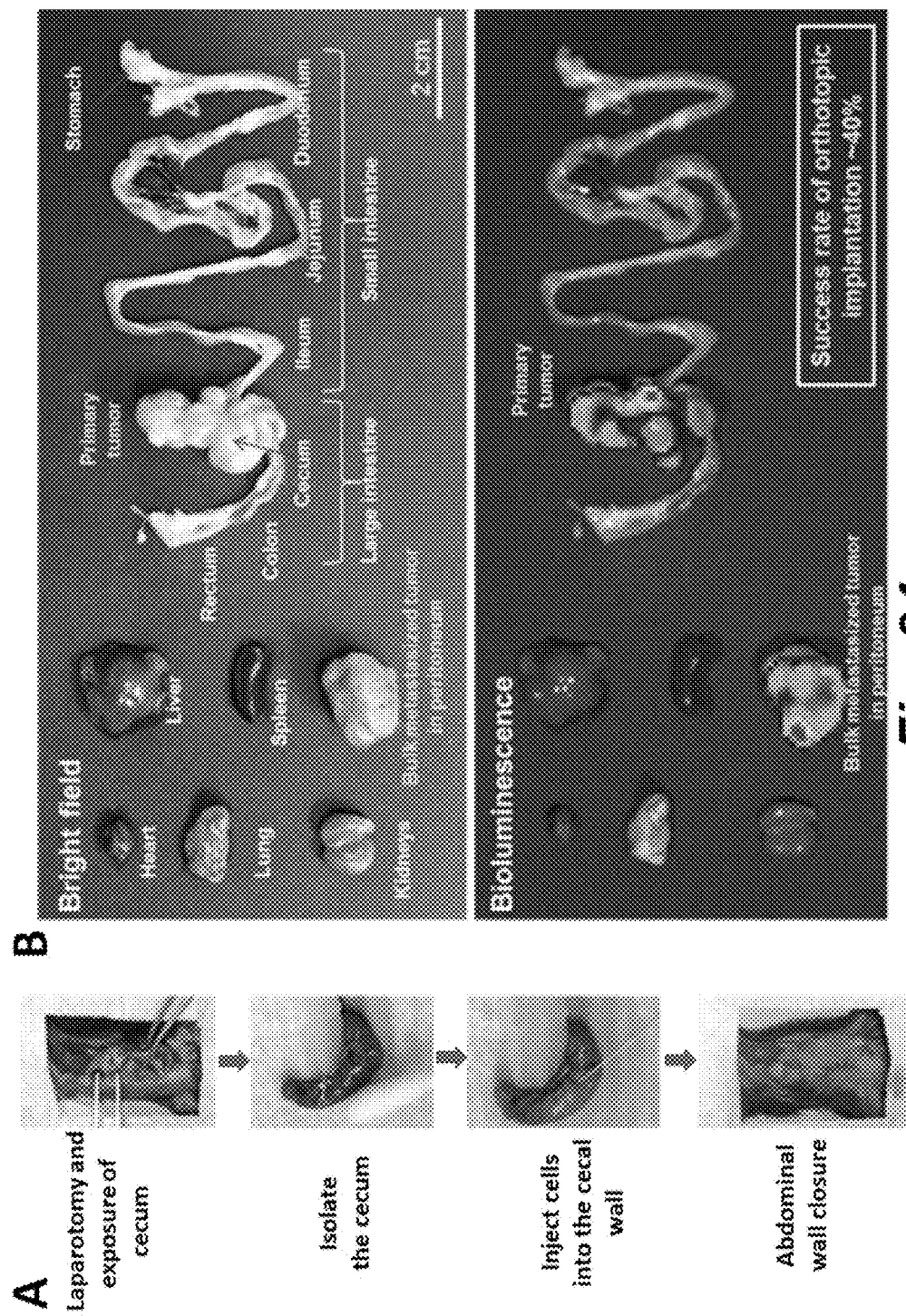
FIG. 24, panels A and B, illustrate characteristics of an orthotopic colon cancer model by injection of MC38-luc cell suspension into the cecum wall. Panel A) The traditional surgical procedure involves injection of luciferase-expressing MC38 cells between the mucosal and the muscularis layers of the cecum wall in C57BL/6 mice. Panel B) While this technique is successful for establishing an orthotopic model that resembles the tumor chunk model, as demonstrated in the above autopsy and IVIS imaging results (~4 wks post-surgery), we could only obtain successful tumor engraftment in ~40% mice. This prompted the development of the tumor chunk model which was successful in 95% of animals in our hands (see FIG. 10).

In order to establish a rigorous orthotopic model for colon cancer, the classic approach of injecting MC38 cells into the wall of the cecum in C57BL/6 mice had to be changed since the procedure was only successful in ~40% of mice in our hands due to uncertainty about the exact depth of orthotopic cell injection (FIG. 24) (McIntyre et al. (2015) *BioEssays,* 37: 909-920). To improve the tumor engraftment rate, we developed an orthotopic model, in which tumor chunks were fastened to the cecum wall by a stitch (Tseng et al. (2007) *Vis. Exp.* 10: 484). The tumor chunks were obtained from subcutaneous growth of MC38 tumors in C57BL/6 mice (FIG. 10, panel A). This approach helped to establish successful orthotopic tumor growth in >95% animals, while also avoiding seepage of bowel content from the cecum to the peritoneum. Hematoxylin and eosin (H&E) staining of a biopsy taken from the primary attachment site demonstrated the presence of orthotopic tumor invasion into the cecal wall (FIG. 10, panel B). Using luciferase-expressing MC38 cells (MC38-luc) to non-invasively monitor orthotopic tumor growth by IVIS imaging, it was possible to discern a primary tumor mass within a week (FIG. 10, panel C), whereupon exponential growth ultimately leads to metastatic spread and the occurrence of ascites, leading to a moribund state within 4 weeks (FIG. 10, panel D).

Pharmacokinetic Profile and Irinotecan Levels in the Orthotopic MC38 Tumors

Figure 11:
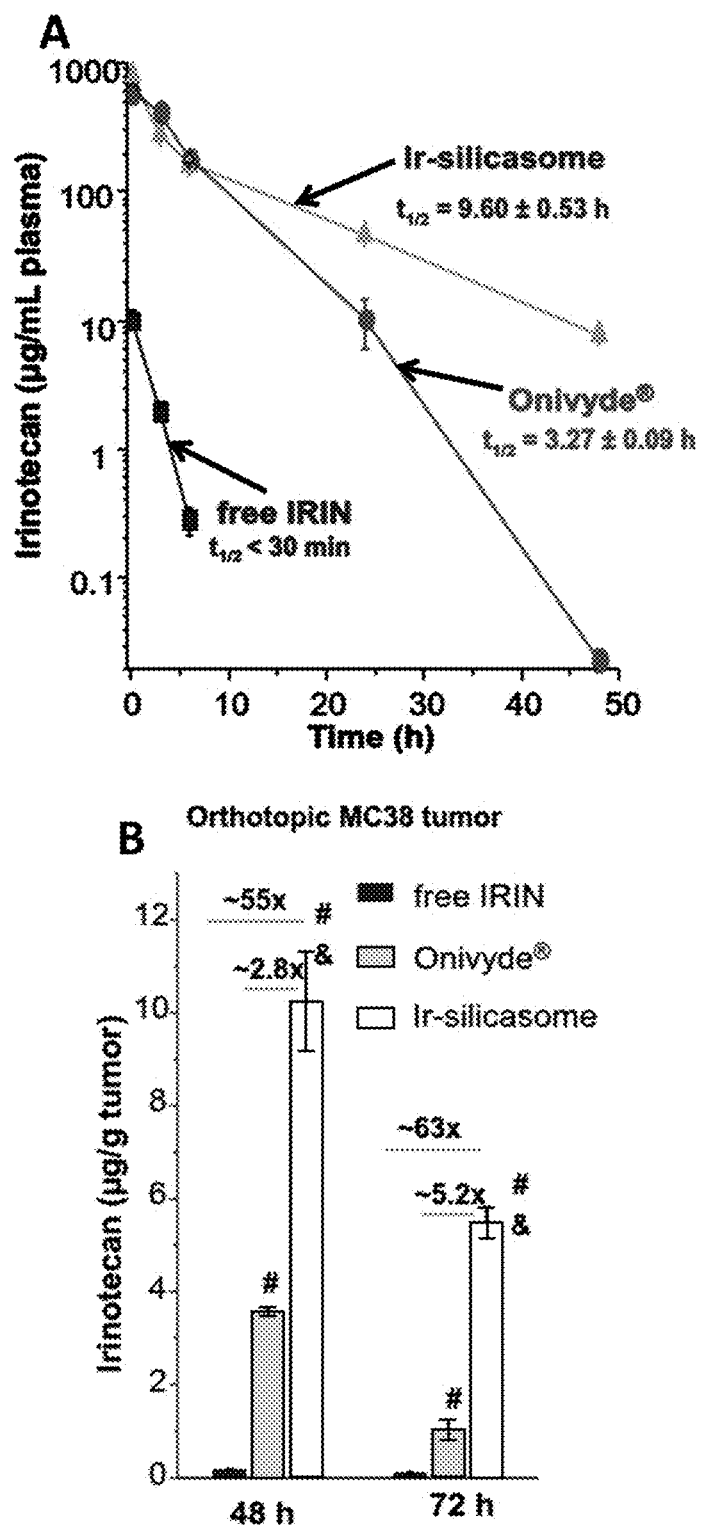
FIG. 11, panels A-E, shows improved PK and tumor irinotecan concentrations using the silicasome carrier for treating orthotopic tumor-bearing mice. Panel A) PK profile after a single IV injection of free drug or the nanocarriers at an irinotecan (IRIN) dose equivalent of 40 mg/kg (n=3). Circulatory t1/2 values were calculated using PKSolver software. Panel B) Drug content at the tumor site after 48 hr and 72 hr in animals receiving an IV injection of 40 mg/kg irinotecan by the different carriers. Panel C) Ex vivo IVIS imaging of tumor-bearing mice receiving IV injection of DyLight680-labeled silicasomes at the identical dose in panel A. Tumor tissue and major organs were harvested at 48 hr. Panel D) ICP-OES was used to quantify the percent injected Si dose (% ID) at the different sites after 48 hr. Panel E) Confocal microscopy to show the intratumoral distribution of the NIR silicasome particles used in the same experiment as in panel C. Color code: Red, NIR silicasome particles; green, blood vessel staining with anti-CD31 antibody; blue, nuclear stained with DAPI. Bars represent 25 m. Data represent mean±SEM. *$p<0.05$ compared to saline; #$p<0.05$ compared to free IRIN; &$p<0.05$ compared to ONIVYDE® (1-way ANOVA followed by a Tukey's test).

The pharmacokinetic (PK) studies were performed in healthy C57BL/6 mice, which received a single intravenous (IV) injection of the silicasome to deliver an irinotecan dose of 40 mg/kg ONIVYDE® and the free drug, used at equivalent doses, were used as controls. A dose of 40 mg/kg was chosen based on literature that this is equal to ~⅔ of the free irinotecan maximal tolerated dose (MTD) in mice (Drummond et al. (2006) *Cancer Res.* 66: 3271-3277; Liu et al. (2016) *ACS Nano*, 10: 2702-2715; Messerer et al. (2004) *Clin. Cancer Res.* 10: 6638-6649). Plasma samples collected at different time points were used to quantify the irinotecan concentration in plasma, using UPLC-MS. The PK data were fitted in a one-compartment model, using PKSolver software (Zhang et al. (2010) *Comput. Meth. Programs Biomed.* 99: 306-314). These calculations demonstrated that the circulatory half-life ($t_{1/2}$) of Ir-silicasome was ~9.6 h compared to ~3.3 h for ONIVYDE® (FIG. 11, panel A). Free irinotecan was rapidly cleared from the circulation, with a $t_{12}$ of <30 min. The detailed PK parameters are summarized in Table 4.

TABLE 4

PK parameters for ONIVYDE ® and the Ir-silicasome in female C57BL/6 mice after a single IV administration (irinotecan: 40 mg/kg). The PK study was performed as described in FIG. 11, panel A.

| Parameter | Unit | ONIVYDE ® | Ir-silicasome |
| --- | --- | --- | --- |
| Cmax | µg/mL | 602.5 ± 38.6 | 792.6 ± 114.9 |
| λz | 1/h | 0.212 ± 0.003 | 0.072 ± 0.002* |
| t½ | h | 3.27 ± 0.05 | 9.60 ± 0.31* |
| AUC 0-t | µg/mL*h | 4299.3 ± 393.4 | 4848.9 ± 286.4 |
| AUC 0-inf | µg/mL*h | 4299.4 ± 393.4 | 4957 ± 284.0 |
| MRT | H | 4.75 ± 0.37 | 9.63 ± 0.57* |
| Vz | (µg)/(µg/mL) | 0.897 ± 0.103 | 2.258 ± 0.201* |
| Cl | (µg)/(µg/mL) | 0.189 ± 0.19 | 0.163 ± 0.010 |

N = 3, data represent mean ± SD,
*p < 0.05 (Student's t-test).
Cmax: maximum plasma concentration; λz: terminal elimination rate; t½: half-life; AUC: area under the curve; MRT: mean residence time; Vz: volume of distribution; Cl systemic clearance.
*indicate statistical significance (p < 0.05)

Please notice that our PK data did not include the measurement of SN-38, which is the active metabolite into which the irinotecan is converted at the tumor site (Mathijssen et al. (2001) *Clin. Cancer Res.* 7: 2182-2194). While published human data from ONIVYDE® has demonstrated that it was possible to detect an SN-38 concentration that was ~7800-fold less than the measurable blood content of irinotecan (i.e., SN-38 $C_{max}$ of ~9.2 ng/mL vs 72 µg/mL for irinotecan) (Chen et al. (2008) *J. Clin. Oncol.* 26: 2565-2565), it was not possible to detect SN-38 in the limited blood volumes that could be obtained from mice (where the lowest level of detection was ~30 ng/mL).

The drug biodistribution to the MC38 orthotopic tumor site was determined by injecting a dose equivalent of 40 mg/kg irinotecan intravenously, followed by animals sacrifice after 48 and 72 h. Drug delivery by the silicasome resulted in a ~55-fold and ~2.8-fold higher drug content at the tumor site compared to free drug and ONIVYDE® at 48 hr, respectively (FIG. 11, panel B).

Figure 25:
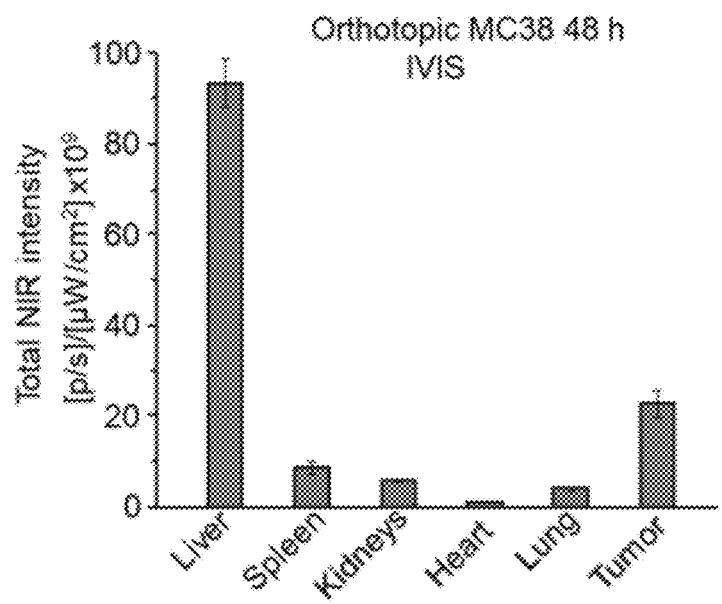
FIG. 25 shows quantitative NIR fluorescence intensity analysis for tumors and organs of animals sacrificed at 48 hr after IV injections of DyLight 680 labeled silicasomes in FIG. 11, panel C. Animals not injected with particles served as the blank for subtracting background tissue autofluorescence. Data represent mean±SEM (n=3).

The comparable increases after 72 h were ~63-fold and ~5.3-fold, respectively (FIG. 11, panel B). Utilizing near infrared (NIR) labeled silicasomes (Liu et al. (2016) *ACS Nano*, 10: 2702-2715; Liu et al. (10'7) *J. Clin. Invest.* 127: 2007-2018), we could also follow carrier biodistribution by IVIS fluorescence imaging of explanted tumor tissue and organs (FIG. 11, panel C). This demonstrated that the particles showed abundant distribution to the primary tumor site, liver and spleen, with some fluorescence associated with the kidneys. A semi-quantitative display of NIR image intensity is shown in FIG. 25. These results were also confirmed by coupled plasma optical emission spectrometry (ICP-OES) to display Si abundance, demonstrating that ~5% of the injected dose (ID) distributed to the orthotopic tumor site after 48 h (FIG. 11, panel D). It was also possible to view the NIR-labeled silicasomes at the tumor site by confocal microscopy (FIG. 11, panel E). We found a heterogeneous particle distribution in the tumor microenvironment, with a relatively high particle density in the vicinity of the $CD31^+$ tumor blood vessels (FIG. 11, panel E). This compatible with the previous demonstration of the micro-heterogeneity of MSNP distribution in pancreatic and breast cancer xenograft tumor sites (Meng et al. (2013) *ACS Nano*, 7: 994-1005; Meng et al. (2013) *ACS Nano*, 7: 10048-10065).

Figure 12:
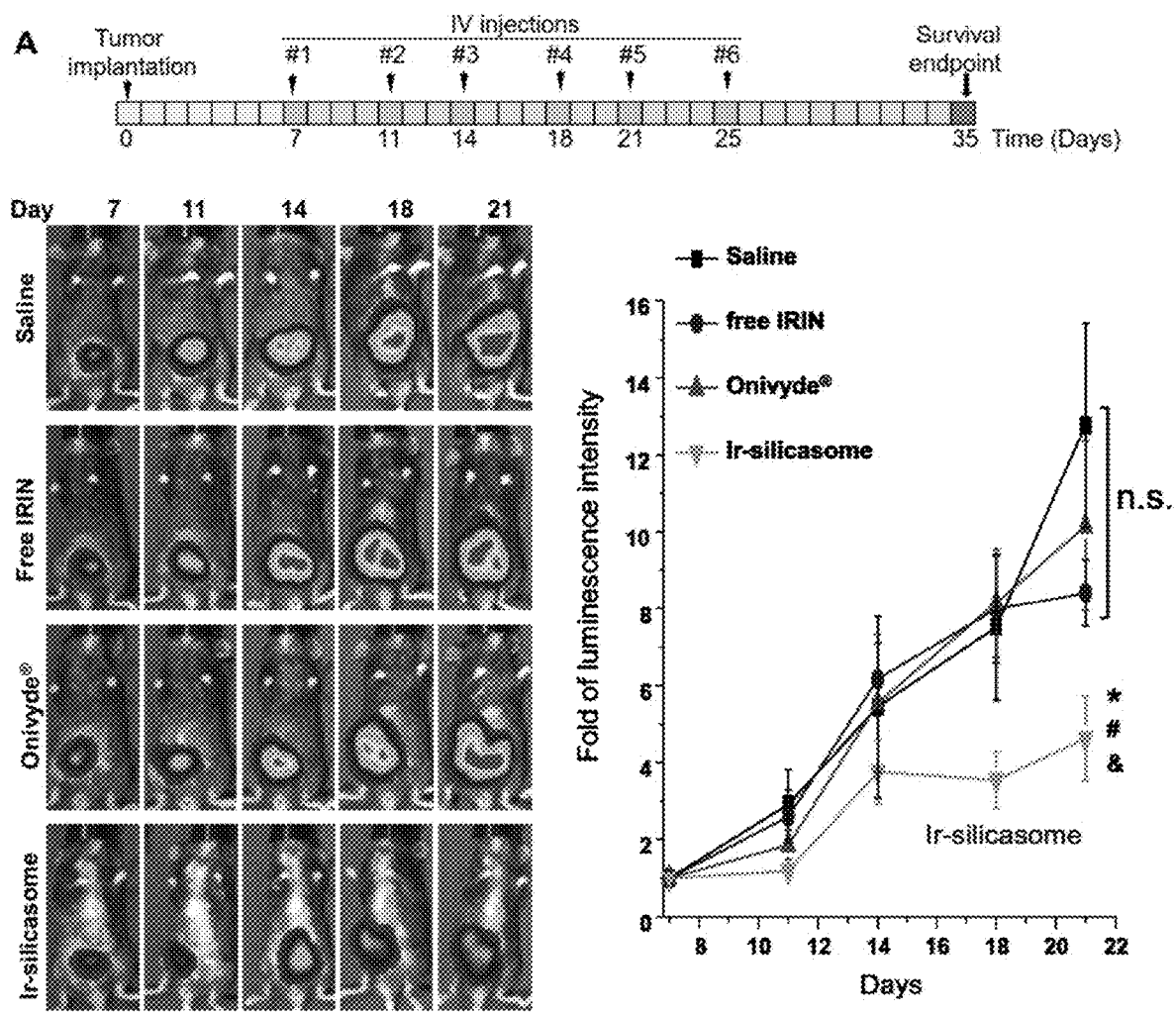
FIG. 12, panels A-D, shows comparative efficacy testing of the Ir-silicasome in the orthotopic MC38 model. Panel A) A survival experiment was performed, in the course of which IVIS imaging was used to compare tumor growth up to day 21, beyond which metastatic peritoneal spread interfered in image detection. MC38 tumor-bearing mice (n=6) received free irinotecan, ONIVYDE® or Ir-silicasome at an irinotecan dose equivalent of 40 mg/kg twice per week for up to six IV administrations. Saline was used as the negative control. Representative images are shown in the left panel, with quantitative data display of bioluminescence intensity at the ROI, using IVIS software. Panel B) Kaplan-Meier plots to display the survival rate of the different animal groups in the same experiment (*$p<0.05$, Log Rank test). Panel C) In a separate experiment, the tumor-bearing mice received similar doses as in panel A twice a week for a total of four administrations (n=3). Animals were sacrificed at 24 hr after the last treatment (day 18). Orthotopic tumors were collected and weighed. Panel D) IHC analysis of cleaved caspase-3 (CC-3) expression in the orthotopic tumors harvested in panel C. Quantification of the number of $CC-3^+$ cells, using ImageScope software (right panel). Bar=100 μm. Data represent mean±SEM; *$p<0.05$ compared to saline; #$p<0.05$ compared to free IRIN; $p<0.05$ compared to ONIVYDE®. "n.s." indicates$p>0.05$.

Prolonged Animal Survival in the CRC Orthotopic Tumor Model During Treatment with the Ir-Silicasome Treatment efficacy and animal survival were determined in the orthotopic tumor model by IV injection of an irinotecan dose equivalent of 40 mg/kg free drug, Ir-silicasomes or ONIVYDE® every third or fourth day, as shown in FIG. 12, panel A (upper panel). Tumor growth (n=6) was monitored by IVIS imaging up to day 21, where the appearance of peritoneal metastases and ascites interfered in quantifying the bioluminescence intensity (FIG. 12, panel A, bottom left) (Terracina et al. (2015) *J. Surg. Res.* 199: 106-114). Quantitative display of the imaging data was shown in the bottom right panel in FIG. 12, panel A, which demonstrated clear tumor inhibition by the Ir-silicasome. Noteworthy, no significant tumor growth inhibition was seen in mice receiving identical doses and frequency of free drug or ONIVYDE® administration. Continued daily monitoring of the animals to the point of moribund health status or spontaneous animal death, allowed us to generate comparative survival data (Liu et al. (10'7) *J. Clin. Invest.* 127: 2007-2018; Olive et al. (2009) *Science*, 324: 1457-1461). Data expression by Kaplan-Meier plots and Log-rank testing (SPSS 19.0 software) (Kuriyama et al. (1999) *Int. J. Oncol.* 14: 321-326; Kleinbaum & Klein (2012) Kaplan-Meier Survival Curves and the Log-Rank Test. In *Survival Analysis*; Springer New York: New York, NY, pp 55-96) demonstrated a statistically significant survival benefit (p <0.05) for the Ir-silicasome as compared to saline, free irinotecan, and ONIVYDE® (FIG. 12, panel B). However, no significant survival benefit was seen for free irinotecan or ONIVYDE®.

A repeat of the efficacy experiment (n=3) to harvest tumor tissue 24 h after the $4^{th}$ IV injection, allowed us to generate quantitative data for tumor weight and histological characteristics (FIG. 12, panel C). This demonstrated a significant reduction in tumor weight for the silicasome vs. free drug or ONIVYDE® (FIG. 12, panel C). Moreover, we also confirmed using immunohistochemistry (IHC) staining for cleaved caspase-3 (CC-3), differences in the rate of apoptosis amongst the treatment groups (FIG. 12, panel D). Thus, while the rate of apoptosis was ~16% for the Ir-silicasome treated group, the values were ~2.5% and ~6.5% for free drug and ONIVYDE®, respectively.

Figure 13:
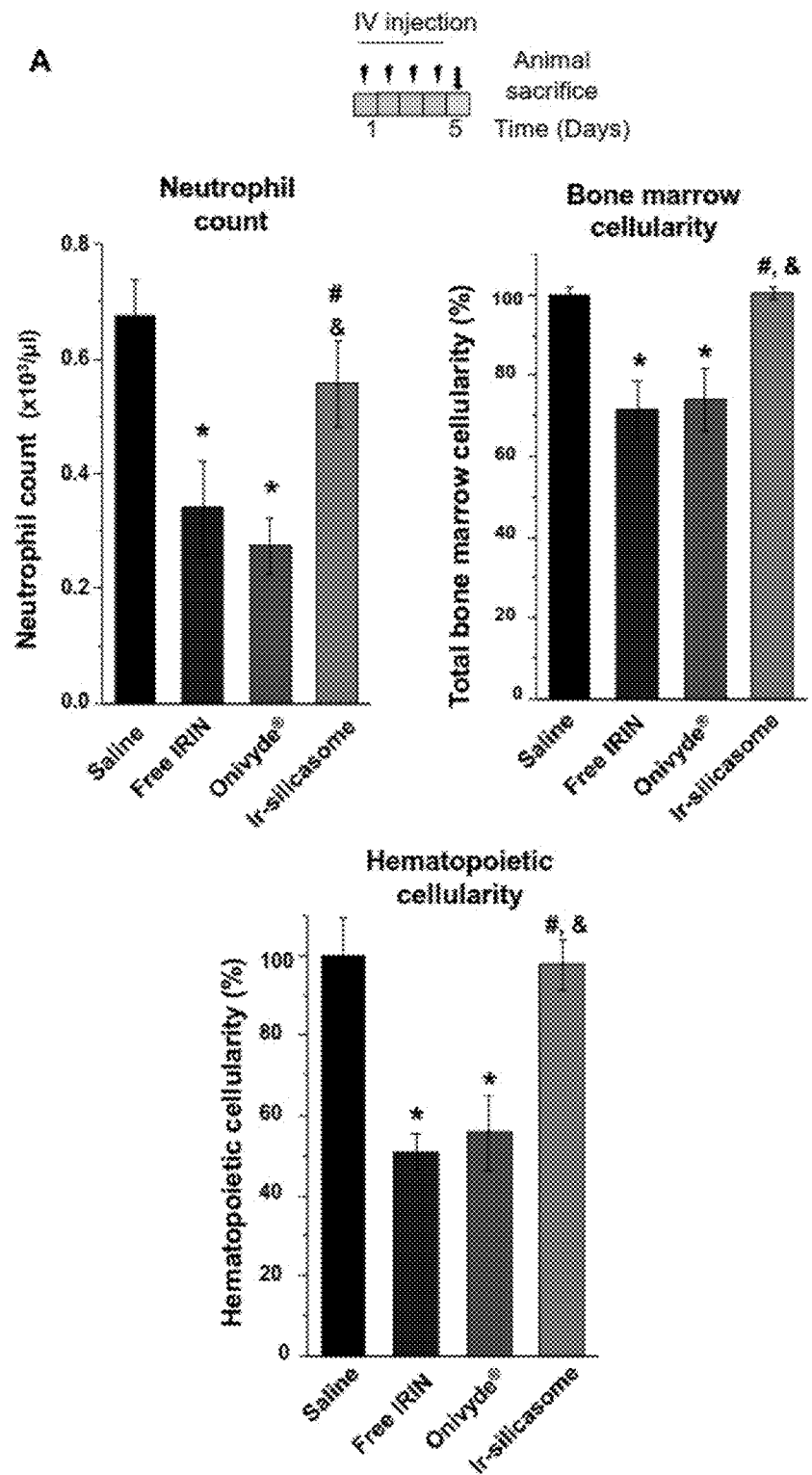
FIG. 13, panels A-D, shows reduction of bone marrow and GI tract toxicity by encapsulated irinotecan delivery by the silicasome. Panel A) Peripheral blood was collected to obtain differential WBC and neutrophil counts in non-tumor-bearing animals 24 hr after receiving 4 IV injections of the various irinotecan formulations at 40 mg/kg. Bone marrow toxicity was evaluated by H&E staining of sternal tissue. Normalized total bone marrow cellularity was determined by using Aperio ImageScope software to calculate the surface area occupied by all cell types (middle panel), as well as the surface area occupied by nucleated hematopoietic cells (right panel). Panel B) Representative H&E images of the sternums. Both low (bar=400 μm) and high (bar=50 μm) magnification pictures are shown. Panel C) GI tract toxicity evaluated by IHC analysis to discern the number of intestinal groups displaying cleaved caspase-3 (CC-3). The intestines were collected from the experiment in panel A. Representative CC-3 IHC staining images in low (bar=100 μm) and high (bar=50 μm) magnification are shown. Panel D) Quantitative display of the percentage $CC-3^+$ cells. Data represent mean±SEM. *p<0.05 compared to saline; #p<0.05 compared to free IRIN; p<0.05 compared to ONIVYDE®.
Figure 26:
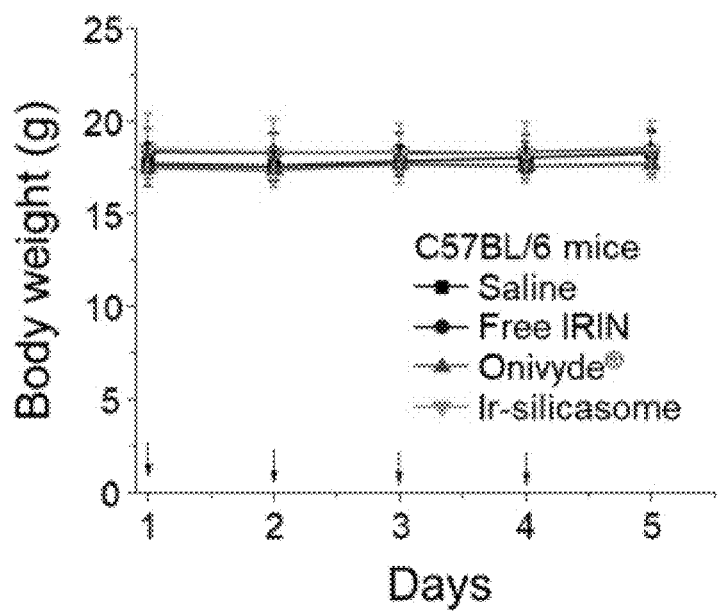
FIG. 26 show body weight profile of animals in the toxicity study described in FIG. 13. No obvious body weight change was observed during treatment. Data represent mean±SD (n=4).

Major Toxicity Reduction in the Bone Marrow and the GI Tract, as a Result of Silicasome Use Irinotecan exerts major systemic toxicological effects (e.g., neutropenia and diarrhea) when used as a free drug monotherapy or in combination with 5-FU (i.e., FOLFIRI regimen) in CRC (Cunningham et al. (1998) *The Lancet*, 352, 1413-1418; Rougier et al. (1998) *The Lancet*, 352: 1407-1412; Saltz et al. (2000) *N. Engl. J Med.* 343: 905-914). This constitutes one of the principal reasons for considering encapsulated irinotecan delivery. To study acute bone marrow toxicity, we designed the toxicity study based on a literature-recommended protocol where the mice were sacrificed at 24 h after receiving six daily irinotecan IV injections to allow for the detection of acute myelosuppression and overall change in health status (Wang et al. (2006) *Curr. Cancer Ther. Rev.* 2: 271-279; Feng et al. (2016) *Basic Clin. Pharmacol. Toxicol.* 119: 428-435; Iusuf et al. (2014) *Mol. Cancer Ther.* 13: 492-503). Thus, an independent experiment was performed in C57BL/6 mice receiving an initial plus three follow-up doses of 40 mg/kg irinotecan IV injections (FIG. 13, panel A) (Iusuf et al. (2014) *Mol. Cancer Ther.* 13: 492-503). The possibility of acute myelosuppression effects was assessed by the collection of whole blood 24 h after the last IV injection, as well as looking at bone marrow cellularity (Id.). No effect was seen on animal weight (FIG. 26), while assessment of differential WBC counts demonstrated a significant degree of neutropenia in animals treated with free irinotecan or ONIVYDE® (FIG. 13, panel A, left panel). The toxicity was reduced by treating with the Ir-silicasome, which yielded essentially a normal neutrophil count compared to the saline group. Sternums were collected to evaluate bone marrow cellularity by H&E staining (FIG. 13, panel B). While both the free drug and ONIVYDE® exhibited significant myelosuppressive effects as evidenced by estimation of total marrow cellularity or the presence of nucleated hematopoietic cells (Id.), no obvious change in cellularity was observed in Ir-silicasome treated animals (FIG. 13, panel B). The visual appearance was confirmed by computer software that semi-quantitatively scored the total marrow cellularity and hematopoietic nuclei in the histology images (FIG. 13, panel A) (Travlos (2006) *Toxicol. Pathol.* 34: 548-565). Thus, while the total and hematopoietic cellularity were reduced by ~26% and ~44% in the ONIVYDE® treated group, the corresponding values were ~0% and ~3% in the Ir-silicasome treated group.

Figure 27:
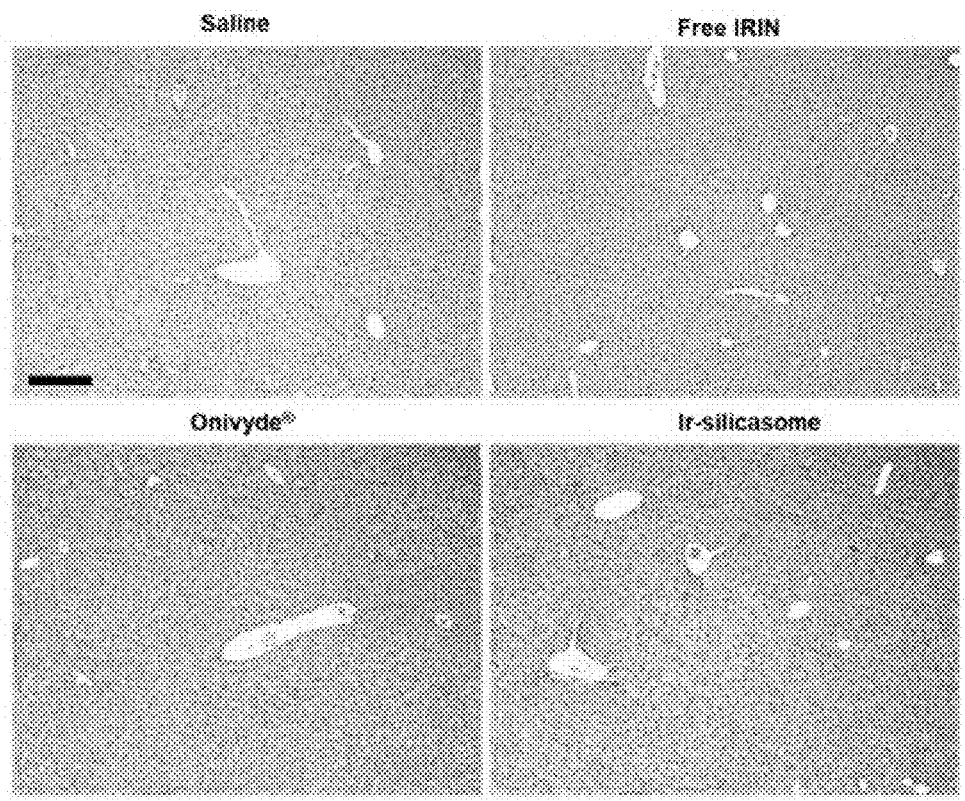
FIG. 27 shows representative H&E staining images of liver tissue taken from the animals in the toxicity study in FIG. 13. Bar=200 m. No obvious liver damage was found in all C57BL/6 mouse strain groups.

In addition to the bone marrow assessment, sections of the small bowel were used to evaluate the presence of apoptotic cells in the intestinal crypts, using IHC to detect cleaved caspase-3 (FIG. 13, panel C) (Tian et al. (2017) *Cancer Res.* 77: 112-122). This demonstrated a significant reduction in the number of $CC-3^+$ cells in animals treated with the silicasome carrier compared to the free drug and ONIVYDE® (FIG. 13, panel D). Curiously, we did not observe significant liver toxicity by any of the treatment modules in C57BL/6 mice, which differs from the higher rates of toxicity seen in a previous study in B6129SF1/J mice (FIG. 27) (Liu et al. (2016) *ACS Nano*, 10: 2702-2715; Ahowesso et al. (2010) *Toxicol. Lett.* 192: 395-401; Okyar et al. (2011) *PLoS ONE*, 6: e20393). All considered, the aforementioned data demonstrate that the custom-designed Ir-silicasome carrier provides favorable toxicity reduction compared to free irinotecan and ONIVYDE®.

Figure 14:
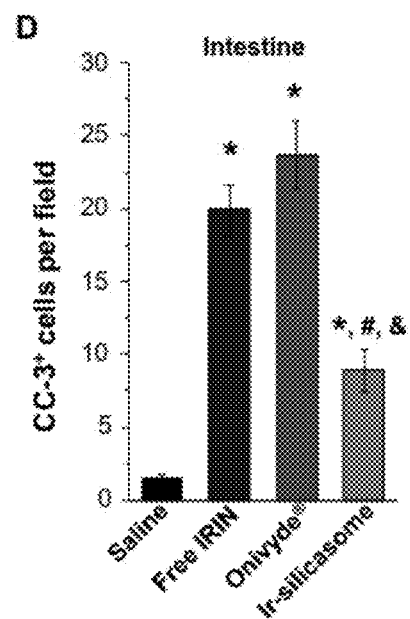
FIG. 14, panels A-C, shows that the custom designed Ir-silicasome demonstrate increased efficacy over ONIVYDE® in an orthotopic PDAC model. Panel A) Intratumoral irinotecan content in orthotopic KPC tumor bearing mice that received a single IV injection of the Ir-silicasome, ONIVYDE®, or free drug at an irinotecan dose equivalent of 40 mg/kg. The mice were sacrificed after 48 hr or 72 hr, and irinotecan content at the harvested tumor sites was determined by UPLC-MS as described in FIG. 11, panel B. Panel B) Efficacy experiment to compare the effects of various irinotecan formulations on primary tumor growth and metastasis. Orthotopic KPC tumor bearing animals received treatments at an irinotecan dose of 40 mg/kg twice per week or saline, for a total of three IV administrations (n=3). Animals were sacrificed at 24 h after the last treatment; autopsy and ex vivo bioluminescence imaging were performed to evaluate the primary and metastatic tumor burden in each group. IHC analysis of CC-3 was performed on primary tumors. Panel C) An independent experiment was conducted to determine the survival outcome between Ir-silicasome vs. ONIVYDE® (n=8). Orthotopic KPC-bearing mice received IV injections of an equivalent dose of 40 mg/kg irinotecan twice per week for a total of six administrations. Overall survival rate was determined as described in FIG. 12 (left bottom panel, *p<0.05, Log Rank test), and orthotopic tumor growth was monitored by live animal tumor bioluminescence imaging (Right bottom panel, FIG. 31). Data represent mean±SEM. *p<0.05 compared to saline; #p<0.05 compared to free IRIN; &p<0.05 compared to ONIVYDE®.
Figure 14:
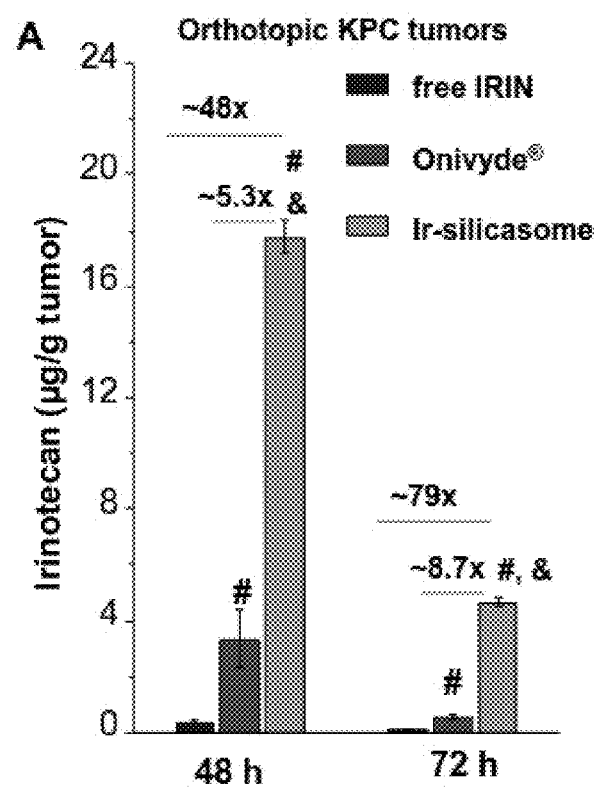
Figure 28:
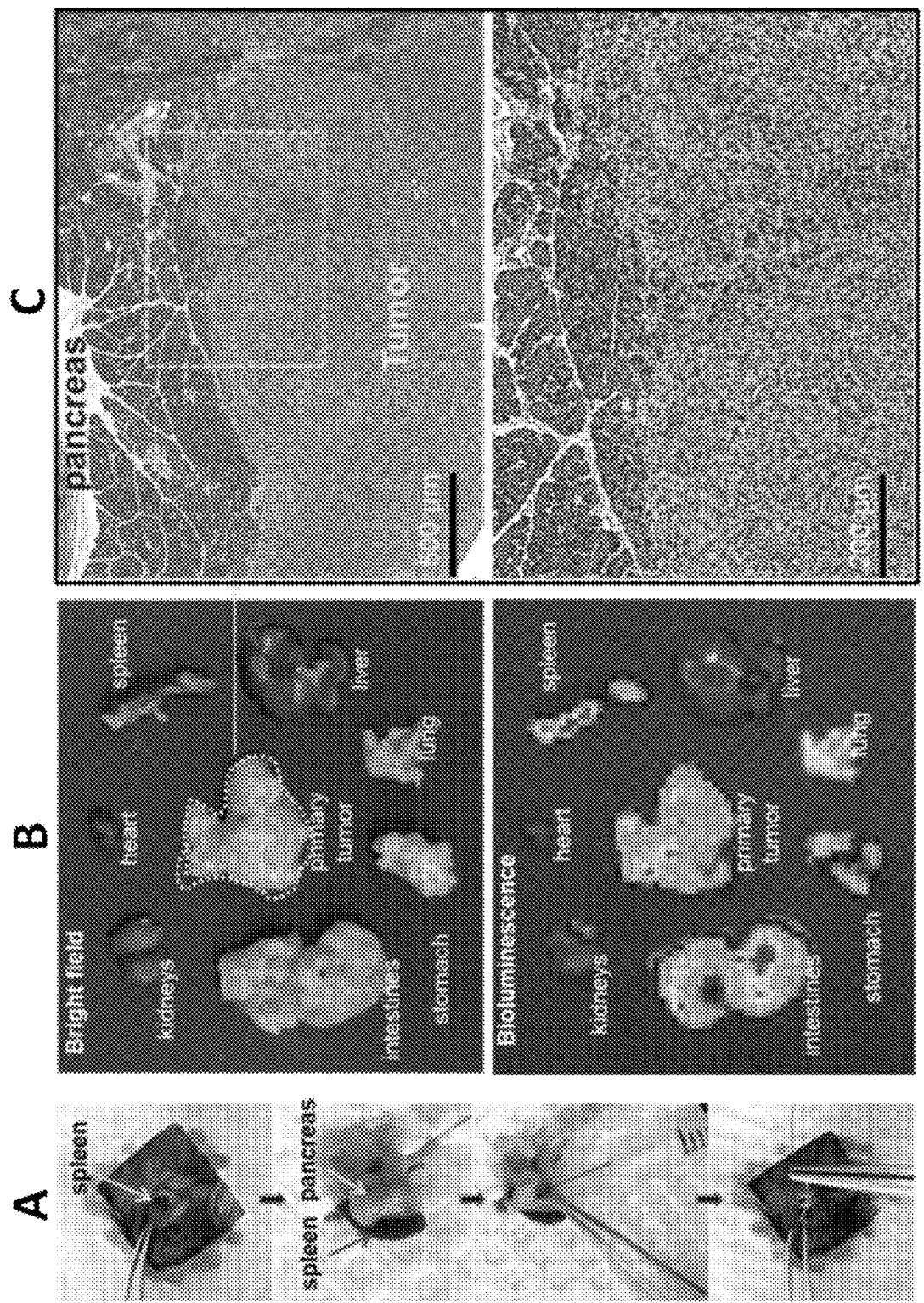
FIG. 28, panels A-C, illustrates various the features of the orthotopic KPC-derived PDAC model in B6/129SF1/J mice. Panel A) The orthotopic KPC model involves injection of KPC-luc cells into the tail of the pancreas in immunocompetent mice using a rapid surgical procedure, as previously described by us (Saltz et al. (2000) *N. Engl. J. Med.* 343: 905-914; Khalid et al. (2017) *Expert Opin. Drug Deliv.* 14: 865-877). Panel B) Animal autopsy and IVIS imaging confirm the presence of primary PDAC and its metastasis to a variety of organs. Panel C) H&E staining of primary tumor tissue confirmed the invasive orthotopic tumor growth.
Figure 29:
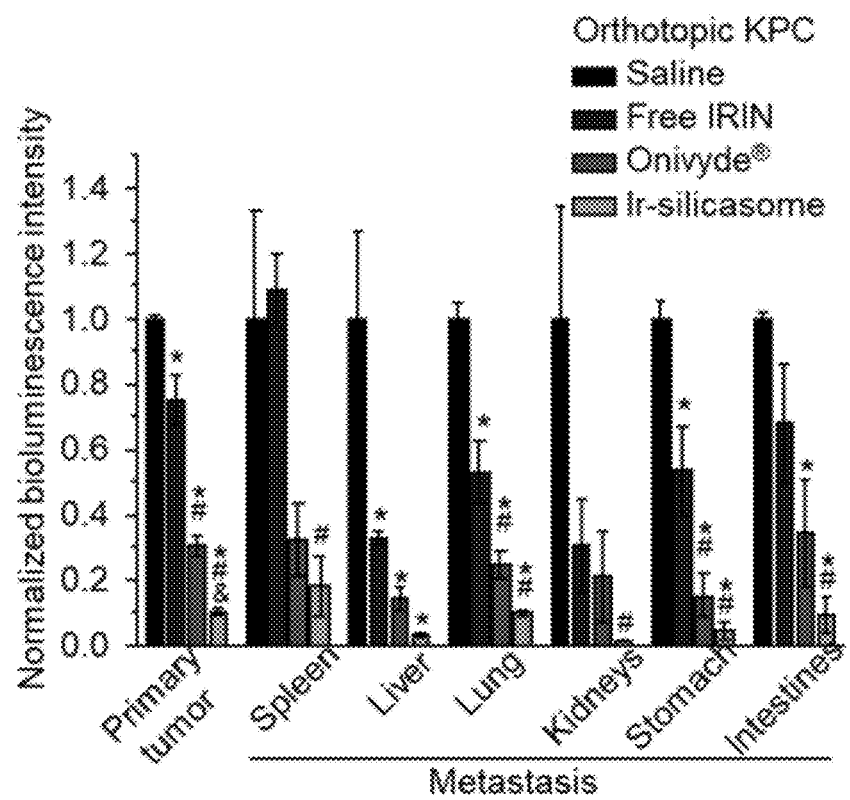
FIG. 29 shows quantitative bioluminescence intensity analysis for the primary and metastatic tumors shown in FIG. 14, panel B. KPC orthotopic tumor mice (n=3) received three IV injections of free irinotecan, ONIVYDE® or Ir-silicasome at the same irinotecan dose (40 mg/kg) twice per week. Saline was used as a control. Animals were sacrificed at 24 h after the last treatment. The data represent mean±SEM, $*p<0.05$ compared to saline, $\#p<0.05$ compared to free IRIN, $p<0.05$ compared to ONIVYDE® (1-way ANOVA followed by a Tukey's test).
Figure 30:
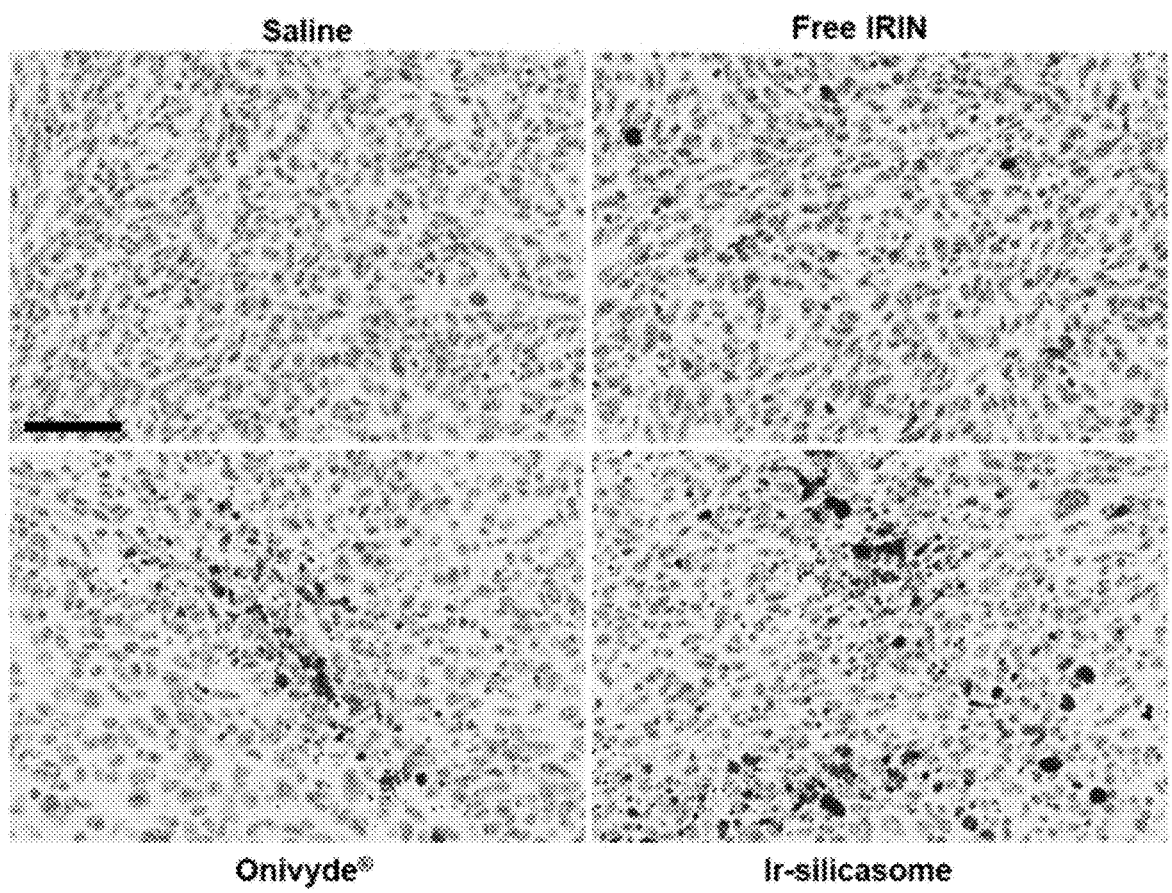
FIG. 30 shows representative IHC images of CC-3 (apoptosis marker) staining in primary tumor sections related to the animals in the efficacy study, described in FIG. 14, panel B. Bar=100 m.
Figure 31:
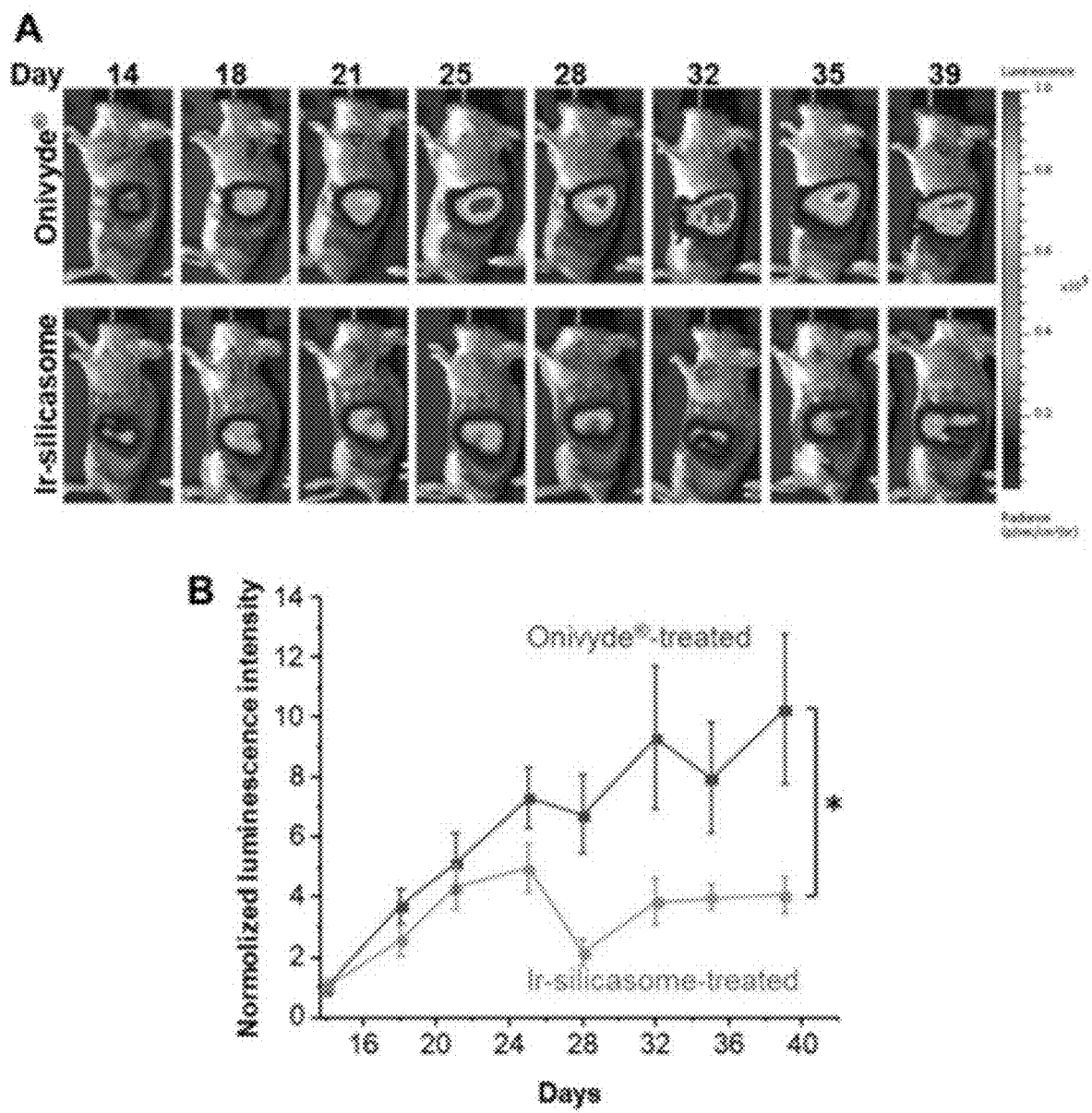
FIG. 31. Panel A) Representative IVIS imaging of the animals used in the survival study of orthotopic PDAC model in FIG. 14, panel C. Panel B) Tumor bioluminescence intensity was analyzed in the operator defined region-of-interest (ROI). N=8, data represent mean±SEM, $*p<0.05$ (Student's t-test).

Confirmation of the Efficacy of the Next-Generation Ir-Silicasome in a PDAC Model The first silicasome generation provided an effective anti-tumor effect free irinotecan in an orthotopic animal model. In order to see how the efficacy of the newly synthesized silicasome compare to ONIVYDE®, we made use of the $Kras^{LSL}$-$G^{12D}$/+/$Trp53^{L}$SL-$R^{172}$H/+/Pdx-1-Cre (KPC) derived PDAC model (Liu et al. (2016) *ACS Nano*, 10: 2702-2715), which is explained in FIG. 28. Assessment of tumor drug content demonstrated that the Ir-silicasome could provide a ~5.3-fold and ~48-fold increase in the PDAC drug content compared to ONIVYDE® and free drug, after 48 h, respectively (FIG. 14, panel A). The differences were even more significant after 72 h, amounting to 8.7-fold and 79-fold increases, respectively (FIG. 14, panel A). Therapeutic efficacy was assessed at either a fixed time point (FIG. 14, panel B) or when the tumor-bearing mice approached moribund status (FIG. 14, panel C). The IVIS imaging data and CC-3 IHC results showed that the Ir-silicasome significantly reduced primary tumor growth and suppression of metastases (FIGS. 14, panel B and 29). While free irinotecan led to inefficient tumor inhibition on primary tumor growth and metastasis, ONIVYDE® had a modest impact on both parameters. Clearly, the Ir-silicasome had the most robust effect on apoptosis at the PDAC site compared to other treatments (FIG. 14, panel B and FIG. 30). The use of Kaplan-Meier analysis in a survival experiment also demonstrated a significantly increased lifespan (p=0.047) through the use of the Ir-silicasome compared to ONIVYDE® (FIG. 14, panel C, left panel). This effect is also reflected by the comparative IVIS imaging data shown in FIG. 14, panel C (right panel) and quantification of bioluminescence intensity in the operator-defined region of interest at the tumor sites (FIG. 31).

DISCUSSION

In this example, we demonstrate that the use of a custom-designed irinotecan-delivering silicasome can improve drug delivery in an orthotopic colon cancer model, leading to an improved treatment outcome and significant toxicity reduction compared to the free drug and ONIVYDE®. Our data demonstrate that the improved PK of the silicasome was accompanied by at least an order of magnitude increase in the drug concentration at the tumor site compared to free irinotecan. The improved drug biodistribution was accompanied by dramatic tumor shrinkage and increased tumor cell death. Moreover, the silicasome also outperformed the ONIVYDE® liposome with respect to PK properties, tumor drug levels, and efficacy, particularly at later time points. Additionally, there were also clear differences between the nanocarriers in terms of adverse outcomes in the bone marrow and GI tract. We also demonstrated that the increased efficacy of the silicasome in the colon model could be reproduced in PDAC, similar to the previous comparative study with a first generation silicasome vs. an in-house liposome (Liu et al. (2016) *ACS Nano*, 10: 2702-2715). Based on these observations, we propose that the Ir-silicasome could also be considered as a treatment option for colon cancer, where the reduction of irinotecan toxicity, coupled with improved efficacy, could advance the Ir-silicasome to be more frequently considered as a treatment consideration for encapsulated drug delivery.

Although liposomal irinotecan has been approved as a $2^{nd}$-line treatment option for PDAC, a Phase II clinical trial using ONIVYDE® for CRC treatment yielded disappointing results, leading to temporary abandonment of the therapeutic effort for this cancer indication (Chibaudel et al. (2016) *Cancer Med.* 5: 676-683). However, it should be possible to revisit the option of irinotecan monotherapy for CRC with the development of our newly designed Ir-silicasome carrier. We should also consider the use of the Ir-silicasome as a substitute for free irinotecan in GI cancer treatment combinations such as FOLFIRINOX (5-FU, folinic acid, irinotecan, oxaliplatin), FOLFIRI (5-FU, folinic acid, irinotecan), XELIRI (irinotecan, capecitabine), FOLFIRI plus the vascular endothelial growth factor (VEGF) antibody, bevacizumab, or the epidermal growth factor (EGFR) antibody, cetuximab (Saltz et al. (2000) *N. Engl. J. Med.* 343: 905-914; Fuchs et al. (2006) *Cancer Treat. Rev.* 32: 491-503; Hurwitz et al. (2004) *N. Engl. J. Med.* 350: 2335-2342; Cunningham et al. (2004) *N. Engl. J. Med.* 351: 337-345). This being stated, it is important to consider that each of these treatment options involve consideration of specific variables that may be introduced by each treatment, e.g., normalization of blood vessels by VGEF blockage, which could impact permeability and egress to the tumor site (Chauhan et al. (2012) *Nat. Nanotechnol.* 7: 383-388). This could have a bearing on the efficacy of various carrier characteristics such as size and the ability of the particle to change its shape during egress through the blood vessel wall (Chauhan et al. (2012) *Nat. Nanotechnol.* 7: 383-388; Jain et al. (2014) *Annu. Rev. Biomed. Eng.* 16: 321-346; Shi et al. (2017) *Nat. Rev. Cancer,* 17: 20-37). Recently, a modified FOLFIRINOX (mFOLFIRINOX) regimen, which adjusts the 5-FU and irinotecan dosing schedule, has attracted attention due to a significant disease-free survival improvement compared to gemcitabine (21.6 vs. 12.8 months) in non-metastatic PDAC (Conroy et al. (2018) *J. Clin. Oncol.* 36: LBA4001). It is possible that the silicasome can further improve these therapeutic combinations, in addition to the major effect on the irinotecan toxicity reduction.

Figure 32:
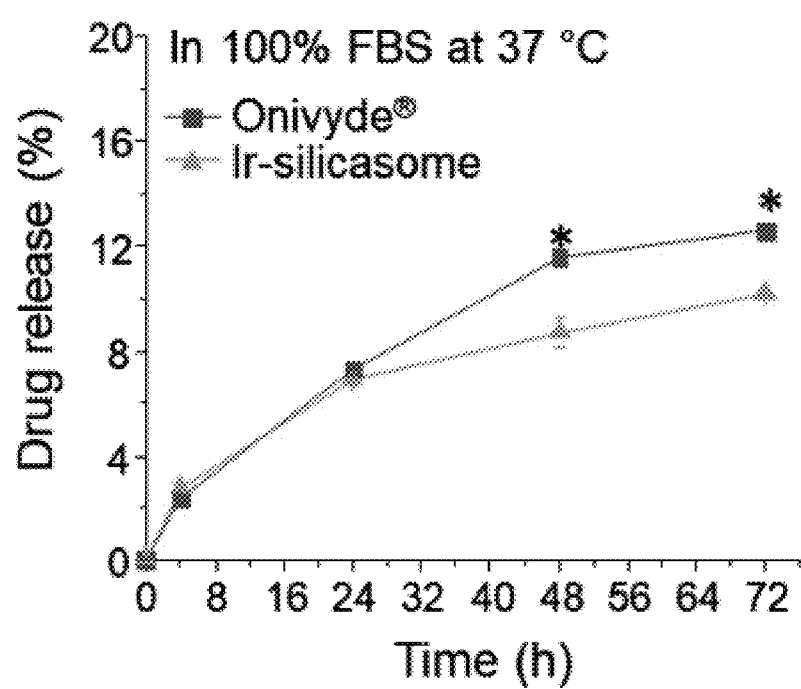
FIG. 32 shows irinotecan release profiles from the ONIVYDE® and Ir-silicasome carriers during incubation in 100% serum at 37° C. for 72 hr, using an irinotecan concentration of 100 μg/mL. Abiotic drug release was analyzed according to our established protocol (Liu et al. (2016) *ACS Nano,* 10: 2702-2715). The irinotecan concentration was determined by HPLC. Compared to the Ir-silicasome, ONIVYDE® exhibited a slightly faster rate of release at 48 and 72 hr. N=3, data represent mean±SD, $*p<0.05$ (Student's t-test).

In this study, a key discovery is the increased potency of the Ir-silicasome compared to ONIVYDE® in two orthotopic tumor models. An obvious advantage is the improved PK and tumor drug content of the silicasome over the liposome. This improved performance is derived from the structural composition and design features of the silicasome compared to the liposome. First, the support provided by the mesoporous silica core allows improved stability of the LB compared to that of the liposome (Liu et al. (2016) *ACS Nano*, 10: 2702-2715; Liu et al. (2009) *J. Am. Chem. Soc.* 131:1354-1355; Cauda et al. (2010) *Nano Lett.* 10: 2484-2492; Ashley et al. (2011) *Nat. Mater.* 10: 389-397; Wang & Liu (2014) *Small,* 10: 3927-3931). This stability improvement is reflected by prolonged circulatory half-life. Second, the porous structure of the coated MSNP provide a large surface area for drug packaging against the side walls of the pores as result of electrostatic and van der Waals interactions (Slowing et al. (20080 *Adv. DrugDeliv. Rev.* 60: 1278-1288; He et al. (2011) *J. Mater. Chem.* 21: 5845; Tang et al. (2012) *Adv. Mater.* 24: 1504-1534). Thus, the large internal surface area of the MSNPs (~800 $m^2/g$) allows more drug encapsulation than for a liposome of equal size. This feature also accounts for the slower drug release rate from the Ir-slicasome compared to ONIVYDE® under abiotic testing conditions (FIG. 32). A third major differential feature from a formulation perspective, is the increased PEG2000 density of the Ir-silicasome (3 mol %) vs. ONIVYDE® (0.3 mol %). In a simulation study, it was demonstrated that the PEG2000 chain assumed a hemispherical ("mushroom") conformation on the lipid bilayer at low density (e.g., <1.6 mol %) (Lee & Larson (2016) *Biomacromolecules*, 17: 1757-1765). However, at higher PEG grafting density, the PEG2000 molecules exhibit an extended "brush" conformation, which is associated with reduced plasma protein binding to the nanoparticle surface under experimental and simulation conditions (Lee & Larson (2016) *Biomacromolecules*, 17: 1757-1765; Perry et al. (2012) *Nano Lett*. 12: 5304-5310; Hak et al. (2012) *ACS Nano*, 6: 5648-5658; Kumagai et al. (2010) *Macromol. Rapid Commun*. 31: 1521-1528). Based on the quantitative assessment of the Flory radius or grafting point distance for PEG in the literature (Lee & Larson (2016) *Biomacromolecules*, 17: 1757-1765), we propose that the PK data could reasonably be interpreted to imply that the 3 mol % PEG density in silicasome assumes a brush-like confirmation that reduces mononuclear phagocyte system (MPS) uptake, leading to a prolonged circulatory $t_{1/2}$. (Hak et al. (2012) *ACS Nano*, 6: 5648-5658; Li & Huang (2010) *J. Controlled Release*, 145: 178-181; Otsuka et al. (2012) *Adv. DrugDeliv. Rev*. 64: 246-255; Liu et al. (2013) *Biomaterials*, 34: 8370-8381; Suk et al. (2016) *Adv. Drug Deliv. Rev*. 99: 28-51; Lucas et al. (2017) *Int. J. Pharm*. 526: 443-454). In contrast, the simulation studies for PEG2000 would suggest that the lesser 0.3 mol % PEG density of the liposome assumes a "mushroom" shape, which is associated with faster clearance from the blood (Lee & Larson (2016) *Biomacromolecules*, 17: 1757-1765). Collectively, the combination of improved stability, large internal surface area and increased PEGylation density of the silicasome likely contributes to the improved PK and tumor drug content during treatment with this carrier.

Finally, a major benefit of using the silicasome vs. the liposome for irinotecan delivery in PDAC and colon cancer is toxicity reduction in the bone marrow and the gastrointestinal tract, as demonstrated in our study. This is in agreement with a previous PDAC study (performed before the commercial availability of ONIVYDE®) in which we demonstrated that the silicasome could outperform an in-house liposome due to reduced irinotecan leakage and a slower rate of drug release (Liu et al. (2016) *ACS Nano*, 10: 2702-2715). One possible explanation is the decreased rate of premature drug release from the silicasome due to increased lipid bilayer stability. Another explanation for the differential toxicity could be the differences in the level of PEGylation of the carriers, which could allow increased opsonization of the lesser PEGylated liposomal membrane to lead to increased phago-endocytosis by the reticuloendothelial cells in the myeloid bone marrow (Sarin, (2010) *J. Angiogenesis Res*. 2: 14). From this perspective, it has specifically been demonstrated in imaging studies that 60 nm PEG-coated nanoparticles are capable of being phagoendocytosed by bone marrow reticuloendothelial cells and released across the capillary wall into the myeloid bone marrow interstitium (Sarin, (2010) *J. Angiogenesis Res*. 2: 14; Illum & Davis (1987) *Life Sci*., 40: 1553-1560; Porter et al. (1992) *Int. J. Pharm*. 83: 273-276). It is possible that the carrier size and the deformability of the carrier could possibly play a role in favoring liposome over silicasome uptake in the bone marrow, leading to increased toxicity.

CONCLUSIONS

In summary, we demonstrated the establishment of a next generation silicasome proved to be more efficacious with reduced toxicity during Irinotecan delivery to orthotopic CRC and PDAC models. Since ONIVYDE® resulted in a disappointing outcome in a phase II clinical study in CRC, the availability of an alternative carrier, which can be produced in large quantities, could allow the pursuit of human clinical studies with the silicasome in patients with CRC, in addition to the potential treatment benefit in PDAC. Moreover, the silicasome nanocarrier can also be used to deliver other chemotherapeutic agents, such as weak basic drugs that can be remotely loaded into the carrier, including the ability to co-encapsulate synergistic drug combinations.

Methods

Materials

Tetraethylorthosicate (TEOS), triethanolamine (TEA-ol), (3-aminopropyl)triethoxysilane (APTES), cetyltrimethylammonium chloride solution (CTAC, 25 wt % in water) and Dowex 50WX8 resin were purchased from Sigma-Aldrich, USA. Sucrose octasulfate (SOS) sodium salt was purchased from Toronto Research Chemicals, Inc, Canada. Triethylamine (TEA) was purchased from Acros, USA. Sepharose CL-4B was purchased from GE Healthcare, USA. Irinotecan hydrochloride trihydrate was purchased from LC Laboratories, USA. ONIVYDE® (Ipsen Biopharmaceuticals, Inc., 4.3 mg/mL irinotecan free base, 10 mL/vial) was purchased through the UCLA health pharmacy. 1,2-Distearoyl-sn-glycero-3-phosphocholine (DSPC), 1,2-distearoyl-sn-glycero-3-phosphoethanol amine-N-[methoxy(polyethylene glycol)-2000] (ammonium salt) ($DSPE-PEG_{2000}$), and cholesterol (Chol) were purchased from Avanti Polar Lipids, USA. Penicillin, streptomycin, Dulbecco's modified Eagle medium (DMEM) and Roswell Park Memorial Institute (RPMI) 1640 medium were purchased from Invitrogen. Fetal bovine serum (FBS) was purchased from Gemini Bio Products. Rabbit mAb antibody (catlog. #9664), which detects activated (cleaved) caspase-3, was purchased from Cell Signaling. Anti-CD31 antibody (catalog #553708) was purchased from BD Pharmingen™, USA. ALEXA FLUOR® 488 conjugated goat anti-rabbit IgG (H+L) secondary antibody (catalog #A11008), and DyLight 680 NHS ester were purchased from Thermo Fisher Scientific Inc, USA. MATRIGEL™ Matrix Basement Membrane was purchased from BD Bioscience.

Synthesis, Purification, and Characterization of Ir-Silicasomes

Synthesis of Bare MSNPs:

17.1 L pure water was added to a 20 L beaker. 0.9 L CTAC solution (25 wt. % in $H_2O$) was gently added while stirring at 185 rpm, using an overhead stirrer shaft. The solution was heated to 85° C. while stirring and then 72 g triethanolamine in 300 mL $H_2O$ was added when the solution reached a temperature of 85° C. After stirring the solution for another 30 min at 85° C., 600 mL TEOS at 85° C. was gently added, followed by stirring at the same temperature for another ~4 hr. This yielded a milky particle suspension, which was allowed to cool down naturally to room temperature. Six L of ethanol was added to the suspension to precipitate the silica particles, followed by centrifugation at 10,000 rpm for 10 mins. To remove the CTAC, the particles pellets were resuspended in acidic ethanol (HCl/ethanol, 4:100 v/v) by sonication through repeated centrifugation (10,000 rpm×60 mins) and resuspension, which was repeated 5 times. This was followed by washing in pure ethanol 3 times. The primary size and morphology of the particles were characterized using TEM (JEOL 1200-EX). The presence of residual CTAC in the MSNP was tested by FTIR and high-performance liquid chromatography (HPLC, Infinity 1260, Agilent), using an Acclaim Surfactant Plus column. A charged aerosol detector was used for CTAC quantification. Surface area, pore volume, and pore size of the purified MSNP were tested by (Brunauer-Emmett-Teller) BET measurement, as described before (Liu et al. (10'7) *J. Clin. Invest.* 127: 2007-2018).

Lipid Coating Using an Ethanol Exchange Method:

Briefly, a mixture of lipids (16 g DSPC, 5.4 g, cholesterol (Chol) and 2.8 g DSPE-PEG$_{2000}$, yielding a DSPC/Chol/DSPE-PEG$_{2000}$ molar ratio of 3:2:0.15) was dissolved in 50 mL pure ethanol at ~65° C. 500 mL of a preheated (~65° C.) solution, containing a 40 mg/mL MSNP suspension into which 80 mM TEA$_8$SOS trapping agent was soaked, was poured into the lipid solution while stirring at ~1,000 rpm. The TEA$_8$SOS trapping agent was made based on our established protocol (Liu et al. (2016) *ACS Nano,* 10: 2702-2715). The mixture was treated by probe sonication (power=200 W) using a 15 s/5 s on/off cycle for 2 hr. In between, the sample was stirred at ~500 rpm, followed by centrifugation at 4,000 rpm for 5 min to remove any aggregates.

Removal of Free TEA$_8$SOS and Remote Loading of the Irinotecan into the Silicasomes:

Unentrapped free TEA$_8$SOS was removed by size exclusion chromatography over a Sepharose CL-4B column, using a HEPES-buffered dextrose solution (5 mM HEPES, 5% dextrose, pH 6.5) for elution. 10 g irinotecan was dissolved in 1 L HEPES buffered dextrose (5 mM HEPES, 5% dextrose, pH=6.5) and mixed with the TEA$_8$SOS-loaded silicasome suspension. The mixture was incubated at ~65° C. for 30 min, before quenching the sample in ice water for ~30 min. The drug loaded silicasome were washed 3 times using a HEPES-buffered NaCl solution (4.05 mg/mL HEPES, 8.42 mg/mL NaCl, pH 7.2). The supernatant was collected and filtered with a 0.45 µm syringe filter, followed by a 0.2 µm filter for sterilization.

Characterization of the Ir-Silicasomes

The irinotecan concentration was determined by either UV spectroscopy (360 nm) or HPLC. The free base form of the drug was prepared at 4.3 mg/mL. MSNP mass and lipid mass in the final product were determined by TGA and HPLC, respectively. Particle hydrodynamic size and zeta potential were measured by a ZETAPALS instrument (Brookhaven Instruments Corporation). The DLS size measurement was performed by diluting the MSNP to ~100 µg/mL in DI water. The zeta potential was assessed by diluting the particles in 10 mM NaCl solution, at a concentration of 100 µg/mL. The final product was visualized by cryoEM (TF20 FEI Tecnai-G2 in CNSI) to confirm the uniformity and integrity of the coated lipid bilayer. Endotoxin levels were tested using a chromogenic LAL assay (QCL-1000 300 Test Kit, Lonza). Sterilization of the final product was confirmed by performing tests for microbial contamination (HPC Count sampler, Millipore Corp., MHPC 10025) or the presence of yeasts and molds (Yeast and mold sampler, Millipore Corp., MY0010025).

Cell Culture

The dimethylhydrazine-induced murine MC38 colon adenocarcinoma cell line (Corbett et al. (1975) *Cancer Res.* 35: 2434-2439), which is syngeneic for a C57BL/6 background, was kindly provided by Dr. Siwen Hu-Lieskovan at UCLA. The KPC murine pancreatic adenocarcinoma cell line was derived from a spontaneous tumor originating in a transgenic Kras$^{LSL-G12D/+}$; Trp53$^{LSL-R172H/+}$; Pdx-1-Cre mouse (B6/129 background) (Liu et al. (2016) *ACS Nano,* 10: 2702-2715). To allow bioluminescence tumor imaging, both cells were permanently transfected with a luciferase-based lentiviral vector in the UCLA vector core facility, followed by a limiting dilution cloning (Liu et al. (2016) *ACS Nano,* 10: 2702-2715; Meng et al. (2015) *ACS Nano,* 9: 3540-3557). Detailed cell culture conditions, cytotoxicity, testing and screening for IL-1β release are described in Supplementary Materials.

Development of an Orthotopic MC38 Tumor Chunk Transplantation Model

Female C57BL/6 mice were purchased from Charles River Laboratories and maintained under pathogen-free conditions. All animal experiments were performed according to protocols approved by the UCLA Animal Research Committee. In order to prepare a tumor that can be sliced into tumor chunks, MC38-luc cells were subcutaneously injected (~2×10$^6$ cells suspended in 100 LL of DMEM/Matrigel, 1:1 v/v) in the flank of C57BL/6 mice (6~8 weeks). The mice were euthanized when the tumor size reached ~1 cm$^3$. The tumor was removed under sterile conditions and cut into ~1.5 mm×~3 mm tumor chunks (Tseng et al. (2007) *Vis. Exp.* 10: 484). The orthotopic placement of the tumor chunks involved a short surgical procedure in anesthetized (isoflurane, ketamine and xylazine) C57BL/6 mice (10-12 weeks). We also administered the 1$^{st}$ dose of pain medication (carprofen 5 mg/kg, subcutaneous) pre-operatively. The surgical area (abdomen) was shaved with a #40 blade and sterilized with betadine and 70% ethanol. The animals were placed on a heat pad and sterilely draped with gauze to expose the surgical site. A 2-3 cm abdominal incision was made to expose the cecum, which was exteriorized and isolated from the rest of the abdominal content by packed gauze. Warm saline was used to keep the cecum moist. A figure of 8 stitch was placed superficially in the cecum wall, using size 6-0 absorbable sutures (PDS II, Ethicon). The tumor piece was tied onto the wall, which was lightly abraded with tweezers to facilitate tissue level contact with the tumor chunk. After attaching the tumor chunk, the cecum was returned to the abdominal cavity. The inner (fascial) layer was closed with size 6-0 absorbable sutures (PDS II, Ethicon) and the exterior skin was closed with size 5-0 sized non-absorbable sutures (PROLENE, Ethicon). The mice were kept on the warming pads until full recovery from anesthesia, and then transferred to clean cages. The efficacy study was performed in the tumor-bearing mice approximately one week after implantation, at which point the tumors had grown to ~0.5 cm. For the biodistribution experiments, the tumor-bearing mice were used ~2 weeks after tumor implantation, at which point the tumors had grown to a size of ~1.0 cm. The orthotopic implantation of KPC cells in the pancreas of B6/129 mice have been previously described (Liu et al. (2016) *ACS Nano,* 10: 2702-2715; Luo et al. (2015) *Wiley Interdiscip. Rev. Nanomed. Nanobiotechnol.* 7: 169-188).

Assessment of Irinotecan Pharmacokinetics (PK), Using the Silicasome

The PK study was performed on 10~12 week old healthy female C57BL/6 mice. The animals received IV injections of free irinotecan, ONIVYDE® or Ir-silicasome at an irinotecan dose of 40 mg/kg, followed by collection of blood samples at 5 min, 3, 6, 24, and 48 hrs. After separation of the plasma fraction, the drug was extracted in an acidic methanol solution (0.1 mol/L phosphoric acid/methanol, 1:4 v/v) (Liu et al. (2016) *ACS Nano,* 10: 2702-2715). The irinotecan concentration was measured by UPLC-MS (Waters LCT Premier ESI), using gradient elution of acetonitrile in water at a flow rate of 1.00 mL/min (Lu et al. (2017) *Nat. Commun.* 8: 1811). The PK data were analyzed by PKSolver software, using a one-compartment model (Zhang et al. (2010) *Comput. Meth. Programs Biomed.* 99: 306-314).

Tumor Drug Content and Intratumoral Biodistribution

Drug content was determined in the tumor tissue obtained from both the MC38 and KPC orthotopic models. Tumor bearing mice received IV injections of free irinotecan, ONIVYDE® or Ir-silicasome at dose of 40 mg/kg irinotecan. Animals were sacrificed after 48 and 72 hr for collection of tumor tissue, estimation of tumor weight, and homogenization in acidic methanol to measure the drug concentration by UPLC-MS (Liu et al. (2016) *ACS Nano*, 10: 2702-2715; Lu et al. (2017) *Nat. Commun.* 8: 1811). To track the silicasome biodistribution by IVIS imaging, silicasomes were labeled with NIR dye by modifying the MSNP with APTES to react with NHS-DyLight 680 NHS ester (Liu et al. (2016) *ACS Nano*, 10: 2702-2715; Liu et al. (10'7) *J. Clin. Invest.* 127: 2007-2018), following which tumor-bearing mice were IV injected with 100 mg/kg MSNP. Animals were sacrificed after 48 hr to collect tumor tissue and major organs for performance of ex vivo IVIS imaging and assessment of Si content by ICP-OES. Tumor slices were also cryo-embedded in OCT reagent to prepare tumor sections for confocal microscopy (SP8-SMD, Leica). The tumor blood vessels were stained with a primary anti-CD31 antibody (1:500), followed by an ALEXAFLUOR® 488-conjugated secondary antibody (1:500). DAPI was used to localize the cellular nuclei.

Assessment of Treatment Efficacy in the Orthotopic Tumor Models

Seven days after MC38 tumor chunk implantation, the tumor-bearing mice were randomly assigned into 4 groups (n=6) (FIG. 12, panels A-B). Animals in each group received IV injections of free irinotecan, ONIVYDE®, or Ir-silicasome at an irinotecan dose equivalent of 40 mg/kg, twice per week for a total of 4 to 6 administrations (depending on animal survival).

Saline was used as a negative control. To assess survival rate, animals were monitored daily up to the point of spontaneous death or approaching moribund status (Liu et al. (10'7) *J. Clin. Invest.* 127: 2007-2018; Olive et al. (2009) *Science*, 324: 1457-1461). Live bioluminescence imaging was used to monitor the orthotopic tumor burden twice per week, as previously described (Liu et al. (2016) *ACS Nano*, 10: 2702-2715). We also performed an efficacy study in the orthotopic MC38 model to obtain tumor tissue for weighing and histological analysis (FIG. 12, panels C-D). This study was conducted using a total of four injections as described above, followed by sacrifice on day 18 (24 hr after the $4^{th}$ IV injection). The orthotopic tumors were harvested and weighed, then fixed in 10% formalin for H&E or assessment of cleaved caspase 3 (CC-3) expression by IHC staining in the UCLA Translational Pathology Core Laboratory. (TPCL). The images were assessed by using Aperic ImageScope software (Leica). The efficacy study in PDAC orthotopic model was provided online.

Safety Assessment of Encapsulated Versus Free Irinotecan Delivery

To compare the toxicity of different irinotecan formulations, a toxicity study was performed in healthy female C57BL/6 mice using a published protocol (Iusuf et al. (2014) *Mol. Cancer Ther.* 13: 492-503). Animals received daily IV injections of different irinotecan formulations at a drug dose of 40 mg/kg. A total of four administrations were performed (Id). The mice were sacrificed 24 hr after the final injection. Blood was drawn to perform complete blood count and sternums and other organs collected for histological analysis and IHC. IHC staining to assess CC-3 expression in the small intestine was performed as described above. H&E staining to assess bone marrow and hematopoietic cellularity in the sternum was analyzed by Aperio ImageScope software (Travlos (2006) *Toxicol. Pathol.* 34: 548-565).

Statistical Analysis

Comparative analysis of differences between groups was performed using the 2-tailed Student's t-test (Excel software, Microsoft) for two-group comparison. A One-way ANOVA followed by a Tukey's test (Origin software, OriginLab) was performed for multiple group comparisons. Data were expressed as mean±SD or SEM, as stated in the figure legends. The survival analysis was performed by Log Rank testing (Mantel-Cox) using SPSS 2.0 software. The software instructions for the Log Rank testing indicates that multiple comparisons analysis is possible, including pairwise comparisons in case three or more groups. A statistically significant difference was considered at $p<0.05$.

Supplement Methods.

Cell Culture and In Vitro Cell Study:

MC38 and KPC cells were cultured in DMEM, containing 10% FBS, 100 U/mL penicillin, 100 µg/mL streptomycin, and 2 mM L-glutamine. THP-1 cells were obtained from ATCC (Manassas, VA) and cultured in RPMI 1640 medium supplemented with 10% FBS.

MTS Cytotoxicity Assay:

The cytotoxicity of purified MSNPs was assessed in a standard MTS assay (CellTiter 96® AQueous One Solution Cell Proliferation Assay, Promega). KPC or MC38 cells were plated at a density of $5 \times 10^3$ cells per well in a 96-well plate and cultured for 24 hr. The medium was replaced with fresh medium containing the different NPs at the indicated concentrations. Non-treated cells were used as control. After a 48 hr treatment, the medium was replaced with 100 µL fresh medium containing MTS solution (5:1, v/v medium/CellTiter 96® Aqueous stock solution) for further culture at 37° C. for 1 hr. The absorbance of the culture wells at 490 nm was directly recorded by a microplate reader (M5e, Molecular Device, USA). Wells without cells but contained the same MTS solution were used as blank. The relative cell viability (%) is [(the absorption of treated well−blank)/(the absorption of control well−blank)]×100.

ELISA to Determine IL-1β Release from THP-1-Cells:

ELISA was used to assess IL-1β release, as previously shown by us (Jiang et al. (2017) *ACS Nano*, 11: 1869-1883). Briefly, THP-1 cells in 100 µL of tissue culture medium were plated at a density of $3 \times 10^4$ cells per well in a 96-well plate. The cells were treated with 1 µg/mL phorbol 12-myristate 13-acetate (PMA) for 16 h. After replenishment with fresh culture medium, the differentiated THP-1 cells were treated with MSNPs in the presence of 10 ng/mL lipopolysaccharide (LPS) for an additional 24 h. The supernatants were collected for measuring IL-1β by and ELISA kit, according to the manufacturer's instructions (BD Biosciences, San Diego, CA). Concentrations were expressed as pg/mL.

Establishment of Orthotopic KPC-Derived PDAC Tumor Model:

We have previously described the establishment of a KPC-derived orthotopic tumor model (Liu et al. (2016) *ACS Nano*, 10: 2702-2715; Liu et al. (2017) *J. Clin. Invest.* 127: 2007-2018). Briefly, female B6/129SF1/J mice were purchased from The Jackson Laboratory, and maintained under pathogen-free conditions. All animal experiments were performed under protocols approved by the UCLA Animal Research Committee. The orthotopic model was developed by injecting 50 iL of DMEM/Matrigel (1:1 v/v) containing $2 \times 10^6$ KPC-luc cells into the tail of the pancreas in female B6129SF1/J mice (8-10 weeks) by a rapid surgery procedure (Liu et al. (2016) *ACS Nano*, 10: 2702-2715; Liu et al.

(2017) *J. Clin. Invest.* 127: 2007-2018). The efficacy study was performed in tumor-bearing mice ~2 weeks after implantation, at which point the primary tumors had grown to ~0.5 cm. For the biodistribution experiments, the tumor-bearing mice were used ~2 weeks after tumor implantation, at which point the primary tumors had grown to a size of ~0.8 cm.

Efficacy Studies on Orthotopic KPC-Derived PDAC Tumor Model:

Orthotopic KPC bearing mice were used to determine the anti-tumor efficacy and survival outcome of different irinotecan formulations. In the survival experiment, the animals received IV injections of Onivyde® or Ir-silicasome both at the same irinotecan dose of 40 mg/kg twice every week, for a total of 6 administrations (n=8) (FIG. 14, panel C). We also included additional controls, free drug and saline, in the antitumor efficacy experiment as described in FIG. 14, panel B. Live animal imaging was used to monitor the orthotopic tumor burden twice per week; the tumor burden was quantitatively expressed as bioluminescence intensity in the ROI measured, using software. Drug induced apoptosis was analyzed by CC-3 IHC staining.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for large-scale preparation of mesoporous silica nanoparticles suitable for use in pharmaceuticals, said method comprising:
   providing a cationic surfactant in water at a concentration greater than a critical micellar concentration (CMC) of said cationic surfactant to form an aqueous mixture of micelles, where said cationic surfactant comprises cetyltrimethylammonium chloride (CTAC) or cetyltrimethylammonium bromide (CTAB);
   adding triethanolamine (TEA) and tetraethylorthosilicate (TEOS) to said aqueous mixture of micelles at a molar ratio of water: cationic surfactant: TEA:TEOS ranging from 100 to 150 water: 0.06 to 0.10 cationic surfactant: 0.04 to 0.08 TEA: 0.08 to 1.2 TEOS; and
   stirring or agitating said aqueous mixture of micelles to allow said cationic surfactant, said TEA, and said TEOS in said aqueous mixture of micelles to react to form a population of mesoporous silica nanoparticles (MSNPs), wherein said method produces at least 30 grams of mesoporous silica nanoparticles in a single batch, and
   wherein the providing of the cationic surfactant at the concentration greater than the CMC maintains a size of MSNPs in presence of said TEA.

2. The method of claim 1, wherein said cationic surfactant is CTAC.

3. The method of claim 1, wherein said method further comprises adding ethanol to said aqueous mixture of micelles after said population of MSNPs is formed to precipitate said population of MSNPs.

4. The method of claim 1, wherein the molar ratio of water:cationic surfactant:TEA:TEOS is 125:0.08:0.06:1.

5. The method of claim 1, wherein said reaction proceeds until at least one of the following: 1) a hydrodynamic size of said population of MSNPs is constant or 2) a yield of said population of MSNPs is constant.

6. The method of claim 1, wherein said method produces said population of MSNPs characterized by at least one of the following features:
   a monotonic size distribution;
   a size distribution having a coefficient of variation of less than 0.10;
   said population of MSNPs having an average diameter ranging from 40 nm up to 100 nm; and
   an average pore size ranging from 2.2 to 3.4 nm.

7. The method of claim 1, wherein said method further comprises:
   providing a plurality of lipids in a polar solvent forming a dispersion of lipid in a solvent;
   introducing said population of MSNPs into said dispersion to form a dispersion containing said population of MSNPs; and
   sonicating or homogenizing said dispersion containing said population of MSNPs to provide a population of MSNPs encased in a lipid bilayer.

8. The method of claim 7, wherein said polar solvent comprises a solvent selected from the group consisting of ethanol, methanol, ethanol containing an aqueous solvent with the organic phase greater than 30%, methanol containing the aqueous solvent with an organic phase greater than 30%, pure acetone, and acetone aqueous solution with acetone concentration of 50% or greater.

9. The method of claim 7, wherein the ratio of the population of MSNPs to the lipid ranges from 1:0.5 to 1:5 w/w.

10. The method of claim 7, wherein said sonication proceeds at an energy and duration sufficient to provide a clear suspension of said population of MSNPs encased in said lipid bilayer.

11. The method of claim 7, wherein:
   said plurality of lipids comprise a phospholipid, cholesterol (CHOL), and an mPEG phospholipid and said lipid bilayer encapsulating said population of MSNPs comprises said phospholipid, cholesterol (CHOL), and mPEG phospholipid; or
   said lipid bilayer comprises 1,2-distearoyl-sn-glycero-3-phosphoethanolamine-PEG (DSPE-PEG); or
   said lipid bilayer comprises DPPC/Chol/DSPE-PEG or DSPC/Chol/DSPE-PEG; or said lipid bilayer comprises a phospholipid, cholesterol, and mPEG phospholipid at a ratio of 50-90 mol % phospholipid:10-50 mol % CHOL:1-10 mol % mPEG phospholipid.

12. The method of claim 7, wherein said lipid bilayer forms a continuous uniform and intact bilayer encompassing an entire nanoparticle within the population of MSNPs.

13. The method of claim 7, wherein said providing said population of MSNPs comprises providing said population of MSNPs loaded with a protonating agent and wherein said population of MSNPs encased in said lipid bilayer formed by said method contain said protonating agent.

14. The method of claim 13, wherein said protonating agent is selected from the group consisting of triethylammonium sucrose octasulfate (TEA8SOS), proton-generating dissociable salts, a trimethylammonium salt, a triethylammonium salt, an acidic buffer, a metal salt, and calcium acetate.

15. The method of claim 13, wherein said method comprises remote loading said population of MSNPs encased in said lipid bilayer with a drug by incubating said population of MSNPs encased in said lipid bilayer containing said protonating agent with one or more drugs comprising at least one weakly basic group capable of being protonated.

16. The method of claim 15, wherein said drug comprises one or more of the following:
   at least one weakly basic group capable of being protonated, and the protonating agent comprises at least one anionic group;
a pKa greater than 7 and less than 11;
a primary, secondary, or tertiary amine; a water solubility index of 2 to 25 mg/mL;
an octanol/water partition coefficient or log P value of −3.0 to 3.0; or
a size smaller than the average or median size of the pores of the silica nanoparticle.

17. The method of claim 16, wherein: said drug comprises an anticancer drug; or said drug comprises irinotecan, a substantially pure D isomer of irinotecan, or a substantially pure L isomer of irinotecan; or said drug comprises one or more drugs independently selected from the group consisting of a topoisomerase inhibitor, an antitumor anthracycline antibiotic, a mitotic inhibitor, an alkaloid, an alkaline alkylating agent, a purine or pyrimidine derivative, and a protein kinase inhibitor; or said drug comprises a drug selected from the group consisting of topotecan, 10-hydroxycamptothecin, belotecan, rubitecan, vinorelbine, LAQ824, doxorubicin, mitoxantrone, vinblastine, vinorelbine, cyclophosphamide, mechlorethamine, temozolomide, 5-fluorouracil, 5'-deoxy-5-fluorouridine, gemcitabine, imatinib, osimertinib and sunitinib pazopanib, enzastaurin, vandetanib, erlotinib, dasatinib, nilotinib, abemaciclib, palbociclib, and ribociclib.

18. The method of claim 16, wherein said drug comprises irinotecan, a pure D isomer of irinotecan, or a pure L isomer of irinotecan.

19. The method of claim 15, wherein:
said population of MSNPs encased in said lipid bilayer have a drug loading capacity of at least 5% w/w, or at least 10% w/w, or at least 20% w/w, or at least 30% w/w, or greater than 40% w/w, or greater than 50% w/w, or greater than 60% w/w, or greater than 70% w/w, or greater than 80% w/w; and/or
said lipid bilayer comprises a hydrophobic drug that is introduced into said lipid bilayer before encapsulation of said population of MSNPs; and/or
said lipid bilayer comprises a hydrophobic drug that is introduced into said lipid bilayer before encapsulation of said population of MSNPs where said lipid bilayer comprises a hydrophobic drug selected from the group consisting of paclitaxel, ellipticine, camptothecan, SN-38, and a lipid prodrug.

20. The method of claim 7, wherein said population of MSNPs encased in said lipid bilayer are each conjugated to a moiety selected from the group consisting of a targeting moiety, a fusogenic peptide, and a transport peptide.

21. The method of claim 7, wherein said method produces said population of MSNPs encased in said lipid bilayer in suspension that comprises one or more of the following properties:
is stable for at least 1 month, or at least 2 months, or at least 3 months, or at least 4 months, or at least 5 months, or at least 6 months when stored at 4° C.;
shows a size distribution having a full width half maximum of less than 30 nm, or less than 20 nm, or less than 10 nm, or less than 5 nm, or less than 3 nm, or less than 2 nm;
shows a unimodal size distribution;
shows a PDI less than 0.2, or less than 0.1; and shows a coefficient of variation in size less than 0.1 or less than 0.05, or less than 1.7/120.

22. The method of claim 1, wherein the molar ratio of water:cationic surfactant:_TEA:TEOS is 125:0.08:0.06:0.33.

23. The method of claim 22, wherein said method produces greater than 100 grams of mesoporous silica nanoparticles in a single batch.

24. The method of claim 23, wherein said method produces about 120 grams to about 140 grams of mesoporous silica nanoparticles in a single batch.

25. The method of claim 1, wherein said method produces at least 60 grams of mesoporous silica nanoparticles in a single batch.

26. The method of claim 1, wherein said method has a yield of greater than about 80%.

* * * * *